US012774350B2

(12) United States Patent
Bruenker et al.

(10) Patent No.: US 12,774,350 B2
(45) Date of Patent: Oct. 27, 2026

(54) ANTIBODIES BINDING TO CD3 AND FOLR1

(71) Applicant: Hoffmann-La Roche Inc., Little Falls, NJ (US)

(72) Inventors: Peter Bruenker, Hittnau (CH); Martina Geiger, Obfelden (CH); Christian Klein, Weilheim (DE); Alexander Knaupp, Wackersberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 840 days.

(21) Appl. No.: 18/066,526

(22) Filed: Dec. 15, 2022

(65) Prior Publication Data

US 2023/0416411 A1 Dec. 28, 2023

Related U.S. Application Data

(63) Continuation of application No. PCT/EP2021/066348, filed on Jun. 17, 2021.

(30) Foreign Application Priority Data

Jun. 19, 2020 (EP) .................................... 20181022

(51) Int. Cl.
*C07K 16/46* (2006.01)
*A61P 35/00* (2006.01)

(52) U.S. Cl.
CPC ............ *C07K 16/468* (2013.01); *A61P 35/00* (2018.01); *C07K 2317/31* (2013.01); *C07K 2317/52* (2013.01); *C07K 2317/55* (2013.01); *C07K 2317/565* (2013.01)

(58) Field of Classification Search
CPC .................................................. A61K 47/6879
See application file for complete search history.

(56) References Cited

U.S. PATENT DOCUMENTS

| | | | |
|---|---|---|---|
| 4,676,980 | A | 6/1987 | Segal et al. |
| 4,737,456 | A | 4/1988 | Weng et al. |
| 5,208,020 | A | 5/1993 | Chari et al. |
| 5,500,362 | A | 3/1996 | Robinson et al. |
| 5,547,668 | A | 8/1996 | Kranz et al. |
| 5,571,894 | A | 11/1996 | Wels et al. |
| 5,587,458 | A | 12/1996 | King et al. |
| 5,591,828 | A | 1/1997 | Bosslet et al. |
| 5,731,168 | A | 3/1998 | Carter et al. |
| 5,821,337 | A | 10/1998 | Carter et al. |
| 5,869,046 | A | 2/1999 | Presta et al. |
| 6,248,516 | B1 | 6/2001 | Winter et al. |
| 6,737,056 | B1 | 5/2004 | Presta et al. |
| 6,809,185 | B1 | 10/2004 | Schoonjans et al. |
| 6,982,321 | B2 | 1/2006 | Winter et al. |
| 7,087,409 | B2 | 8/2006 | Barbas et al. |
| 7,332,581 | B2 | 2/2008 | Presta et al. |
| 7,521,541 | B2 | 4/2009 | Eigenbrot et al. |
| 7,527,791 | B2 | 5/2009 | Adams et al. |
| 7,608,413 | B1 | 10/2009 | Joseloff et al. |
| 7,695,936 | B2 | 4/2010 | Carter et al. |
| 7,855,275 | B2 | 12/2010 | Eigenbrot et al. |
| 8,227,577 | B2 | 7/2012 | Klein et al. |
| 8,242,247 | B2 | 8/2012 | Klein et al. |
| 8,309,300 | B2 | 11/2012 | Junutula et al. |
| 8,703,132 | B2 | 4/2014 | Imhof-Jung et al. |
| 8,709,421 | B2 | 4/2014 | Heiss et al. |
| 8,796,424 | B2 | 8/2014 | Croasdale et al. |
| 8,834,877 | B2 | 9/2014 | O'Shannessy |
| 8,969,526 | B2 | 3/2015 | Baehner et al. |
| 9,000,130 | B2 | 4/2015 | Bhakta et al. |
| 9,068,008 | B2 | 6/2015 | Mossner et al. |
| 9,207,238 | B2 | 12/2015 | Ando et al. |
| 9,266,938 | B2 | 2/2016 | Ast et al. |
| 9,266,967 | B2 | 2/2016 | Klein et al. |
| 9,382,323 | B2 | 7/2016 | Brinkmann et al. |
| 9,447,159 | B2 | 9/2016 | Ast et al. |
| 9,522,196 | B2 | 12/2016 | Matsuyama et al. |
| 9,526,797 | B2 | 12/2016 | Gerdes et al. |
| 10,781,262 | B2 | 9/2020 | Klein et al. |
| 11,242,390 | B2 | 2/2022 | Bruenker et al. |
| 11,591,397 | B2 | 2/2023 | Freimoser-Grundschober et al. |
| 11,608,376 | B2 | 3/2023 | Georges et al. |
| 11,613,587 | B2 | 3/2023 | Klein et al. |
| 11,672,858 | B2 | 6/2023 | Freimoser-Grundschober et al. |
| 11,780,920 | B2 | 10/2023 | Freimoser-Grundschober et al. |

(Continued)

FOREIGN PATENT DOCUMENTS

| | | | |
|---|---|---|---|
| CN | 103037900 | A | 4/2013 |
| CN | 103748114 | A | 4/2014 |

(Continued)

OTHER PUBLICATIONS

Ma et al. (Front. Immunol, vol. 12, May 2021).*
Almagro, J., et al., "Humanization of antibodies" Front Biosci 13:1619-1633 (Jan. 1, 2008).
Atwell, S., et al., "Stable Heterodimers from Remodeling the Domain Interface of a Homodimer using a Phage Display Library" J Mol Biol 270(1):26-35 (Jul. 4, 1997).
Baca, M., et al., "Antibody humanization using monovalent phage display" J Biol Chem 272(16):10678-10684 (Apr. 18, 1997).
Bacac, M., et al., "CEA TCB: A novel head-to-tail 2:1 T cell bispecific antibody for treatment of CEA-positive solid tumors" Oncoimmunology 5(8 SUPPL e1203498):1-3 (Jun. 24, 2016).

(Continued)

*Primary Examiner* — Gary B Nickol
(74) *Attorney, Agent, or Firm* — Clark & Elbing LLP; Karen L. Elbing

(57) ABSTRACT

The present invention generally relates to bispecific antibodies that bind to CD3 and Folate Receptor 1 (FolR1), e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

44 Claims, 58 Drawing Sheets

Specification includes a Sequence Listing.

(56) References Cited

U.S. PATENT DOCUMENTS

| | | | |
|---|---|---|---|
| 12,215,155 | B2 | 2/2025 | Freimoser-Grundschober et al. |
| 12,466,889 | B2 | 11/2025 | Bujotzek et al. |
| 12,473,373 | B2 | 11/2025 | Freimoser-Grundschober et al. |
| 2003/0157108 | A1 | 8/2003 | Presta et al. |
| 2004/0093621 | A1 | 5/2004 | Shitara et al. |
| 2004/0110282 | A1 | 6/2004 | Yutaka et al. |
| 2004/0132140 | A1 | 7/2004 | Satoh et al. |
| 2004/0259150 | A1 | 12/2004 | Nakamura et al. |
| 2005/0031613 | A1 | 2/2005 | Nakamura et al. |
| 2007/0111281 | A1 | 5/2007 | Sondermann et al. |
| 2008/0069820 | A1 | 3/2008 | Fuh et al. |
| 2008/0241152 | A1 | 10/2008 | Alitalo et al. |
| 2009/0252683 | A1 | 10/2009 | Kischel et al. |
| 2010/0015133 | A1 | 1/2010 | Igawa et al. |
| 2010/0150918 | A1 | 6/2010 | Kufer et al. |
| 2010/0233079 | A1 | 9/2010 | Jakob et al. |
| 2010/0310571 | A1 | 12/2010 | Cheung |
| 2010/0316645 | A1 | 12/2010 | Imhof-Jung et al. |
| 2011/0293613 | A1 | 12/2011 | Brinkmann et al. |
| 2012/0164137 | A1 | 6/2012 | Sass et al. |
| 2012/0189620 | A1 | 7/2012 | Oyesiku |
| 2012/0225071 | A1 | 9/2012 | Klein et al. |
| 2012/0276125 | A1 | 11/2012 | Ast et al. |
| 2013/0022601 | A1 | 1/2013 | Brinkmann et al. |
| 2013/0045492 | A1 | 2/2013 | Babb et al. |
| 2013/0058936 | A1 | 3/2013 | Bruenker et al. |
| 2013/0058937 | A1 | 3/2013 | Auer et al. |
| 2013/0060011 | A1 | 3/2013 | Bruenker et al. |
| 2013/0078249 | A1 | 3/2013 | Ast et al. |
| 2013/0171095 | A1 | 7/2013 | Bernett et al. |
| 2013/0266579 | A1 | 10/2013 | Wei et al. |
| 2013/0273054 | A1 | 10/2013 | Bossenmaier et al. |
| 2014/0088295 | A1 | 3/2014 | Smith et al. |
| 2014/0099254 | A1 | 4/2014 | Chang et al. |
| 2014/0112914 | A1 | 4/2014 | Nezu et al. |
| 2014/0120096 | A1 | 5/2014 | Bakker et al. |
| 2014/0154254 | A1 | 6/2014 | Kannan et al. |
| 2014/0205610 | A1 | 7/2014 | Ando et al. |
| 2014/0242079 | A1 | 8/2014 | Bacac et al. |
| 2014/0242080 | A1 | 8/2014 | Jaeger et al. |
| 2014/0288275 | A1 | 9/2014 | Moore et al. |
| 2014/0294823 | A1 | 10/2014 | Moore et al. |
| 2014/0294833 | A1 | 10/2014 | Desjarlais et al. |
| 2014/0302064 | A1 | 10/2014 | Moore |
| 2014/0308285 | A1 | 10/2014 | Yan et al. |
| 2014/0322217 | A1 | 10/2014 | Moore et al. |
| 2014/0363426 | A1 | 12/2014 | Moore et al. |
| 2014/0370013 | A1 | 12/2014 | Desjarlais et al. |
| 2014/0377270 | A1 | 12/2014 | Moore et al. |
| 2015/0079088 | A1 | 3/2015 | Lowman et al. |
| 2015/0094451 | A1 | 4/2015 | Fischer et al. |
| 2015/0166661 | A1 | 6/2015 | Chen et al. |
| 2015/0218274 | A1 | 8/2015 | Sabatos-Peyton et al. |
| 2015/0274845 | A1 | 10/2015 | Bruenker et al. |
| 2015/0315296 | A1 | 11/2015 | Schaefer et al. |
| 2015/0343088 | A1 | 12/2015 | Matsuyama et al. |
| 2015/0368351 | A1 | 12/2015 | Vu et al. |
| 2015/0376287 | A1 | 12/2015 | Vu et al. |
| 2016/0075785 | A1 | 3/2016 | Ast et al. |
| 2016/0130347 | A1 | 5/2016 | Bruenker et al. |
| 2016/0145354 | A1 | 5/2016 | Bacac et al. |
| 2016/0175397 | A1 | 6/2016 | Umana et al. |
| 2016/0208017 | A1 | 7/2016 | Ast et al. |
| 2016/0208019 | A1 | 7/2016 | Bacac et al. |
| 2016/0263240 | A1 | 9/2016 | Ast et al. |
| 2016/0297881 | A1 | 10/2016 | Vu et al. |
| 2016/0368985 | A1 | 12/2016 | Hotzel et al. |
| 2017/0008971 | A1 | 1/2017 | Dennis et al. |
| 2017/0096485 | A1 | 4/2017 | Bacac et al. |
| 2017/0096495 | A1 | 4/2017 | Bacac et al. |
| 2017/0114146 | A1 | 4/2017 | Klein et al. |
| 2017/0174786 | A1 | 6/2017 | Bacac et al. |
| 2017/0190783 | A1 | 7/2017 | Bacac et al. |
| 2017/0209573 | A1 | 7/2017 | Bacac et al. |
| 2017/0253670 | A1 | 9/2017 | Klein et al. |
| 2017/0267783 | A1 | 9/2017 | Nezu et al. |
| 2017/0306018 | A1 | 10/2017 | Vu et al. |
| 2017/0306036 | A1 | 10/2017 | Vu et al. |
| 2017/0306044 | A1 | 10/2017 | Vu et al. |
| 2017/0327579 | A1 | 11/2017 | Vu et al. |
| 2017/0327580 | A1 | 11/2017 | Vu et al. |
| 2017/0349666 | A1 | 12/2017 | Klein et al. |
| 2019/0031784 | A1 | 1/2019 | Bacac et al. |
| 2019/0119383 | A1 | 4/2019 | Bruenker et al. |
| 2020/0172633 | A1 | 6/2020 | Klein et al. |
| 2020/0199234 | A1 | 6/2020 | Georges et al. |
| 2020/0270347 | A1 | 8/2020 | Freimoser-Grundschober et al. |
| 2021/0087291 | A1 | 3/2021 | Klein et al. |
| 2021/0403562 | A1 | 12/2021 | Freimoser-Grundschober et al. |
| 2022/0010014 | A1 | 1/2022 | Freimoser-Grundschober et al. |
| 2022/0213199 | A1 | 7/2022 | Bujotzek et al. |
| 2022/0213224 | A1 | 7/2022 | Klein et al. |
| 2022/0220224 | A1 | 7/2022 | Bacac et al. |
| 2022/0259318 | A1 | 8/2022 | Bujotzek et al. |
| 2023/0119537 | A1 | 4/2023 | Bruenker et al. |
| 2023/0159642 | A1 | 5/2023 | Bujotzek et al. |
| 2023/0277662 | A1 | 9/2023 | Freimoser-Grundschober et al. |
| 2023/0416365 | A1 | 12/2023 | Georges et al. |
| 2024/0002498 | A1 * | 1/2024 | Avanzino ................ A61P 35/00 |
| 2024/0042022 | A1 | 2/2024 | Freimoser-Grundschober et al. |
| 2024/0043535 | A1 | 2/2024 | Amann et al. |
| 2024/0132590 | A1 | 4/2024 | Freimoser-Grundschober et al. |
| 2025/0277035 | A1 | 9/2025 | Freimoser-Grundschober et al. |

FOREIGN PATENT DOCUMENTS

| | | | |
|---|---|---|---|
| CN | 103842030 | A | 6/2014 |
| EA | 201791121 | A1 | 4/2018 |
| EP | 0404097 | B1 | 12/1990 |
| EP | 1870459 | A1 | 12/2007 |
| EP | 2578230 | A1 | 4/2013 |
| EP | 2647707 | A1 | 10/2013 |
| EP | 2982694 | A1 | 2/2016 |
| EP | 1870459 | B1 | 6/2016 |
| EP | 2101823 | B1 | 11/2016 |
| JP | 2012-522523 | A | 9/2012 |
| TW | 201439117 | A | 10/2014 |
| WO | WO-91/03493 | A1 | 3/1991 |
| WO | 93/01161 | A1 | 1/1993 |
| WO | 93/16185 | A2 | 8/1993 |
| WO | 94/11026 | A2 | 5/1994 |
| WO | 94/11026 | A3 | 5/1994 |
| WO | WO-96/01126 | A1 | 1/1996 |
| WO | 96/027011 | A1 | 9/1996 |
| WO | WO-96/40210 | A1 | 12/1996 |
| WO | 97/30087 | A1 | 8/1997 |
| WO | 98/050431 | A2 | 11/1998 |
| WO | 98/050431 | A3 | 11/1998 |
| WO | 98/58964 | A1 | 12/1998 |
| WO | 99/22764 | A1 | 5/1999 |
| WO | 99/54342 | A1 | 10/1999 |
| WO | 01/77342 | A1 | 10/2001 |
| WO | WO-02/09573 | A2 | 2/2002 |
| WO | 03/011878 | A2 | 2/2003 |
| WO | 03/085107 | A1 | 10/2003 |
| WO | 2004/056312 | A2 | 7/2004 |
| WO | 2004/056312 | A3 | 7/2004 |
| WO | 2004/065540 | A2 | 8/2004 |
| WO | 2004/106381 | A1 | 12/2004 |
| WO | WO-2004/113388 | A2 | 12/2004 |
| WO | WO-2005/044859 | A2 | 5/2005 |
| WO | 2005/061547 | A2 | 7/2005 |
| WO | WO-2005/080431 | A2 | 9/2005 |
| WO | 2005/100402 | A1 | 10/2005 |
| WO | 2006/029879 | A2 | 3/2006 |
| WO | 2006/029879 | A3 | 3/2006 |
| WO | 2006/082515 | A2 | 8/2006 |
| WO | WO-2006/099141 | A2 | 9/2006 |
| WO | WO-2006/116592 | A2 | 11/2006 |
| WO | WO-2006/121168 | A1 | 11/2006 |
| WO | WO-2007/024715 | A2 | 3/2007 |
| WO | 2007/042261 | A2 | 4/2007 |
| WO | WO-2006/116592 | A3 | 4/2007 |
| WO | WO-2007/075270 | A2 | 7/2007 |

(56) References Cited

FOREIGN PATENT DOCUMENTS

| | | | |
|---|---|---|---|
| WO | 2007/110205 | A2 | 10/2007 |
| WO | 2007/147901 | A1 | 12/2007 |
| WO | WO-2007/146968 | A2 | 12/2007 |
| WO | 2008/024715 | A2 | 2/2008 |
| WO | WO-2008/031577 | A1 | 3/2008 |
| WO | 2008/119567 | A2 | 10/2008 |
| WO | WO-2007/024715 | A3 | 10/2008 |
| WO | WO-2008/119566 | A2 | 10/2008 |
| WO | WO-2007/024715 | A9 | 4/2009 |
| WO | WO-2009/070642 | A1 | 6/2009 |
| WO | 2009/080251 | A1 | 7/2009 |
| WO | 2009/080252 | A1 | 7/2009 |
| WO | 2009/080253 | A1 | 7/2009 |
| WO | 2009/089004 | A1 | 7/2009 |
| WO | WO-2009/080254 | A1 | 7/2009 |
| WO | WO-2010/096838 | A2 | 8/2010 |
| WO | 2010/112193 | A1 | 10/2010 |
| WO | 2010/115589 | A1 | 10/2010 |
| WO | WO-2010/115551 | A1 | 10/2010 |
| WO | WO-2010/115553 | A1 | 10/2010 |
| WO | 2010/136172 | A1 | 12/2010 |
| WO | 2010/145792 | A1 | 12/2010 |
| WO | WO-2010/145793 | A1 | 12/2010 |
| WO | 2010/129304 | A2 | 2/2011 |
| WO | 2010/129304 | A3 | 2/2011 |
| WO | 2011/034605 | A2 | 3/2011 |
| WO | WO-2011/028952 | A1 | 3/2011 |
| WO | 2011/090754 | A1 | 7/2011 |
| WO | 2011/090762 | A1 | 7/2011 |
| WO | WO-2011/106528 | A1 | 9/2011 |
| WO | 2011/143545 | A1 | 11/2011 |
| WO | WO-2011/159877 | A2 | 12/2011 |
| WO | WO-2012/054654 | A2 | 4/2012 |
| WO | WO-2012/061759 | A2 | 5/2012 |
| WO | 2012/058768 | A1 | 6/2012 |
| WO | 2012/058768 | A8 | 6/2012 |
| WO | WO-2012/073985 | A1 | 6/2012 |
| WO | 2012/130831 | A1 | 10/2012 |
| WO | WO-2012/135675 | A2 | 10/2012 |
| WO | WO-2012/158818 | A2 | 11/2012 |
| WO | WO-2012/162067 | A2 | 11/2012 |
| WO | WO-2013/006490 | A2 | 1/2013 |
| WO | WO-2013/012722 | A1 | 1/2013 |
| WO | 2013/026831 | A1 | 2/2013 |
| WO | 2013/026833 | A1 | 2/2013 |
| WO | 2013/026839 | A1 | 2/2013 |
| WO | WO-2013/019906 | A1 | 2/2013 |
| WO | WO-2013/026837 | A1 | 2/2013 |
| WO | WO-2013/072406 | A1 | 5/2013 |
| WO | 2013/096291 | A2 | 6/2013 |
| WO | 2013/096291 | A3 | 6/2013 |
| WO | 2013/120929 | A1 | 8/2013 |
| WO | 2013/157953 | A1 | 10/2013 |
| WO | 2013/157954 | A1 | 10/2013 |
| WO | WO-2013/172951 | A1 | 11/2013 |
| WO | WO-2014/004549 | A2 | 1/2014 |
| WO | WO-2014/022540 | A1 | 2/2014 |
| WO | WO-2014/028560 | A2 | 2/2014 |
| WO | WO-2014/047231 | A1 | 3/2014 |
| WO | WO-2014/051433 | A1 | 4/2014 |
| WO | WO-2014/056783 | A1 | 4/2014 |
| WO | WO-2014/028560 | A3 | 5/2014 |
| WO | WO-2014/081955 | A1 | 5/2014 |
| WO | WO-2014/087863 | A1 | 6/2014 |
| WO | WO-2014/104270 | A1 | 7/2014 |
| WO | WO-2014/110601 | A1 | 7/2014 |
| WO | WO-2014/122143 | A1 | 8/2014 |
| WO | WO-2014/122144 | A1 | 8/2014 |
| WO | WO-2014/122251 | A2 | 8/2014 |
| WO | 2014/131712 | A1 | 9/2014 |
| WO | WO-2014/131694 | A1 | 9/2014 |
| WO | WO-2014/141152 | A2 | 9/2014 |
| WO | WO-2014/144357 | A1 | 9/2014 |
| WO | WO-2014/144722 | A2 | 9/2014 |
| WO | WO-2014/151910 | A1 | 9/2014 |
| WO | WO-2014/153002 | A1 | 9/2014 |
| WO | WO-2014/122251 | A3 | 10/2014 |
| WO | WO-2014/161845 | A1 | 10/2014 |
| WO | WO-2014/163684 | A1 | 10/2014 |
| WO | WO-2014/167022 | A1 | 10/2014 |
| WO | WO-2014/141152 | A3 | 12/2014 |
| WO | WO-2014/191113 | A1 | 12/2014 |
| WO | WO-2015/001085 | A1 | 1/2015 |
| WO | WO-2015/013671 | A1 | 1/2015 |
| WO | WO-2014/191113 | A8 | 2/2015 |
| WO | WO-2015/018085 | A1 | 2/2015 |
| WO | WO-2015/048272 | A1 | 4/2015 |
| WO | 2015/095539 | A1 | 6/2015 |
| WO | 2015/150447 | A1 | 10/2015 |
| WO | WO-2016/014974 | A2 | 1/2016 |
| WO | 2016/016299 | A1 | 2/2016 |
| WO | 2016/020309 | A1 | 2/2016 |
| WO | WO-2016/020065 | A1 | 2/2016 |
| WO | WO-2016/020332 | A1 | 2/2016 |
| WO | 2016/040856 | A2 | 3/2016 |
| WO | WO-2016/036678 | A1 | 3/2016 |
| WO | WO-2016/055592 | A1 | 4/2016 |
| WO | WO-2016/055593 | A1 | 4/2016 |
| WO | 2016/079076 | A1 | 5/2016 |
| WO | WO-2016/077505 | A2 | 5/2016 |
| WO | WO-2016/079050 | A1 | 5/2016 |
| WO | WO-2016/079081 | A1 | 5/2016 |
| WO | WO-2016/079177 | A1 | 5/2016 |
| WO | WO-2016/087531 | A1 | 6/2016 |
| WO | WO-2016/146894 | A1 | 9/2016 |
| WO | 2016/172485 | A2 | 10/2016 |
| WO | WO-2016/179003 | A1 | 11/2016 |
| WO | WO-2017/021450 | A1 | 2/2017 |
| WO | 2017/072210 | A1 | 5/2017 |
| WO | 2019/122046 | A1 | 6/2019 |
| WO | 2020/127619 | A1 | 6/2020 |
| WO | WO-2020/127618 | A1 | 6/2020 |
| WO | WO-2021/018859 | A2 | 2/2021 |
| WO | WO-2021/255138 | A1 | 12/2021 |
| WO | WO-2021/255143 | A1 | 12/2021 |
| WO | WO-2021/255146 | A1 | 12/2021 |

OTHER PUBLICATIONS

Brennan, M., et al., "Preparation of Biospecific Antibodies by Chemical Recombination of Monoclonal Immunoglobulin G1 Fragments" Science 229(4708):81-83 (Jul. 5, 1985).
Bruggemann, M., et al., "Comparison of the Effector Functions of Human Immunogobulins Using a Matched set of Chimeric Antibodies" J Exp Med 166(5):1351-1361 (Oct. 1, 1987).
Carter, P., et al., "Bispecific human IgG by design" J Immunol Methods 248(1-2):7-15 (Feb. 1, 2001).
Carter, P., et al., "Humanization of an anti-p185 HER2 antibody for human cancer therapy" PNAS USA 89(10):4285-4289 (May 15, 1992).
Chari, R., et al., "Immunoconjugates containing novel maytansinoids: Promising anticancer drugs" Cancer Res 52(1):127-131 (Jan. 1, 1992).
Clifton, G., et al., "Folate receptor α: a storied past and promising future in immunotherapy" Hum Vaccin 7(2):183-190 (Feb. 1, 2011).
Clynes, R., et al., "Fc receptors are required in passive and active immunity to melanoma" PNAS USA 95(2):652-656 (Jan. 1, 1998).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Cui, H., et al., "Chemically Programmed Bispecific Antibodies That Recruit and Activate T Cells" J Biol Chem 287(34):28206-28214 (Aug. 17, 2012).
Dall'Acqua, W., et al., "Antibody humanization by framework shuffling" Methods 36(1):43-60 (Jan. 17, 2005).
Ferrara, C., et al., "Modulation of Therapeutic Antibody Effector Functions by Glycosylation Engineering: Influence of Golgi Enzyme

(56) References Cited

OTHER PUBLICATIONS

Localization Domain and Co-Expression of Heterologous β1, 4-N-acetylglucosaminyltransferase III and Golgi α-mannosidase II" Biotechnol Bioeng 93(5):851-861 (Jan. 24, 2006).
Fingl, E., et al. Basis of Therapeutics "Ch. 1—General Principles" Fifth edition, New York: Macmillan Publishing Co., Inc.,:1-46 (Jan. 1, 1975).
Gazzano-Santoro, H., et al., "A non-radioactive complement-dependent cytotoxicity assay for anti-CD20 monoclonal antibody" J Immunol Methods 202(2):163-171 (Mar. 28, 1997).
Gerngross, T., "Advances in the Production of Human Therapeutic Proteins in Yeasts and Filamentous Fungi" Nat Biotechnol 22(11):1409-1414 (Nov. 22, 2004).
Gruber, M. et al., "Efficient tumor cell lysis mediated by a bispecific single chain antibody expressed in *Escherichia coli*" J Immunol 152(11):5368-5374 (Jun. 1, 1994).
Hellstrom, I., et al., "Antitumor effects of L6, an IgG2a antibody that reacts with most human carcinomas" PNAS USA 83(18):7059-7063 (Sep. 1, 1986).
Hellstrom, I., et al., "Strong antitumor activities of IgG3 antibodies to a human melanoma-associated ganglioside" PNAS USA 82(5):1499-1502 (Mar. 1, 1985).
Holliger, P., et al., "Diabodies: Small Bivalent and Bispecific Antibody Fragments" PNAS USA 90(14):6444-6448 (Jul. 15, 1993).
Holliger, P., et al., "Engineered antibody fragments and the rise of single domains" Nat Biotechnol 23(9):1126-1136 (Sep. 1, 2005).
Holliger, P., et al., "Specific killing of lymphoma cells by cytotoxic T-cells mediated by a bispecific diabody" Protein Eng 9(3):299-305 (Mar. 1, 1996).
Hudson, P., et al., "Engineered antibodies" Nat Med 9(1):129-134 (Jan. 1, 2003).
"International Preliminary Report on Patentability—PCT/EP2021/066348" (Report Issuance Date: Dec. 13, 2022; Chapter I), :pp. 1-10 (Dec. 29, 2022).
"International Search Report—PCT/EP2021/066348" (w/Written Opinion), :pp. 1-15 (Sep. 7, 2021).
Johnson, S., et al., "Effector Cell Recruitment with Novel Fv-based Dual-affinity Re-targeting Protein Leads to Potent Tumor Cytolysis and in Vivo B-cell Depletion" J Mol Biol 399(3):436-449 (Jun. 11, 2010).
Kanda, Y. et al., "Comparison of Cell Lines for Stable Production of Fucose-Negative Antibodies with Enhanced ADCC" Biotechnol Bioeng 94(4):680-688 (Jul. 1, 2006).
Kandalaft, L., et al., "A phase I clinical trial of adoptive transfer of folate receptor-alpha redirected autologous T cells for recurrent ovarian cancer" J Transl Med 10(157):1-10 (Aug. 3, 2012).
Kashmiri, S., et al., "SDR grafting—a new approach to antibody humanization" Methods 36:25-34 (Jan. 1, 2005).
Kelemen, L.,, "The role of folate receptor alpha in cancer development, progression and treatment: cause, consequence or innocent bystander?" Int J Cancer 119(2):243-250 (Jul. 15, 2006).
Kipriyanov, S., et al., "Bispecific Tandem Diabody for Tumor Therapy with Improved Antigen Binding and Pharmacokinetics" J Mol Biol 293(1):41-56 (Oct. 15, 1999).
Klein, C. et al., "The use of CrossMAb technology for the generation of bi- and multispecific antibodies" MABS 8(6):1010-1020 (Aug. 31, 2016).
Klimka, A. et al., "Human anti-CD30 recombinant antibodies by guided phage antibody selection using cell panning" Brit J Cancer 83(2):252-260 (Jun. 15, 2000).
Kostelny, S., et al., "Formation of a bispecific antibody by the use of leucine zippers" J Immunol 148(5):1547-1553 (Mar. 1, 1992).
Kranz, D.M., et al., "Conjugates of folate and anti-T-cell-receptor antibodies specifically target folate-receptor-positive tumor cells for lysis" PNAS 92(20):9057-9061 (Sep. 26, 1995).
Lamars, C.H. et al., "Inhibition of bispecific monoclonal antibody (bsAb)-targeted cytolysis by human anti-mouse antibodies in ovarian carcinoma patients treated with bsAb-targeted activated T-lymphocytes" Int J Cancer 60(4):450-457 (Feb. 8, 1995).
Li, H., et al., "Optimization of humanized IgGs in glycoengineered Pichia pastoris" Nat Biotechnol 24(2):210-215 (Feb. 1, 2006).
Marks, J.D., et al., "By-passing immunization. Human antibodies from V-gene libraries displayed on phage" J Mol Biol 222(3):581-597 (Dec. 5, 1991).
Mather, J., "Establishment and characterization of two distinct mouse testicular epithelial cell lines" Biol Reprod 23(1):243-252 (Aug. 1, 1980).
Mather, J., et al., "Culture of Testicular Cells in Hormone-Supplemented Serum-Free Medium" Ann NY Acad Sci 383:44-68 (Jan. 1, 1982).
Mezzanzanica, D., et al., "Human ovarian carcinoma lysis by cytotoxic T cells targeted by bispecific monoclonal antibodies: analysis of the antibody components" Int J Cancer 41(4):609-615 (Apr. 15, 1988).
Milstein, C., et al., "Hybrid hybridomas and their use in immunohistochemistry" Nature 305(5934):537-539 (Oct. 6, 1983).
Nagorsen, D., et al., "Immunomodulatory therapy of cancer with T cell-engaging BiTE antibody blinatumomab" Exp Cell Res 317(9):1255-1260 (May 15, 2011).
Osbourn, J. et al., "From rodent reagents to human therapeutics using antibody guided selection" Methods 36(1):61-68 (May 1, 2005).
Pace, C., et al., "How to measure and predict the molar absorption coefficient of a protein" Protein Sci 4(11):2411-2423 (Nov. 1, 1995).
Padlan, E. et al., "A possible procedure for reducing the immunogenicity of antibody variable domains while preserving their ligand-binding properties" Mol Immunol 28(4-5):489-498 (Apr. 30, 1991).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Pluckthun, A. et al. The Pharmacology of Monoclonal Antibodies "Antibodies from *Escherichia coli*" Rosenberg & Moore, vol. 113:269-315 (1994).
Polakis, P. et al., "Antibody Drug Conjugates for Cancer Therapy" Pharmacol Rev 68(1):3-19 (Jan. 1, 2016).
Presta, L., et al., "Humanization of an Antibody Directed Against IgE" J Immunol 151(5):2623-2632 (Sep. 1, 1993).
Queen, C., et al., "A humanized antibody that binds to the interleukin 2 receptor" PNAS USA 86(24):10029-10033 (Dec. 1, 1989).
Ridgway, J., et al., "Knobs-into-holes engineering of antibody CH3 domains for heavy chain heterodimerization" Protein Eng 9(7):617-621 (Jul. 1, 1996).
Riechmann, L., et al., "Reshaping human antibodies for therapy" Nature 332:323-327 (Mar. 24, 1988).
Ripka, J., et al., "Two Chinese Hamster Ovary Glycosylation Mutants Affected in the Conversion of GDP-Mannose to GDP-Fucose" Arch Biochem Biophys 249(2):533-545 (Sep. 1, 1986).
Rosok, M., et al., "A combinatorial library strategy for the rapid humanization of anticarcinoma BR96 Fab" J Biol Chem 271(37):22611-22618 (Sep. 13, 1996).
Roy, E., et al., "Folate-mediated targeting of T cells to tumors" Adv Drug Deliv Rev 56(8):1219-1231 (Apr. 29, 2004).
Schaefer, W., et al., "Immunoglobulin domain crossover as a generic approach for the production of bispecific IgG antibodies" PNAS USA 108(27):11187-11192 (Jul. 5, 2011).
Seimetz, D., et al., "Development and approval of the trifunctional antibody catumaxomab (anti-EpCAM x anti-CD3) as a target cancer immunotherapy" Cancer Treat Rev 36(6):458-467 (Oct. 1, 2010).
Sims, M., et al., "A Humanized CD18 Antibody Can Block Function Without Cell Destruction" J Immunol 151(4):2296-2308 (Aug. 15, 1993).
Spiess, C., et al., "Alternative molecular formats and therapeutic applications for bispecific antibodies" Mol Immunol 67( SUPPL 2 Pt A):95-106 (Jan. 27, 2015).
Stadler, C., et al., "Elimination of large tumors in mice by mRNA-encoded bispecific antibodies" Nat Med 23(7):815-817 (Jun. 12, 2017).
Stubenrauch, K., et al., "Impact of molecular processing in the hinge region of therapeutic IgG4 antibodies on disposition profiles in cynomolgus monkeys" Drug Metab Dispos 38(1):84-91 (Jan. 1, 2010).

(56) References Cited

OTHER PUBLICATIONS

Teng, L., et al., "Clinical translation of folate receptor-targeted therapeutics" Expert Opin Drug Deliv 9(8):901-908 (Aug. 1, 2012).
Thompson, S., et al., "Preclinical evaluation of light-activatable, bispecific anti-human CD3 antibody conjugates as anti-ovarian cancer therapeutics" MABS 1(4):348-356 (Jul. 19, 2009).
Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).
Umana, P., et al., "Engineered Glycoforms of an Antineuroblastoma IgG1 with Optimized Antibody-Dependent Cellular Cytotoxic Activity" Nat Biotechnol 17(2): 176-180 (Feb. 1, 1999).
UNIPROT.org, Other Database, UniProt—CD3E_Human, P07766, (T-cell surface glycoprotein CD3 epsilon chain; Sequence Version 2), pp. 1-9; Creation Date Aug. 1, 1988 https://www.uniprot.org/uniprotkb/P07766/entry.
UNIPROT.org, Other Database, UniprotKB-P15328-FOLR1_Human, (Folate receptor alpha; Sequence Version 3; FOLR1_Human), pp. 1-10; Modified Date Jun. 1, 1994 https://www.uniprot.org/uniprotkb/P15328/entry.
UNIPROT.org, Other Database, UniProtKB-EGFR-Human-P00533, (Sequence Version 2; EGFR-Human), pp. 1-54; Modified Date Nov. 1, 1997 https://www.uniprot.org/uniprotkb/P00533/entry.
UNIPROT.org, Other Database, UniProtKB-TYRP1_Human, P17643, (Sequence Version, 2; TYRP1_Human; 5,6-dihydroxyindole-2-carboxylic acid oxidase), pp. 1-10; Modified Date Jan. 11, 2001 https://www.uniprot.org/uniprotkb/P17643/entry.
Urlaub, G., et al., "Isolation of Chinese hamster cell mutants deficient in Dihydrofolate reductase activity" PNAS US 77(7):4216-4220 (Jul. 1, 1980).
Vaitilingam, B., et al., "A folate receptor-α-specific ligand that targets cancer tissue and not sites of inflammation" J Nucl Med 53(7 SUPPL 34):1127-1134 (Jul. 1, 2012).
Van Dam, G., et al., "Intraoperative tumor-specific fluorescence imaging in ovarian cancer by folate receptor-α targeting: first in-human results" Nat Med 17(10):1315-1319 (Sep. 18, 2011).
Vitetta, E. et al., "Redesigning nature's poisons to create anti-tumor reagents" Science 238(4830):1098-1104 (Nov. 20, 1987).
Wright, A., et al., "Effect of Glycosylation on Antibody Function: Implications for Genetic Engineering" Trends Biotechnol 15(1):26-32 (Jan. 1, 1997).
Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki, P. J., et al. Methods in Molecular Biology "Expression of recombinant antibodies in mammalian cell lines" Lo, B.K.C. (ed.), Totowa, NJ: Humana Press, vol. 248:255-268 (2004)
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC 70(8 Suppl) Abstract 5621 (2010) (1 page).
Carreno et al., "Cross-species reactivity of the anti-idiotype anti-OKT3 cascade between mice and humans," Hum Immunol. 33(4):249-58 (1992).
Carreno et al., "First step toward the murine idiotypic network generated by OKT3," Human Immunology. 32:12:8.4 (1991) (Abstract only) (1 page).
Casset et al., "A peptide mimetic of an anti-CD4 monoclonal antibody by rational design," Biochem Biophys Res Commun. 307(1):198-205 (2003).
Chan et al., "Variable region domain exchange in human IgGs promotes antibody complex formation with accompanying structural changes and altered effector functions," Mol Immunol. 41(5):527-38 (2004).
Chen et al., "Selection and analysis of an optimized anti-VEGF antibody: crystal structure of an affinity-matured Fab in complex with antigen," J Mol Biol. 293(4):865-81 (1999).
Curran et al., "PD-1 and CTLA-4 combination blockade expands infiltrating T cells and reduces regulatory T and myeloid cells within B16 melanoma tumors," Proc Natl Acad Sci U S A. 107(9):4275-80 (2010).
De Genst et al., "Antibody repertoire development in camelids," Dev Comp Immunol. 30(1-2):187-98 (2006).
De Pascalis et al., "Grafting of 'abbreviated' complementarity-determining regions containing specificity-determining residues essential for ligand contact to engineer a less immunogenic humanized monoclonal antibody," J Immunol. 169(6):3076-84 (2002).
Deyev et al., "Modern Technologies for Creating Synthetic Antibodies for Clinical application," Acta Naturae. 1(1):32-50 (2009) (19 pages).
Diamond et al., "Somatic mutation of the T15 heavy chain gives rise to an antibody with autoantibody specificity," Proc Natl Acad Sci U S A. 81(18):5841-5844 (1984).
Dilek et al., "Targeting CD28, CTLA-4 and PD-L1 costimulation differentially controls immune synapses and function of human regulatory and conventional T-cells," PLoS One. 8(12):e83139 (2013) (14 pages).
Duraiswamy et al., "Dual Blockade of PD-1 and CTLA-4 Combined with Tumor Vaccine Effectively Restores T-Cell Rejection Function in Tumors," Cancer Res. 73(12): 3591-603 (2013) (14 pages).
Ebel et al., "Preclinical evaluation of MORAb-003, a humanized monoclonal antibody antagonizing folate receptor-alpha," Cancer Immun. 7:6 (2007) (8 pages).
Edelman et al., "The covalent structure of an entire gammaG immunoglobulin molecule," Proc Natl Acad Sci U S A. 63(1):78-85 (1969).
Edwards et al., "The remarkable flexibility of the human antibody repertoire; isolation of over one thousand different antibodies to a single protein, BLyS," J Mol Biol. 334(1):103-18 (2003).
Garcia-Bennett et al., "In search of the Holy Grail: Folate-targeted nanoparticles for cancer therapy," Biochem Pharmacol. 81(8):976-84 (2011) (9 pages).
Hasemann et al., "Mutational analysis of arsonate binding by a CRIA+ antibody. VH and VL junctional diversity are essential for binding activity," J Biol Chem. 266(12):7626-32 (1991) (7 pages).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Jackman et al., "Development of a two-part strategy to identify a therapeutic human bispecific antibody that inhibits IgE receptor signaling," J Biol Chem. 285(27):20850-9 (2010) (11 pages).
Kang et al., "Antibody redesign by chain shuffling from random combinatorial immunoglobulin libraries," Proc Natl Acad Sci U.S. A. 88(24):11120-3 (1991).
Katayose et al., "MUC1-specific targeting immunotherapy with bispecific antibodies: inhibition of xenografted human bile duct carcinoma growth," Cancer Res. 56(18):4205-12 (1996) (9 pages).
Kimura et al., "Molecular cloning of a human MafF homologue, which specifically binds to the oxytocin receptor gene in term myometrium," Biochem Biophys Res Commun. 264(1):86-92 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," mAbs. 4(2):182-97 (2012) (17 pages).
Kopantzev et al., "Differences in gene expression levels between early and later stages of human lung development are opposite to those between normal lung tissue and non-small lung cell carcinoma," Lung Cancer. 62(1):23-34 (2008) (12 pages).
Lamminmäki et al., "Crystal Structure of a Recombinant Anti-Estradiol Fab Fragment in Complex With 17beta-Estradiol," J Biol Chem. 276(39):36687-94 (2001).
Lloyd et al., "Modelling the human immune response: performance of a $10^{11}$ human antibody repertoire against a broad panel of therapeutically relevant antigens". Protein Eng Des Sel. 22(3):159-68 (2009).

(56) References Cited

OTHER PUBLICATIONS

Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).
MacCallum et al., "Antibody-antigen interactions: contact analysis and binding site topography," J Mol Biol. 262(5):732-45 (1996) (14 pages).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Ohno et al., "Antigen-binding specificities of antibodies are primarily determined by seven residues of VH," Proc Natl Acad Sci USA. 82(9):2945-9 (1985).
Osada et al., "CEA/CD3-bispecific T cell-engaging (BiTE) antibody-mediated T lymphocyte cytotoxicity maximized by inhibition of both PD1 and PD-L1," Cancer Immunol Immunother. 64(6):677-88 (2015).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991) (7 pages).
Padlan et al., "Structure of an Antibody-Antigen Complex: Crystal Structure of the HyHEL-10 Fab-lysozyme Complex," Proc Natl Acad Sci USA. 86(15):5938-42 (1989).
Paul, Chapter 9: Structure and Function of Immunoglobulins, *Fundamental Immunology, Third Edition.* Raven Press Ltd., 292-295 (1993) (6 pages).
Pessano et al., "The T3/T cell receptor complex: antigenic distinction between the two 20-kd T3 (T3-delta and T3-epsilon) subunits," EMBO J. 4(2):337-44 (1985).
Riedle et al., "In vivo activation and expansion of T cells by a bi-specific antibody abolishes metastasis formation of human melanoma cells in SCID mice," Int J Cancer. 75(6):908-18 (1998).
Riemer et al., "Matching of trastuzumab (Herceptin®) epitope mimics onto the surface of Her-2/neu—a new method of epitope definition," Mol Immunol. 42(9):1121-1124 (2005) (Abstract only) (2 pages).
Rudikoff et al., "Single amino acid substitution altering antigen-binding specificity," Immunology, 79, pp. 1979-1983 (1982) (5 pages).
Sakuishi et al., "Targeting Tim-3 and PD-1 pathways to reverse T cell exhaustion and restore anti-tumor immunity," J Exp Med. 207(10):2187-94 (2010).
Stancovski et al., "Mechanistic aspects of the opposing effects of monoclonal antibodies to the ERBB2 receptor on tumor growth," Proc Natl Acad Sci U S A. 88(19):8691-8695 (1991).
Sun et al., "Anti-CD20/CD3 T cell-dependent bispecific antibody for the treatment of B cell malignancies," Sci Transl Med. 7(287):287ra70 (2015) (11 pages).
Topalian et al., "Safety, Activity, and Immune Correlates of Anti-PD-1 Antibody in Cancer," N Engl J Med. 366(26):2443-54 (2012).
Torisu-Itakura et al., "Redirected lysis of human melanoma cells by a MCSP/CD3-bispecific BiTE antibody that engages patient-derived T cells," J Immunother. 34(8):597-605 (2011).
Vajdos et al., "Comprehensive functional maps of the antigen-binding site of an anti-ErbB2 antibody obtained with shotgun scanning mutagenesis," J Mol Biol. 320(2):415-28 (2002).
Weidle et al., "The intriguing options of multispecific antibody formats for treatment of cancer," Cancer Genomics Proteomics. 10(1):1-18 (2013).
Wolf et al., "BiTEs: bispecific antibody constructs with unique anti-tumor activity," Drug Discov Today. 10(18):1237-44 (2005).
Wu et al., "Humanization of a murine monoclonal antibody by simultaneous optimization of framework and CDR residues," J Mol Biol. 294(1):151-62 (1999).
Yokosuka et al., "Programmed cell death 1 forms negative costimulatory microclusters that directly inhibit T cell receptor signaling by recruiting phosphatase SHP2," J Exp Med. 209(6):1201-17 (2012).
Yoshinaga et al., "Ig L-chain shuffling for affinity maturation of phage library-derived human anti-human MCP-1 antibody blocking its chemotactic activity," J Biochem. 143(5):593-601 (2008).
Zhu et al., "Identification of heavy chain residues in a humanized anti-CD3 antibody important for efficient antigen binding and T cell activation," J Immunol. 155(4):1903-10 (1995).
Supplementary European Search Report for European Patent Application No. EP06730751, dated Jul. 16, 2010 (7 pages).
Supplementary European Search Report for European Patent Application No. EP11845786, dated Mar. 24, 2014 (4 pages).
U.S. Appl. No. 19/350,812, Genentech, Inc.

* cited by examiner

TYRP1 TCB $CD3_{opt}$ TYRP1 TCB $CD3_{orig}$

TYRP1 TCB $CD3_{opt}$ TYRP1 TCB $CD3_{orig}$

ANTIBODIES BINDING TO CD3 AND FOLR1

CROSS REFERENCE TO RELATED APPLICATIONS

This application is a continuation of International Application No. PCT/EP2021/066348, filed Jun. 17, 2021, which claims priority to European Application No. 20181022.3, filed Jun. 19, 2020, both of which are incorporated herein by reference in its entirety.

SEQUENCE LISTING

This application contains a Sequence Listing which has been submitted electronically in XML format and is hereby incorporated by reference in its entirety. Said XML copy, created on Nov. 30, 2002, is named P36031-US Sequence Listing.xml and is 189,316 bytes in size.

FIELD OF THE INVENTION

The present invention generally relates to bispecific antibodies that bind to CD3 and Folate Receptor 1 (FolR1), e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

CD3 has been extensively explored as drug target. Monoclonal antibodies targeting CD3 have been used as immunosuppressant therapies in autoimmune diseases such as type I diabetes, or in the treatment of transplant rejection. The CD3 antibody muromonab-CD3 (OKT3) was the first monoclonal antibody ever approved for clinical use in humans, in 1985.

A more recent application of CD3 antibodies is in the form of bispecific antibodies, binding CD3 on the one hand and a tumor cell antigen on the other hand. The simultaneous binding of such an antibody to both of its targets will force a temporary interaction between target cell and T cell, causing activation of any cytotoxic T cell and subsequent lysis of the target cell.

FOLR1 is expressed on epithelial tumor cells of various origins, e.g., ovarian cancer, lung cancer, breast cancer, renal cancer, colorectal cancer, endometrial cancer. Several approaches to target FOLR1 with therapeutic antibodies, such as farletuzumab, antibody drug conjugates, or adoptive T cell therapy for imaging of tumors have been described (Kandalaft et al., J Transl Med. 2012 Aug. 3; 10:157. doi: 10.1186/1479-5876-10-157; van Dam et al., Nat Med. 2011 Sep. 18; 17(10):1315-9. doi: 10.1038/nm.2472; Clifton et al., Hum Vaccin. 2011 February; 7(2):183-90. Epub 2011 Feb. 1; Kelemen et al., Int J Cancer. 2006 Jul. 15; 119(2): 243-50; Vaitilingam et al., J Nucl Med. 2012 July; 53(7); Teng et al., 2012 August; 9(8):901-8. doi: 10.1517/17425247.2012.694863. Epub 2012 Jun. 5. Some attempts have been made to target folate receptor-positive tumors with constructs that target the folate receptor and CD3 (Kranz et al., Proc Natl Acad Sci USA. Sep. 26, 1995; 92(20): 9057-9061; Roy et al., Adv Drug Deliv Rev. 2004 Apr. 29; 56(8):1219-31; Huiting Cui et al Biol Chem. Aug. 17, 2012; 287(34): 28206-28214; Lamers et al., Int. J. Cancer. 60(4):450 (1995); Thompson et al., MAbs. 2009 July-August; 1(4):348-56. Epub 2009 Jul. 19; Mezzanzanca et al., Int. J. Cancer, 41, 609-615 (1988). However, the approaches taken so far have many disadvantages. The molecules used thus far could not be readily and reliably produced as they require chemical cross linking. Similarly, hybrid molecules cannot be produced at large scale as human proteins and require the use of rat, murine or other proteins that are highly immunogenic when administered to humans and, thus, of limited therapeutic value. Further, many of the existing molecules retained FcgR binding.

More recently, WO2016/079076 describes T cell activating bispecific antigen binding molecules targeting CD3 and FolR1.

For therapeutic purposes, an important requirement that antibodies have to fulfill is sufficient stability both in vitro (for storage of the drug) an in vivo (after administration to the patient).

Modifications like asparagine deamidation are typical degradations for recombinant antibodies and can affect both in vitro stability and in vivo biological functions.

Given the tremendous therapeutic potential of antibodies, particularly bispecific antibodies for the activation of T cells, there is a need for bispecific CD3/FolR1 antibodies with optimized properties.

SUMMARY OF THE INVENTION

The present invention provides antibodies, including multispecific (e.g. bispecific) antibodies, that bind to CD3 and are resistant to degradation by e.g. asparagine deamidation and thus particularly stable as required for therapeutic purposes. The (multispecific) antibodies provided further combine good efficacy and produceability with low toxicity and favorable pharmacokinetic properties.

As is shown herein, the antibodies, including multispecific antibodies, that bind to CD3, provided by the present invention, retain more than about 90% binding activity to CD3 after 2 weeks at pH 7.4, 37 °C, relative to the binding activity after 2 weeks at pH 6, −80 °C, as determined by surface plasmon resonance (SPR).

In particular aspect, the present invention provides bispecific antibodies that bind to CD3 and Folate receptor 1 (FolR1) that retain more than about 90% binding activity to CD3 after 2 weeks at pH 7.4, 37 °C, relative to the binding activity after 2 weeks at pH 6, −80 °C, as determined by surface plasmon resonance (SPR).

In one aspect, provided is bispecific antibody that binds to CD3 and Folate receptor 1 (FolR1), wherein the bispecific antibody comprises (i) a first antigen binding domain capable of specific binding to CD3, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10, and (ii) a second antigen binding domain capable of specific binding to FolR1.

In one aspect, provided is a bispecific antibody, wherein the VH of the first antigen binding domain comprises an amino acid sequence that is at least about 95%, 96%, 97%, 98%, 99% or 100% identical to the amino acid sequence of SEQ ID NO: 7, and/or the VL comprises an amino acid sequence that is at least about 95%, 96%, 97%, 98%, 99% or 100% identical to the amino acid sequence of SEQ ID NO: 11.

In one aspect, the bispecific antibody binds to CD3 and FolR1, wherein the bispecific antibody comprises (i) a first antigen binding domain capable of specific binding to CD3, comprising a VH sequence of SEQ ID NO: 7 and a VL sequence of SEQ ID NO: 11, and (ii) a second antigen binding domain capable of specific binding to FolR1.

In one aspect, the first antigen binding domain is a Fab molecule.

In one aspect, the bispecific antibody comprises an Fc domain composed of a first and a second subunit.

In one aspect, the bispecific antibody, comprises a third antigen binding domain capable of specific binding to FolR1.

In one aspect, the second and/or, where present, the third antigen binding domain is a Fab molecule.

In one aspect, the first antigen binding domain is a Fab molecule wherein the variable domains VL and VH or the constant domains CL and CH1, particularly the variable domains VL and VH, of the Fab light chain and the Fab heavy chain are replaced by each other.

In one aspect, the second and, where present, the third antigen binding domain is a conventional Fab molecule.

In one aspect, the second and, where present, the third antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, the first and the second antigen binding domain are fused to each other, optionally via a peptide linker.

In one aspect, the first and the second antigen binding domain are each a Fab molecule and either (i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.

In one aspect, the first, the second and, where present, the third antigen binding domain are each a Fab molecule and the bispecific antibody comprises an Fc domain composed of a first and a second subunit; and wherein either (i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and the third antigen binding domain, where present, is fused at the C-terminus of the Fab heavy chain to the N-terminus of the second subunit of the Fc domain.

In one aspect, the Fc domain is an IgG, particularly an $IgG_1$, Fc domain.

In one aspect, the Fc domain is a human Fc domain.

In one aspect, the Fc comprises a modification promoting the association of the first and the second subunit of the Fc domain.

In one aspect, the Fc domain comprises one or more amino acid substitution that reduces binding to an Fc receptor and/or effector function.

In one aspect, the second and, where present, the third antigen binding domain comprises a VH comprising a HCDR 1 of SEQ ID NO: 124, a HCDR 2 of SEQ ID NO: 125, and a HCDR 3 of SEQ ID NO: 126, and a VL comprising a LCDR 1 of SEQ ID NO: 8, a LCDR 2 of SEQ ID NO: 9 and a LCDR 3 of SEQ ID NO: 10.

In one aspect, provided is the bispecific antibody as described herein above, wherein the second and, where present, the third antigen binding domain comprises a VH comprising an amino acid sequence that is at least about 95%, 96%, 97%, 98%, 99% or 100% identical to the amino acid sequence of SEQ ID NO: 123, and/or a VL comprising an amino acid sequence that is at least about 95%, 96%, 97%, 98%, 99% or 100% identical to the amino acid sequence of SEQ ID NO: 11.

In one aspect, provided is an isolated polynucleotide encoding the bispecific antibody of the invention.

In one aspect, provided is a host cell comprising the isolated polynucleotide.

In one aspect, provided is a method of producing a bispecific antibody that binds to CD3 and FolR1, comprising the steps of (a) culturing the host cell under conditions suitable for the expression of the bispecific antibody and optionally (b) recovering the bispecific antibody.

In one aspect, provided is a bispecific antibody that binds to CD3 and FolR1 produced by the method of as described herein above.

In one aspect, provided is a pharmaceutical composition comprising the bispecific antibody of the invention and a pharmaceutically acceptable carrier.

In one aspect, provided is the bispecific antibody of the invention or the pharmaceutical composition of the invention for use as a medicament.

In one aspect, provided is the bispecific antibody of the invention or the pharmaceutical composition of the invention for use in the treatment of cancer.

In one aspect, provided is the use of the bispecific antibody of the invention or the pharmaceutical composition of the invention in the manufacture of a medicament.

In one aspect, provided is use of the bispecific antibody of the invention or the pharmaceutical composition of the invention in the manufacture of a medicament for the treatment of cancer.

In one aspect, provided is a method of treating a disease in an individual, comprising administering to said individual an effective amount of the bispecific antibody of the invention or the pharmaceutical composition of the invention.

In one aspect, the disease is cancer.

BRIEF DESCRIPTION OF THE DRAWINGS

(FIG. 1A, FIG. 1D) Illustration of the "1+1 CrossMab" molecule. (FIG. 1X, FIG. 1Z) Illustration of the "$(Crossfab)_2$-Fab" molecule. Black dot: optional modification in the Fc domain promoting heterodimerization. ++, −−: amino acids of opposite charges optionally introduced in the CH1 and CL domains. Crossfab molecules are depicted as comprising an exchange of VH and VL regions, but may—in aspects wherein no charge modifications are introduced in CH1 and CL domains—alternatively comprise an exchange of the CH1 and CL domains.

FIG. 11A-FIG. 11R. Tumor cell killing and T cell activation with TYRP1 TCBs comprising original or optimized CD3 binders. Killing of the melanoma cell line M150543 upon treatment with TYRP1 TCB $CD3_{orig}$ and TYRP1 TCB $CD3_{opt}$ by PBMCs from three different healthy donors (FIG. 11A-FIG. 11F: donor 1, FIG. 11M-FIG. 11R: donor 3) was determined by LDH release after 24 h (FIG. 11A, FIG. 11G, FIG. 11M) and 48 h (FIG. 11B, FIG. 11H, FIG. 11N). In parallel, CD25 (FIG. 11C, FIG. 11E, FIG. 11I, FIG. 11K, FIG. 11O, FIG. 11Q) and CD69 (FIG. 11D, FIG. 11F, FIG. 11J, FIG. 11L, FIG. 11P, FIG. 11R) upregulation on CD8 (FIG. 11E, FIG. 11F, FIG. 11K, FIG. 11L, FIG. 11Q, FIG. 11R) and CD4 (FIG. 11C, FIG. 11D, FIG. 11I, FIG. 11J, FIG. 11O, FIG. 11P) T cells within PBMCs was measured by flow cytometry as a marker for T cell activation after 48 h.

Figures 16A, 16B, 16C, 16D:
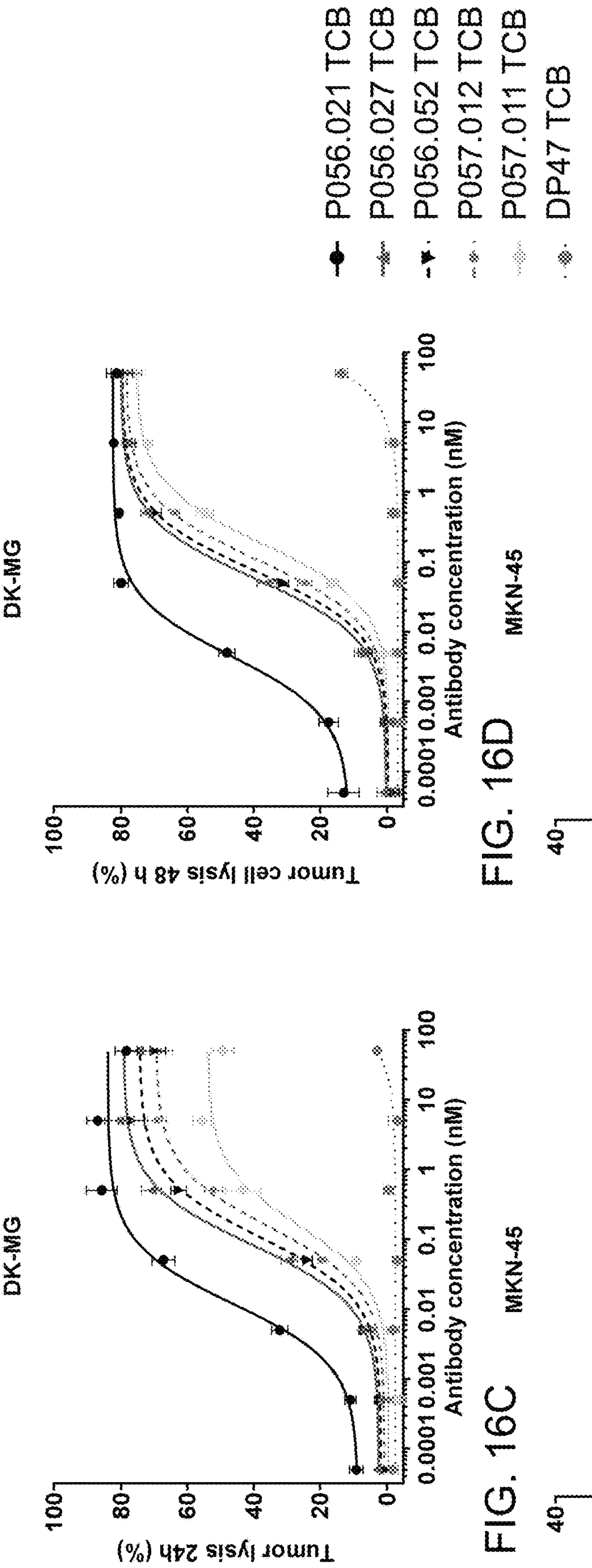
Figures 17A, 17B, 17C, 17D:
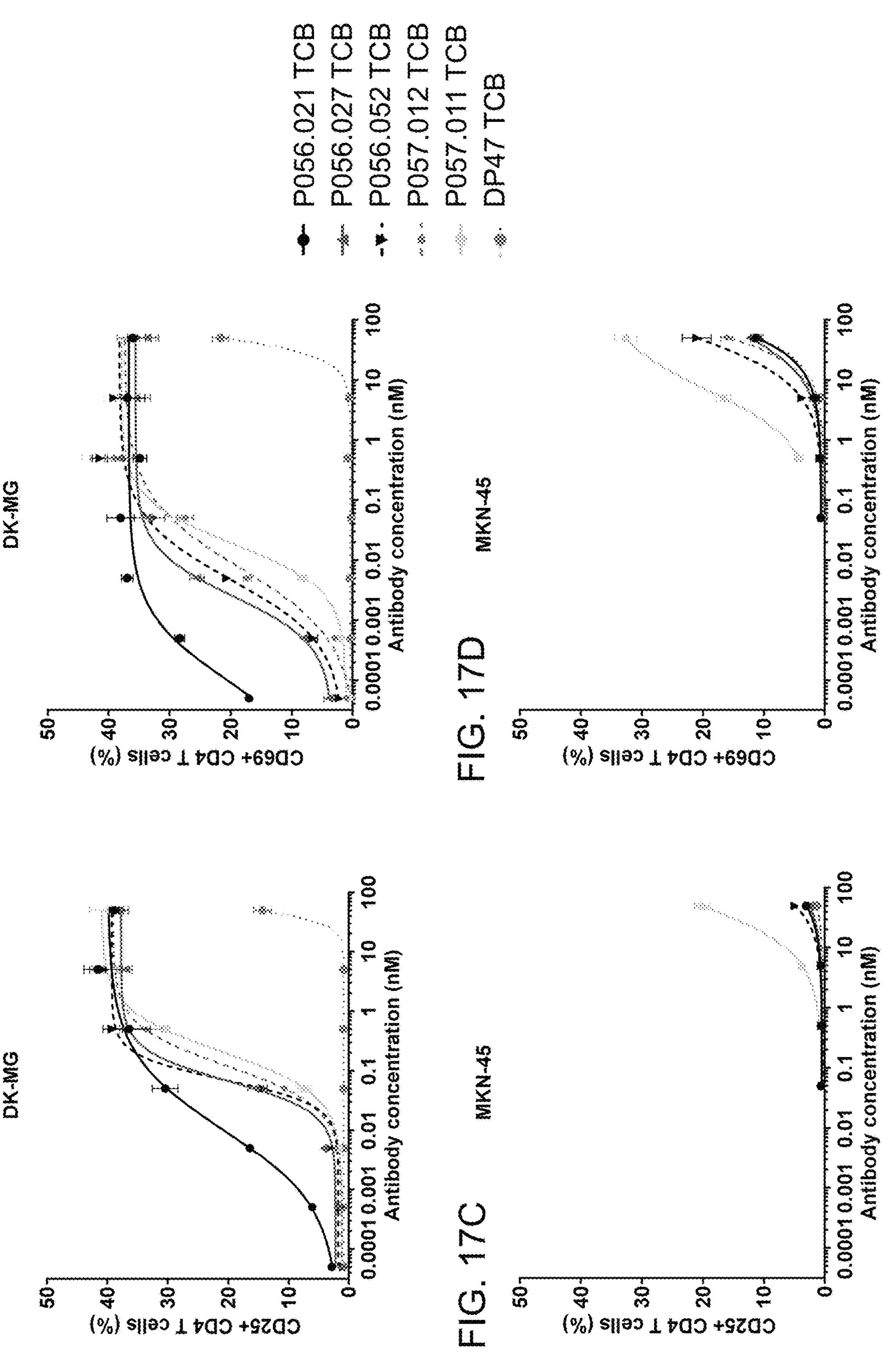
Figures 17E, 17F, 17G, 17H:
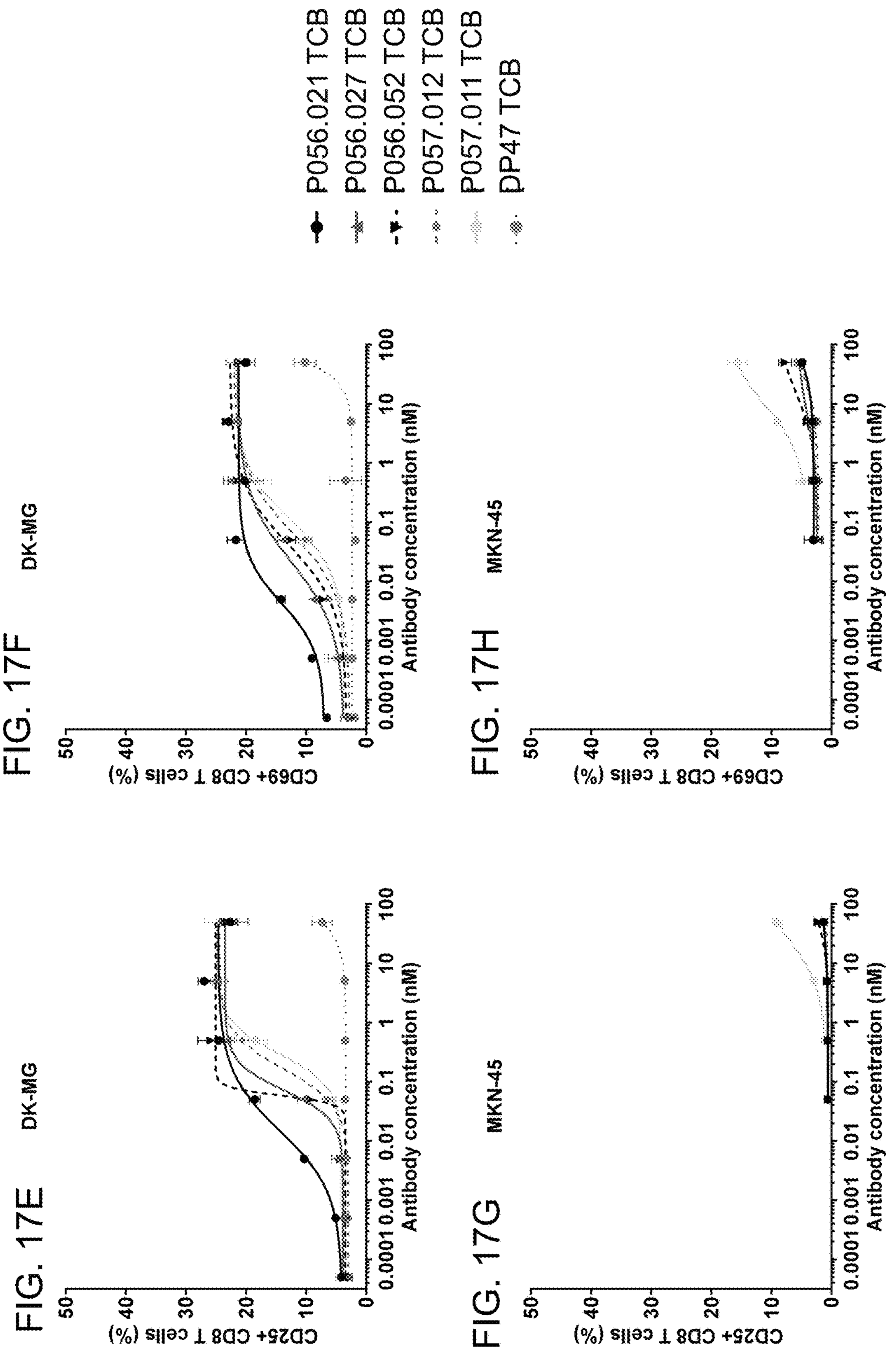

FIG. 16A-FIG. 16D. Tumor cell lysis with EGFRvIII TCBs. Induction of specific tumor cell lysis by EGFRvIII TCBs was determined upon co-culture with freshly isolated PBMCs and either EGFRvIII positive DK-MG cells (FIG. 16A, FIG. 16B) or EGFRwt positive MKN-45 cells (FIG. 16C, FIG. 16D) for 24 h (FIG. 16A, FIG. 16C) or 48 h (FIG. 16B, FIG. 16D).

FIG. 17A-FIG. 17H. T cell activation with EGFRvIII TCBs. Induction of T cell activation by EGFRvIII TCBs was determined upon co-culture with freshly isolated PBMCs and either EGFRvIII positive DK-MG cells (FIG. 17A, FIG. 17B, FIG. 17E, FIG. 17F) or EGFRwt positive MKN-45 cells (FIG. 17C, FIG. 17D, FIG. 17G, FIG. 17H) using activation markers CD25 (FIG. 17A, FIG. 17C, FIG. 17E, FIG. 17G) or CD69 (FIG. 17B, FIG. 17D, FIG. 17F, FIG. 17H) on CD4 T cells (FIG. 17A-FIG. 17D) or CD8 T cells (FIG. 17E-FIG. 17H).

Figure 18A:
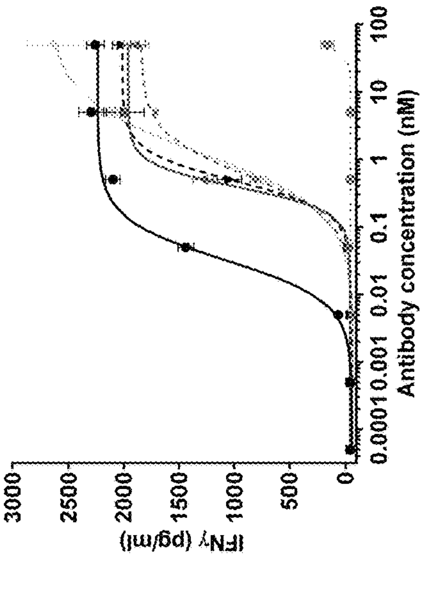
Figure 18B:
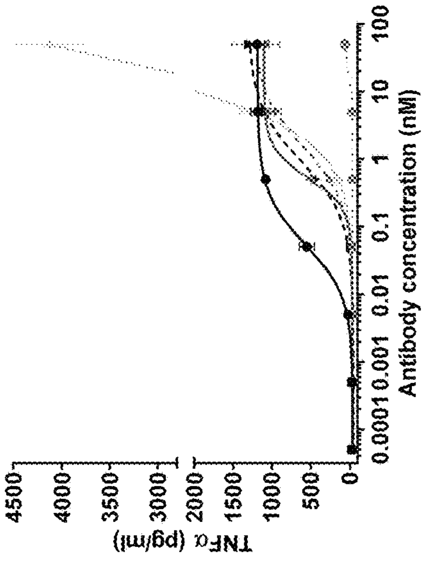
Figure 18C:
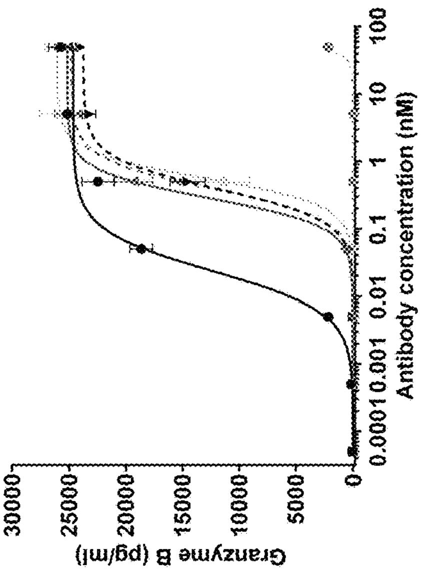
Figure 18D:
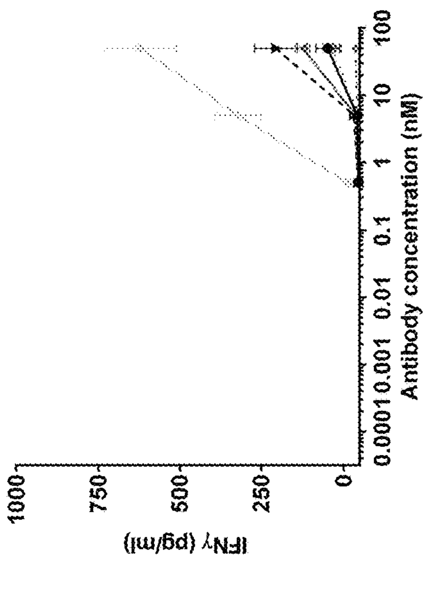
Figure 18E:
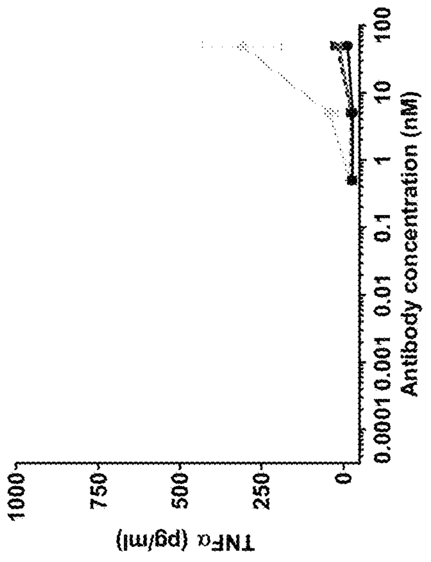
Figure 18F:
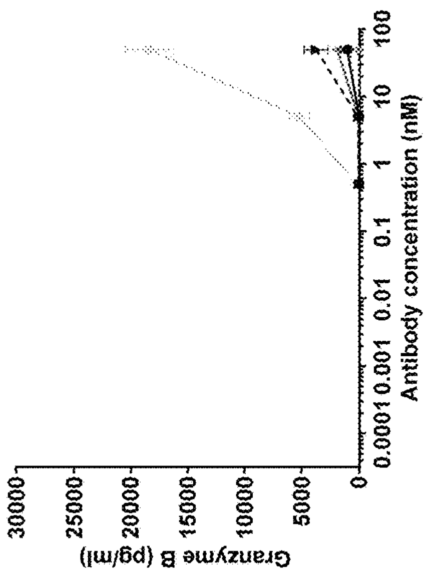

FIG. 18A-FIG. 18F. Cytokine release with EGFRvIII TCBs. Induction of release of IFNγ (FIG. 18A, FIG. 18D), TNFα (FIG. 18B, FIG. 18E) and Granzyme B (FIG. 18C, FIG. 18F) by EGFRvIII TCBs was determined upon co-culture with freshly isolated PBMCs and either EGFRvIII positive DK-MG cells (FIG. 18A-FIG. 18C) or EGFRwt positive MKN-45 cells (FIG. 18D-FIG. 18F).

Figure 19A:
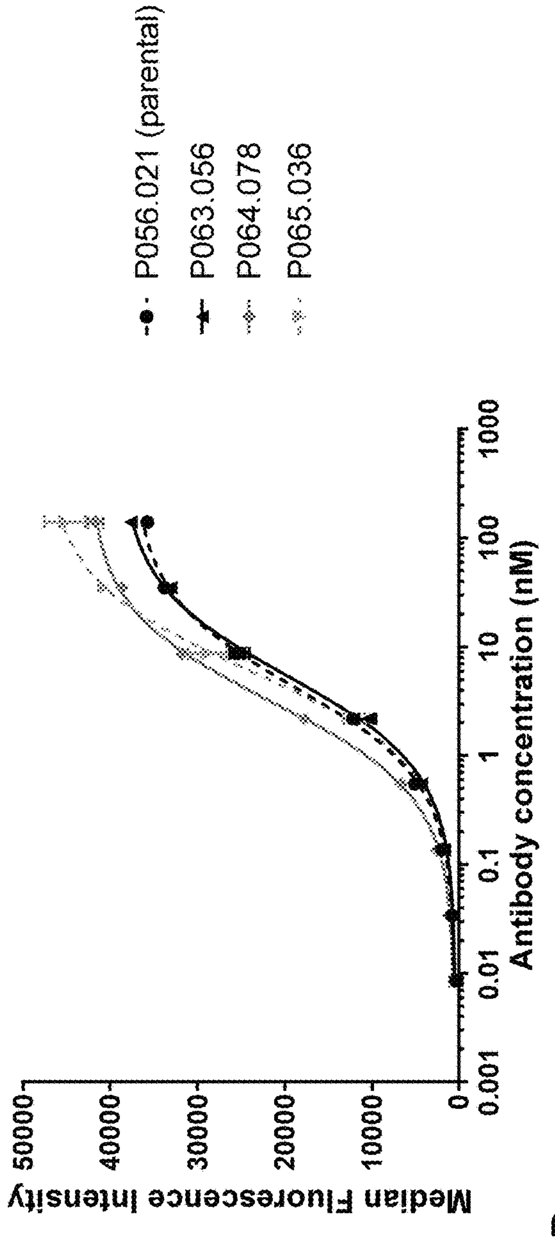
Figure 19B:
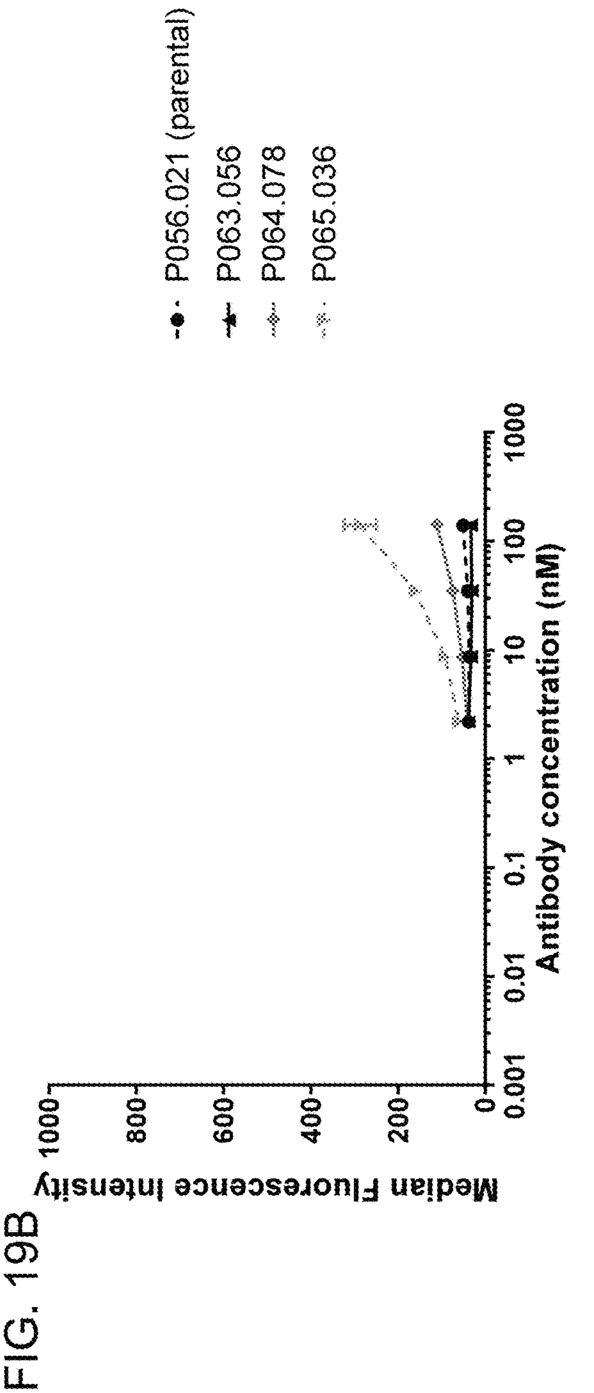

FIG. 19A and FIG. 19B. Specific binding of affinity matured EGFRvIII IgG PGLALA. Specific binding of affinity matured EGFRvIII antibodies to EGFRvIII was compared to the parental EGFRvIII binder on U87MG-EGFRvIII cells (FIG. 19A) and on the EGFRwt positive cell line MKN-45 (FIG. 19B).

Figure 20A:
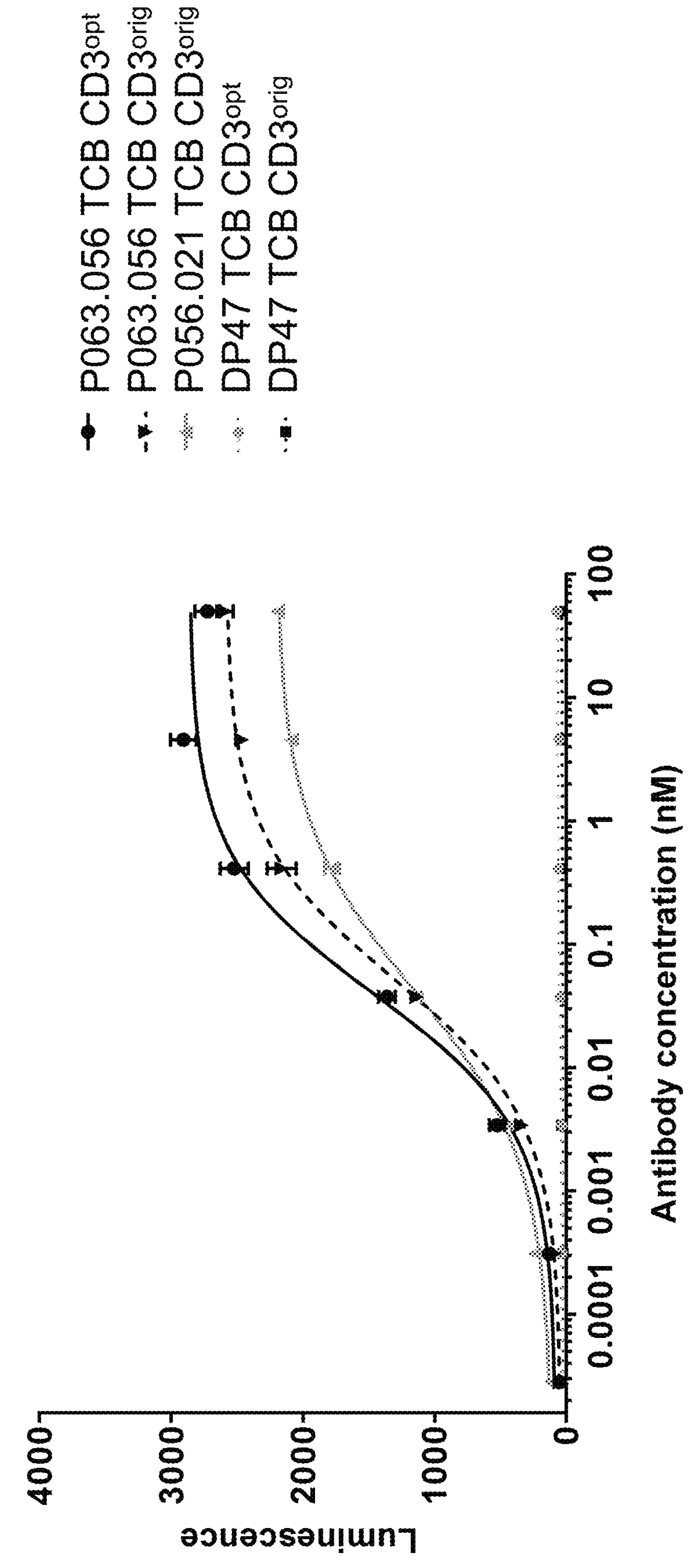
Figure 20B:
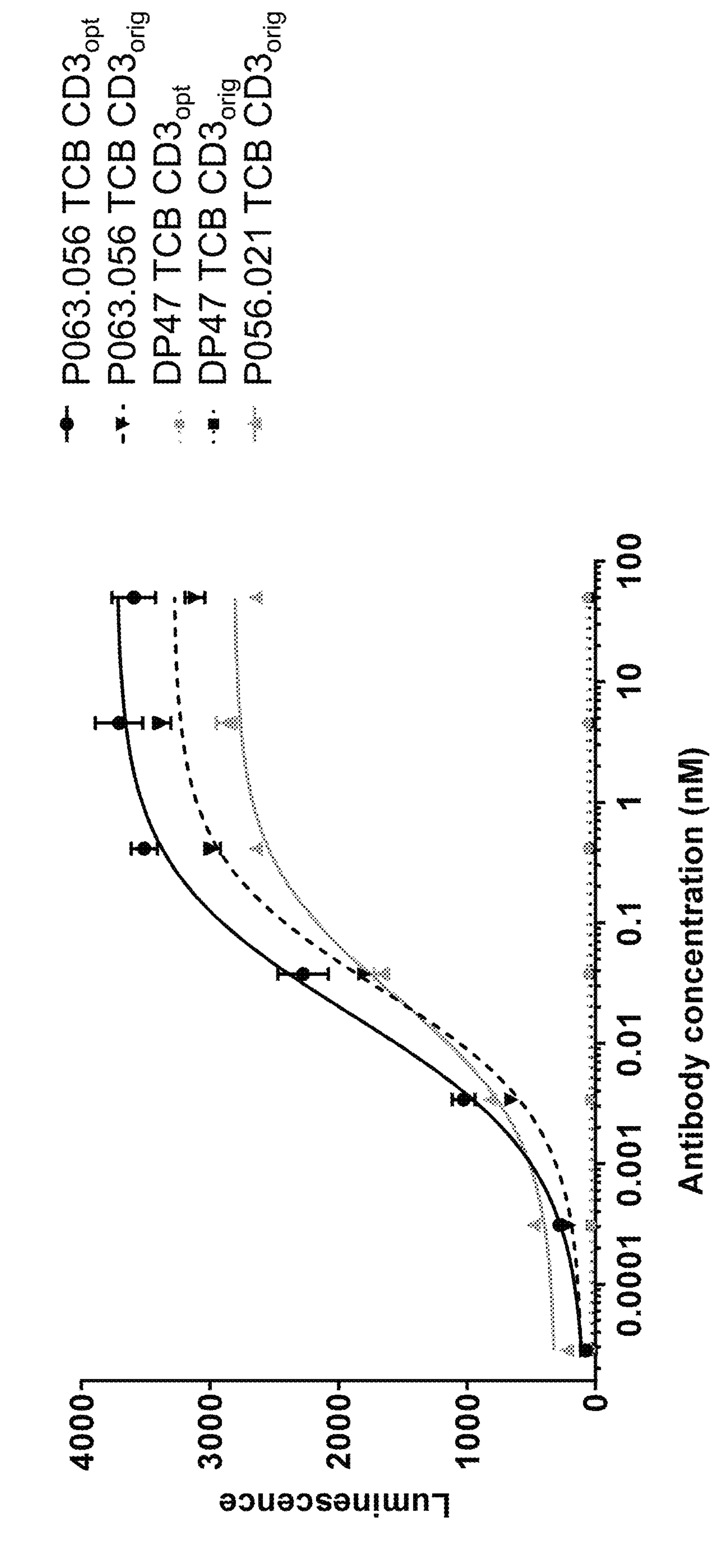
Figure 20C:
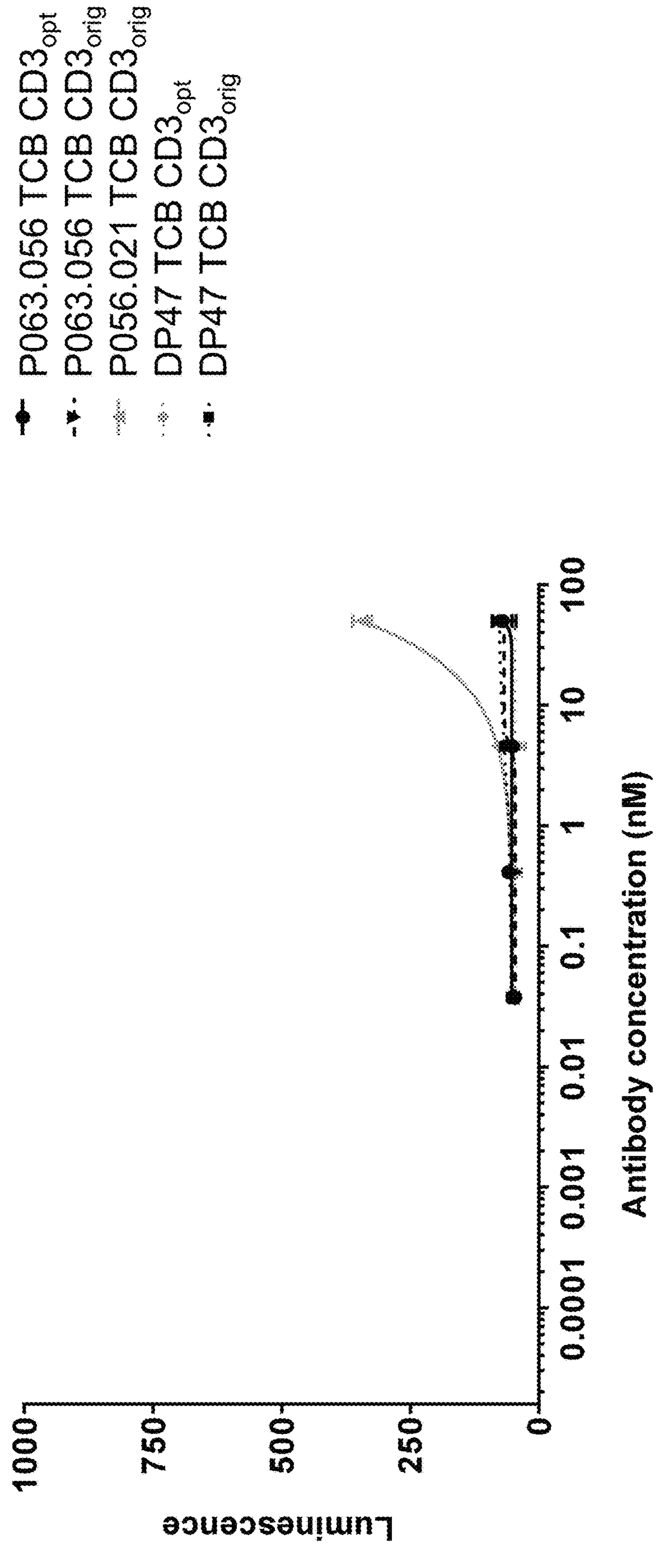

FIG. 20A-FIG. 20C Jurkat NFAT activation by EGFRvIII TCBs. Jurkat NFAT activation was determined as a marker for CD3 engagement with EGFRvIII TCBs in the presence of EGFRvIII positive DK-MG cells (FIG. 20A), U87MG-EGFRvIII cells (FIG. 20B) and MKN-45 cells (FIG. 20C). DP47 TCB was included as negative control.

Figure 21:
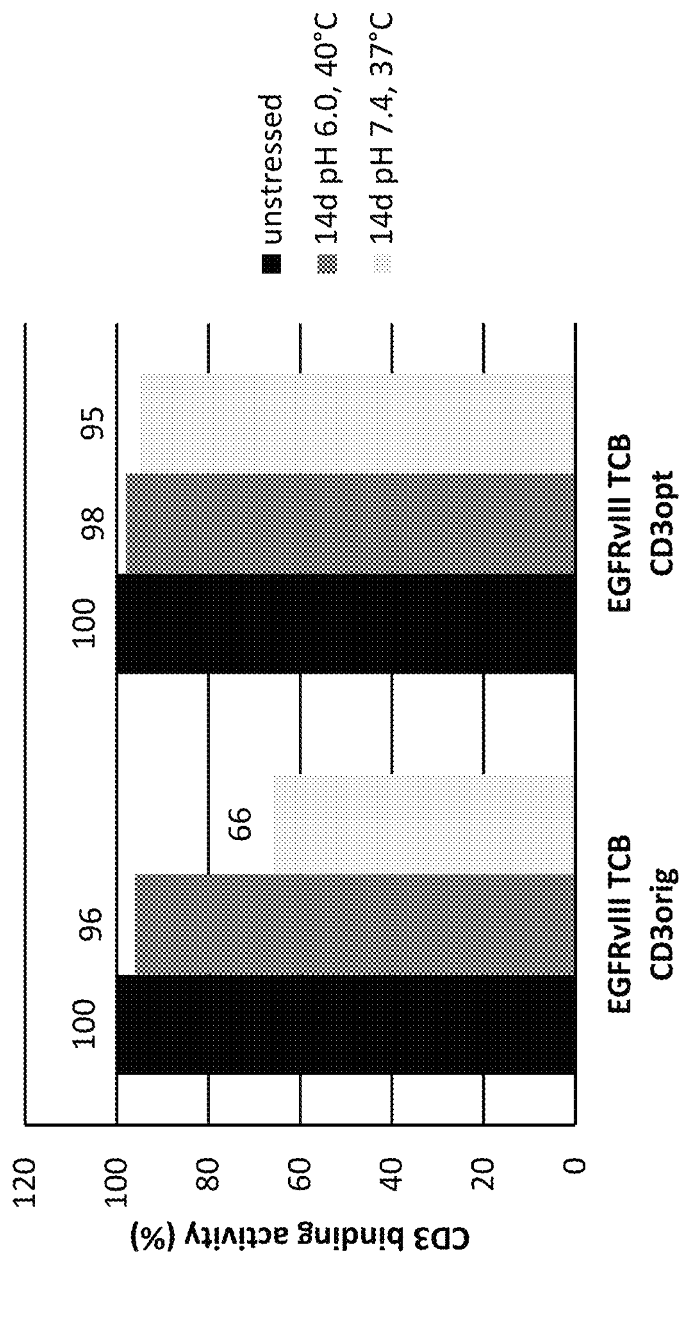

FIG. 21. Relative binding activity of EGFRvIII TCBs comprising original or optimized CD3 binders, $CD3_{orig}$ or $CD3_{opt}$, to recombinant CD3 as measured by SPR in unstressed condition, after 14 d at 40 °C. pH 6, or after 14 d at 37 °C. pH 7.4.

Figure 22:
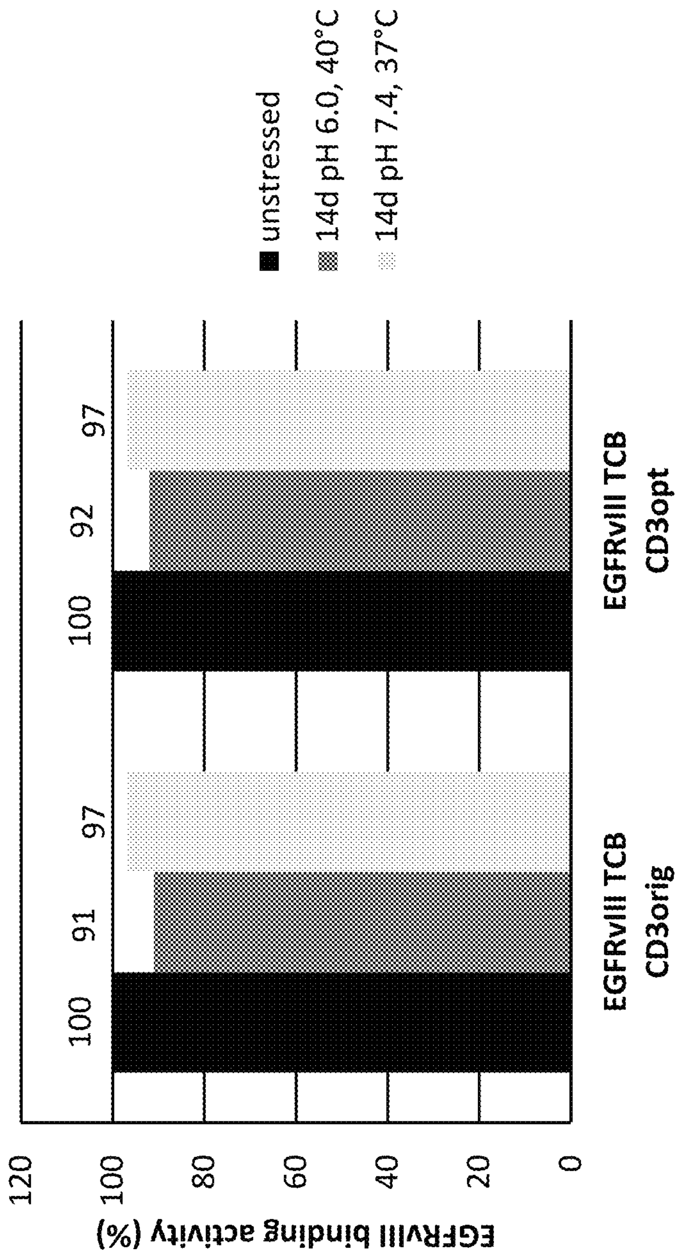

FIG. 22. Relative binding activity of EGFRvIII TCBs comprising original or optimized CD3 binders, $CD3_{orig}$ or $CD3_{opt}$, to recombinant EGFRvIII as measured by SPR in unstressed condition, after 14 d at 40 °C. pH 6, or after 14 d at 37 °C. pH 7.4.

Figure 23:
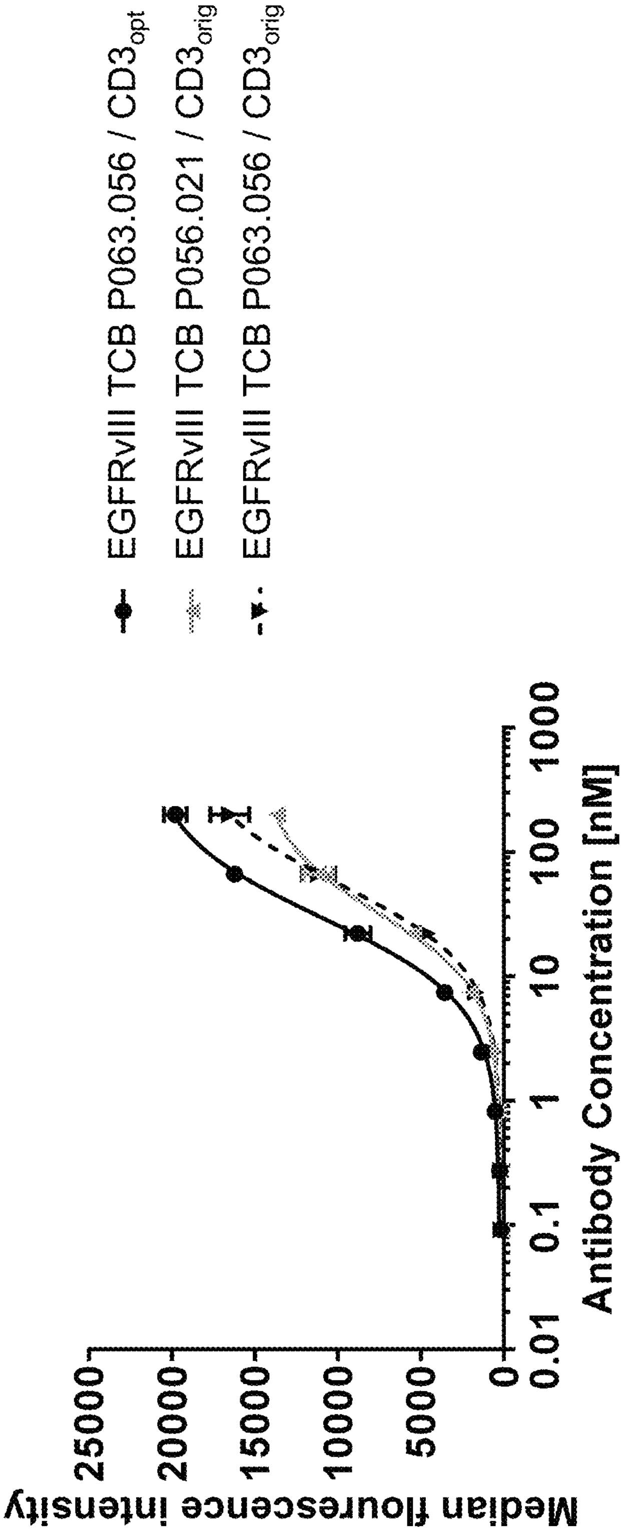

FIG. 23. Binding of EGFRvIII TCBs comprising original or optimized CD3 binders, $CD3_{orig}$ or $CD3_{opt}$, to Jurkat NFAT cells as measured by flow cytometry. TCBs bound to Jurkat NFAT cells were detected with a fluorescently labeled anti-human Fc specific secondary antibody.

Figure 24:
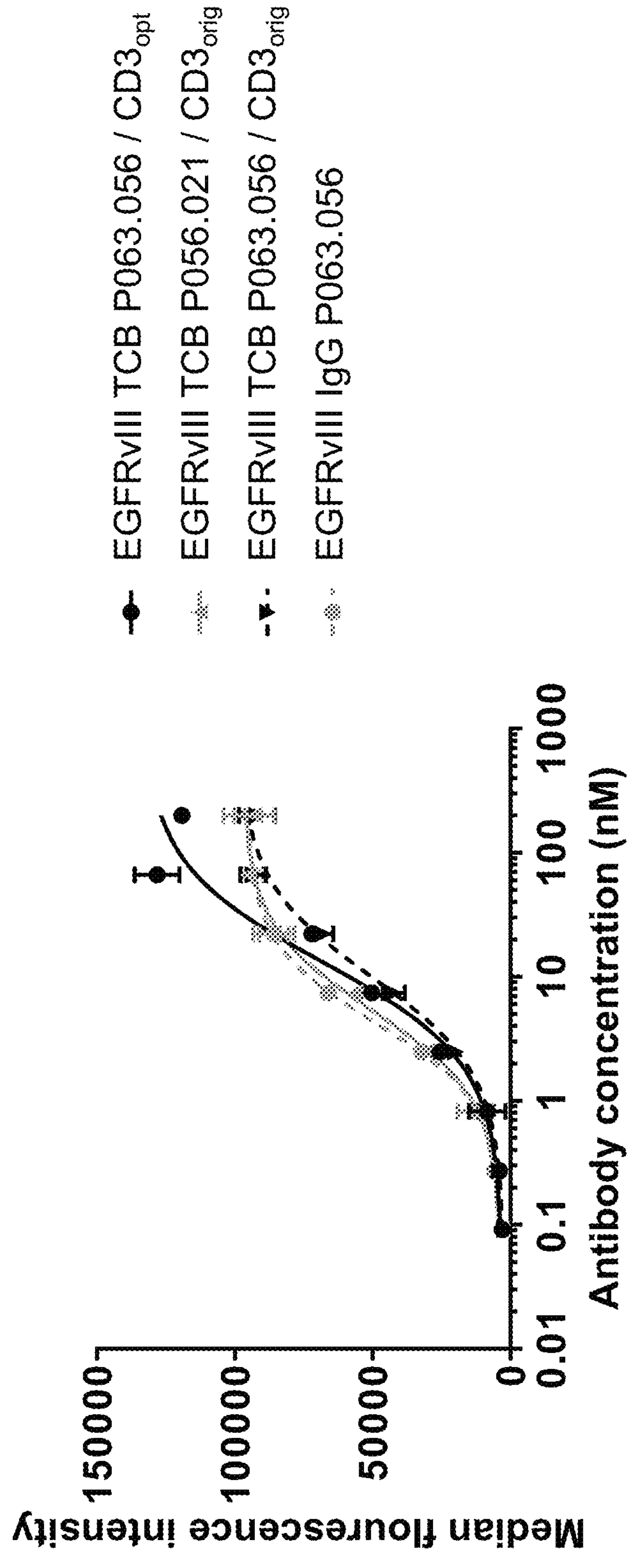

FIG. 24. Binding of EGFRvIII TCBs comprising P063.056 or P056.021 EGFRvIII binder to U87MG-EGFRvIII cells as measured by flow cytometry. TCBs bound to U87MG-EGFRvIII cells were detected with a fluorescently labeled anti-human Fc specific secondary antibody.

Figure 25A:
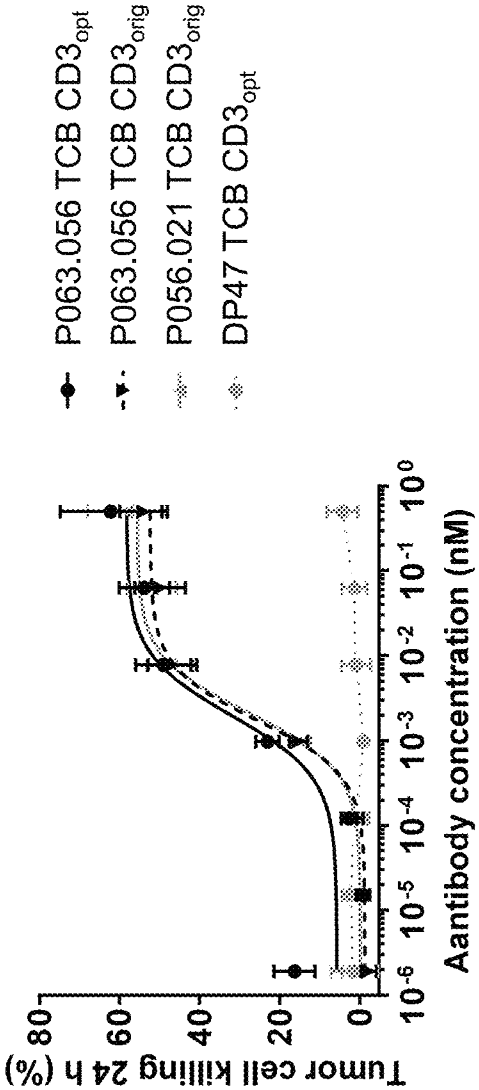
Figure 25B:
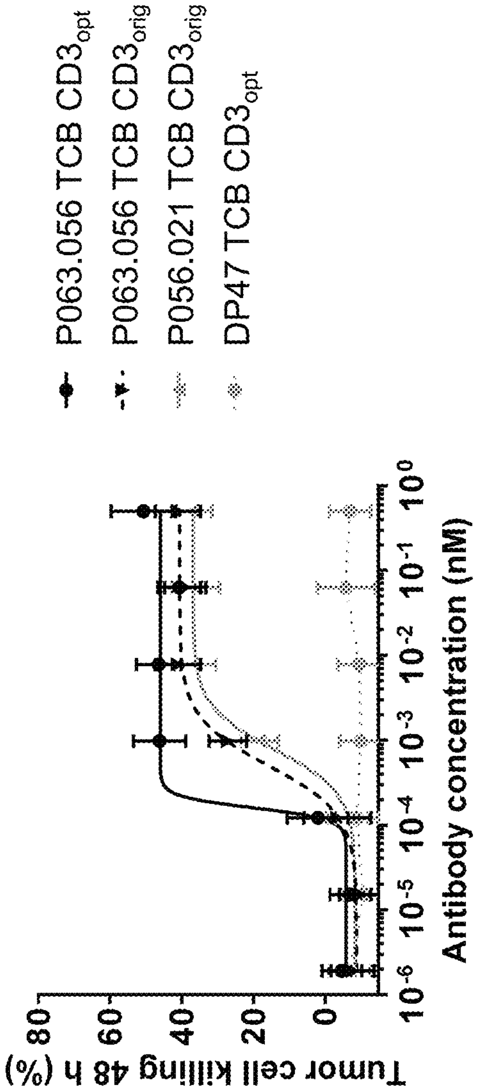
Figure 25C:
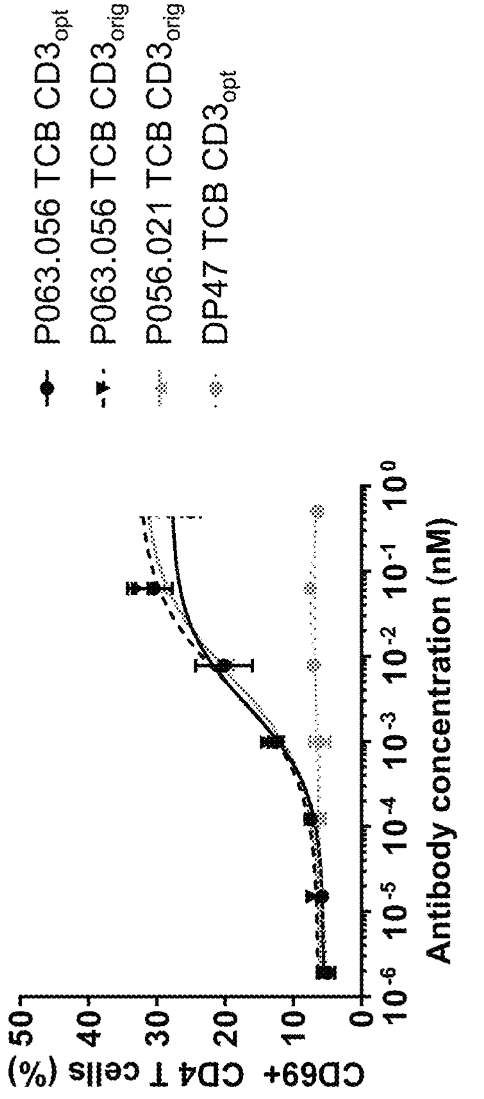
Figure 25D:
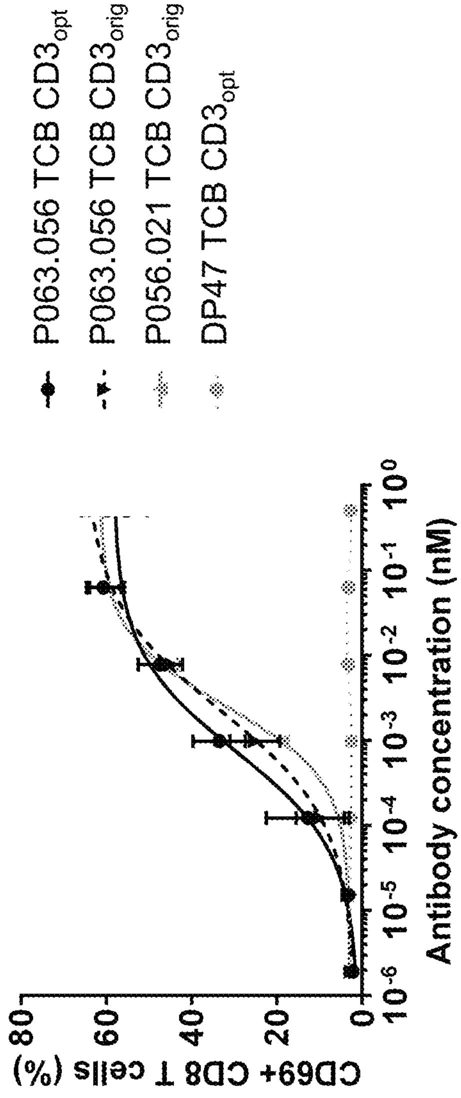

FIG. 25A-FIG. 25D. Tumor cell lysis and T cell activation with EGFRvIII TCBs. Induction of specific tumor cell lysis (FIG. 25A, FIG. 25B) and T cell activation (FIG. 25C, FIG. 25D) by EGFRvIII TCBs was determined upon co-culture with freshly isolated PBMCs and U87MG-EGFRvIII cells for 24 h (FIG. 25A, FIG. 25C) or 48 h (FIG. 25B, FIG. 25D). DP47 TCB was included as negative control.

Figure 26:
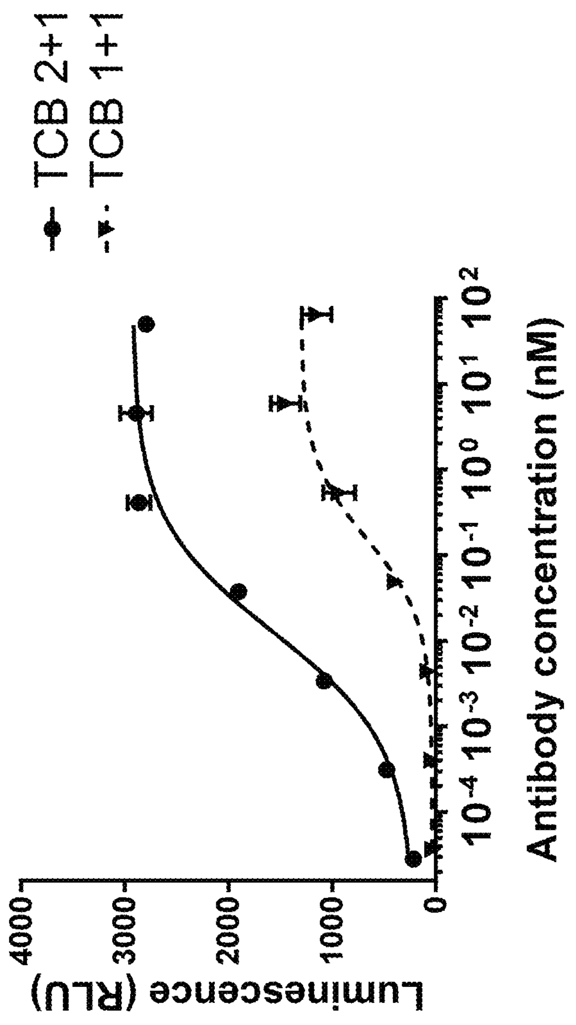

FIG. 26. Jurkat NFAT activation comparing EGFRvIII TCB 2+1 format and 1+1 format. Jurkat NFAT activation was determined as a marker for CD3 engagement with EGFRvIII TCB in the 2+1 inverted format and in the 1+1 head-to-tail format in the presence of EGFRvIII positive U87MG-EGFRvIII cells.

Figure 27A:
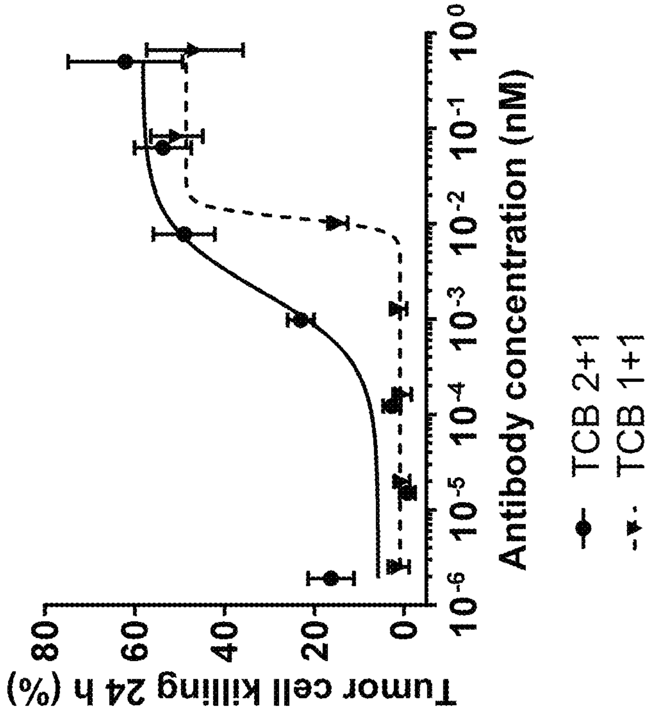
Figure 27B:
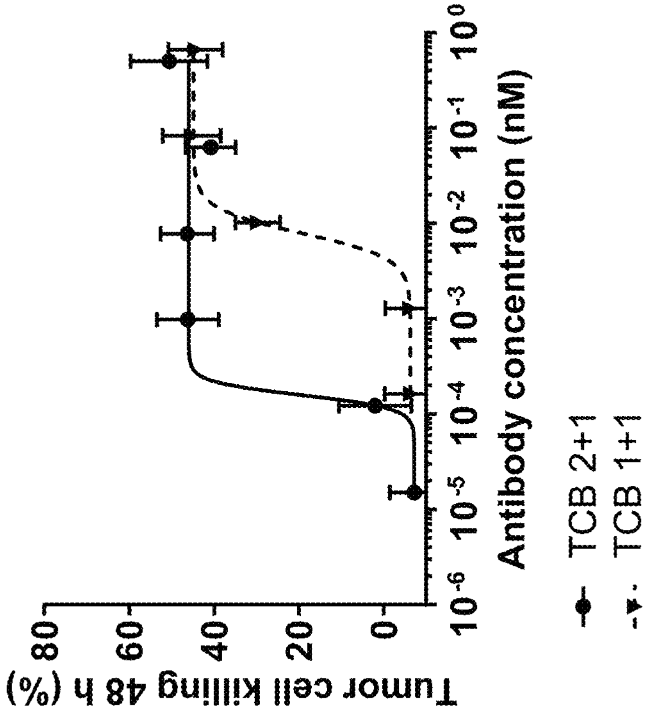
Figure 27C:
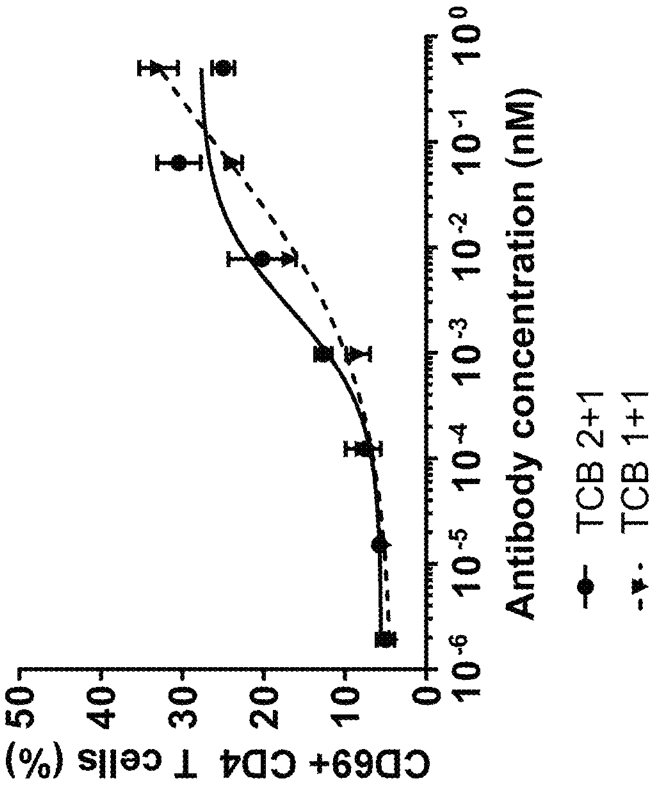
Figure 27D:
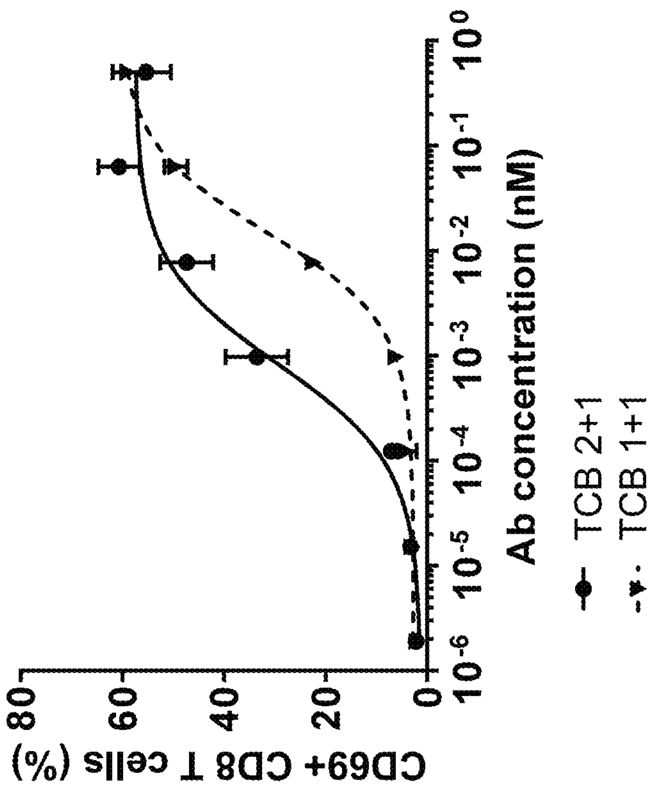
Figure 28A:
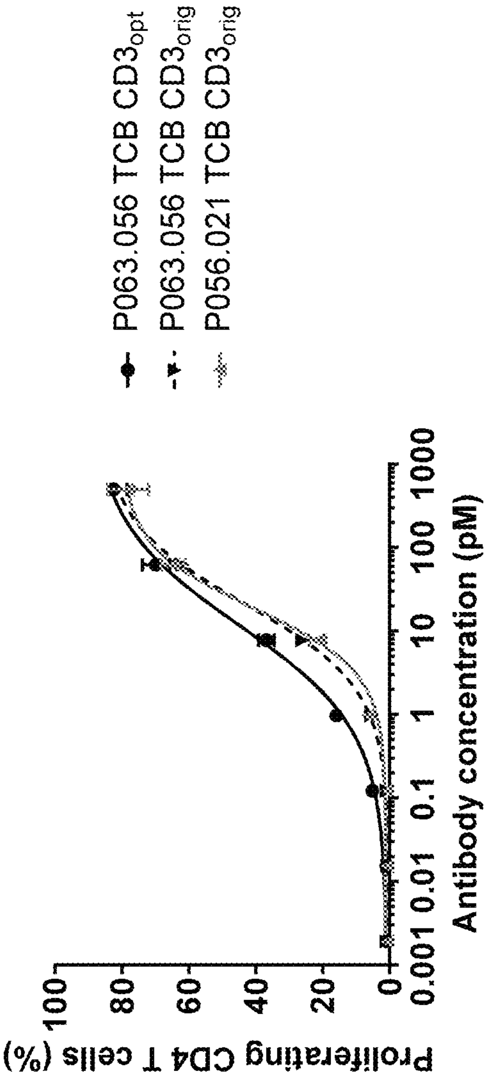
Figure 28B:
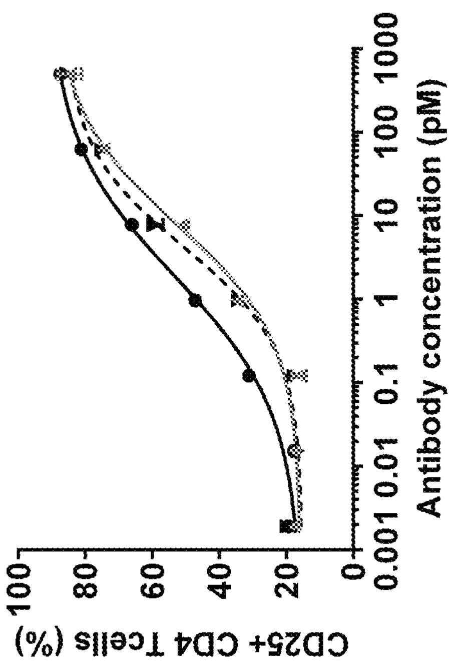
Figure 28C:
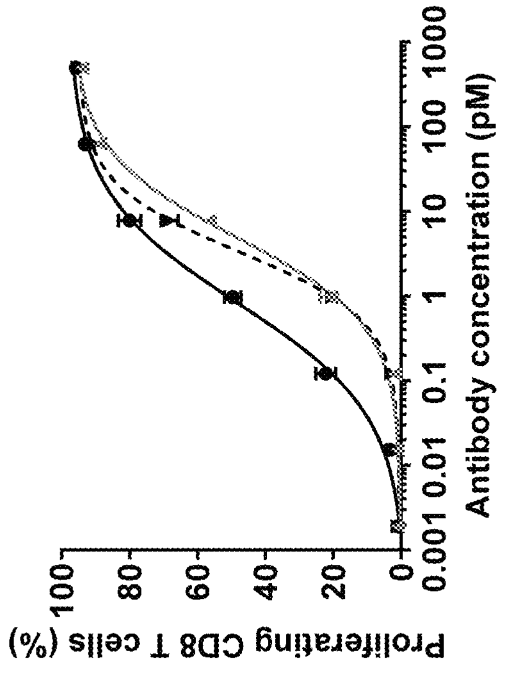
Figure 28D:
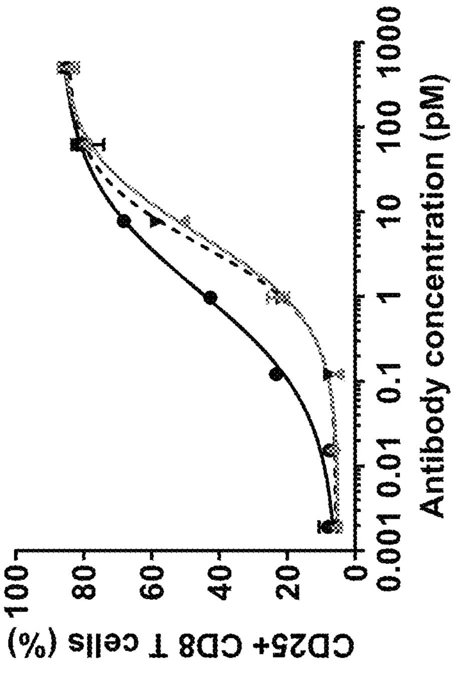
Figure 29A:
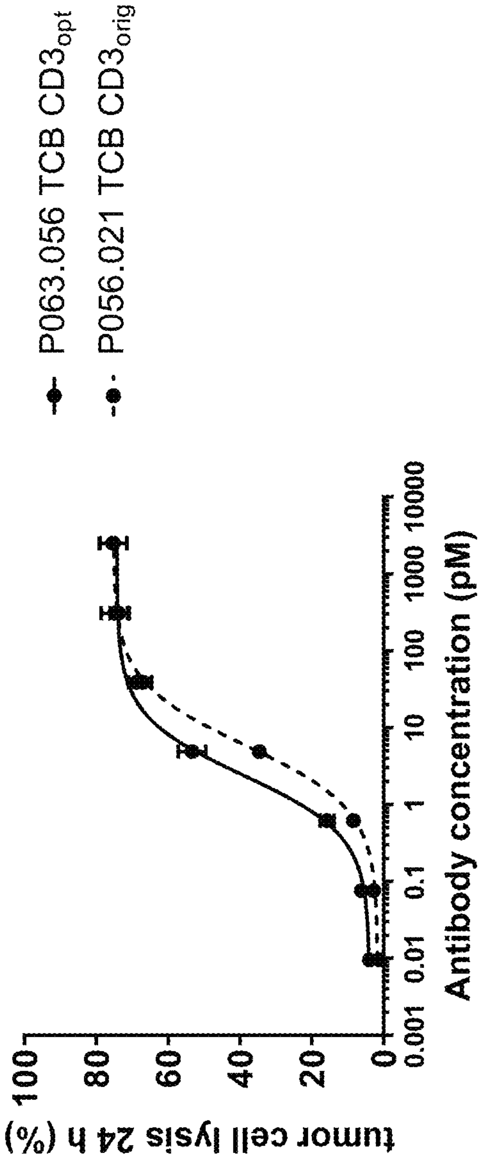
Figure 29B:
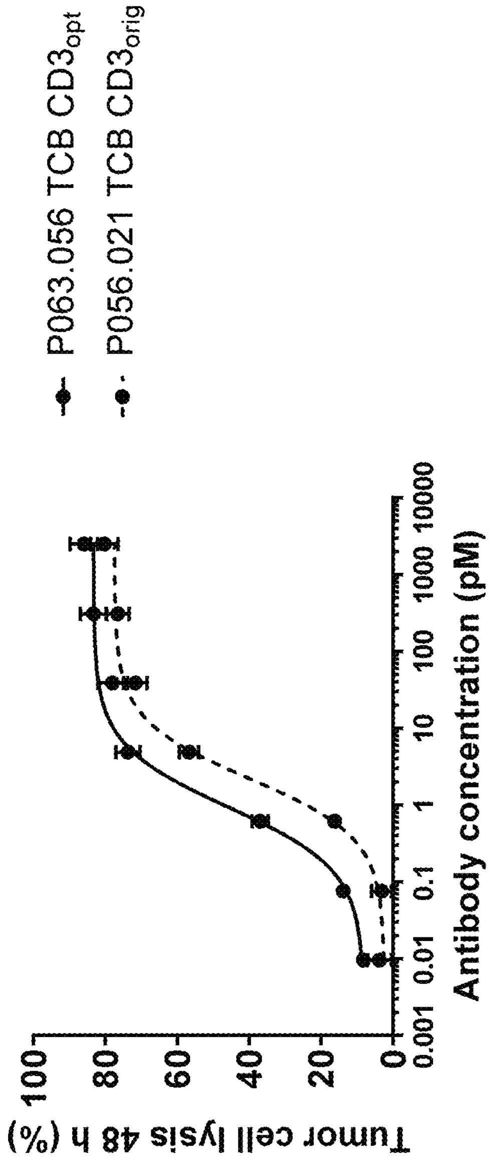
Figure 29C:
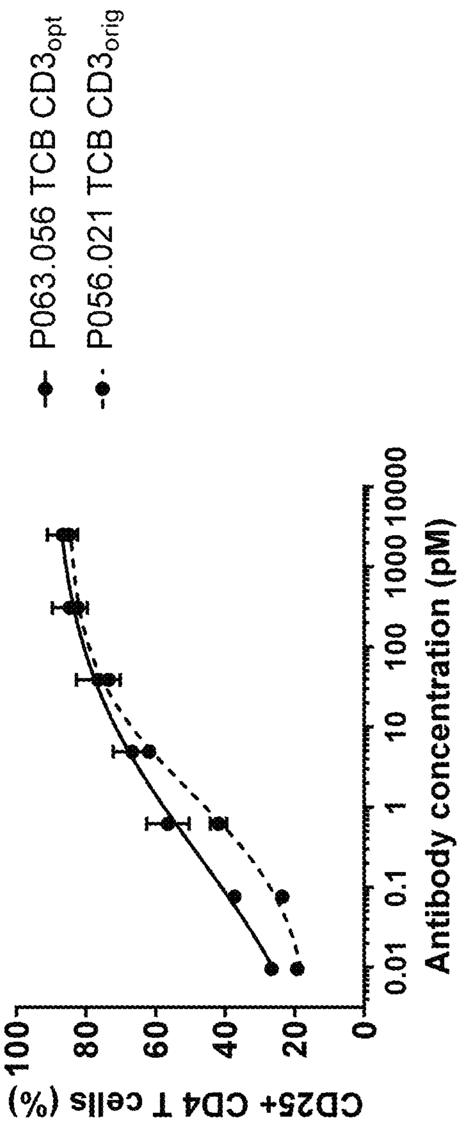
Figure 29D:
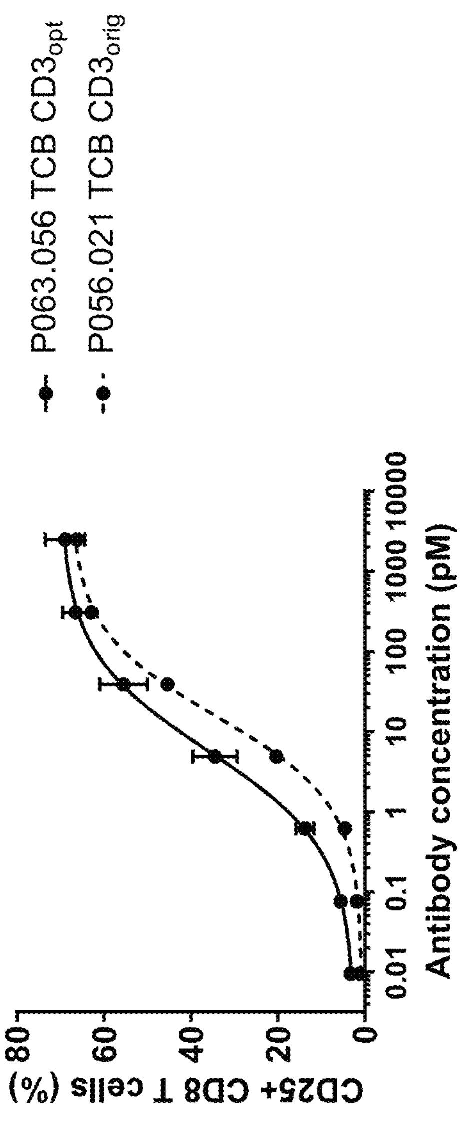
Figure 29E:
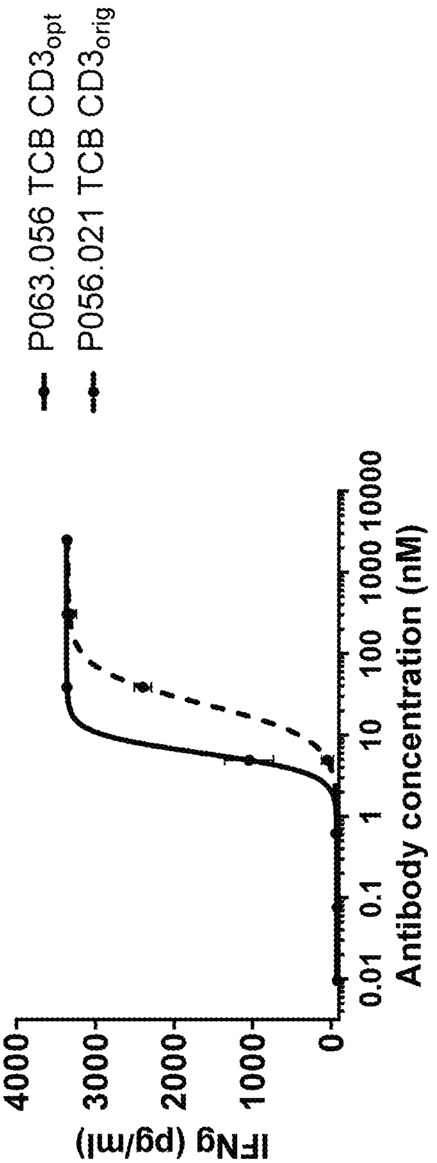
Figure 29F:
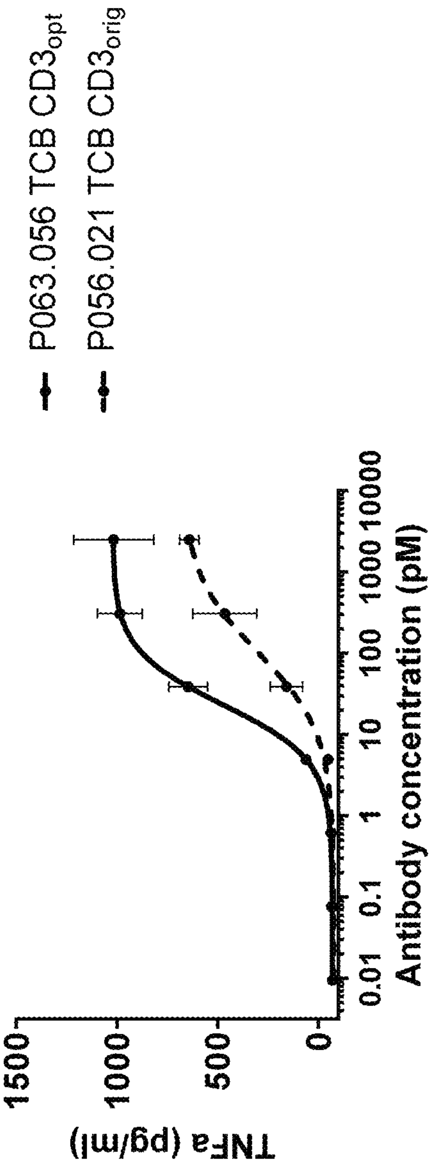
Figure 30A:
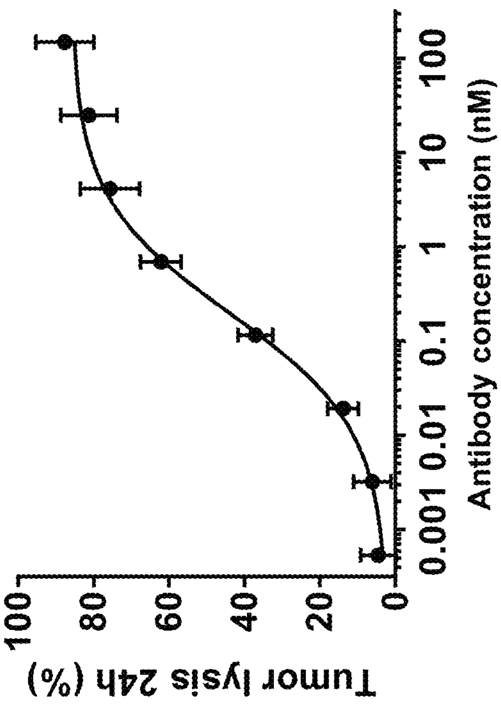
Figure 30B:
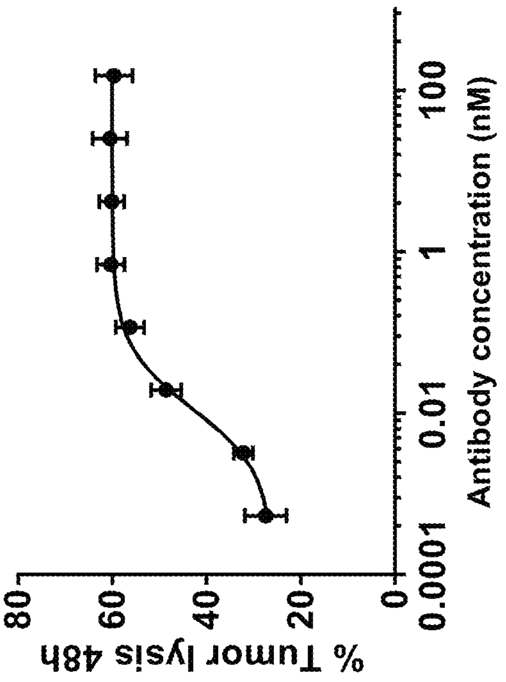
Figure 30C:
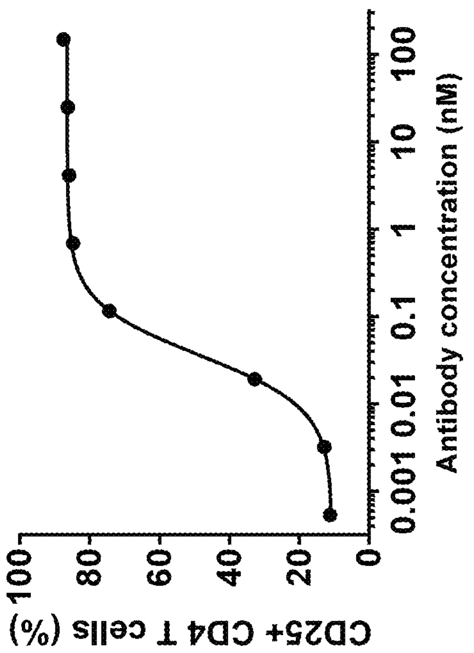
Figure 30D:
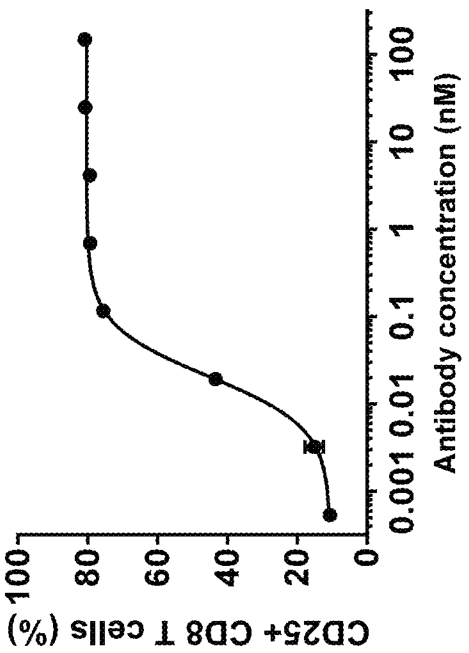
Figure 30E:
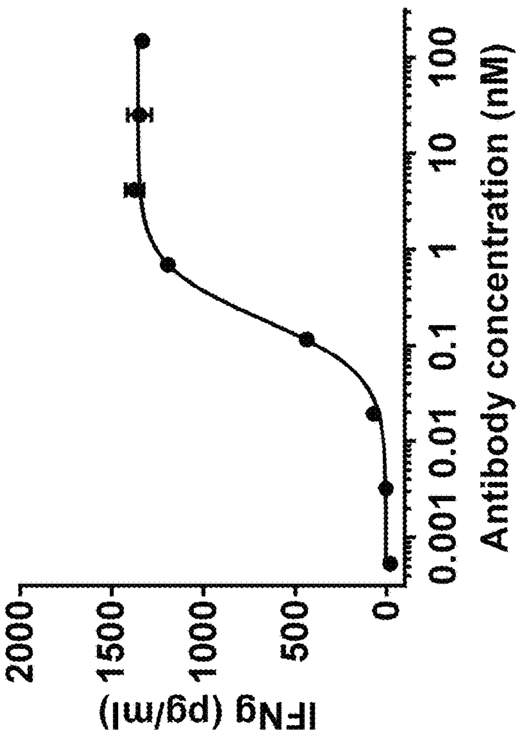
Figure 30F:
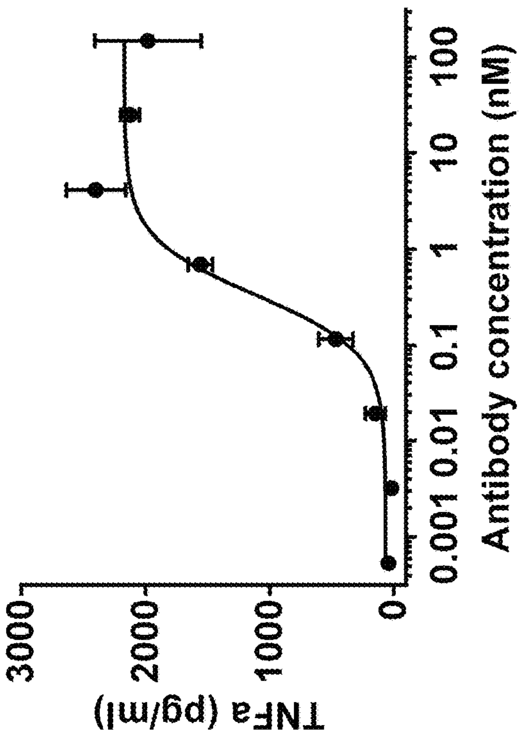

FIG. 27A-FIG. 27D. Tumor cell lysis and T cell activation comparing EGFRvIII TCB 2+1 format and 1+1 format. Induction of specific tumor cell lysis (FIG. 27A, FIG. 27B) and T cell activation (FIG. 27C, FIG. 27D) by EGFRvIII TCB in the 2+1 inverted format and in the 1+1 head-to-tail format was determined upon co-culture with freshly isolated PBMCs and U87MG-EGFRvIII cells for 24 h (FIG. 27A, FIG. 27C) or 48 h (FIG. 27B, FIG. 27D).

FIG. 28A-FIG. 28D. T cell activation and proliferation with EGFRvIII TCBs. Induction of T cell proliferation (FIG. 28A, FIG. 28C) and T cell activation of CD4 T cells (FIG. 28A, FIG. 28B) and CD8 T cells (FIG. 28C, FIG. 28D) by EGFRvIII TCBs was determined upon co-culture of U87MG-EGFRvIII and PBMCs isolated from healthy donors.

FIG. 29A-FIG. 29F. Tumor cell lysis, T cell activation and cytokine release with EGFRvIII TCBs. Induction of tumor cell lysis (FIG. 29A, FIG. 29B), T cell activation (FIG. 29C, FIG. 29D) and release of IFNγ and TNFα (FIG. 29E, FIG. 29F) by EGFRvIII TCBs was determined upon co-culture of U87MG-EGFRvIII cells with PBMCs. Tumor cell lysis was measured after 24 h and 48 h of treatment, T cell activation and cytokine release was measured after 48 h.

FIG. 30A-FIG. 30F. Tumor cell lysis, T cell activation and cytokine release with TYRP-1 TCB. Induction of tumor cell lysis (FIG. 30A, FIG. 30B), T cell activation (FIG. 30C, FIG. 30D) and release of IFNγ and TNFα (FIG. 30E, FIG. 30F) by TYRP-1 TCB was determined upon co-culture with the patient derived melanoma cell line M150543 with PBMCs. Tumor cell lysis was measured after 24 h and 48 h of treatment, T cell activation and cytokine release was measured after 48 h.

Figure 31:
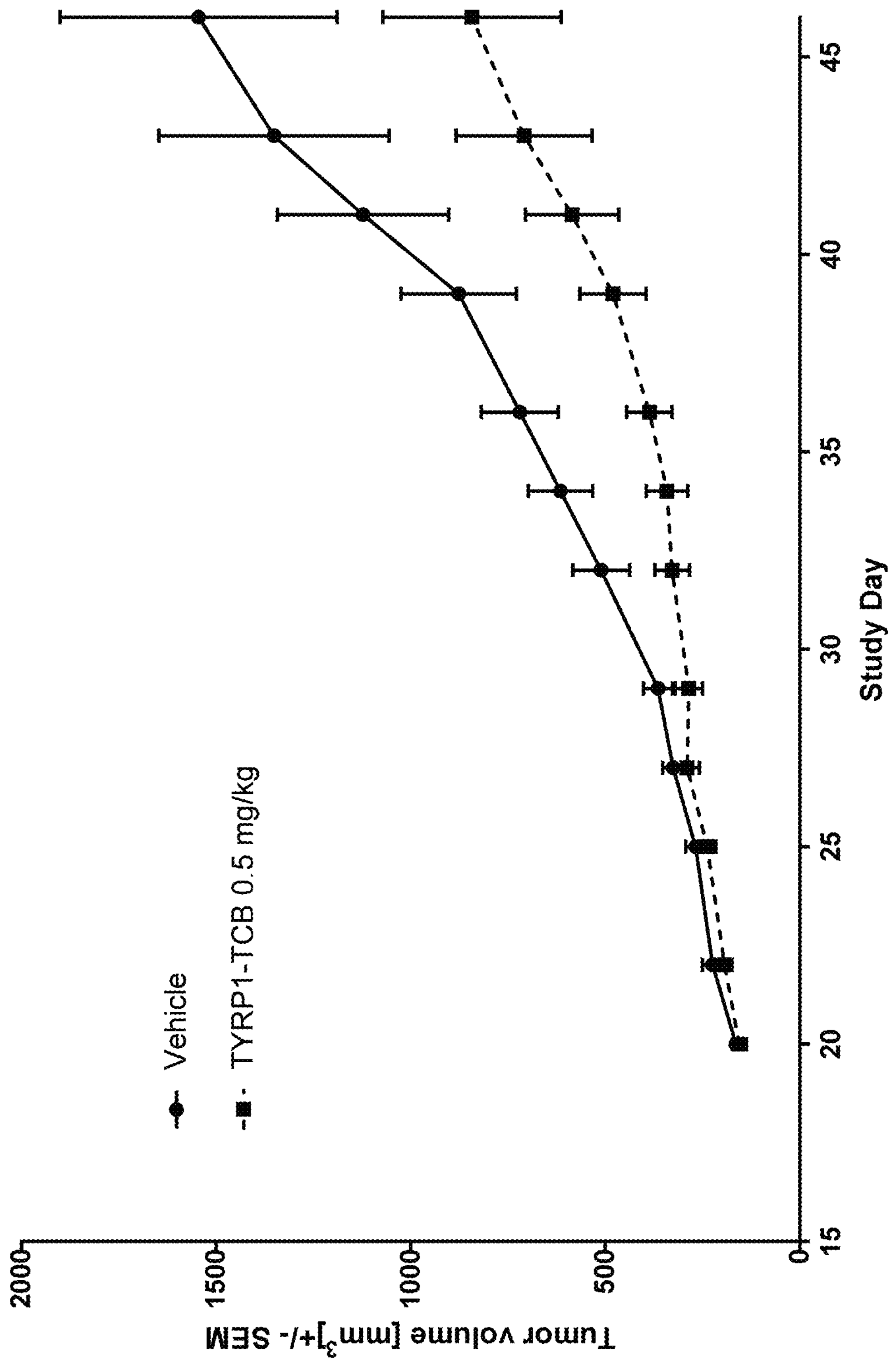

FIG. 31. In vivo efficacy of TYRP-1 TCB. The IGR-1 human melanoma cell line was injected subcutaneously in humanized NSG mice to study tumor growth inhibition in a melanoma subcutaneous xenograft model. Significant tumor growth inhibition (TGI) was observed in the TYRP-1 TCB group (68% TGI, p=0.0058*) compared to vehicle group.

Figure 32:
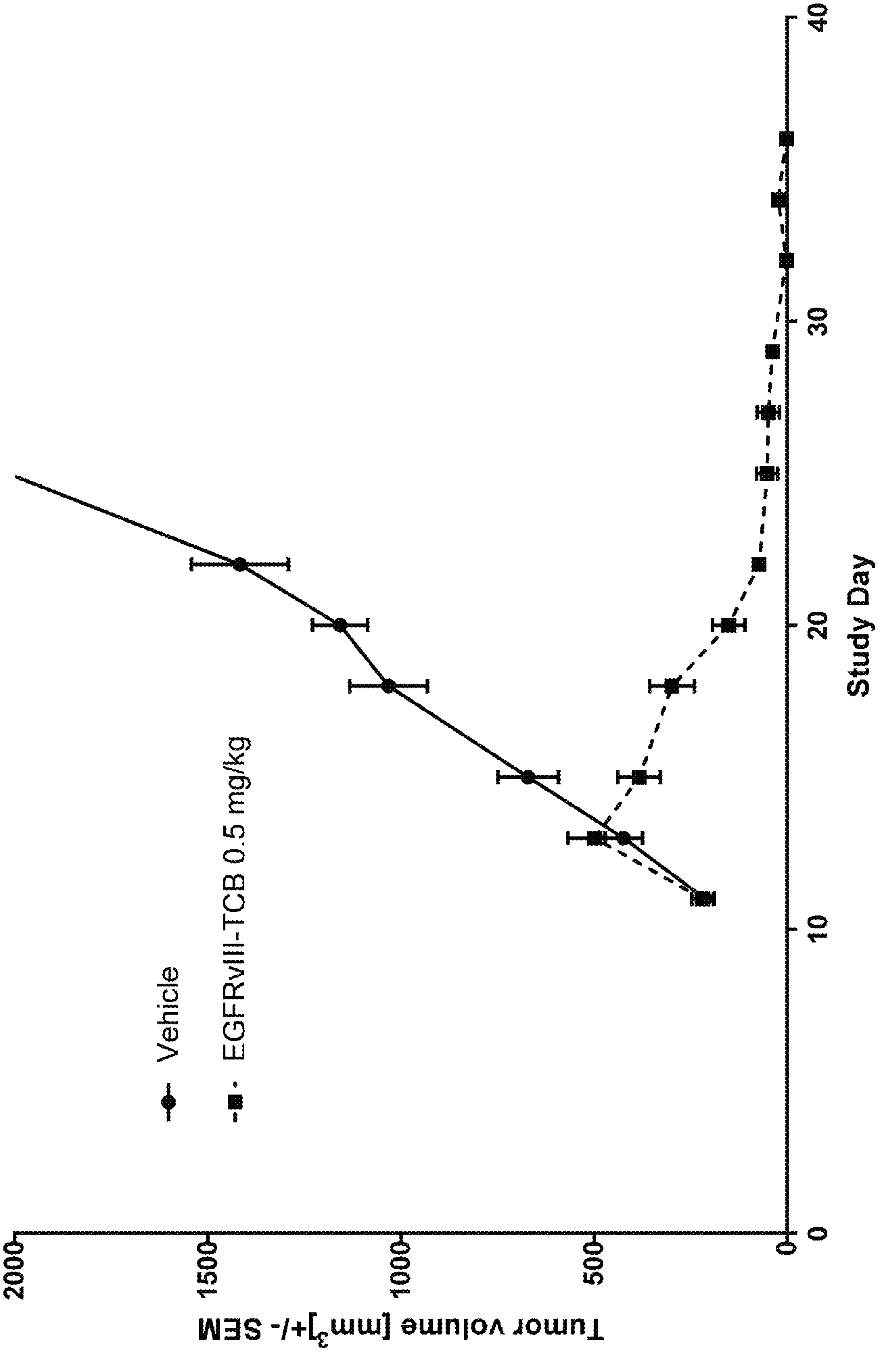

FIG. 32. In vivo efficacy of EGFRvIII TCB. The U87-huEGFRvIII human glioblastoma cell line was injected subcutaneously in humanized NSG mice to study tumor growth inhibition in a glioblastoma subcutaneous xenograft model. Significant tumor control was observed in the EGFRvIII TCB group with all mice achieving complete remission.

Figure 33A:
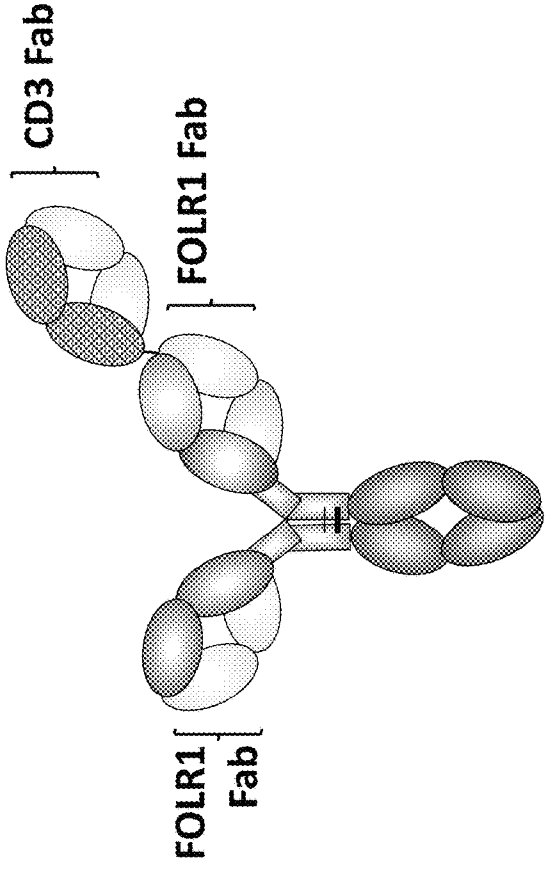
Figure 33B:
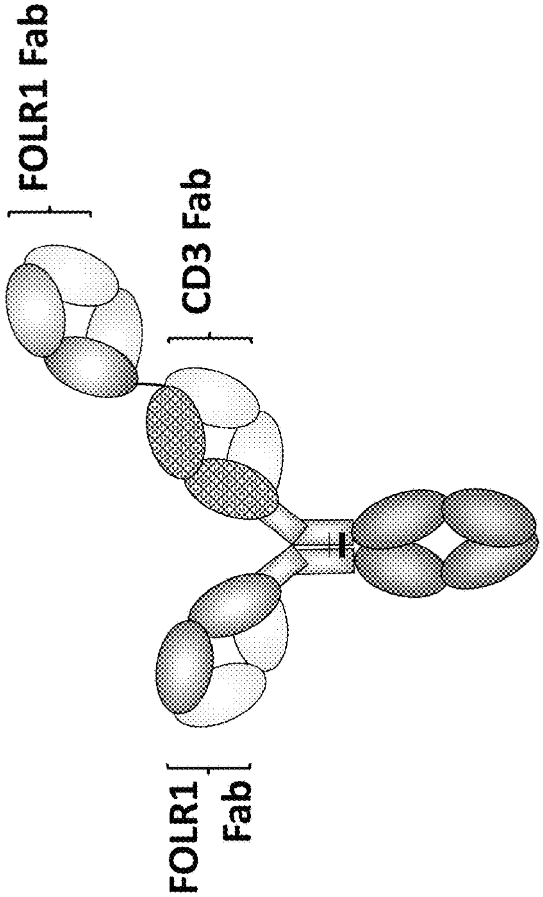
Figure 33D:
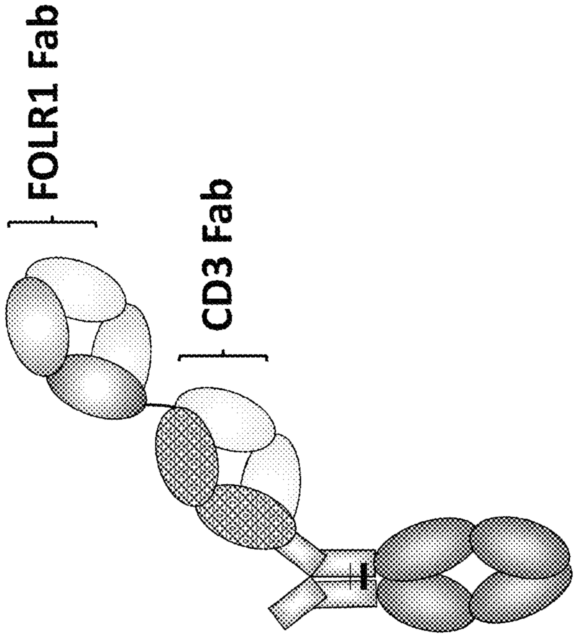
Figure 33C:
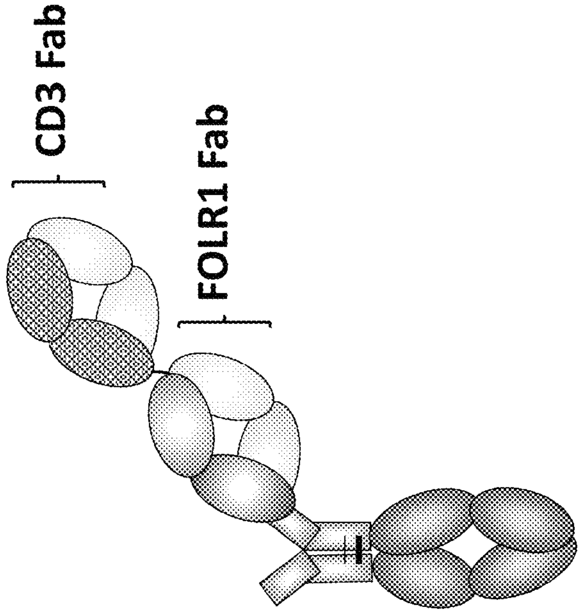
Figure 33E:
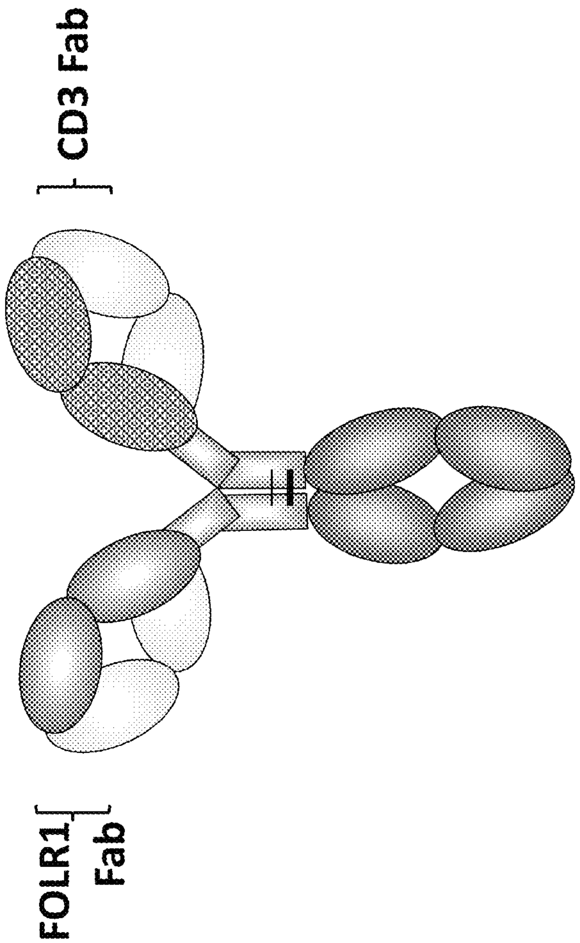

FIG. 33A-FIG. 33E. Formats of FolR1 TCB molecules. FIG. 33A: Classical 2+1 TCB molecule with a CD3 Fab fused via a (G4S)2 linker to VH of inner FOLR1 Fab. Heterodimerization by knob-into-hole technology, PGLALA mutation in Fc. FIG. 33B: Inverted 2+1 FOLR1 TCB with $CD3_{opt}$ Fab inside of Fc knob chain. FIG. 33C. Classical 1+1 head-to-tail FOLR1 TCB molecule with a $CD3_{opt}$ Fab fused via a (G4S)2 linker to VH of inner FOLR1 Fab. Heterodimerization by knob-into-hole technology, PGLALA mutation in Fc. FIG. 33D. Inverted 1+1 head-to-tail FOLR1 TCB with $CD3_{opt}$ Fab inside of Fc knob chain. FIG. 33E: 1+1 IgG like FOLR1 TCB molecule with a $CD3_{opt}$ Fab on the Fc knob chain and FOLR1 Fab on Fc hole chain. Fab. Heterodimerization by knob-into-hole technology, PGLALA mutation in Fc.

Figure 34:
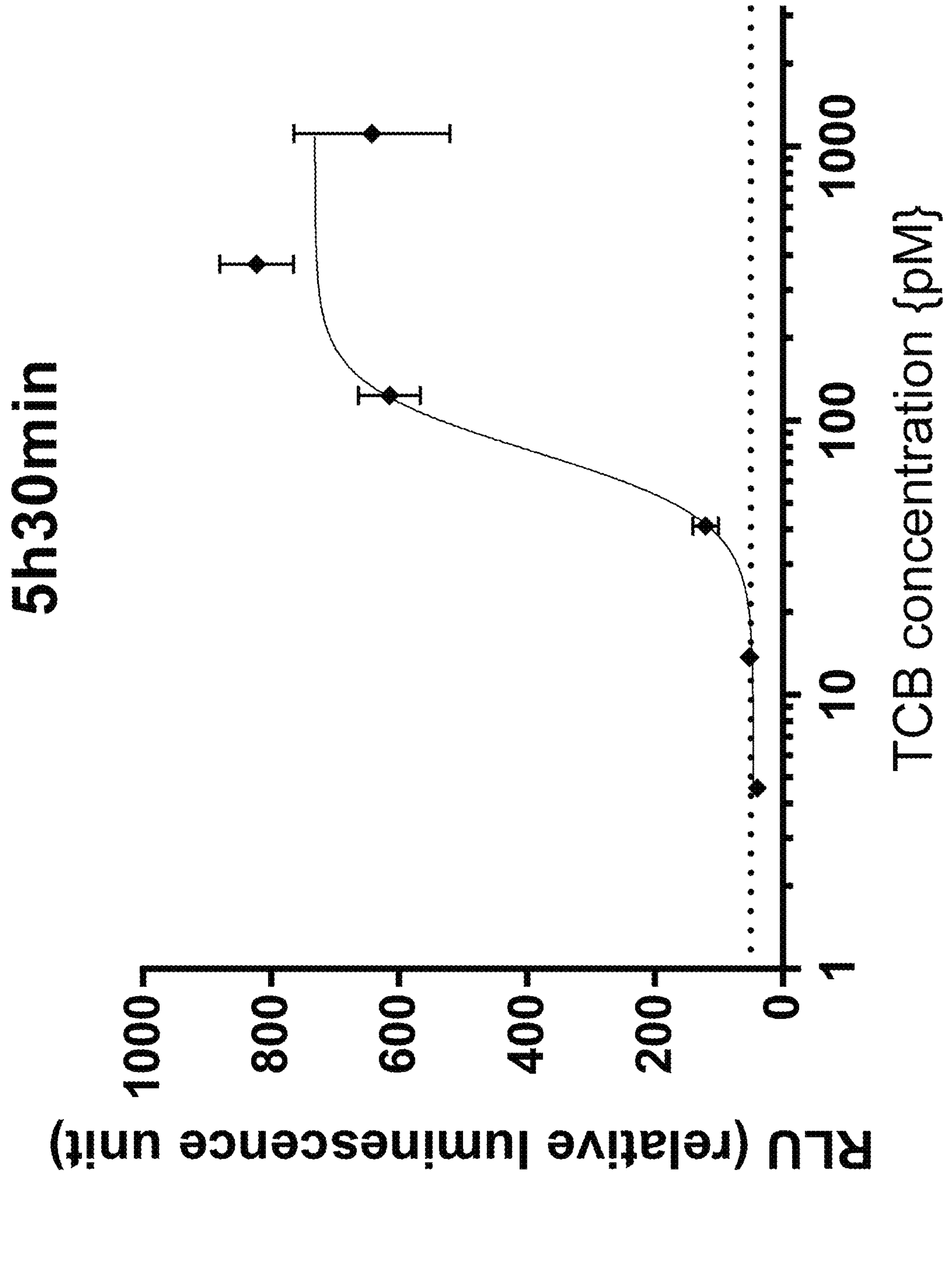

FIG. 34. Jurkat NFAT activation mediated by FOLR1-TCB ($CD3_{opt}$). Jurkat NFAT activation mediated by FOLR1-TCB with $CD3_{opt}$ is shown. FOLR1-TCB was incubated with huFOLR1 coated beads and and Jurkat NFAT effector cells for 5.5 h at 37 °C. Dotted line represents the beads with Jurkat cells without TCB. Each point represents the mean of technical triplicates. Standard deviation is indicated by error bars (n=1).

Figure 35A:
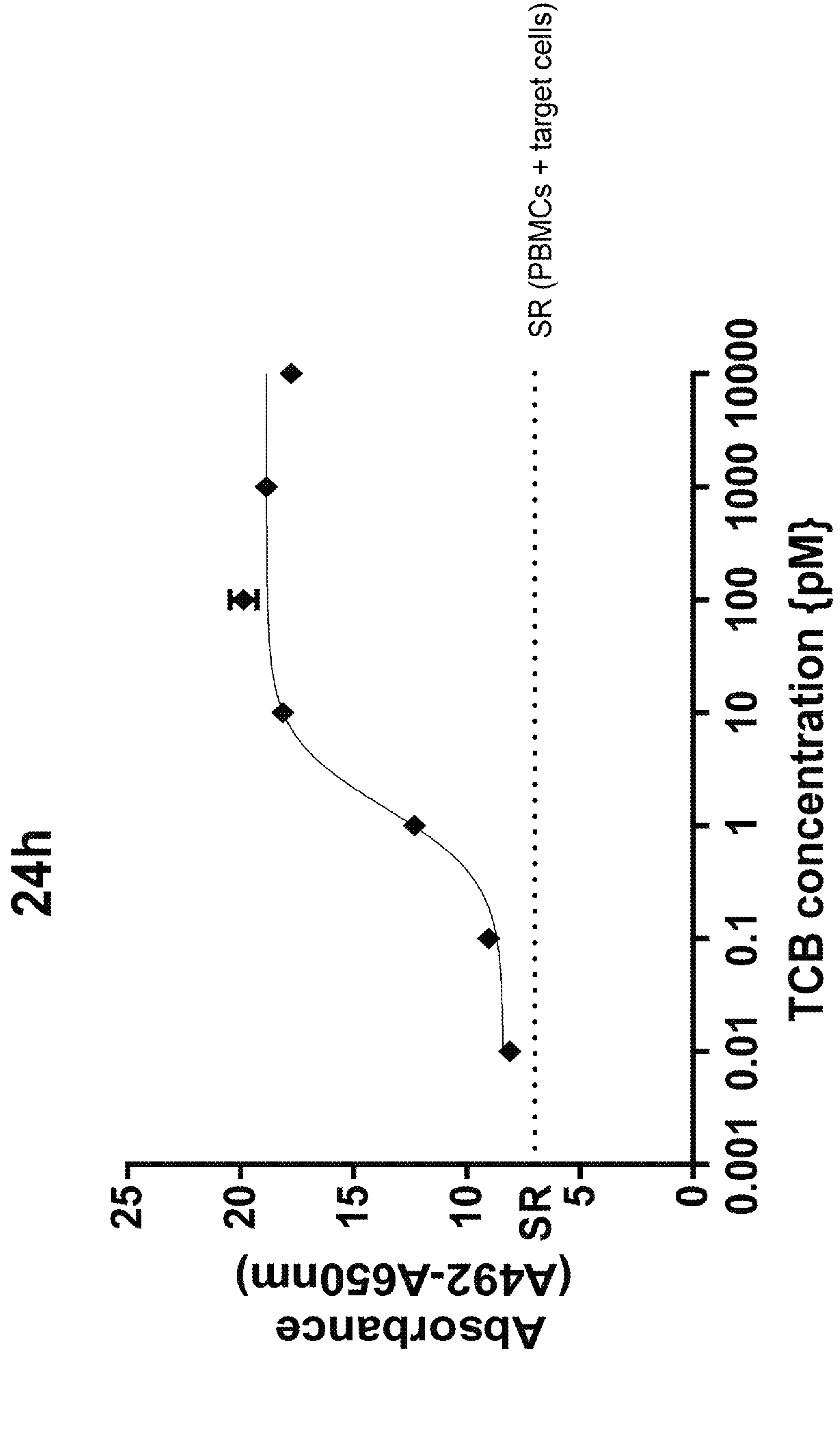
Figure 35B:
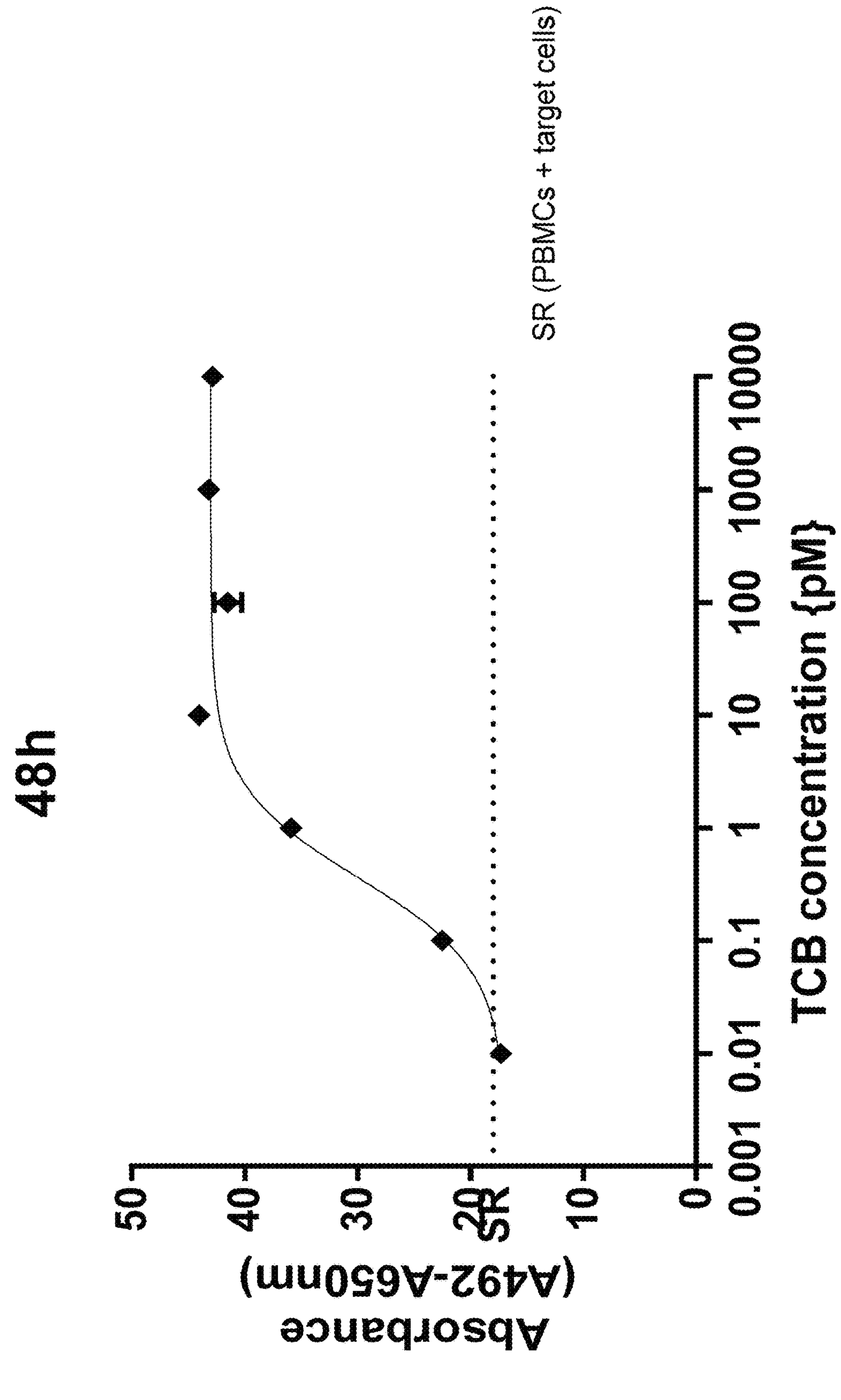
Figure 35D:
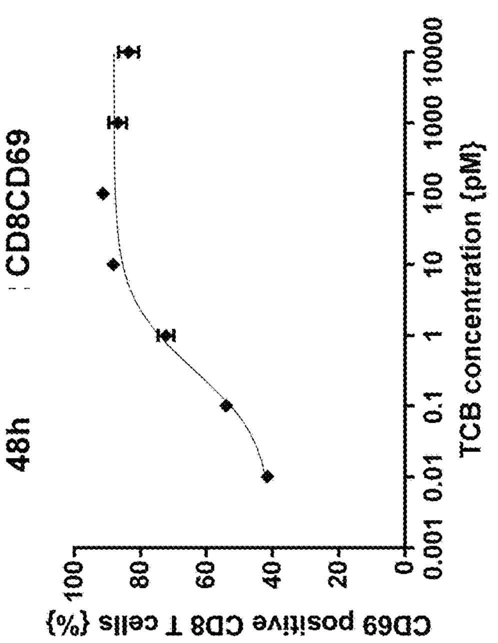
Figure 35F:
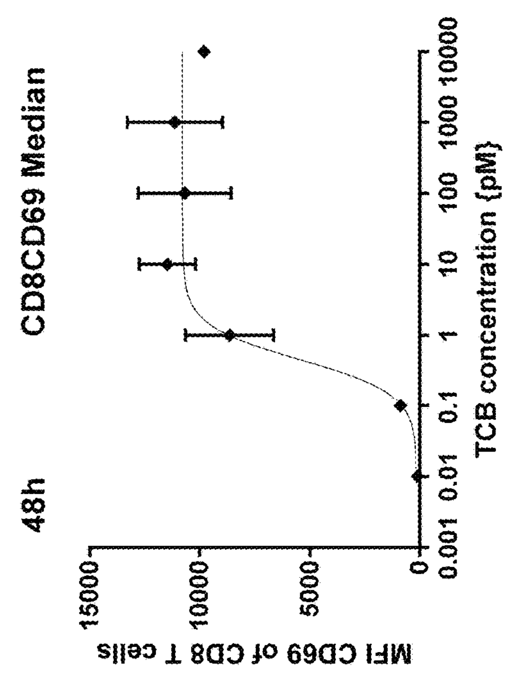
Figure 35C:
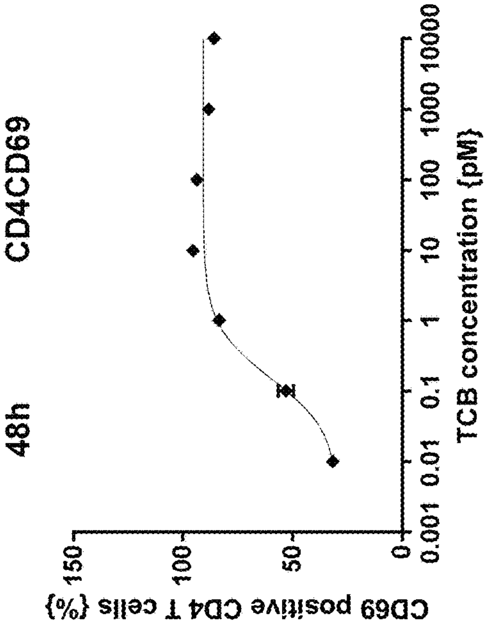
Figure 35E:
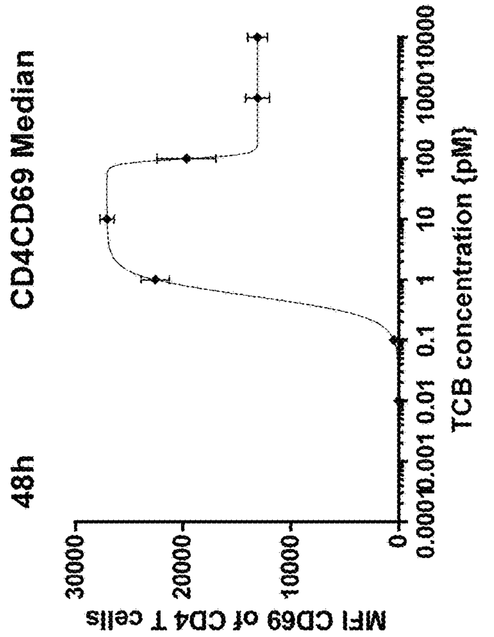

FIG. 35A-FIG. 35F. Tumor cell lysis and T cell activation with FOLR1 (pro-) TCB ($CD3_{opt}$). Dose-dependent tumor cell lysis and T cell activation were analyzed after co-incubation of human PBMCs (effector cells) and FOLR1-positive target cells (Ovcar-3) with FOLR1 TCB after 24 h and 48 h of incubation (E:T=10:1, effectors are human PBMCs). Induction of tumor cell lysis after 24 h and 48 h (FIG. 35A and FIG. 35B). T cell activation was measured after 48 h of treatment by quantification of CD69 for CD4 and CD8 T cells by FACS. CD69 positive CD4 T cells (FIG. 35C) and CD8 T cells (FIG. 35D) are shown in the upper panel. In the lower panel Median for CD69 {PE} was plotted for CD4 (FIG. 35E) and CD8 (FIG. 35F) positive T cells. Each point represents the mean of technical tripilicates. Standard deviation is indicated by error bars.

DETAILED DESCRIPTION OF THE INVENTION

I. Definitions

Terms are used herein as generally used in the art, unless otherwise defined in the following.

As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one aspect, the extent of binding of an anti-CD3 antibody to an unrelated, non-CD3 protein is less than about 10% of the binding of the antibody to CD3 as measured, e.g., by surface plasmon resonance (SPR). In certain aspects, an antibody that binds to CD3 has a dissociation constant ($K_D$) of ≤1 μM, ≤500 nM, ≤200 nM, or ≤100 nM. An antibody is said to "specifically bind" to CD3 when the antibody has a $K_D$ of 1 μM or less, as measured, e.g., by SPR. In certain aspects, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g. scFv and scFab), single-domain antibodies, and multispecific antibodies formed from antibody fragments. For a review of certain antibody fragments, see Hollinger and Hudson, Nature Biotechnology 23:1126-1136 (2005).

The terms "full-length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC, affinity chromatography, size exclusion chromatography) methods. For review of methods for assessment of antibody purity, see, e.g., Flatman et al., *J. Chromatogr. B* 848:79-87 (2007). In some aspects, the antibodies provided by the present invention are isolated antibodies.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some aspects, some FR residues in a humanized antibody are substituted with corresponding residues from a non-human antibody (e.g., the antibody from which the CDR residues are derived), e.g., to restore or improve antibody specificity or affinity. A "humanized form" of an antibody, e.g. of a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain aspects, a human antibody is derived from a non-human transgenic mammal, for example a mouse, a rat, or a rabbit. In certain aspects, a human antibody is derived from a hybridoma cell line. Antibodies or antibody fragments isolated from human antibody libraries are also considered human antibodies or human antibody fragments herein.

The term "antigen binding domain" refers to the part of an antibody that comprises the area which binds to and is complementary to part or all of an antigen. An antigen binding domain may be provided by, for example, one or more antibody variable domains (also called antibody variable regions). In preferred aspects, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and complementarity determining regions (CDRs). See, e.g., Kindt et al., *Kuby Immunology,* $6^{th}$ ed., W.H. Freeman & Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein in connection with variable region sequences, "Kabat numbering" refers to the numbering system set forth by Kabat et al., *Sequences of Proteins of Immunological Interest,* 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., *Sequences of Proteins of Immunological Interest,* 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, hinge, CH2 and CH3), which is herein further clarified by referring to "numbering according to Kabat EU index" or "Kabat EU index numbering" in this case.

The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system. "Framework" or "FR" refers to variable domain residues other than complementarity determining regions (CDRs). The FR of a variable domain generally consists of four FR domains: FR1, FR2, FR3, and FR4. Accordingly, the HVR and FR sequences generally appear in the following order in VH (or VL): FR1-HCDR1(LCDR1)-FR2-HCDR2(LCDR2)-FR3-HCDR3(LCDR3)-FR4. Unless otherwise indicated, CDR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes is 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence. A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3.

The term "immunoglobulin molecule" herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called $\alpha$ (IgA), $\delta$ (IgD), $\varepsilon$ (IgE), $\gamma$ (IgG), or $\mu$ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa ($\kappa$) and lambda ($\lambda$), based on the amino acid sequence of its constant domain. An immunoglobulin essentially consists of two Fab molecules and an Fc domain, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

In certain embodiments, the invention relates to bispecific molecules wherein at least two binding moieties have identical light chains and corresponding remodeled heavy chains that confer the specific binding to the respective antigens (e.g. CD3 and FolR1). The use of this so-called "common light chain" principle, i.e. combining two or more binders that share one light chain but still have separate specificities, prevents light chain mispairing. Thus, there are less side products during production, facilitating the homogenous preparation of the bispecific molecules.

The term "Fc domain" or "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region (or a subunit of an Fc domain as defined herein) are denoted herein without C-terminal glycine-lysine dipeptide if not indicated otherwise. In one aspect, a heavy chain including an Fc region (subunit) as specified herein, comprised in an antibody according to the invention, comprises an additional C-terminal glycine-lysine dipeptide (G446 and K447, numbering according to Kabat EU index). In one aspect, a heavy chain including an Fc region (subunit) as specified herein, comprised in an antibody according to the invention, comprises an additional C-terminal glycine residue (G446, numbering according to Kabat EU index). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, M D, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain. By "fused" is meant that the components (e.g. a Fab molecule and an Fc domain subunit) are linked by peptide bonds, either directly or via one or more peptide linkers.

The term "multispecific" means that the antibody is able to specifically bind to at least two distinct antigenic determinants. A multispecific antibody can be, for example, a bispecific antibody. Typically, a bispecific antibody comprises two antigen binding sites, each of which is specific for a different antigenic determinant. In certain aspects the multispecific (e.g. bispecific) antibody is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigenic determinant" or "antigen" refers to a site (e.g. a contiguous stretch of amino acids or a conformational configuration made up of different regions of non-contiguous amino acids) on a polypeptide macromolecule to which an antigen binding domain binds, forming an antigen binding domain-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). In a preferred aspect, the antigen is a human protein.

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one aspect, CD3 is human CD3, particularly the epsilon subunit of human CD3 (CD3ε). The amino acid sequence of human CD3ε is shown in SEQ ID NO: 112 (without signal peptide). See also UniProt (www.uniprot.org) accession no. P07766 (version 189), or NCBI (www.ncbi.nlm.nih.gov/) RefSeq NP_000724.1. In another aspect, CD3 is cynomolgus (*Macaca fascicularis*) CD3, particularly cynomolgus CD3c. The amino acid sequence of cynomolgus CD3ε is shown in SEQ ID NO: 113 (without signal peptide). See also NCBI GenBank no. BAB71849.1. In certain aspects the antibody of the invention binds to an epitope of CD3 that is conserved among the CD3 antigens from different species, particularly human and cynomolgus CD3. In preferred aspects, the antibody binds to human CD3.

A "target cell antigen" as used herein refers to an antigenic determinant presented on the surface of a target cell, for example a cell in a tumor such as a cancer cell or a cell of the tumor stroma (in that case a "tumor cell antigen"). Preferably, the target cell antigen is not CD3, and/or is expressed on a different cell than CD3. In one aspect, the target cell antigen is TYRP-1, particularly human TYRP-1. In another aspect, the target cell antigen is EGFRvIII, particularly human EGFRvIII. In a preferred embodiment, the target antigen is Folate receptor 1 (FolR1).

"FolR1" stands for Folate receptor 1 (synonyms include but are not limited to Folate receptor alpha (FRA), Folate binding protein (FBP), MOv18, P15328, FRA1, FRAI) is a protein receptor mediating the update of folic acid and reduced folic acid derivatives to the interior of cells. The sequence of human FolR1 is shown in SEQ ID NO:137. See also UniProt entry no. P15328. "FolR1 as used herein refers to any native FolR1 from any vertebrate source, including mammals such as primates (e.g. humans), non-human primates (e.g. cynomolgus monkeys) and rodents (e.g. mice and rats), unless otherwise indicated. The term encompasses "full-length," unprocessed FolR1 as well as any form of FolR11 that results from processing in the cell. The term also encompasses naturally occurring variants of FolR1, e.g., splice variants or allelic variants. In one aspect, FolR1 is human FolR1.

"TYRP1" or "TYRP-1" stands for tyrosine-related protein 1, which is an enzyme involved in melanin synthesis. The mature form of TYRP1, also originally called gp75, is a 75 kDa transmembrane glycoprotein. The sequence of human TYRP1 is shown in SEQ ID NO: 114 (without signal peptide). See also UniProt entry no. P17643 (version 185). "TYRP1" as used herein refers to any native TYRP1 from any vertebrate source, including mammals such as primates (e.g. humans), non-human primates (e.g. cynomolgus monkeys) and rodents (e.g. mice and rats), unless otherwise indicated. The term encompasses "full-length," unprocessed TYRP1 as well as any form of TYRP1 that results from processing in the cell. The term also encompasses naturally occurring variants of TYRP1, e.g., splice variants or allelic variants. In one aspect, TYRP1 is human TYRP1.

"EGFRvIII" stands for Epidermal Growth Factor Receptor Variant III, which is a mutant of EGFR, formed by an in-frame deletion of exons 2-7, leading to deletion of 267 amino acids with a glycine substitution at the junction. The sequence of human EGFRvIII is shown in SEQ ID NO: 115 (without signal peptide). The sequence of wild-type human EGFR is shown in SEQ ID NO: 116 (without signal peptide). See also UniProt entry no. P00533 (version 258). "EGFRvIII" as used herein refers to any native EGFRvIII from any vertebrate source, including mammals such as primates (e.g. humans), non-human primates (e.g. cynomolgus monkeys) and rodents (e.g. mice and rats), unless otherwise indicated. The term encompasses "full-length," unprocessed EGFRvIII (but not wild-type EGFR) as well as any form of EGFRvIII that results from processing in the cell (e.g. EGFRvIII without signal peptide). In one aspect, EGFRvIII is human EGFRvIII.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., an antibody and an antigen). The affinity of a molecule X for its partner Y can generally be represented by the dissociation constant ($K_D$). Affinity can be measured by well-established methods known in the art, including those described herein. A preferred method for measuring affinity is Surface Plasmon Resonance (SPR).

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein preferably includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which may be non-identical in the sense that further components fused to each of the subunits (e.g. antigen binding domains) are not the same. In some aspects, the modification promoting the association of the first and the second subunit of the Fc domain comprises an amino acid mutation in the Fc domain, specifically an amino acid substitution. In a preferred aspect, the modification promoting the association of the first and the second subunit of the Fc domain comprises a separate amino acid mutation, specifically an amino acid substitution, in each of the two subunits of the Fc domain. The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Preferred amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, % amino acid sequence identity values are generated using the ggsearch program of the FASTA package version 36.3.8c or later with a BLOSUM50 comparison matrix. The FASTA program package was authored by W. R. Pearson and D. J. Lipman ("Improved Tools for Biological Sequence Analysis", PNAS 85 (1988) 2444-2448), W. R. Pearson ("Effective protein sequence comparison" Meth. Enzymol. 266 (1996) 227-258), and Pearson et. al. (Genomics 46 (1997) 24-36) and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" or "nucleic acid molecule" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group.

Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

An "isolated" nucleic acid molecule refers to a nucleic acid molecule that has been separated from a component of its natural environment. An isolated nucleic acid molecule includes a nucleic acid molecule contained in cells that ordinarily contain the nucleic acid molecule, but the nucleic acid molecule is present extrachromosomally or at a chromosomal location that is different from its natural chromosomal location.

"Isolated polynucleotide (or nucleic acid) encoding an antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one aspect, the host cell of the invention is a eukaryotic cell, particularly a mammalian cell. In one aspect, the host cell is not a cell within a human body.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human.

An "effective amount" of an agent, e.g., a pharmaceutical composition, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

II. Compositions and Methods

The invention provides bispecific antibodies that bind CD3 and FolR1. The antibodies show superior stability, combined with other favorable properties for therapeutic application, e.g. with respect to efficacy and safety, pharmacokinetics, as well as produceability. Antibodies of the invention as useful, e.g., for the treatment of diseases such as cancer.

A. Bispecific Anti-CD3 Anti-FolR1 Antibodies

In one aspect, the invention provides bispecific antibodies that bind to CD3 and FolR1. In one aspect, provided are isolated bispecific antibodies that bind to CD3 and FolR1. In one aspect, the invention provides bispecific antibodies that specifically bind to CD3 and FolR1. In certain aspects, the bispecific anti-CD3 anti-FolR1 antibodies retain more than about 90% binding activity to CD3 after 2 weeks at pH 7.4, 37 °C, relative to the binding activity after 2 weeks at pH 6, −80 °C, as determined by surface plasmon resonance (SPR).

In one aspect, the invention provides a bispecific antibody that binds to CD3 and FolR1, wherein the antibody comprises a first antigen binding domain, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10.

In one aspect, the antibody is a humanized antibody. In one aspect, the antigen binding domain is a humanized antigen binding domain (i.e. an antigen binding domain of a humanized antibody).

In one aspect, the VH and/or the VL is a humanized variable region.

In one aspect, the VH and/or the VL comprises an acceptor human framework, e.g. a human immunoglobulin framework or a human consensus framework.

In one aspect, the VH comprises one or more heavy chain framework sequence (i.e. the FR1, FR2, FR3 and/or FR4 sequence) of the heavy chain variable region sequence of SEQ ID NO: 7. In one aspect, the VH comprises an amino acid sequence that is at least about 95%, 96%, 97%, 98%, or 99% identical to the amino acid sequence of SEQ ID NO: 7. In one aspect, the VH comprises an amino acid sequence that is at least about 95% identical to the amino acid sequence of SEQ ID NO: 7. In one aspect, the VH comprises an amino acid sequence that is at least about 98% identical to the amino acid sequence of SEQ ID NO: 7. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 7. In certain aspects, substitutions, insertions, or deletions occur in regions outside the CDRs (i.e., in the FRs).

In one aspect, the VH comprises the amino acid sequence of SEQ ID NO: 7. Optionally, the VH comprises the amino acid sequence of SEQ ID NO: 7, including post-translational modifications of that sequence.

In one aspect, the VL comprises one or more light chain framework sequence (i.e. the FR1, FR2, FR3 and/or FR4 sequence) of the light chain variable region sequence of SEQ ID NO: 11. In one aspect, the VL comprises an amino acid sequence that is at least about 95%, 96%, 97%, 98%, or 99% identical to the amino acid sequence of SEQ ID NO: 11. In one aspect, the VL comprises an amino acid sequence that is at least about 95% identical to the amino acid sequence of SEQ ID NO: 11. In one aspect, the VL comprises an amino acid sequence that is at least about 98% identical to the amino acid sequence of SEQ ID NO: 11. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 11. In certain aspects, substitutions, insertions, or deletions occur in regions outside the CDRs (i.e., in the FRs). In one aspect, the VL comprises the amino acid sequence of SEQ ID NO: 11. Optionally, the VL comprises the amino acid sequence of SEQ ID NO: 11, including post-translational modifications of that sequence.

In one aspect, the VH comprises an amino acid sequence that is at least about 95%, 96%, 97%, 98%, or 99% identical to the amino acid sequence of SEQ ID NO: 7, and the VL comprises an amino acid sequence that is at least about 95%, 96%, 97%, 98%, or 99% identical to the amino acid sequence of SEQ ID NO: 11. In one aspect, the VH comprises the amino acid sequence of SEQ ID NO: 7 and the VL comprises the amino acid sequence of SEQ ID NO: 11.

In a further aspect, the invention provides an antibody that binds to CD3, wherein the antibody comprises a first antigen binding domain comprising a VH comprising the amino acid sequence of SEQ ID NO: 7 and a VL comprising the amino acid sequence of SEQ ID NO: 11.

In a further aspect, the invention provides a bispecific antibody that binds to CD3 and FolR1, wherein the antibody comprises a first antigen binding domain comprising a VH sequence of SEQ ID NO: 7 and a VL sequence of SEQ ID NO: 11.

In another aspect, the invention provides a bispecific antibody that binds to CD3 and FolR1, wherein the antibody comprises a first antigen binding domain comprising a VH comprising the heavy chain CDR sequences of the VH of SEQ ID NO: 7, and a VL comprising the light chain CDR sequences of the VL of SEQ ID NO: 11.

In a further aspect, the first antigen binding domain comprises the HCDR1, HCDR2 and HCDR3 amino acid sequences of the VH of SEQ ID NO: 7 and the LCDR1, LCDR2 and LCDR3 amino acid sequences of the VL of SEQ ID NO: 11.

In one aspect, the VH comprises the heavy chain CDR sequences of the VH of SEQ ID NO: 7 and a framework of at least 95%, 96%, 97%, 98% or 99% sequence identity to the framework sequence of the VH of SEQ ID NO: 7. In one aspect, the VH comprises the heavy chain CDR sequences of the VH of SEQ ID NO: 7 and a framework of at least 95% sequence identity to the framework sequence of the VH of SEQ ID NO: 7. In another aspect, the VH comprises the heavy chain CDR sequences of the VH of SEQ ID NO: 7 and a framework of at least 98% sequence identity to the framework sequence of the VH of SEQ ID NO: 7.

In one aspect, the VL comprises the light chain CDR sequences of the VL of SEQ ID NO: 11 and a framework of at least 95%, 96%, 97%, 98% or 99% sequence identity to the framework sequence of the VL of SEQ ID NO: 11. In one aspect, the VL comprises the light chain CDR sequences of the VL of SEQ ID NO: 11 and a framework of at least 95% sequence identity to the framework sequence of the VL of SEQ ID NO: 11. In another aspect, the VL comprises the light chain CDR sequences of the VL of SEQ ID NO: 11 and a framework of at least 98% sequence identity to the framework sequence of the VL of SEQ ID NO: 11.

In one aspect, the invention provides a bispecific antibody that binds to CD3 and FolR1, wherein the antibody comprises a first antigen binding domain comprising a VH sequence as in any of the aspects provided above, and a VL sequence as in any of the aspects provided above.

In one aspect, the bispecific antibody comprises a human constant region. In one aspect, the bispecific antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 120 and 121 (human kappa and lambda CL domains, respectively) and SEQ ID NO: 122 (human IgG1 heavy chain constant domains CH1-CH2-CH3). In one aspect, the bispecific antibody comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. In one aspect, the bispecific antibody comprises a heavy chain constant region comprising an amino acid sequence that is at least about 95%, 96%, 97%, 98%, 99% or 100% identical to the amino acid sequence of SEQ ID NO: 122. Particularly, the heavy chain constant region may comprise amino acid mutations in the Fc domain as described herein.

In one aspect, the first antigen binding domain comprises a human constant region. In one aspect, the first antigen binding moiety is a Fab molecule comprising a human constant region, particularly a human CH1 and/or CL domain. In one aspect, the first antigen binding domain comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. Particularly, the light chain constant region may comprise amino acid mutations as described herein under “charge modifications” and/or may comprise deletion or substitutions of one or more (particularly two) N-terminal amino acids if in a crossover Fab molecule. In some aspects, the first antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 122. Particularly, the heavy chain constant region (specifically CH1 domain) may comprise amino acid mutations as described herein under “charge modifications”.

In one aspect, the bispecific antibody is a monoclonal antibody.

In one aspect, the bispecific antibody is an IgG, particularly an $IgG_1$, antibody. In one aspect, the bispecific antibody is a full-length antibody.

In another aspect, the first and/or the second and/or further antigen binding domain(s) are/is an antibody fragment(s) selected from the group of (a) Fv molecule(s), (a) scFv molecule(s), (a) Fab molecule(s), and (a) $F(ab')_2$ molecule (s); particularly (a) Fab molecule(s). In another aspect, the antibody fragment(s) is/are (a) diabody(ies), (a) triabody)ies or (a) tetrabodyies.

In one aspect, the first antigen binding domain is a Fab molecule. In a preferred aspect the first antigen binding domain is a Fab molecule wherein the variable domains VL and VH or the constant domains CL and CH1, particularly the variable domains VL and VH, of the Fab light chain and the Fab heavy chain are replaced by each other (i.e. the first antigen binding domain is a crossover Fab molecule).

In a further aspect, the antibody according to any of the above aspects may incorporate any of the features, singly or in combination, as described in sections II. A. 1.-8. below.

In a preferred aspect, the antibody comprises an Fc domain, particularly an IgG Fc domain, more particularly an $IgG_1$ Fc domain. In one aspect the Fc domain is a human Fc domain. In one aspect, the Fc domain is a human $IgG_1$ Fc domain. The Fc domain is composed of a first and a second subunit and may incorporate any of the features, singly or in combination, described hereinbelow in relation to Fc domain variants (section II. A. 8.).

In another preferred aspect, the antibody comprises a second and optionally a third antigen binding domain which binds to a second antigen (i.e. the antibody is a multispecific antibody, as further described hereinbelow (section II. A. 7.).

1. Antibody Fragments

In certain aspects, an antigen binding domain provided herein is an antibody fragment.

In one aspect, the antibody fragment is a Fab, Fab', Fab'-SH, or $F(ab')_2$ molecule, in particular a Fab molecule as described herein. “Fab’ molecule” differ from Fab molecules by the addition of residues at the carboxy terminus of the CH1 domain including one or more cysteines from the antibody hinge region. Fab'-SH are Fab' molecules in which the cysteine residue(s) of the constant domains bear a free thiol group. Pepsin treatment yields an $F(ab')_2$ molecule that has two antigen-binding sites (two Fab molecules) and a part of the Fc region.

In another aspect, the antibody fragment is a diabody, a triabody or a tetrabody. “Diabodies” are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab molecule. A “single chain Fab molecule” or “scFab” is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab molecules are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A “single-chain variable fragment” or “scFv” is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. “Single-domain antibodies” are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., *E. coli*), as described herein.

2. Humanized Antibodies

In certain aspects, an antibody (e.g. bispecific antibody) provided herein is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

3. Glycosylation Variants

In certain aspects, an antibody (e.g. bispecific antibody) provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.,* 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

4. Cysteine Engineered Antibody Variants

In certain aspects, it may be desirable to create cysteine engineered antibodies, e.g., THIOMAB™ antibodies, in which one or more residues of an antibody are substituted with cysteine residues. In preferred aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

5. Antibody Derivatives

In certain aspects, an antibody (e.g. bispecific antibody) provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

6. Immunoconjugates

The invention also provides immunoconjugates comprising an anti-CD3/anti-FolR1 antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody of the invention conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody of the invention conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as $I^{123}$, $I^{131}$, $In^{111}$, $F^{19}$, $C^{13}$, $N^{15}$, $O^{17}$, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

7. Multispecific Antibodies

An antibody provided herein is a multispecific antibody, particularly a bispecific antibody. Multispecific antibodies are monoclonal antibodies that have binding specificities for at least two different antigenic determinants (e.g., two different proteins, or two different epitopes on the same protein). In certain aspects, the multispecific antibody has three or more binding specificities. In certain aspects, one of the binding specificities is for CD3 and the other specificity is for FolR1. In certain aspects, multispecific antibodies may bind to two (or more) different epitopes of CD3. Multispecific (e.g., bispecific) antibodies may also be used to localize cytotoxic agents or cells to cells which express CD3. Multispecific antibodies may be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The multispecific antibody or antigen binding fragment thereof also includes a "Dual Acting FAb" or "DAF" comprising an antigen binding site that binds to CD3 as well as another different antigen, or two different epitopes of CD3 (see, e.g., US 2008/0069820 and WO 2015/095539).

Multi-specific antibodies may also be provided in an asymmetric form with a domain crossover in one or more binding arms of the same antigen specificity (so-called "CrossMab" technology), i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Multi-specific antibodies wherein the binding arms of different specificity share a common light chain are also be provided. The inventors of the present invention generated a bispecific antibody wherein the binding moieties share a common light chain that retains the specificity and efficacy of the parent monospecific antibody for CD3 and can bind a second antigen (e.g., FolR1) using the same light chain. The generation of a bispecific molecule with a common light chain that retains the binding properties of the parent antibody is not straight-forward as the common CDRs of the hybrid light chain have to effectuate the binding specificity for both targets. In one aspect the present invention provides a T cell activating bispecific antigen binding molecule comprising a first and a second antigen binding moiety, one of which is a Fab molecule capable of specific binding to CD3 and the other one of which is a Fab molecule capable of specific binding to FolR1, wherein the first and the second Fab molecule have identical VLCL light chains. In one embodiment said identical light chain (VLCL) comprises the light chain CDRs of SEQ ID NO: 8, SEQ ID NO: 9 and SEQ ID NO: 10. In one embodiment said identical light chain (VLCL) comprises SEQ ID NO: 129.

Various further molecular formats for multispecific antibodies are known in the art and are included herein (see e.g., Spiess et al., Mol Immunol 67 (2015) 95-106).

A particular type of multispecific antibodies, also included herein, are bispecific antibodies designed to simultaneously bind to a surface antigen, such as FolR1, on a target cell, e.g., a tumor cell, and to an activating, invariant component of the T cell receptor (TCR) complex, such as CD3, for retargeting of T cells to kill target cells. Hence, in preferred aspects, an antibody provided herein is a multispecific antibody, particularly a bispecific antibody, wherein one of the binding specificities is for CD3 and the other is for FolR1.

Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

Preferred aspects of the multispecific antibodies of the present invention are described in the following.

In one aspect, the invention provides an antibody that binds to CD3, comprising a first antigen binding domain that binds to CD3, as described herein, and comprising a second and optionally a third antigen binding domain which binds to FolR1.

According to preferred aspects of the invention, the antigen binding domains comprised in the antibody are Fab molecules (i.e. antigen binding domains composed of a heavy and a light chain, each comprising a variable and a constant domain). In one aspect, the first, the second and/or, where present, the third antigen binding domain is a Fab molecule. In one aspect, said Fab molecule is human. In a preferred aspect, said Fab molecule is humanized. In yet another aspect, said Fab molecule comprises human heavy and light chain constant domains.

In a preferred aspect according to the invention, the (multispecific) antibody is capable of simultaneous binding to the first antigen (i.e. CD3), and the second antigen (i.e. FolR1). In one aspect, the (multispecific) antibody is capable of crosslinking a T cell and a target cell by simultaneous binding to CD3 and FolR1. In an even more preferred aspect, such simultaneous binding results in lysis of the target cell, particularly a target cell antigen (i.e. FolR1)-expressing tumor cell. In one aspect, such simultaneous binding results in activation of the T cell. In other aspects, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one aspect, binding of the (multispecific) antibody to CD3 without simultaneous binding to FolR1 does not result in T cell activation.

In one aspect, the (multispecific) antibody is capable of re-directing cytotoxic activity of a T cell to a target cell. In a preferred aspect, said re-direction is independent of MHC-mediated peptide antigen presentation by the target cell and and/or specificity of the T cell.

Preferably, a T cell according to any of the aspects of the invention is a cytotoxic T cell. In some aspects the T cell is a $CD4^+$ or a $CD8^+$ T cell, particularly a $CD8^+$ T cell.

a) First Antigen Binding Domain

The (multispecific) antibody of the invention comprises at least one antigen binding domain (the first antigen binding domain) that binds to CD3. In preferred aspects, CD3 is human CD3 (SEQ ID NO: 112) or cynomolgus CD3 (SEQ ID NO: 113) most particularly human CD3. In one aspect the first antigen binding domain is cross-reactive for (i.e. specifically binds to) human and cynomolgus CD3. In some aspects, CD3 is the epsilon subunit of CD3 (CD3 epsilon).

In a preferred aspect, the (bispecific) antibody comprises not more than one antigen binding domain that binds to CD3. In one aspect the (bispecific) antibody provides monovalent binding to CD3.

In one aspect, the antigen binding domain that binds to CD3 is an antibody fragment selected from the group of an Fv molecule, a scFv molecule, a Fab molecule, and a $F(ab')_2$ molecule. In a preferred aspect, the antigen binding domain that binds to CD3 is a Fab molecule.

b) Second (and Third) Antigen Binding Domain

In certain aspects, the (multispecific) antibody of the invention comprises at least one antigen binding domain, particularly a Fab molecule, that binds to a second antigen. The second antigen preferably is not CD3, i.e. different from CD3. In one aspect, the second antigen is an antigen expressed on a different cell than CD3 (e.g. expressed on a cell other than a T cell). In one aspect, the second antigen is a target cell antigen, particularly a tumor cell antigen. In a preferred embodiment, the second antigen is FolR1. The second antigen binding domain is able to direct the (multispecific) antibody to a target site, for example to a specific type of tumor cell that expresses the second antigen.

In one aspect, the antigen binding domain that binds to the second antigen (i.e. FolR1) is an antibody fragment selected from the group of an Fv molecule, a scFv molecule, a Fab molecule, and a $F(ab')_2$ molecule. In a preferred aspect, the antigen binding domain that binds to the second antigen is a Fab molecule.

In certain aspects, the (multispecific) antibody comprises two antigen binding domains, particularly Fab molecules, that bind to the second antigen. In a preferred such aspect, each of these antigen binding domains binds to the same antigenic determinant. In an even more preferred aspect, all of these antigen binding domains are identical, i.e. they have the same molecular format (e.g. conventional Fab molecule) and comprise the same amino acid sequences including the same amino acid substitutions in the CH1 and CL domain as described herein (if any). In one aspect, the (multispecific) antibody comprises not more than two antigen binding domains, particularly Fab molecules, that bind to the second antigen.

In one aspect, the second (and, where present, third) antigen binding domain comprises a human constant region. In one aspect, the second (and, where present, third) antigen binding domain is a Fab molecule comprising a human constant region, particularly a human CH1 and/or CL domain. Exemplary sequences of human constant domains are given in SEQ ID NOs 120 and 121 (human kappa and lambda CL domains, respectively) and SEQ ID NO: 122 (human IgG1 heavy chain constant domains CH1-CH2-CH3). In one aspect, the second (and, where present, third) antigen binding domain comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the second (and, where present, third) antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 122. Particularly, the heavy chain constant region (specifically CH1 domain) may comprise amino acid mutations as described herein under "charge modifications".

TYRP-1

In some aspects of the disclosure, the second antigen is TYRP-1, particularly human TYRP-1 (SEQ ID NO: 114).

In one aspect, the second (and, where present, third) antigen binding domain comprises a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody).

In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, third) antigen binding domain comprises one or more heavy chain framework sequence (i.e. the FR1, FR2, FR3 and/or FR4 sequence) of SEQ ID NO: 18. In one aspect, the VH comprises an amino acid sequence that is at least about 95%, 96%, 97%, 98%, or 99% identical to the amino acid sequence of SEQ ID NO: 18. In one aspect, the VH comprises an amino acid sequence that is at least about 95% identical to the amino acid sequence of SEQ ID NO: 18. In one aspect, the VH comprises an amino acid sequence that is at least about 98% identical to the amino acid sequence of SEQ ID NO: 18. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to TYRP-1. In certain aspects, a total of 1 to 10 amino acids have been substituted, inserted and/or deleted in the amino acid sequence of SEQ ID NO: 18. In certain aspects, substitutions, insertions, or deletions occur in regions outside the CDRs (i.e., in the FRs). In one aspect, the VH comprises the amino acid sequence of SEQ ID NO: 18. Optionally, the VH comprises the amino acid sequence of SEQ ID NO: 18, including post-translational modifications of that sequence.

In one aspect, the VL of the second (and, where present, third) antigen binding domain comprises one or more light chain framework sequence (i.e. the FR1, FR2, FR3 and/or FR4 sequence) of SEQ ID NO: 22. In one aspect, the VL comprises an amino acid sequence that is at least about 95%, 96%, 97%, 98%, or 99% identical to the amino acid sequence of SEQ ID NO: 22. In one aspect, the VL comprises an amino acid sequence that is at least about 95% identical to the amino acid sequence of SEQ ID NO: 22. In one aspect, the VL comprises an amino acid sequence that is at least about 98% identical to the amino acid sequence of SEQ ID NO: 22. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to TYRP-1. In certain aspects, a total of 1 to 10 amino acids have been substituted, inserted and/or deleted in the amino acid sequence of SEQ ID NO: 22. In certain aspects, substitutions, insertions, or deletions occur in regions outside the CDRs (i.e., in the FRs). In one aspect, the VL comprises the amino acid sequence of SEQ ID NO: 22. Optionally, the VL comprises the amino acid sequence of SEQ ID NO: 22, including post-translational modifications of that sequence.

In one aspect, the VH of the second (and, where present, third) antigen binding domain comprises an amino acid sequence that is at least about 95%, 96%, 97%, 98%, or 99% identical to the amino acid sequence of SEQ ID NO: 18, and the VL of the second (and, where present, third) antigen binding domain comprises an amino acid sequence that is at least about 95%, 96%, 97%, 98%, or 99% identical to the amino acid sequence of SEQ ID NO: 22. In one aspect, the VH comprises the amino acid sequence of SEQ ID NO: 18 and the VL comprises the amino acid sequence of SEQ ID NO: 22.

In a further aspect, the second (and, where present, third) antigen binding domain comprises a VH comprising the sequence of SEQ ID NO: 18 and a VL comprising the sequence of SEQ ID NO: 22.

In a further aspect, the second (and, where present, third) antigen binding domain comprises a VH sequence of SEQ ID NO: 18 and a VL sequence of SEQ ID NO: 22.

In another aspect, the second (and, where present, third) antigen binding domain comprises a VH comprising the heavy chain CDR sequences of the VH of SEQ ID NO: 18, and a VL comprising the light chain CDR sequences of the VL of SEQ ID NO: 22.

In a further aspect, the second (and, where present, third) antigen binding domain comprises the HCDR1, HCDR2 and HCDR3 amino acid sequences of the VH of SEQ ID NO: 18 and the LCDR1, LCDR2 and LCDR3 amino acid sequences of the VL of SEQ ID NO: 22.

In one aspect, the VH of the second (and, where present, third) antigen binding domain comprises the heavy chain CDR sequences of the VH of SEQ ID NO: 18 and a framework of at least 95%, 96%, 97%, 98% or 99% sequence identity to the framework sequence of the VH of SEQ ID NO: 18. In one aspect, the VH comprises the heavy chain CDR sequences of the VH of SEQ ID NO: 18 and a framework of at least 95% sequence identity to the framework sequence of the VH of SEQ ID NO: 18. In another aspect, the VH comprises the heavy chain CDR sequences of the VH of SEQ ID NO: 18 and a framework of at least 98% sequence identity to the framework sequence of the VH of SEQ ID NO: 18.

In one aspect, the VL of the second (and, where present, third) antigen binding domain comprises the light chain CDR sequences of the VL of SEQ ID NO: 22 and a framework of at least 95%, 96%, 97%, 98% or 99% sequence identity to the framework sequence of the VL of SEQ ID NO: 22. In one aspect, the VL comprises the light chain CDR sequences of the VL of SEQ ID NO: 22 and a framework of at least 95% sequence identity to the framework sequence of the VL of SEQ ID NO: 22. In another aspect, the VL comprises the light chain CDR sequences of the VL of SEQ ID NO: 22 and a framework of at least 98% sequence identity to the framework sequence of the VL of SEQ ID NO: 22.

EGFRvIII

In some aspects of the disclosure, the second antigen is EGFRvIII, particularly human EGFRvIII (SEQ ID NO: 115).

In one aspect, the second (and, where present, third) antigen binding domain comprises a heavy chain variable region (VH) comprising a heavy chain complementary determining region (HCDR) 1 of SEQ ID NO: 85, a HCDR 2 of SEQ ID NO: 86, and a HCDR 3 of SEQ ID NO: 87, and a light chain variable region (VL) comprising a light chain complementarity determining region (LCDR) 1 of SEQ ID NO: 89, a LCDR 2 of SEQ ID NO: 90 and a LCDR 3 of SEQ ID NO: 91.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody).

In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, third) antigen binding domain comprises one or more heavy chain framework sequence (i.e. the FR1, FR2, FR3 and/or FR4 sequence) of SEQ ID NO: 88. In one aspect, the VH comprises an amino acid sequence that is at least about 95%, 96%, 97%, 98%, or 99% identical to the amino acid sequence of SEQ ID NO: 88. In one aspect, the VH comprises an amino acid sequence that is at least about 95% identical to the amino acid sequence of SEQ ID NO: 88. In one aspect, the VH comprises an amino acid sequence that is at least about 98% identical to the amino acid sequence of SEQ ID NO: 88. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to EGFRvIII. In certain aspects, a total of 1 to 10 amino acids have been substituted, inserted and/or deleted in the amino acid sequence of SEQ ID NO: 88. In certain aspects, substitutions, insertions, or deletions occur in regions outside the CDRs (i.e., in the FRs). In one aspect, the VH comprises the amino acid sequence of SEQ ID NO: 88. Optionally, the VH comprises the amino acid sequence of SEQ ID NO: 88, including post-translational modifications of that sequence.

In one aspect, the VL of the second (and, where present, third) antigen binding domain comprises one or more light chain framework sequence (i.e. the FR1, FR2, FR3 and/or FR4 sequence) of SEQ ID NO: 92. In one aspect, the VL comprises an amino acid sequence that is at least about 95%, 96%, 97%, 98%, or 99% identical to the amino acid sequence of SEQ ID NO: 92. In one aspect, the VL comprises an amino acid sequence that is at least about 95% identical to the amino acid sequence of SEQ ID NO: 92. In one aspect, the VL comprises an amino acid sequence that is at least about 98% identical to the amino acid sequence of SEQ ID NO: 92. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to EGFRvIII. In certain aspects, a total of 1 to 10 amino acids have been substituted, inserted and/or deleted in the amino acid sequence of SEQ ID NO: 92. In certain aspects, substitutions, insertions, or deletions occur in regions outside the CDRs (i.e., in the FRs). In one aspect, the VL comprises the amino acid sequence of SEQ ID NO: 92. Optionally, the VL comprises the amino acid sequence of SEQ ID NO: 92, including post-translational modifications of that sequence.

In one aspect, the VH of the second (and, where present, third) antigen binding domain comprises an amino acid sequence that is at least about 95%, 96%, 97%, 98%, or 99% identical to the amino acid sequence of SEQ ID NO: 88, and the VL of the second (and, where present, third) antigen binding domain comprises an amino acid sequence that is at least about 95%, 96%, 97%, 98%, or 99% identical to the amino acid sequence of SEQ ID NO: 92. In one aspect, the VH comprises the amino acid sequence of SEQ ID NO: 88 and the VL comprises the amino acid sequence of SEQ ID NO: 92.

In a further aspect, the second (and, where present, third) antigen binding domain comprises a VH comprising the sequence of SEQ ID NO: 88 and a VL comprising the sequence of SEQ ID NO: 92.

framework of at least 95% sequence identity to the framework sequence of the VH of SEQ ID NO: 88. In another aspect, the VH comprises the heavy chain CDR sequences of the VH of SEQ ID NO: 88 and a framework of at least 98% sequence identity to the framework sequence of the VH of SEQ ID NO: 88.

In one aspect, the VL of the second (and, where present, third) antigen binding domain comprises the light chain CDR sequences of the VL of SEQ ID NO: 92 and a framework of at least 95%, 96%, 97%, 98% or 99% sequence identity to the framework sequence of the VL of SEQ ID NO: 92. In one aspect, the VL comprises the light chain CDR sequences of the VL of SEQ ID NO: 92 and a framework of at least 95% sequence identity to the framework sequence of the VL of SEQ ID NO: 92. In another aspect, the VL comprises the light chain CDR sequences of the VL of SEQ ID NO: 92 and a framework of at least 98% sequence identity to the framework sequence of the VL of SEQ ID NO: 92.

In alternative aspects, the second (and, where present, third) antigen binding domain comprises a VH sequence as in any of the aspects provided in this section above in relation to EGFRvIII, and a VL sequence as in any of the aspects provided in this section above in relation to EGFRvIII, but based on the following sequences (ordered in rows) instead of SEQ ID NOs 85 (HCDR1), 86 (HCDR2), 87 (HCDR3), 88 (VH), 89 (LCDR1), 90 (LCDR2), 91 (LCDR3) and 92 (VL):

| HCDR1 | HCDR2 | HCDR3 | VH | LCDR1 | LCDR2 | LCDR3 | VL |
|---|---|---|---|---|---|---|---|
| SEQ ID NO: 37 | SEQ ID NO: 38 | SEQ ID NO: 39 | SEQ ID NO: 40 | SEQ ID NO: 41 | SEQ ID NO: 42 | SEQ ID NO: 43 | SEQ ID NO: 44 |
| SEQ ID NO: 45 | SEQ ID NO: 46 | SEQ ID NO: 47 | SEQ ID NO: 48 | SEQ ID NO: 49 | SEQ ID NO: 50 | SEQ ID NO: 51 | SEQ ID NO: 52 |
| SEQ ID NO: 53 | SEQ ID NO: 54 | SEQ ID NO: 55 | SEQ ID NO: 56 | SEQ ID NO: 57 | SEQ ID NO: 58 | SEQ ID NO: 59 | SEQ ID NO: 60 |
| SEQ ID NO: 61 | SEQ ID NO: 62 | SEQ ID NO: 63 | SEQ ID NO: 64 | SEQ ID NO: 65 | SEQ ID NO: 66 | SEQ ID NO: 67 | SEQ ID NO: 68 |
| SEQ ID NO: 69 | SEQ ID NO: 70 | SEQ ID NO: 71 | SEQ ID NO: 72 | SEQ ID NO: 73 | SEQ ID NO: 74 | SEQ ID NO: 75 | SEQ ID NO: 76 |
| SEQ ID NO: 77 | SEQ ID NO: 78 | SEQ ID NO: 79 | SEQ ID NO: 80 | SEQ ID NO: 81 | SEQ ID NO: 82 | SEQ ID NO: 83 | SEQ ID NO: 84 |
| SEQ ID NO: 93 | SEQ ID NO: 94 | SEQ ID NO: 95 | SEQ ID NO: 96 | SEQ ID NO: 97 | SEQ ID NO: 98 | SEQ ID NO: 99 | SEQ ID NO: 100 |
| SEQ ID NO: 101 | SEQ ID NO: 102 | SEQ ID NO: 103 | SEQ ID NO: 104 | SEQ ID NO: 105 | SEQ ID NO: 106 | SEQ ID NO: 107 | SEQ ID NO: 108 |

In a further aspect, the second (and, where present, third) antigen binding domain comprises a VH sequence of SEQ ID NO: 88 and a VL sequence of SEQ ID NO: 92.

In another aspect, the second (and, where present, third) antigen binding domain comprises a VH comprising the heavy chain CDR sequences of the VH of SEQ ID NO: 88, and a VL comprising the light chain CDR sequences of the VL of SEQ ID NO: 92.

In a further aspect, the second (and, where present, third) antigen binding domain comprises the HCDR1, HCDR2 and HCDR3 amino acid sequences of the VH of SEQ ID NO: 88 and the LCDR1, LCDR2 and LCDR3 amino acid sequences of the VL of SEQ ID NO: 92.

In one aspect, the VH of the second (and, where present, third) antigen binding domain comprises the heavy chain CDR sequences of the VH of SEQ ID NO: 88 and a framework of at least 95%, 96%, 97%, 98% or 99% sequence identity to the framework sequence of the VH of SEQ ID NO: 88. In one aspect, the VH comprises the heavy chain CDR sequences of the VH of SEQ ID NO: 88 and a FolR1

In some aspects of the disclosure, the second antigen is FolR1, particularly human FolR1 (SEQ ID NO: 137).

In one aspect, the second (and, where present, third) antigen binding domain comprises a heavy chain variable region (VH) comprising a heavy chain complementary determining region (HCDR) 1 of SEQ ID NO: 124, a HCDR 2 of SEQ ID NO: 125, and a HCDR 3 of SEQ ID NO: 126, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody). In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, third) antigen binding domain comprises one or more heavy chain framework sequence (i.e. the FR1, FR2, FR3 and/or FR4 sequence) of SEQ ID NO: 123. In one aspect, the VH comprises an amino acid sequence that is at least about 95%, 96%, 97%, 98%, or 99% identical to the amino acid sequence of SEQ ID NO: 123. In one aspect, the VH comprises an amino acid sequence that is at least about 95% identical to the amino acid sequence of SEQ ID NO: 123. In one aspect, the VH comprises an amino acid sequence that is at least about 98% identical to the amino acid sequence of SEQ ID NO: 123. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to FolR1. In certain aspects, a total of 1 to 10 amino acids have been substituted, inserted and/or deleted in the amino acid sequence of SEQ ID NO: 123. In certain aspects, substitutions, insertions, or deletions occur in regions outside the CDRs (i.e., in the FRs). In one aspect, the VH comprises the amino acid sequence of SEQ ID NO: 123. Optionally, the VH comprises the amino acid sequence of SEQ ID NO: 123, including post-translational modifications of that sequence.

In one aspect, the VL of the second (and, where present, third) antigen binding domain comprises one or more light chain framework sequence (i.e. the FR1, FR2, FR3 and/or FR4 sequence) of SEQ ID NO: 11. In one aspect, the VL comprises an amino acid sequence that is at least about 95%, 96%, 97%, 98%, or 99% identical to the amino acid sequence of SEQ ID NO: 11. In one aspect, the VL comprises an amino acid sequence that is at least about 95% identical to the amino acid sequence of SEQ ID NO: 11. In one aspect, the VL comprises an amino acid sequence that is at least about 98% identical to the amino acid sequence of SEQ ID NO: 11. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to FolR1. In certain aspects, a total of 1 to 10 amino acids have been substituted, inserted and/or deleted in the amino acid sequence of SEQ ID NO: 11. In certain aspects, substitutions, insertions, or deletions occur in regions outside the CDRs (i.e., in the FRs). In one aspect, the VL comprises the amino acid sequence of SEQ ID NO: 11. Optionally, the VL comprises the amino acid sequence of SEQ ID NO: 11, including post-translational modifications of that sequence.

In one aspect, the VH of the second (and, where present, third) antigen binding domain comprises an amino acid sequence that is at least about 95%, 96%, 97%, 98%, or 99% identical to the amino acid sequence of SEQ ID NO: 123, and the VL of the second (and, where present, third) antigen binding domain comprises an amino acid sequence that is at least about 95%, 96%, 97%, 98%, or 99% identical to the amino acid sequence of SEQ ID NO: 11. In one aspect, the VH comprises the amino acid sequence of SEQ ID NO: 123 and the VL comprises the amino acid sequence of SEQ ID NO: 11.

In a further aspect, the second (and, where present, third) antigen binding domain comprises a VH comprising the sequence of SEQ ID NO: 123 and a VL comprising the sequence of SEQ ID NO: 11.

In a further aspect, the second (and, where present, third) antigen binding domain comprises a VH sequence of SEQ ID NO: 123 and a VL sequence of SEQ ID NO: 11.

In another aspect, the second (and, where present, third) antigen binding domain comprises a VH comprising the heavy chain CDR sequences of the VH of SEQ ID NO: 123, and a VL comprising the light chain CDR sequences of the VL of SEQ ID NO: 11.

In a further aspect, the second (and, where present, third) antigen binding domain comprises the HCDR1, HCDR2 and HCDR3 amino acid sequences of the VH of SEQ ID NO: 123 and the LCDR1, LCDR2 and LCDR3 amino acid sequences of the VL of SEQ ID NO: 11.

In one aspect, the VH of the second (and, where present, third) antigen binding domain comprises the heavy chain CDR sequences of the VH of SEQ ID NO: 123 and a framework of at least 95%, 96%, 97%, 98% or 99% sequence identity to the framework sequence of the VH of SEQ ID NO: 123. In one aspect, the VH comprises the heavy chain CDR sequences of the VH of SEQ ID NO: 123 and a framework of at least 95% sequence identity to the framework sequence of the VH of SEQ ID NO: 123. In another aspect, the VH comprises the heavy chain CDR sequences of the VH of SEQ ID NO: 123 and a framework of at least 98% sequence identity to the framework sequence of the VH of SEQ ID NO: 123.

In one aspect, the VL of the second (and, where present, third) antigen binding domain comprises the light chain CDR sequences of the VL of SEQ ID NO: 11 and a framework of at least 95%, 96%, 97%, 98% or 99% sequence identity to the framework sequence of the VL of SEQ ID NO: 11. In one aspect, the VL comprises the light chain CDR sequences of the VL of SEQ ID NO: 11 and a framework of at least 95% sequence identity to the framework sequence of the VL of SEQ ID NO: 11. In another aspect, the VL comprises the light chain CDR sequences of the VL of SEQ ID NO: 11 and a framework of at least 98% sequence identity to the framework sequence of the VL of SEQ ID NO: 11.

In one aspect, the second (and, where present, third) antigen binding domain comprises a VH sequence as in any of the aspects provided in this section above, and a VL sequence as in any of the aspects provided in this section above.

Anti-TYRP-1 and Anti-EGFRvIII Antibodies

The disclosure also provides an antibody that binds to TYRP-1, comprising a VH sequence as in any of the aspects provided in this section above in relation to TYRP-1, and a VL sequence as in any of the aspects provided in this section above in relation to TYRP-1 (for example, an antibody that binds to TYRP-1 comprising a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21; or an antibody that binds to TYRP-1 comprising a VH comprising the sequence of SEQ ID NO: 18 and a VL comprising the sequence of SEQ ID NO: 22).

The disclosure also provides an antibody that binds to EGFRvIII, comprising a VH sequence as in any of the aspects provided in this section above in relation to EGFRvIII, and a VL sequence as in any of the aspects provided in this section above in relation to EGFRvIII (for example, an antibody that binds to EGFRvIII comprising a heavy chain variable region (VH) comprising a heavy chain complementary determining region (HCDR) 1 of SEQ ID NO: 85, a HCDR 2 of SEQ ID NO: 86, and a HCDR 3 of SEQ ID NO: 87, and a light chain variable region (VL) comprising a light chain complementarity determining region (LCDR) 1 of SEQ ID NO: 89, a LCDR 2 of SEQ ID NO: 90 and a LCDR 3 of SEQ ID NO: 91; or an antibody that binds to TYRP-1 comprising a VH comprising the sequence of SEQ ID NO: 88 and a VL comprising the sequence of SEQ ID NO: 92).

Anti-FolR1 Antibodies

The invention provides an antibody that binds to FolR1, comprising a VH sequence as in any of the aspects provided in this section above in relation to FolR1, and a VL sequence as in any of the aspects provided in this section above in relation to FolR1 (for example, an antibody that binds to FolR1 comprising a heavy chain variable region (VH) comprising a heavy chain complementary determining region (HCDR) 1 of SEQ ID NO: 124, a HCDR 2 of SEQ ID NO: 125, and a HCDR 3 of SEQ ID NO: 126, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10; or an antibody that binds to FolR1 comprising a VH comprising the sequence of SEQ ID NO: 123 and a VL comprising the sequence of SEQ ID NO: 11).

In a further aspect of the invention, the antibodies that bind to FolR1 according to any of the above aspects may incorporate any of the features, singly or in combination, as described in relation to the antibody that binds to CD3 (unless clearly specific to the anti-CD3 antibody, such as the binding sequences).

c) Charge Modifications

The (bispecific) antibody of the invention may comprise amino acid substitutions in Fab molecules comprised therein which are particularly efficient in reducing mispairing of light chains with non-matching heavy chains (Bence-Jones-type side products), which can occur in the production of Fab-based multispecific antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired (bispecific) antibody compared to undesired side products, in particular Bence Jones-type side products occurring in multispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some aspects wherein the first and the second (and, where present, third) antigen binding domain of the (bispecific) antibody are both Fab molecules, and in one of the antigen binding domains (particularly the first antigen binding domain) the variable domains VL and VH of the Fab light chain and the Fab heavy chain are replaced by each other, i) in the constant domain CL of the second (and, where present, third) antigen binding domain the amino acid at position 124 is substituted by a positively charged amino acid (numbering according to Kabat), and wherein in the constant domain CH1 of the second (and, where present, third) antigen binding domain the amino acid at position 147 or the amino acid at position 213 is substituted by a negatively charged amino acid (numbering according to Kabat EU index); or ii) in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index).

The (bispecific) antibody does not comprise both modifications mentioned under i) and ii). The constant domains CL and CH1 of the antigen binding domain having the VH/VL exchange are not replaced by each other (i.e. remain unexchanged).

In a more specific aspect, i) in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 or the amino acid at position 213 is substituted independently by glutamic acid (E), or aspartic acid (D) (numbering according to Kabat EU index); or ii) in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In one such aspect, in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 or the amino acid at position 213 is substituted independently by glutamic acid (E), or aspartic acid (D) (numbering according to Kabat EU index).

In a further aspect, in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 is substituted independently by glutamic acid (E), or aspartic acid (D) (numbering according to Kabat EU index).

In a preferred aspect, in the constant domain CL of the second (and, where present, third) antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more preferred aspect, in the constant domain CL of the second (and, where present, third) antigen binding domain the amino acid at position 124 is substituted by lysine (K) (numbering according to Kabat) and the amino acid at position 123 is substituted by lysine (K) (numbering according to Kabat), and in the constant domain CH1 of the second (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In an even more preferred aspect, in the constant domain CL of the second (and, where present, third) antigen binding domain the amino acid at position 124 is substituted by lysine (K) (numbering according to Kabat) and the amino acid at position 123 is substituted by arginine (R) (numbering according to Kabat), and in the constant domain CH1 of the second (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In preferred aspects, if amino acid substitutions according to the above aspects are made in the constant domain CL and the constant domain CH1 of the second (and, where present, third) antigen binding domain, the constant domain CL of the second (and, where present, third) antigen binding domain is of kappa isotype.

Alternatively, the amino acid substitutions according to the above aspects may be made in the constant domain CL and the constant domain CH1 of the first antigen binding domain instead of in the constant domain CL and the constant domain CH1 of the second (and, where present, third) antigen binding domain. In preferred such aspects, the constant domain CL of the first antigen binding domain is of kappa isotype.

Accordingly, in one aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In a further aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index).

In still another aspect, in the constant domain CL of the first antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, in the constant domain CL of the first antigen binding domain the amino acid at position 124 is substituted by lysine (K) (numbering according to Kabat) and the amino acid at position 123 is substituted by lysine (K) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In another aspect, in the constant domain CL of the first antigen binding domain the amino acid at position 124 is substituted by lysine (K) (numbering according to Kabat) and the amino acid at position 123 is substituted by arginine (R) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In a preferred aspect, the (bispecific) antibody of the invention comprises (a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10, and (b) a second and optionally a third antigen binding domain that binds to a target antigen; wherein in the constant domain CL of the second (and, where present, third) antigen binding domain the amino acid at position 124 is substituted independently by lysine (K), arginine (R) or histidine (H) (numbering according to Kabat) (in a preferred aspect independently by lysine (K) or arginine (R)) and the amino acid at position 123 is substituted independently by lysine (K), arginine (R) or histidine (H) (numbering according to Kabat) (in a preferred aspect independently by lysine (K) or arginine (R)), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

d) Multispecific Antibody Formats

Figure 1A:
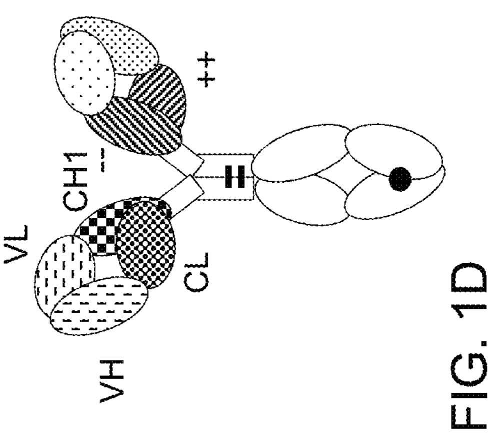
FIG. 1A-FIG. 1Z. Exemplary configurations of the (multispecific) antibodies of the invention.
Figure 1B:
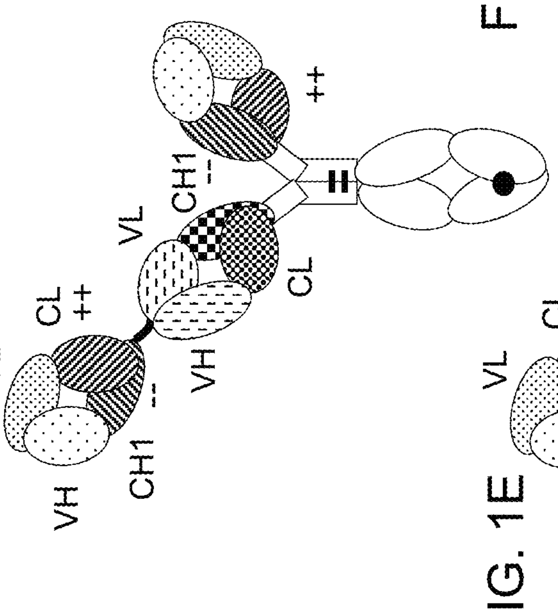
(FIG. 1B, FIG. 1E) Illustration of the "2+1 IgG Crossfab" molecule with alternative order of Crossfab and Fab components ("inverted").
Figure 1C:
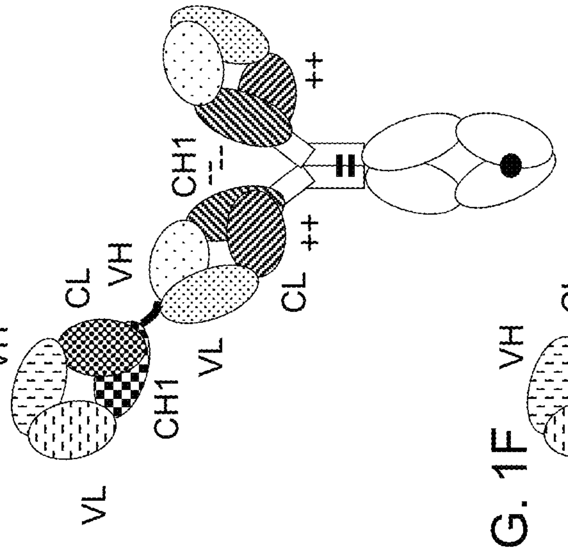
(FIG. 1C, FIG. 1F) Illustration of the "2+1 IgG Crossfab" molecule.
Figure 1D:
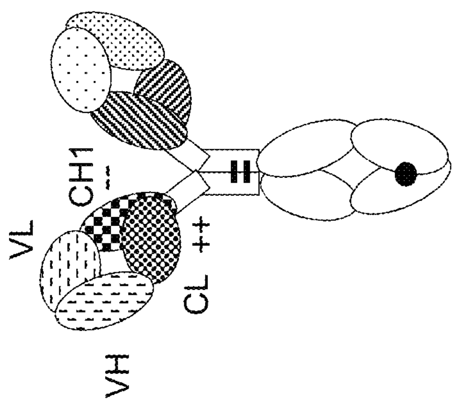
Figure 1E:
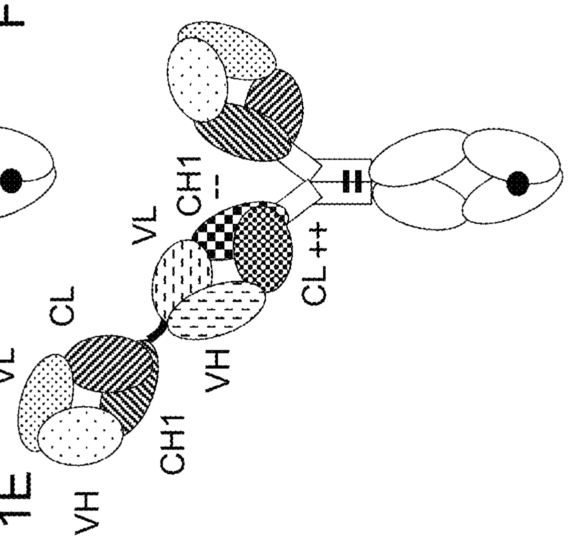
Figure 1F:
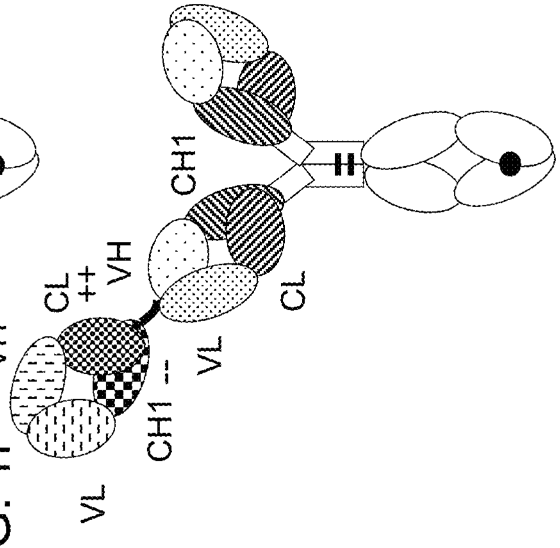
Figure 1G:
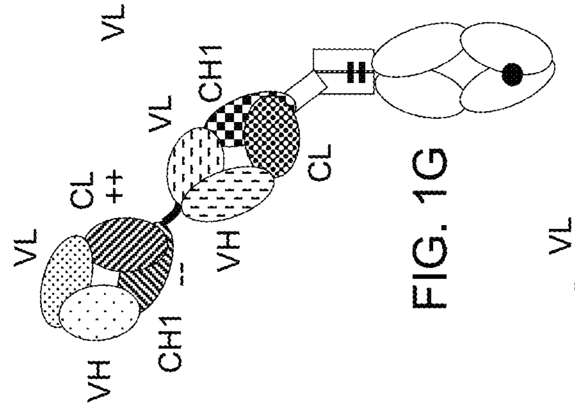
(FIG. 1G, FIG. 1K) Illustration of the "1+1 IgG Crossfab" molecule with alternative order of Crossfab and Fab components ("inverted").
Figure 1H:
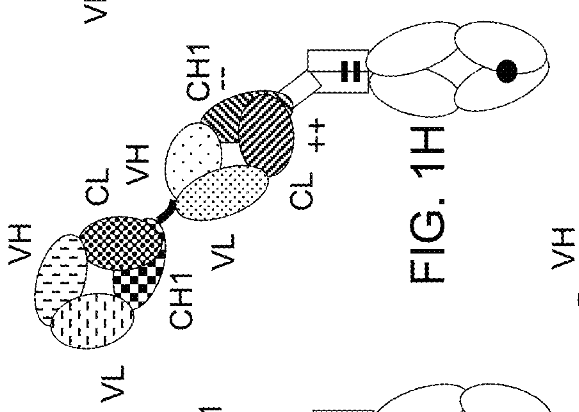
(FIG. 1H, FIG. 1L) Illustration of the "1+1 IgG Crossfab" molecule.
Figure 1I:
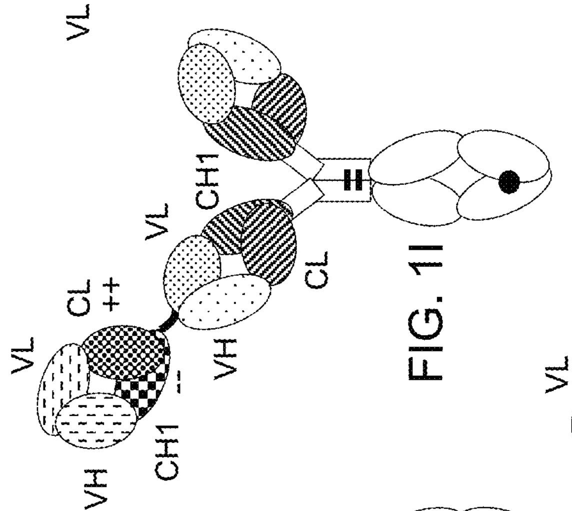
(FIG. 1I, FIG. 1M) Illustration of the "2+1 IgG Crossfab" molecule with two CrossFabs.
Figure 1J:
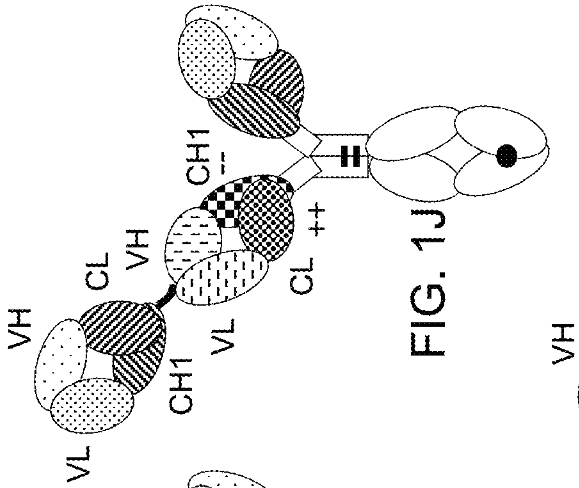
(FIG. 1J, FIG. 1N) Illustration of the "2+1 IgG Crossfab" molecule with two CrossFabs and alternative order of Crossfab and Fab components ("inverted").
Figure 1K:
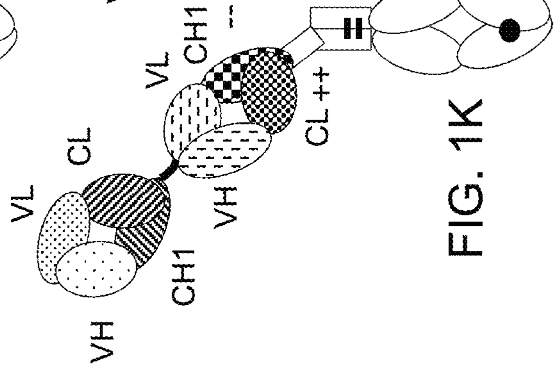
Figure 1L:
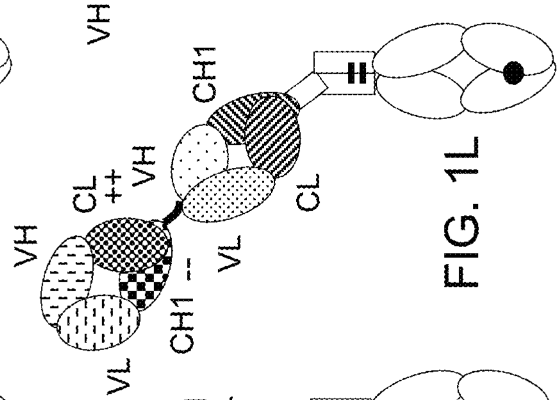
Figure 1M:
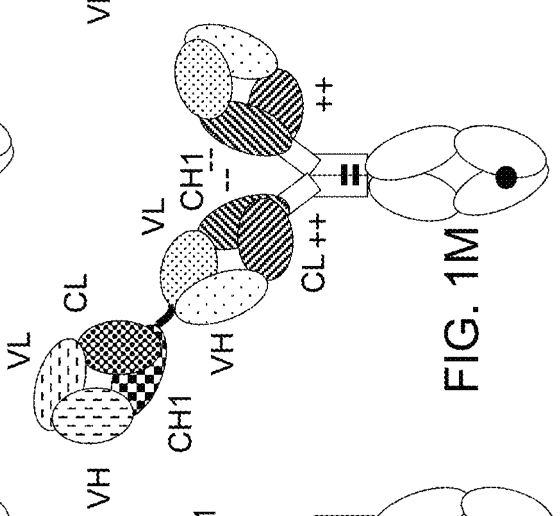
Figure 1N:
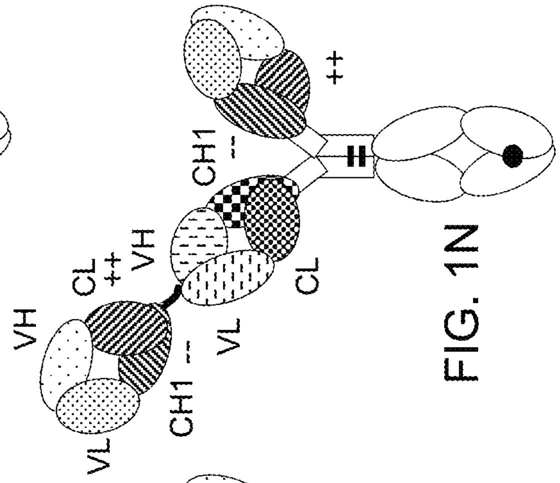
Figure 1O:
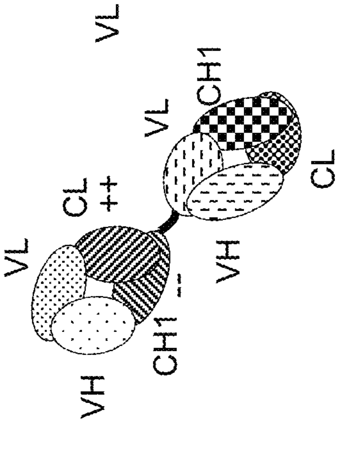
(FIG. 1O, FIG. 1S) Illustration of the "Fab-Crossfab" molecule.
Figure 1P:
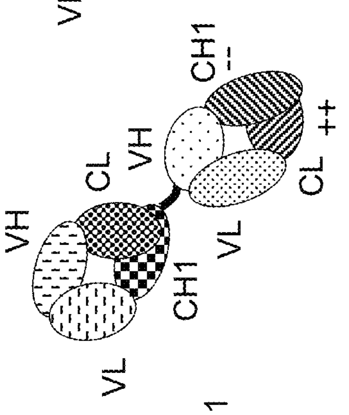
(FIG. 1P, FIG. 1T) Illustration of the "Crossfab-Fab" molecule.
Figure 1Q:
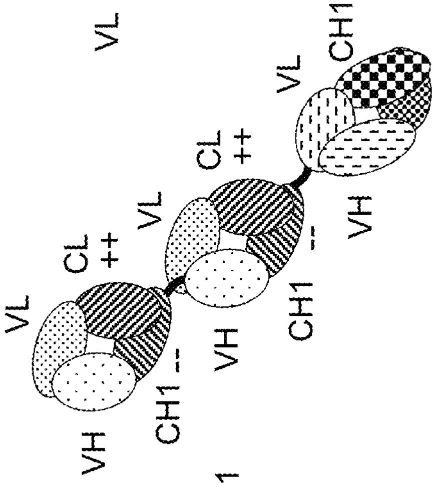
(FIG. 1Q, FIG. 1U) Illustration of the "$(Fab)_2$-Crossfab" molecule.
Figure 1R:
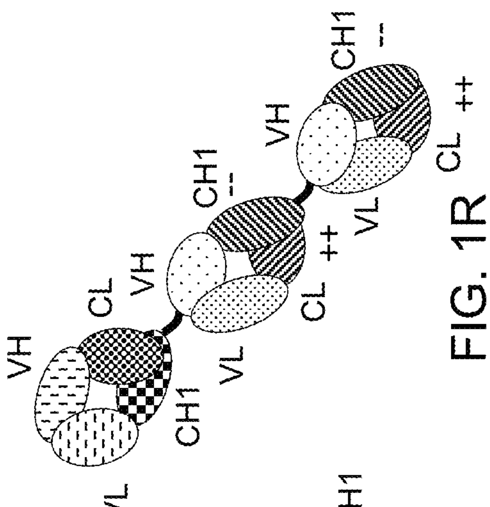
(FIG. 1R, FIG. 1V) Illustration of the "Crossfab-$(Fab)_2$" molecule.
Figure 1S:
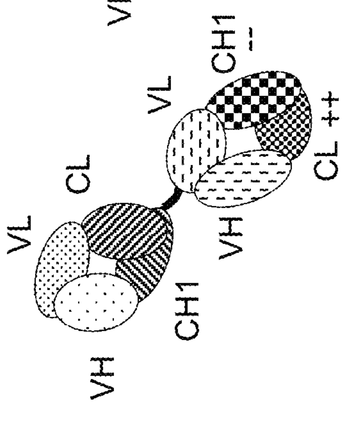
Figure 1T:
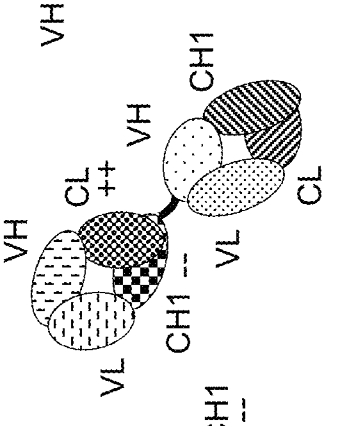
Figure 1U:
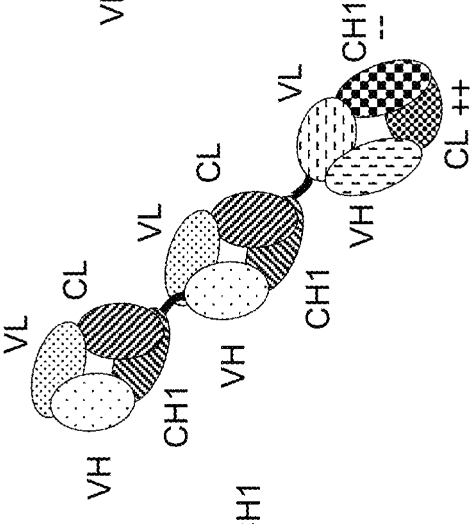
Figure 1V:
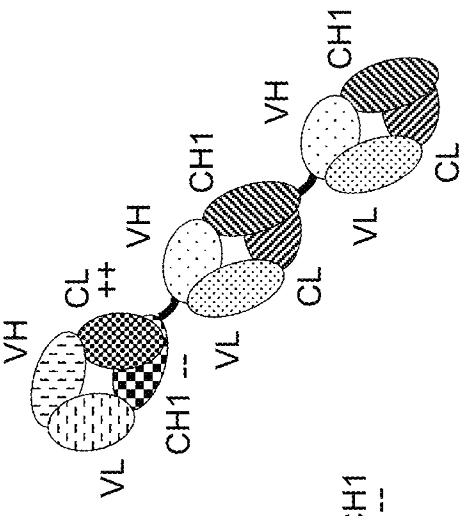
Figure 1W:
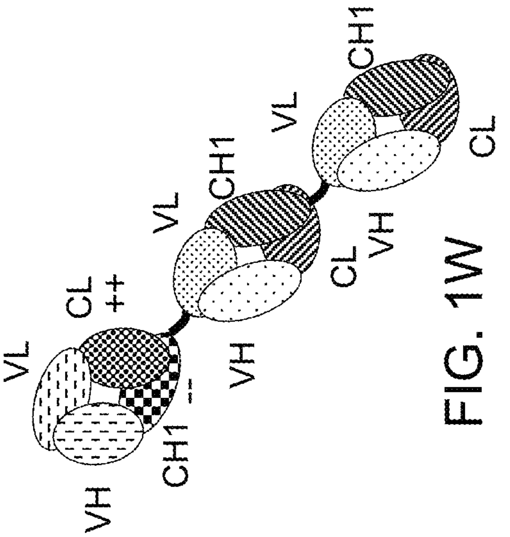
(FIG. 1W, FIG. 1Y) Illustration of the "Fab-$(Crossfab)_2$" molecule.
Figure 1X:
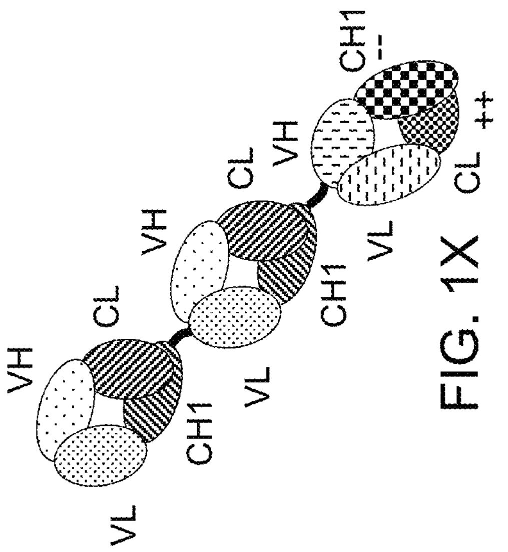
Figure 1Y:
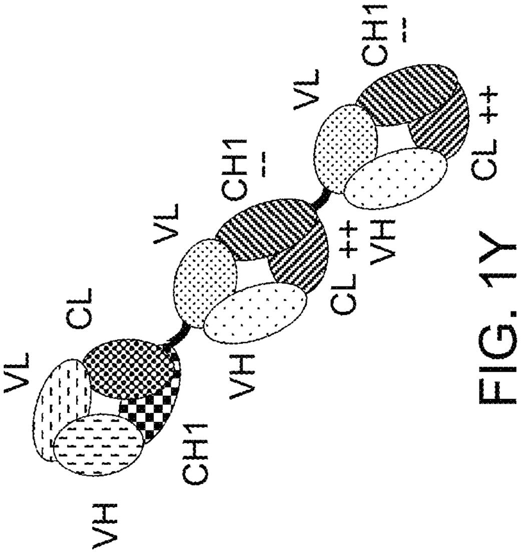
Figure 1Z:
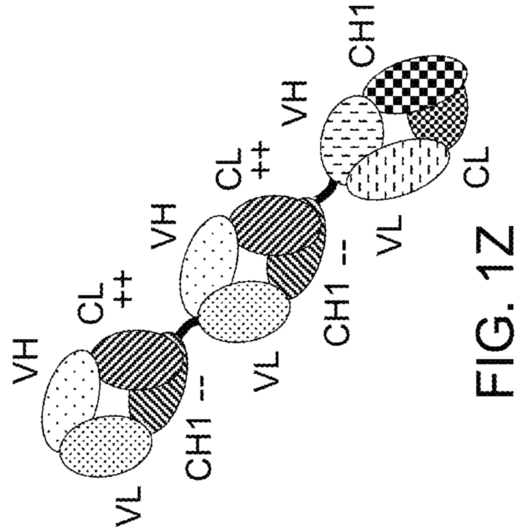

The (bispecific and/or multispecific) antibody according to the present invention can have a variety of configurations. Exemplary configurations are depicted in FIG. 1A-FIG. 1Z.

In preferred aspects, the antigen binding domains comprised in the (multispecific) antibody are Fab molecules. In such aspects, the first, second, third etc. antigen binding domain may be referred to herein as first, second, third etc. Fab molecule, respectively.

In one aspect, the first and the second antigen binding domain of the (bispecific) antibody are fused to each other, optionally via a peptide linker. In preferred aspects, the first and the second antigen binding domain are each a Fab molecule. In one such aspect, the first antigen binding domain is fused at the C-terminus of the Fab heavy chain to the N-terminus of the Fab heavy chain of the second antigen binding domain. In another such aspect, the second antigen binding domain is fused at the C-terminus of the Fab heavy chain to the N-terminus of the Fab heavy chain of the first antigen binding domain. In aspects wherein either (i) the first antigen binding domain is fused at the C-terminus of the Fab heavy chain to the N-terminus of the Fab heavy chain of the second antigen binding domain or (ii) the second antigen binding domain is fused at the C-terminus of the Fab heavy chain to the N-terminus of the Fab heavy chain of the first antigen binding domain, additionally the Fab light chain of the first antigen binding domain and the Fab light chain of the second antigen binding domain may be fused to each other, optionally via a peptide linker.

A (bispecific) antibody with a single antigen binding domain (such as a Fab molecule) capable of specific binding to a second antigen, e.g. a target cell antigen such as FolR1, (for example as shown in FIG. 1A, FIG. 1D, FIG. 1G, FIG. 1H, FIG. 1K, FIG. 1L) is useful, particularly in cases where internalization of the second antigen is to be expected following binding of a high affinity antigen binding domain. In such cases, the presence of more than one antigen binding domain specific for the second antigen may enhance internalization of the second antigen, thereby reducing its availability.

In other cases, however, it will be advantageous to have a (bispecific) antibody comprising two or more antigen binding domains (such as Fab molecules) specific for a second antigen, e.g. a target cell antigen (see examples shown in FIG. 1B, FIG. 1C, FIG. 1E, FIG. 1F, FIG. 1I, FIG. 1J, FIG. 1M, FIG. 1N, FIG. 33A, FIG. 33B), for example to optimize targeting to the target site or to allow crosslinking of target cell antigens.

Accordingly, in preferred aspects, the (multispecific, e.g. bispecific) antibody according to the present invention comprises a third antigen binding domain.

In one aspect, the third antigen binding domain binds to the second antigen, e.g. a target cell antigen such as FolR1. In one aspect, the third antigen binding domain is a Fab molecule.

In one aspect, the third antigen domain is identical to the second antigen binding domain.

In some aspects, the third and the second antigen binding domain are each a Fab molecule and the third antigen binding domain is identical to the second antigen binding domain. Thus, in these aspects, the second and the third antigen binding domain comprise the same heavy and light chain amino acid sequences and have the same arrangement of domains (i.e. conventional or crossover). Furthermore, in these aspects, the third antigen binding domain comprises the same amino acid substitutions, if any, as the second antigen binding domain. For example, the amino acid substitutions described herein as "charge modifications" will be made in the constant domain CL and the constant domain CH1 of each of the second antigen binding domain and the third antigen binding domain. Alternatively, said amino acid substitutions may be made in the constant domain CL and the constant domain CH1 of the first antigen binding domain (which in preferred aspects is also a Fab molecule), but not in the constant domain CL and the constant domain CH1 of the second antigen binding domain and the third antigen binding domain.

Like the second antigen binding domain, the third antigen binding domain preferably is a conventional Fab molecule. All the Fab molecules may share a common light chain. However, aspects wherein the second and the third antigen binding domains are crossover Fab molecules (and the first antigen binding domain is a conventional Fab molecule) are, however, also contemplated. Thus, in some aspects, the second and the third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other.

In other aspects, the second and the third antigen binding domains are each a crossover Fab molecule and the first antigen binding domain is a conventional Fab molecule.

If a third antigen binding domain is present, in a preferred aspect the first antigen domain binds to CD3, and the second and third antigen binding domain bind to a second antigen, particularly a target cell antigen, such as FolR1.

As depicted above and in FIG. 33A-FIG. 33E, in one embodiment the T cell activating bispecific antigen binding molecules comprise at least two Fab fragments having identical light chains (VLCL) and having different heavy chains (VHCL) which confer the specificities to two different antigens, i.e. one Fab fragment is capable of specific binding to a T cell activating antigen CD3 and the other Fab fragment is capable of specific binding to the target cell antigen FolR1.

In preferred aspects, the (multispecific) antibody of the invention comprises an Fc domain composed of a first and a second subunit. The first and the second subunit of the Fc domain are capable of stable association.

The (multispecific, e.g. bispecific) antibody according to the invention can have different configurations, i.e. the first, second (and optionally third) antigen binding domain may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some aspects, the first and the second antigen binding domain are each a Fab molecule and the first antigen binding domain is fused at the C-terminus of the Fab heavy chain to the N-terminus of the first or the second subunit of the Fc domain. In such aspects, the second antigen binding domain may be fused at the C-terminus of the Fab heavy chain to the N-terminus of the Fab heavy chain of the first antigen binding domain or to the N-terminus of the other one of the subunits of the Fc domain. In preferred such aspects, the second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, the second antigen binding domain is a crossover Fab molecule and the first antigen binding domain is a conventional Fab molecule.

In one aspect, the first and the second antigen binding domain are each a Fab molecule, the first antigen binding domain is fused at the C-terminus of the Fab heavy chain to the N-terminus of the first or the second subunit of the Fc domain, and the second antigen binding domain is fused at the C-terminus of the Fab heavy chain to the N-terminus of the Fab heavy chain of the first antigen binding domain. In a specific aspect, the (multispecific, e.g. bispecific) antibody essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIG. 1G and FIG. 1K (with the first antigen binding domain in these examples being a VH/VL crossover Fab molecule). Optionally, the Fab light chain of the first Fab molecule and the Fab light chain of the second Fab molecule may additionally be fused to each other.

In another aspect, the first and the second antigen binding domain are each a Fab molecule and the first and the second antigen binding domain are each fused at the C-terminus of the Fab heavy chain to the N-terminus of one of the subunits of the Fc domain. In a specific aspect, the (multispecific, e.g. bispecific) antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D (in these examples with the first antigen binding domain being a VH/VL crossover Fab molecule and the second antigen binding domain being a conventional Fab molecule) and in FIG. 33E (in this example the light chain of the first and second antigen binding domains is identical). The first and the second Fab molecule may be fused to the Fc domain directly or through a peptide linker. In a preferred aspect the first and the second Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain.

In some aspects, the first and the second antigen binding domain are each a Fab molecule and the second antigen binding domain is fused at the C-terminus of the Fab heavy chain to the N-terminus of the first or the second subunit of the Fc domain. In such aspects, the first antigen binding domain may be fused at the C-terminus of the Fab heavy chain to the N-terminus of the Fab heavy chain of the first antigen binding domain or (as described above) to the N-terminus of the other one of the subunits of the Fc domain. In preferred such aspects, said second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other.

In other such aspects, said second antigen binding domain is a crossover Fab molecule and the first antigen binding domain is a conventional Fab molecule.

In one aspect, the first and the second antigen binding domain are each a Fab molecule, the second antigen binding domain is fused at the C-terminus of the Fab heavy chain to the N-terminus of the first or the second subunit of the Fc domain, and the first antigen binding domain is fused at the C-terminus of the Fab heavy chain to the N-terminus of the Fab heavy chain of the second antigen binding domain. In a specific aspect, the (multispecific, e.g. bispecific) antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1H and FIG. 1L (in these examples with the first antigen binding domain being a VH/VL crossover Fab molecule and the second antigen binding domain being a conventional Fab molecule) and FIG. 33C and FIG. 33D (in these examples the light chain of the first and second antigen binding domains is identical). Optionally, the Fab light chain of the first Fab molecule and the Fab light chain of the second Fab molecule may additionally be fused to each other.

In a preferred such aspect, the first and the third antigen binding domain are each fused at the C-terminus of the Fab heavy chain to the N-terminus of one of the subunits of the Fc domain, and the second antigen binding domain is fused at the C-terminus of the Fab heavy chain to the N-terminus of the Fab heavy chain of the first Fab molecule. In a specific aspect, the (multispecific, e.g. bispecific) antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. The first and the third Fab molecule may be fused to the Fc domain directly or through a peptide linker. In a preferred aspect, the first and the third Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In another such aspect, the second and the third antigen binding domain are each fused at the C-terminus of the Fab heavy chain to the N-terminus of one of the subunits of the Fc domain, and the first antigen binding domain is fused at the C-terminus of the Fab heavy chain to the N-terminus of the Fab heavy chain of the second antigen binding domain. In a specific aspect, the (multispecific, e.g. bispecific) antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. The second and the third Fab molecule may be fused to the Fc domain directly or through a peptide linker. In a preferred aspect the second and the third Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the (multispecific) antibody wherein a Fab molecule is fused at the C-terminus of the Fab heavy chain to the N-terminus of each of the subunits of the Fc domain through an immunoglobulin hinge region, the two Fab molecules, the hinge regions and the Fc domain essentially form an immunoglobulin molecule. In a preferred aspect the immunoglobulin molecule is an IgG class immunoglobulin. In an even more preferred aspect the immunoglobulin is an $IgG_1$ subclass immunoglobulin. In another aspect the immunoglobulin is an $IgG_4$ subclass immunoglobulin. In a further preferred aspect the immunoglobulin is a human immunoglobulin.

In other aspects the immunoglobulin is a chimeric immunoglobulin or a humanized immunoglobulin. In one aspect, the immunoglobulin comprises a human constant region, particularly a human Fc region.

In some of the (multispecific) antibodies of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the (multispecific) antibody of the invention.

The antigen binding domains may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one aspect said peptide linker has a length of at least 5 amino acids, in one aspect a length of 5 to 100, in a further aspect of 10 to 50 amino acids. In one aspect said peptide linker is $(GxS)_n$ or $(GXS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one aspect x=4 and n=2 or 3, in a further aspect x=4 and n=2. In one aspect said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 118 and 119). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In some aspects, the bispecific antigen binding molecule comprises a common light chain. In one aspect the present invention provides a bispecific antigen binding molecule comprising a first and a second antigen binding moiety, one of which is a Fab molecule capable of specific binding to CD3 and the other one of which is a Fab molecule capable of specific binding to FolR1, wherein the first and the second Fab molecule have identical VLCL light chains. In one embodiment said identical light chain (VLCL) comprises the light chain CDRs of SEQ ID NO: 8, SEQ ID NO: 9 and SEQ ID NO: 10. In one embodiment said identical light chain (VLCL) comprises SEQ ID NO. 133.

In one embodiment the present invention provides a T cell activating bispecific antigen binding molecule comprising (i) a first antigen binding moiety which is a Fab molecule capable of specific binding to CD3, and which comprises at least one heavy chain complementarity determining region (CDR) selected from the group consisting of SEQ ID NO: 2, SEQ ID NO: 3 and SEQ ID NO: 5 and at least one light chain CDR selected from the group of SEQ ID NO: 8, SEQ ID NO: 9, SEQ ID NO: 10; (ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 124, SEQ ID NO: 125 and SEQ ID NO: 126 and at least one light chain CDR selected from the group of SEQ ID NO: 8, SEQ ID NO: 9, SEQ ID NO: 10.

In one such embodiment the CD3 antigen binding moiety comprises the heavy chain CDR1 of SEQ ID NO: 2, the heavy chain CDR2 of SEQ ID NO: 3, the heavy chain CDR3 of SEQ ID NO:5, the light chain CDR1 of SEQ ID NO: 8, the light chain CDR2 of SEQ ID NO: 9, and the light chain CDR3 of SEQ ID NO:10 and the FolR1 antigen binding moiety 5 comprises the heavy chain CDR1 of SEQ ID NO: 124, the heavy chain CDR2 of SEQ ID NO: 125, the heavy chain CDR3 of SEQ ID NO:126, the light chain CDR1 of SEQ ID NO: 8, the light chain CDR2 of SEQ ID NO: 9, and the light chain CDR3 of SEQ ID NO:10.

In one embodiment the present invention provides a T cell activating bispecific antigen binding molecule comprising (i) a first antigen binding moiety which is a Fab molecule capable of specific binding to CD3 comprising a variable heavy chain comprising an amino acid sequence of SEQ ID NO: 7 and a variable light chain comprising an amino acid sequence of SEQ ID NO: 11. (ii) a second antigen binding moiety which is a Fab molecule capable of specific binding to Folate Receptor 1 (FolR1) comprising a variable heavy chain comprising an amino acid sequence of SEQ ID NO: 123 and a variable light chain comprising an amino acid sequence of SEQ ID NO: 11.

In one embodiment the present invention provides a T cell activating bispecific antigen binding molecule comprising (i) a first antigen binding moiety which is a Fab molecule capable of specific binding to CD3 comprising a variable heavy chain comprising an amino acid sequence of SEQ ID NO: 7 and a variable light chain comprising an amino acid sequence of SEQ ID NO: 11 (ii) a second antigen binding moiety which is a Fab molecule capable of specific binding to Folate Receptor 1 (FolR1) comprising a variable heavy chain comprising an amino acid sequence of SEQ ID NO: 123 and a variable light chain comprising an amino acid sequence of SEQ ID NO: 11.

In one embodiment the T cell activating bispecific antigen binding molecule additionally comprises (iii) a third antigen binding moiety (which is a Fab molecule) capable of specific binding to FolR1. In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

Hence in one embodiment the present invention provides a T cell activating bispecific antigen binding molecule comprising (i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;

(ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.

(iii) a third antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 5 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 16, the heavy chain CDR2 of SEQ ID NO: 17, the heavy chain CDR3 of SEQ ID NO:18, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising (i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.

(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

(iii) a third antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

Thus, in one embodiment, the invention relates to bispecific molecules wherein at least two binding moieties have identical light chains and corresponding remodeled heavy chains that confer the specific binding to the T cell activating antigen CD3 and the target cell antigen FolR1, respectively. The use of this so-called 'common light chain' principle, i.e. combining two binders that share one light chain but still have separate specificities, prevents light chain mispairing. Thus, there are less side products during production, facilitating the homogenous preparation of T cell activating bispecific antigen binding molecules.

In some embodiments, said T cell activating bispecific antigen binding molecule comprises an Fc domain composed of a first and a second subunit capable of stable association. Below are described exemplary embodiments of T cell activating bispecific antigen binding molecule comprising an Fc domain are described.

In one aspect, the invention provides a (multispecific, e.g. bispecific) antibody comprising a) a first antigen binding domain that binds to CD3, wherein the first antigen binding domain is a Fab molecule, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly FolR1, wherein the second antigen binding domain is a Fab molecule comprising a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

c) an Fc domain composed of a first and a second subunit; wherein (i) the first antigen binding domain under a) is fused at the C-terminus of the Fab heavy chain to the N-terminus of the Fab heavy chain of the second antigen binding domain under b), and the second antigen binding domain under b) is fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) is fused at the C-terminus of the Fab heavy chain to the N-terminus of one of the subunits of the Fc domain under c).

In a preferred aspect, the invention provides a (multispecific) antibody comprising a) a first antigen binding domain that binds to CD3, wherein the first antigen binding domain is a Fab molecule, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second and a third antigen binding domain that bind to a second antigen, particularly a target cell antigen, more particularly FolR1, wherein the second and the third antigen binding domain are each a Fab molecule comprising a light chain variable region (VL) comprising a light chain complementarity determining region (LCDR) 1 of SEQ ID NO: 8, a LCDR 2 of SEQ ID NO: 9 and a LCDR 3 of SEQ ID NO: 10; and c) an Fc domain composed of a first and a second subunit; wherein (i) the first antigen binding domain under a) is fused at the C-terminus of the Fab heavy chain to the N-terminus of the Fab heavy chain of the second antigen binding domain under b), and the second antigen binding domain under b) and the third antigen binding domain under b) are each fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In another aspect, the invention provides a (multispecific) antibody comprising a) a first antigen binding domain that binds to CD3, wherein the first antigen binding domain is a Fab molecule, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly FolR1, wherein the second antigen binding domain is a Fab molecule comprising a light chain variable region (VL) comprising a light chain complementarity determining region (LCDR) 1 of SEQ ID NO: 8, a LCDR 2 of SEQ ID NO: 9 and a LCDR 3 of SEQ ID NO: 10; c) an Fc domain composed of a first and a second subunit;

wherein (i) the first antigen binding domain under a) and the second antigen binding domain under b) are each fused at the C-terminus of the Fab heavy chain to the N-terminus of one of the subunits of the Fc domain under c).

According to any of the above aspects, components of the (multispecific, e.g. bispecific) antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

In a preferred aspect, the invention provides a (bispecific) antibody comprising a) a first antigen binding domain that binds CD3, wherein the first antigen binding domain is a Fab, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5;

b) a second and a third antigen binding domain that bind to FolR1, wherein the second and the third antigen binding domain are each a Fab molecule, and comprise a heavy chain variable region (VH) comprising a heavy chain complementary determining region (HCDR) 1 of SEQ ID NO: 124, a HCDR 2 of SEQ ID NO: 125, and a HCDR 3 of SEQ ID NO: 126;

c) an Fc domain composed of a first and a second subunit; and wherein the first antigen binding domain and the second and third antigen binding domain comprise a light chain variable region (VL) comprising a light chain complementarity determining region (LCDR) 1 of SEQ ID NO: 8, a LCDR 2 of SEQ ID NO: 9 and a LCDR 3 of SEQ ID NO: 10.

In one aspect according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further aspect according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further aspect according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further aspect according to these aspects of the invention, the Fc domain is a human $IgG_1$ Fc domain.

In a preferred specific aspect, the bispecific antibody comprises a polypeptide comprising an amino acid sequence that is at least 95%, 96%, 97%, 98%, or 99% identical to the sequence of SEQ ID NO: 127, a polypeptide comprising an amino acid sequence that is at least 95%, 96%, 97%, 98%, or 99% identical to the sequence of SEQ ID NO: 128, and a polypeptide (particularly three polypeptides) comprising an amino acid sequence that is at least 95%, 96%, 97%, 98%, or 99% identical to the sequence of SEQ ID NO: 129. In a further preferred specific aspect, the (multispecific, e.g. bispecific) antibody comprises a polypeptide comprising the amino acid sequence of SEQ ID NO: 127, a polypeptide comprising the amino acid sequence of SEQ ID NO: 128, and a polypeptide (particularly three polypeptides) comprising the amino acid sequence of SEQ ID NO: 129.

In one preferred aspect the invention provides a bispecific antibody that binds to CD3 and FolR1, comprising a polypeptide comprising an amino acid sequence that is at least 95%, 96%, 97%, 98%, or 99% identical to the sequence of SEQ ID NO: 127, a polypeptide comprising an amino acid sequence that is at least 95%, 96%, 97%, 98%, or 99% identical to the sequence of SEQ ID NO: 128, and a polypeptide (particularly three polypeptides) comprising an amino acid sequence that is at least 95%, 96%, 97%, 98%, or 99% identical to the sequence of SEQ ID NO: 129. In one preferred aspect the invention provides a bispecific antibody that binds to CD3 and FolR1, comprising a polypeptide comprising the amino acid sequence of SEQ ID NO: 127, a polypeptide comprising the amino acid sequence of SEQ ID NO: 128, and a polypeptide (particularly three polypeptides) comprising the amino acid sequence of SEQ ID NO: 129.

In a specific aspect, the bispecific antibody comprises a polypeptide comprising an amino acid sequence that is at least 95%, 96%, 97%, 98%, or 99% identical to the sequence of SEQ ID NO: 130, a polypeptide comprising an amino acid sequence that is at least 95%, 96%, 97%, 98%, or 99% identical to the sequence of SEQ ID NO: 128, and a polypeptide (particularly three polypeptides) comprising an amino acid sequence that is at least 95%, 96%, 97%, 98%, or 99% identical to the sequence of SEQ ID NO: 129. In a further specific aspect, the (multispecific, e.g. bispecific) antibody comprises a polypeptide comprising the amino acid sequence of SEQ ID NO: 130, a polypeptide comprising the amino acid sequence of SEQ ID NO: 128, and a polypeptide (particularly three polypeptides) comprising the amino acid sequence of SEQ ID NO: 129.

In one aspect the invention provides a bispecific antibody that binds to CD3 and FolR1, comprising a polypeptide comprising an amino acid sequence that is at least 95%, 96%, 97%, 98%, or 99% identical to the sequence of SEQ ID NO: 130, a polypeptide comprising an amino acid sequence that is at least 95%, 96%, 97%, 98%, or 99% identical to the sequence of SEQ ID NO: 128, and a polypeptide (particularly three polypeptides) comprising an amino acid sequence that is at least 95%, 96%, 97%, 98%, or 99% identical to the sequence of SEQ ID NO: 129. In one aspect the invention provides a bispecific antibody that binds to CD3 and FolR1, comprising a polypeptide comprising the amino acid sequence of SEQ ID NO: 130, a polypeptide comprising the amino acid sequence of SEQ ID NO: 128, and a polypeptide (particularly three polypeptides) comprising the amino acid sequence of SEQ ID NO: 129.

In a specific aspect, the bispecific antibody comprises a polypeptide comprising an amino acid sequence that is at least 95%, 96%, 97%, 98%, or 99% identical to the sequence of SEQ ID NO: 131, a polypeptide comprising an amino acid sequence that is at least 95%, 96%, 97%, 98%, or 99% identical to the sequence of SEQ ID NO: 132, and a polypeptide (particularly three polypeptides) comprising an amino acid sequence that is at least 95%, 96%, 97%, 98%, or 99% identical to the sequence of SEQ ID NO: 129. In a further specific aspect, the (multispecific, e.g. bispecific) antibody comprises a polypeptide comprising the amino acid sequence of SEQ ID NO: 131, a polypeptide comprising the amino acid sequence of SEQ ID NO: 132, and a polypeptide (particularly three polypeptides) comprising the amino acid sequence of SEQ ID NO: 129.

In one aspect the invention provides a bispecific antibody that binds to CD3 and FolR1, comprising a polypeptide comprising an amino acid sequence that is at least 95%, 96%, 97%, 98%, or 99% identical to the sequence of SEQ ID NO: 131, a polypeptide comprising an amino acid sequence that is at least 95%, 96%, 97%, 98%, or 99% identical to the sequence of SEQ ID NO: 132, and a polypeptide (particularly three polypeptides) comprising an amino acid sequence that is at least 95%, 96%, 97%, 98%, or 99% identical to the sequence of SEQ ID NO: 129. In one aspect the invention provides a bispecific antibody that binds to CD3 and FolR1-1, comprising a polypeptide comprising the amino acid sequence of SEQ ID NO: 131, a polypeptide comprising the amino acid sequence of SEQ ID NO: 132, and a polypeptide (particularly three polypeptides) comprising the amino acid sequence of SEQ ID NO: 129.

In a specific aspect, the bispecific antibody comprises a polypeptide comprising an amino acid sequence that is at least 95%, 96%, 97%, 98%, or 99% identical to the sequence of SEQ ID NO: 133, a polypeptide comprising an amino acid sequence that is at least 95%, 96%, 97%, 98%, or 99% identical to the sequence of SEQ ID NO: 134, and a polypeptide (particularly three polypeptides) comprising an amino acid sequence that is at least 95%, 96%, 97%, 98%, or 99% identical to the sequence of SEQ ID NO: 129. In a further specific aspect, the (multispecific, e.g. bispecific) antibody comprises a polypeptide comprising the amino acid sequence of SEQ ID NO: 133, a polypeptide comprising the amino acid sequence of SEQ ID NO: 134, and a polypeptide (particularly three polypeptides) comprising the amino acid sequence of SEQ ID NO: 129.

In one aspect the invention provides a bispecific antibody that binds to CD3 and FolR1, comprising a polypeptide comprising an amino acid sequence that is at least 95%, 96%, 97%, 98%, or 99% identical to the sequence of SEQ ID NO: 133, a polypeptide comprising an amino acid sequence that is at least 95%, 96%, 97%, 98%, or 99% identical to the sequence of SEQ ID NO: 134, and a polypeptide (particularly three polypeptides) comprising an amino acid sequence that is at least 95%, 96%, 97%, 98%, or 99% identical to the sequence of SEQ ID NO: 129. In one aspect the invention provides a bispecific antibody that binds to CD3 and FolR1, comprising a polypeptide comprising the amino acid sequence of SEQ ID NO: 133, a polypeptide comprising the amino acid sequence of SEQ ID NO: 134, and a polypeptide (particularly three polypeptides) comprising the amino acid sequence of SEQ ID NO: 129.

In a specific aspect, the bispecific antibody comprises a polypeptide comprising an amino acid sequence that is at least 95%, 96%, 97%, 98%, or 99% identical to the sequence of SEQ ID NO: 135, a polypeptide comprising an amino acid sequence that is at least 95%, 96%, 97%, 98%, or 99% identical to the sequence of SEQ ID NO: 136, and a polypeptide (particularly two polypeptides) comprising an amino acid sequence that is at least 95%, 96%, 97%, 98%, or 99% identical to the sequence of SEQ ID NO: 129. In a further specific aspect, the (multispecific, e.g. bispecific) antibody comprises a polypeptide comprising the amino acid sequence of SEQ ID NO: 135, a polypeptide comprising the amino acid sequence of SEQ ID NO: 136, and a polypeptide (particularly two polypeptides) comprising the amino acid sequence of SEQ ID NO: 129.

In one aspect the invention provides a bispecific antibody that binds to CD3 and FolR1, comprising a polypeptide comprising an amino acid sequence that is at least 95%, 96%, 97%, 98%, or 99% identical to the sequence of SEQ ID NO: 135, a polypeptide comprising an amino acid sequence that is at least 95%, 96%, 97%, 98%, or 99% identical to the sequence of SEQ ID NO: 136, and a polypeptide (particularly two polypeptides) comprising an amino acid sequence that is at least 95%, 96%, 97%, 98%, or 99% identical to the sequence of SEQ ID NO: 129. In one aspect the invention provides a bispecific antibody that binds to CD3 and FolR1, comprising a polypeptide comprising the amino acid sequence of SEQ ID NO: 135, a polypeptide comprising the amino acid sequence of SEQ ID NO: 136, and a polypeptide (particularly two polypeptides) comprising the amino acid sequence of SEQ ID NO: 129.

e) Fc Domain Variants

In preferred aspects, the (multispecific, e.g. bispecific) antibody of the invention comprises an Fc domain composed of a first and a second subunit.

The Fc domain of the (multispecific, e.g. bispecific) antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one aspect, the (multispecific, e.g. bispecific) antibody of the invention comprises not more than one Fc domain.

In one aspect, the Fc domain of the (multispecific, e.g. bispecific) antibody is an IgG Fc domain. In a preferred aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further preferred aspect, the Fc domain is a human Fc domain. In an even more preferred aspect, the Fc domain is a human $IgG_1$ Fc domain. An exemplary sequence of a human $IgG_1$ Fc region is given in SEQ ID NO: 117.

f) Fc Domain Modifications Promoting Heterodimerization (Multispecific, e.g. bispecific) antibodies according to the invention comprise different antigen binding domains, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of (multispecific, e.g. bispecific) antibodies in recombinant production, it will thus be advantageous to introduce in the Fc domain of the (multispecific, e.g. bispecific) antibody a modification promoting the association of the desired polypeptides.

Accordingly, in preferred aspects, the Fc domain of the (multispecific, e.g. bispecific) antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the (multispecific, e.g. bispecific) antibody which reduce heavy/light chain mispairing and Bence Jones-type side products.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a preferred aspect, in the CH3 domain of the first subunit of the Fc domain of the (multispecific, e.g. bispecific) antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific aspect, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In a preferred aspect the antigen binding domain that binds to CD3 is fused (optionally via the second antigen binding domain, which binds to a second antigen (i.e. FolR1), and/or a peptide linker) to the first subunit of the Fc domain (comprising the "knob" modification). Without wishing to be bound by theory, fusion of the antigen binding domain that binds CD3 to the knob-containing subunit of the Fc domain will (further) minimize the generation of antibodies comprising two antigen binding domains that bind to CD3 (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one aspect, the heterodimerization approach described in EP 1870459, is used alternatively. This approach is based on the introduction of charged amino acids with opposite charges at specific amino acid positions in the CH3/CH3 domain interface between the two subunits of the Fc domain. A particular aspect for the (multispecific) antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another aspect, the (multispecific, e.g. bispecific) antibody of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another aspect, the (multispecific, e.g. bispecific) antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said (multispecific, e.g. bispecific) antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one aspect, the heterodimerization approach described in WO 2013/157953 is used alternatively. In one aspect, a first CH3 domain comprises amino acid mutation T366K and a second CH3 domain comprises amino acid mutation L351D (numberings according to Kabat EU index). In a further aspect, the first CH3 domain comprises further amino acid mutation L351K. In a further aspect, the second CH3 domain comprises further an amino acid mutation selected from Y349E, Y349D and L368E (particularly L368E) (numberings according to Kabat EU index).

In one aspect, the heterodimerization approach described in WO 2012/058768 is used alternatively. In one aspect a first CH3 domain comprises amino acid mutations L351Y, Y407A and a second CH3 domain comprises amino acid mutations T366A, K409F. In a further aspect the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further aspect a first CH3 domain comprises amino acid mutations L351Y, Y407A and a second CH3 domain comprises amino acid mutations T366V, K409F. In a further aspect, a first CH3 domain comprises amino acid mutation Y407A and a second CH3 domain comprises amino acid mutations T366A, K409F. In a further aspect, the second CH3 domain further comprises amino acid mutations K392E, T411E, D399R and S400R (numberings according to Kabat EU index).

In one aspect, the heterodimerization approach described in WO 2011/143545 is used alternatively, e.g. with the amino acid modification at a position selected from the group consisting of 368 and 409 (numbering according to Kabat EU index).

In one aspect, the heterodimerization approach described in WO 2011/090762, which also uses the knobs-into-holes technology described above, is used alternatively. In one aspect a first CH3 domain comprises amino acid mutation T366W and a second CH3 domain comprises amino acid mutation Y407A. In one aspect, a first CH3 domain comprises amino acid mutation T366Y and a second CH3 domain comprises amino acid mutation Y407T (numberings according to Kabat EU index).

In one aspect, the (multispecific, e.g. bispecific) antibody or its Fc domain is of $IgG_2$ subclass and the heterodimerization approach described in WO 2010/129304 is used alternatively.

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such aspect, a first CH3 domain comprises amino acid substitution of K392 or N392 with a negatively charged amino acid (e.g. glutamic acid (E), or aspartic acid (D), particularly K392D or N392D) and a second CH3 domain comprises amino acid substitution of D399, E356, D356, or E357 with a positively charged amino acid (e.g. lysine (K) or arginine (R), particularly D399K, E356K, D356K, or E357K, and more particularly D399K and E356K). In a further aspect, the first CH3 domain further comprises amino acid substitution of K409 or R409 with a negatively charged amino acid (e.g. glutamic acid (E), or aspartic acid (D), particularly K409D or R409D). In a further aspect the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further aspect, the heterodimerization approach described in WO 2007/147901 is used alternatively. In one aspect, a first CH3 domain comprises amino acid mutations K253E, D282K, and K322D and a second CH3 domain comprises amino acid mutations D239K, E240K, and K292D (numberings according to Kabat EU index).

In still another aspect, the heterodimerization approach described in WO 2007/110205 can be used alternatively.

In one aspect, the first subunit of the Fc domain comprises amino acid substitutions K392D and K409D, and the second subunit of the Fc domain comprises amino acid substitutions D356K and D399K (numbering according to Kabat EU index).

2) Fc Domain Modifications Reducing Fc Receptor Binding and/or Effector Function The Fc domain confers to the (multispecific) antibody favorable pharmacokinetic properties, including a long serum half-life which contributes to good accumulation in the target tissue and a favorable tissue-blood distribution ratio. At the same time it may, however, lead to undesirable targeting of the (multispecific, e.g. bispecific) antibody to cells expressing Fc receptors rather than to the preferred antigen-bearing cells. Moreover, the co-activation of Fc receptor signaling pathways may lead to cytokine release which, in combination with the T cell activating properties and the long half-life of the (multispecific) antibody, results in excessive activation of cytokine receptors and severe side effects upon systemic administration. Activation of (Fc receptor-bearing) immune cells other than T cells may even reduce efficacy of the (multispecific) antibody due to the potential destruction of T cells e.g. by NK cells.

Accordingly, in preferred aspects, the Fc domain of the (multispecific, e.g. bispecific) antibody according to the invention exhibits reduced binding affinity to an Fc receptor and/or reduced effector function, as compared to a native $IgG_1$ Fc domain. In one such aspect the Fc domain (or the (multispecific) antibody comprising said Fc domain) exhibits less than 50%, particularly less than 20%, more particularly less than 10% and most particularly less than 5% of the binding affinity to an Fc receptor, as compared to a native $IgG_1$ Fc domain (or a (multispecific, e.g. bispecific) antibody comprising a native $IgG_1$ Fc domain), and/or less than 50%, particularly less than 20%, more particularly less than 10% and most particularly less than 5% of the effector function, as compared to a native $IgG_1$ Fc domain domain (or a (multispecific, e.g. bispecific) antibody comprising a native $IgG_1$ Fc domain). In one aspect, the Fc domain domain (or the (multispecific, e.g. bispecific) antibody comprising said Fc domain) does not substantially bind to an Fc receptor and/or induce effector function. In a preferred aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa. In one aspect the effector function is one or more selected from the group of CDC, ADCC, ADCP, and cytokine secretion. In a preferred aspect, the effector function is ADCC. In one aspect, the Fc domain domain exhibits substantially similar binding affinity to neonatal Fc receptor (FcRn), as compared to a native $IgG_1$ Fc domain domain. Substantially similar binding to FcRn is achieved when the Fc domain (or the (multispecific, e.g. bispecific) antibody comprising said Fc domain) exhibits greater than about 70%, particularly greater than about 80%, more particularly greater than about 90% of the binding affinity of a native $IgG_1$ Fc domain (or the (multispecific, e.g. bispecific) antibody comprising a native $IgG_1$ Fc domain) to FcRn.

In certain aspects the Fc domain is engineered to have reduced binding affinity to an Fc receptor and/or reduced effector function, as compared to a non-engineered Fc domain. In preferred aspects, the Fc domain of the (multispecific, e.g. bispecific) antibody comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In one aspect, the amino acid mutation reduces the binding affinity of the Fc domain to an Fc receptor by at least 2-fold, at least 5-fold, or at least 10-fold. In aspects where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one aspect the (multispecific, e.g. bispecific) antibody comprising an engineered Fc domain exhibits less than 20%, particularly less than 10%, more particularly less than 5% of the binding affinity to an Fc receptor as compared to a (multispecific, e.g. bispecific) antibody comprising a non-engineered Fc domain. In a preferred aspect, the Fc receptor is an Fcγ receptor. In some aspects, the Fc receptor is a human Fc receptor. In some aspects, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the (multispecific, e.g. bispecific) antibody comprising said Fc domain) exhibits greater than about 70% of the binding affinity of a non-engineered form of the Fc domain (or the (multispecific, e.g. bispecific) antibody comprising said non-engineered form of the Fc domain) to FcRn. The Fc domain, or (multispecific) antibodies of the invention comprising said Fc domain, may exhibit greater than about 80% and even greater than about 90% of such affinity. In certain aspects, the Fc domain of the (multispecific, e.g. bispecific) antibody is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one aspect, the reduced effector function is one or more selected from the group of reduced CDC, reduced ADCC, reduced ADCP, and reduced cytokine secretion. In a preferred aspect, the reduced effector function is reduced ADCC. In one aspect the reduced ADCC is less than 20% of the ADCC induced by a non-engineered Fc domain (or a (multispecific, e.g. bispecific) antibody comprising a non-engineered Fc domain).

In one aspect, the amino acid mutation that reduces the binding affinity of the Fc domain to an Fc receptor and/or effector function is an amino acid substitution. In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an $IgG_1$ Fc domain, particularly a human $IgG_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In preferred aspects, the Fc domain comprises amino acid substitutions at positions P329, L234 and L235 (numberings according to Kabat EU index). In more preferred aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such aspect, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some aspects, the Fc domain of the (multispecific) antibodies of the invention is an $IgG_4$ Fc domain, particularly a human $IgG_4$ Fc domain. In one aspect, the $IgG_4$ Fc domain comprises an amino acid substitution at position S228, specifically the amino acid substitution S228P (numberings according to Kabat EU index). To further reduce its binding affinity to an Fc receptor and/or its effector function, in one aspect, the $IgG_4$ Fc domain comprises an amino acid substitution at position L235, specifically the amino acid substitution L235E (numberings according to Kabat EU index). In another aspect, the $IgG_4$ Fc domain comprises an amino acid substitution at position P329, specifically the amino acid substitution P329G (numberings according to Kabat EU index). In a preferred aspect, the $IgG_4$ Fc domain comprises amino acid substitutions at positions S228, L235 and P329, specifically amino acid substitutions S228P, L235E and P329G (numberings according to Kabat EU index). Such $IgG_4$ Fc domain mutants and their Fcγ receptor binding properties are described in PCT publication no. WO 2012/130831, incorporated herein by reference in its entirety.

In a preferred aspect, the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G, or a human $IgG_4$ Fc domain comprising the amino acid substitutions S228P, L235E and optionally P329G (numberings according to Kabat EU index).

In certain aspects, N-glycosylation of the Fc domain has been eliminated. In one such aspect, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or (multispecific) antibodies comprising an Fc domain for Fc receptors may be evaluated using cell lines known to express particular Fc receptors, such as human NK cells expressing FcγIIIa receptor.

Effector function of an Fc domain, or a (multispecific, e.g. bispecific) antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the Fc domain, or the (multispecific, e.g. bispecific) antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half life determinations can also be performed using methods known in the art (see, e.g., Petkova, S. B. et al., *Int'l. Immunol.* 18(12):1759-1769 (2006); WO 2013/120929).

B. Polynucleotides

The invention further provides an isolated polynucleotide encoding an antibody of the invention. Said isolated polynucleotide may be a single polynucleotide or a plurality of polynucleotides.

The polynucleotides encoding (multispecific, e.g. bispecific) antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the portion of the antibody comprising the heavy chain of the antibody. When co-expressed, the heavy chain polypeptides will associate with the light chain polypeptides to form the antibody. In another example, the portion of the antibody comprising one of the two Fc domain subunits and optionally (part of) one or more Fab molecules could be encoded by a separate polynucleotide from the portion of the antibody comprising the other of the two Fc domain subunits and optionally (part of) a Fab molecule. When co-expressed, the Fc domain subunits will associate to form the Fc domain.

In some aspects, the isolated polynucleotide encodes the entire antibody molecule according to the invention as described herein. In other aspects, the isolated polynucleotide encodes a polypeptide comprised in the antibody according to the invention as described herein.

In certain aspects the polynucleotide or nucleic acid is DNA. In other aspects, a polynucleotide of the present invention is RNA, for example, in the form of messenger RNA (mRNA). RNA of the present invention may be single stranded or double stranded.

C. Recombinant Methods

Antibodies of the invention may be obtained, for example, by solid-state peptide synthesis (e.g. Merrifield solid phase synthesis) or recombinant production. For recombinant production one or more polynucleotide encoding the antibody, e.g., as described above, is isolated and inserted into one or more vectors for further cloning and/or expression in a host cell. Such polynucleotide may be readily isolated and sequenced using conventional procedures. In one aspect a vector, particularly an expression vector, comprising the polynucleotide (i.a. a single polynucleotide or a plurality of polynucleotides) of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., Molecular Cloning: a Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible by tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain aspects, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further aspect, a host cell comprising a polynucleotide (i.e. a single polynucleotide or a plurality of polynucleotides) of the invention is provided. In certain aspects a host cell comprising a vector of the invention is provided. The polynucleotides and vectors may incorporate any of the features, singly or in combination, described herein in relation to polynucleotides and vectors, respectively. In one such aspect a host cell comprises (e.g. has been transformed or transfected with) one or more vector comprising one or more polynucleotide that encodes (part of) an antibody of the invention. As used herein, the term "host cell" refers to any kind of cellular system which can be engineered to generate the antibody of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one aspect, the host cell is a eukaryotic cell, particularly a mammalian cell, such as a Chinese Hamster Ovary (CHO) cell, a human embryonic kidney (HEK) cell or a lymphoid cell (e.g., YO, NS0, Sp20 cell). In one aspect, the host cell is not a cell within a human body.

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one aspect, a method of producing an antibody according to the invention is provided, wherein the method comprises culturing a host cell comprising a polynucleotide encoding the antibody, as provided herein, under conditions suitable for expression of the antibody, and optionally recovering the antibody from the host cell (or host cell culture medium).

The components of the (multispecific, e.g. bispecific) antibody of the invention may be genetically fused to each other. The (multispecific, e.g. bispecific) antibody can be designed such that its components are fused directly to each other or indirectly through a linker sequence. The composition and length of the linker may be determined in accordance with methods well known in the art and may be tested for efficacy. Examples of linker sequences between different components of (multispecific) antibodies are provided herein. Additional sequences may also be included to incorporate a cleavage site to separate the individual components of the fusion if desired, for example an endopeptidase recognition sequence.

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well-known analytical methods including gel electrophoresis, high pressure liquid chromatography, and the like.

D. Assays

Antibodies provided herein may be identified, screened for, or characterized for their physical/chemical properties and/or biological activities by various assays known in the art.

1. Binding Assays

The binding (affinity) of the antibody to an Fc receptor or a target antigen can be determined for example by surface plasmon resonance (SPR), using standard instrumentation such as a BIAcore instrument (GE Healthcare), and receptors or target proteins such as may be obtained by recombinant expression. Alternatively, binding of antibodies to different receptors or target antigens may be evaluated using cell lines expressing the particular receptor or target antigen, for example by flow cytometry (FACS). A specific illustrative and exemplary aspect for measuring binding activity to CD3 is described in the following. The illustrated assay can be easily adapted to measure binding activity to FolR1 by using a FolR1 antigen instead of a CD3 antigen and minor adjustments readily recognizable to the skilled artisan.

In one aspect, the binding activity to CD3 is determined by SPR as follows:

SPR is performed on a Biacore T200 instrument (GE Healthcare). Anti-Fab capturing antibody (GE Healthcare, #28958325) is immobilized on a Series S Sensor Chip CM5 (GE Healthcare) using standard amine coupling chemistry, at a surface density of 4000-6000 resonance units (RU). As running and dilution buffer, HBS-P+ (10 mM HEPES, 150 mM NaCl pH 7.4, 0.05% Surfactant P20) is used. CD3 antibodies with a concentration of 2 μg/ml (in 20 mM His, 140 mM NaCl, pH 6.0) are injected for about 60 s at a flow rate of 5 μl/min. The CD3 antigen used is a heterodimer of CD3 delta and CD3 epsilon ectodomains fused to a human Fc domain with knob-into-hole modifications and a C-terminal Avi-tag (see SEQ ID NOs 28 and 29). CD3 antigen is injected at a concentration of 10 μg/ml for 120 s and dissociation is monitored at a flow rate of 5 μl/min for about 120 s. The chip surface is regenerated by two consecutive injections of 10 mM glycine pH 2.1 for about 60 s each. Bulk refractive index differences are corrected by subtracting blank injections and by subtracting the response obtained from the blank control flow cell. For evaluation, the binding response is taken 5 seconds after injection end. To normalize the binding signal, the CD3 binding is divided by the anti-Fab response (the signal (RU) obtained upon capture of the CD3 antibody on the immobilized anti-Fab antibody). The binding activity to CD3 of an antibody after a certain treatment, relative to the binding activity to CD3 of the antibody after a different treatment (also referred to as relative active concentration (RAC)) is calculated by referencing the binding activity of a sample of the antibody after the certain treatment to the binding activity of a corresponding sample of the antibody after the different treatment.

2. Activity Assays

Biological activity of the (multispecific, e.g. bispecific) antibodies of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

E. Compositions, Formulations, and Routes of Administration

In a further aspect, the invention provides pharmaceutical compositions comprising any of the (multispecific, e.g. bispecific) antibodies provided herein, e.g., for use in any of the below therapeutic methods. In one aspect, a pharmaceutical composition comprises an antibody according to the invention and a pharmaceutically acceptable carrier. In another aspect, a pharmaceutical composition comprises a (multispecific, e.g. bispecific) antibody according to the invention and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise an effective amount of antibody dissolved or dispersed in a pharmaceutically acceptable carrier. The phrase "pharmaceutically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

A (multispecific, e.g. bispecific) antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, particularly in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular aspects, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the (multispecific, e.g. bispecific) antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen. The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

F. Therapeutic Methods and Compositions

Any of the (multispecific, e.g. bispecific) antibodies provided herein may be used in therapeutic methods. Antibodies of the invention may be used as immunotherapeutic agents, for example in the treatment of cancers.

For use in therapeutic methods, (multispecific, e.g. bispecific) antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, (multispecific, e.g. bispecific) antibodies of the invention for use as a medicament are provided. In further aspects, (multispecific, e.g. bispecific) antibodies of the invention for use in treating a disease are provided. In certain aspects, (multispecific, e.g. bispecific) antibodies of the invention for use in a method of treatment are provided. In one aspect, the invention provides a (multispecific, e.g. bispecific) antibody of the invention for use in the treatment of a disease in an individual in need thereof. In certain aspects, the invention provides a (multispecific, e.g. bispecific) antibody for use in a method of treating an individual having a disease comprising administering to the individual an effective amount of the antibody. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. In further aspects, the invention provides an antibody of the invention for use in inducing lysis of a target cell, particularly a tumor cell. In certain aspects, the invention provides a (multispecific, e.g. bispecific) antibody of the invention for use in a method of inducing lysis of a target cell, particularly a tumor cell, in an individual comprising administering to the individual an effective amount of the antibody to induce lysis of a target cell. An "individual" according to any of the above aspects is a mammal, preferably a human.

In a further aspect, the invention provides for the use of a (multispecific, e.g. bispecific) antibody of the invention in the manufacture or preparation of a medicament. In one aspect the medicament is for the treatment of a disease in an individual in need thereof. In a further aspect, the medicament is for use in a method of treating a disease comprising administering to an individual having the disease an effective amount of the medicament. In certain aspects the disease to be treated is a proliferative disorder. In a preferred aspect the disease is cancer. In one aspect, the method further comprises administering to the individual an effective amount of at least one additional therapeutic agent, e.g., an anti-cancer agent if the disease to be treated is cancer. In a further aspect, the medicament is for inducing lysis of a target cell, particularly a tumor cell. In still a further aspect, the medicament is for use in a method of inducing lysis of a target cell, particularly a tumor cell, in an individual comprising administering to the individual an effective amount of the medicament to induce lysis of a target cell. An "individual" according to any of the above aspects may be a mammal, preferably a human.

In a further aspect, the invention provides a method for treating a disease. In one aspect, the method comprises administering to an individual having such disease an effective amount of an antibody of the invention. In one aspect a composition is administered to said individual, comprising the antibody of the invention in a pharmaceutically acceptable form. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. An "individual" according to any of the above aspects may be a mammal, preferably a human.

In a further aspect, the invention provides a method for inducing lysis of a target cell, particularly a tumor cell. In one aspect the method comprises contacting a target cell with an antibody of the invention in the presence of a T cell, particularly a cytotoxic T cell. In a further aspect, a method for inducing lysis of a target cell, particularly a tumor cell, in an individual is provided. In one such aspect, the method comprises administering to the individual an effective amount of an antibody of the invention to induce lysis of a target cell. In one aspect, an "individual" is a human.

In certain aspects, the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects the cancer is selected from the group consisting of kidney cancer, bladder cancer, skin cancer, lung cancer, colorectal cancer, breast cancer, brain cancer, head and neck cancer and prostate cancer. In one aspect, in particular wherein the antibody is a bispecific antibody binding to FolR1 as the second antigen, the cancer is a cancer expressing (or over-expressing) FolR1. In one aspect, in particular wherein the antibody is a bispecific antibody binding to FolR1 as the second antigen, the cancer is a an ovarian cancer, lung cancer, breast cancer, or renal cancer. A skilled artisan readily recognizes that in many cases the antibody may not provide a cure but may only provide partial benefit. In some aspects, a physiological change having some benefit is also considered therapeutically beneficial. Thus, in some aspects, an amount of antibody that provides a physiological change is considered an "effective amount". The subject, patient, or individual in need of treatment is typically a mammal, more specifically a human.

In some aspects, an effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in an effective amount.

For systemic administration, an effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective dose of the antibodies of the invention will generally provide therapeutic benefit without causing substantial toxicity. Toxicity and therapeutic efficacy of an antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one aspect, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The (multispecific, e.g. bispecific) antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular disease being treated, preferably those with complementary activities that do not adversely affect each other. In certain aspects, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a preferred aspect, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the (multispecific, e.g. bispecific) antibody of the invention can occur prior to, simultaneously, and/or following, administration of the additional therapeutic agent and/or adjuvant. Antibodies of the invention may also be used in combination with radiation therapy.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

H. Methods and Compositions for Diagnostics and Detection

In certain aspects, any of the antibodies provided herein is useful for detecting the presence of its target (e.g. CD3, FolR1) in a biological sample. The term "detecting" as used herein encompasses quantitative or qualitative detection. In certain aspects, a biological sample comprises a cell or tissue, such as prostate tissue.

In one aspect, an antibody according to the invention for use in a method of diagnosis or detection is provided. In a further aspect, a method of detecting the presence of CD3 and FolR1 in a biological sample is provided. In certain aspects, the method comprises contacting the biological sample with an antibody of the present invention under conditions permissive for binding of the antibody to CD3 and FolR1, and detecting whether a complex is formed between the antibody and CD3 and FolR1. Such method may be an in vitro or in vivo method. In one aspect, an antibody of the invention is used to select subjects eligible for therapy with an antibody that binds CD3 and FolR1 e.g. where CD3 and FolR1 are biomarkers for selection of patients.

Exemplary disorders that may be diagnosed using an antibody of the invention include cancer, particularly skin cancer or brain cancer.

In certain aspects, an antibody according to the present invention is provided, wherein the antibody is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Sequences

| | Amino Acid Sequence | SEQ ID NO |
|---|---|---|
| $CD3_{orig}$ HCDR1 | TYAMN | 1 |
| $CD3_{opt}$ HCDR1 | SYAMN | 2 |
| $CD3_{orig}$ / $CD3_{opt}$ HCDR2 | RIRSKYNNYATYYADSVKG | 3 |
| $CD3_{orig}$ HCDR3 | HGNFGNSYVSWFAY | 4 |

-continued

| | Amino Acid Sequence | SEQ ID NO |
|---|---|---|
| $CD3_{opt}$ HCDR3 | HTTFPSSYVSYYGY | 5 |
| $CD3_{orig}$ VH | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSS | 6 |
| $CD3_{opt}$ VH | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSS | 7 |
| $CD3_{orig}$ / $CD3_{opt}$ LCDR1 | GSSTGAVTTSNYAN | 8 |
| $CD3_{orig}$ / $CD3_{opt}$ LCDR2 | GTNKRAP | 9 |
| $CD3_{orig}$ / $CD3_{opt}$ LCDR3 | ALWYSNLWV | 10 |
| $CD3_{orig}$ / $CD3_{opt}$ VL | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVL | 11 |
| $CD3_{orig}$ IgG HC | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASTKGPSVFPLAPSSKSTSGGTAALGCLVKDYFPE PVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPPS RDELTKNQVSLTCLVKGFYPSDIAVEWESNGQPENNYKTT PPVLDSDGSFFLYSKLTVDKSRWQQGNVFSCSVMHEALHN HYTQKSLSLSP | 12 |
| $CD3_{opt}$ IgG HC | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSSASTKGPSVFPLAPSSKSTSGGTAALGCLVKDYFPEP VTVSWNSGALTSGVHTFPAVLQSSGLYSLSSVVTVPSSSLG TQTYICNVNHKPSNTKVDKKVEPKSCDKTHTCPPCPAPEA AGGPSVFLFPPKPKDTLMISRTPEVTCVVVDVSHEDPEVKF NWYVDGVEVHNAKTKPREEQYNSTYRVVSVLTVLHQDW LNGKEYKCKVSNKALGAPIEKTISKAKGQPREPQVYTLPPS RDELTKNQVSLTCLVKGFYPSDIAVEWESNGQPENNYKTT PPVLDSDGSFFLYSKLTVDKSRWQQGNVFSCSVMHEALHN HYTQKSLSLSP | 13 |
| $CD3_{orig}$ / $CD3_{opt}$ IgG LC | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVLRTVAAPSVFIFP PSDEQLKSGTASVVCLLNNFYPREAKVQWKVDNALQSGN SQESVTEQDSKDSTYSLSSTLTLSKADYEKHKVYACEVTH QGLSSPVTKSFNRGEC | 14 |
| TYRP1 HCDR1 | DYFLH | 15 |
| TYRP1 HCDR2 | WINPDNGNTVYAQKFQG | 16 |
| TYRP1 HCDR3 | RDYTYEKAALDY | 17 |

-continued

| | Amino Acid Sequence | SEQ ID NO |
|---|---|---|
| TYRP1 VH | QVQLVQSGAEVKKPGASVKVSCKASGFNIKDYFLHWVRQ<br>APGQGLEWMGWINPDNGNTVYAQKFQGRVTMTADTSTST<br>VYMELSSLRSEDTAVYYCTRRDYTYEKAALDYWGQGTLV<br>TVSS | 18 |
| TYRP1 LCDR1 | RASGNIYNYLA | 19 |
| TYRP1 LCDR2 | DAKTLAD | 20 |
| TYRP1 LCDR3 | QHFWSLPFT | 21 |
| TYRP1 VL | DIQMTQSPSSLSASVGDRVTITCRASGNIYNYLAWYQQKPG<br>KVPKLLIYDAKTLADGVPSRESGSGSGTDFTLTISSLQPEDV<br>ATYYCQHFWSLPFTFGQGTKLEIK | 22 |
| TYRP1 VH-CH1(EE) -CD3$_{orig}$/ CD3$_{opt}$ VL-CH1 -Fc (knob, PGLALA) | QVQLVQSGAEVKKPGASVKVSCKASGFNIKDYFLHWVRQ<br>APGQGLEWMGWINPDNGNTVYAQKFQGRVTMTADTSTST<br>VYMELSSLRSEDTAVYYCTRRDYTYEKAALDYWGQGTLV<br>TVSSASTKGPSVFPLAPSSKSTSGGTAALGCLVEDYFPEPVT<br>VSWNSGALTSGVHTFPAVLQSSGLYSLSSVVTVPSSSLGTQ<br>TYICNVNHKPSNTKVDEKVEPKSCDGGGGSGGGGSQAVVT<br>QEPSLTVSPGGTVTLTCGSSTGAVTTSNYANWVQEKPGQA<br>FRGLIGGTNKRAPGTPARFSGSLLGGKAALTLSGAQPEDEA<br>EYYCALWYSNLWVFGGGTKLTVLSSASTKGPSVFPLAPSS<br>KSTSGGTAALGCLVKDYFPEPVTVSWNSGALTSGVHTFPA<br>VLQSSGLYSLSSVVTVPSSSLGTQTYICNVNHKPSNTKVDK<br>KVEPKSCDKTHTCPPCPAPEAAGGPSVFLFPPKPKDTLMISR<br>TPEVTCVVVDVSHEDPEVKFNWYVDGVEVHNAKTKPREE<br>QYNSTYRVVSVLTVLHQDWLNGKEYKCKVSNKALGAPIE<br>KTISKAKGQPREPQVYTLPPCRDELTKNQVSLWCLVKGFY<br>PSDIAVEWESNGQPENNYKTTPPVLDSDGSFFLYSKLTVDK<br>SRWQQGNVFSCSVMHEALHNHYTQKSLSLSP | 23 |
| TYRP1 VH-CH1(EE) -Fc (hole, PGLALA) | QVQLVQSGAEVKKPGASVKVSCKASGFNIKDYFLHWVRQ<br>APGQGLEWMGWINPDNGNTVYAQKFQGRVTMTADTSTST<br>VYMELSSLRSEDTAVYYCTRRDYTYEKAALDYWGQGTLV<br>TVSSASTKGPSVFPLAPSSKSTSGGTAALGCLVEDYFPEPVT<br>VSWNSGALTSGVHTFPAVLQSSGLYSLSSVVTVPSSSLGTQ<br>TYICNVNHKPSNTKVDEKVEPKSCDKTHTCPPCPAPEAAG<br>GPSVFLFPPKPKDTLMISRTPEVTCVVVDVSHEDPEVKENW<br>YVDGVEVHNAKTKPREEQYNSTYRVVSVLTVLHQDWLNG<br>KEYKCKVSNKALGAPIEKTISKAKGQPREPQVCTLPPSRDE<br>LTKNQVSLSCAVKGFYPSDIAVEWESNGQPENNYKTTPPV<br>LDSDGSFFLVSKLTVDKSRWQQGNVFSCSVMHEALHNHY<br>TQKSLSLSP | 24 |
| TYRP1 VL-CL(RK) | DIQMTQSPSSLSASVGDRVTITCRASGNIYNYLAWYQQKPG<br>KVPKLLIYDAKTLADGVPSRFSGSGSGTDFTLTISSLQPEDV<br>ATYYCQHFWSLPFTFGQGTKLEIKRTVAAPSVFIFPPSDRKL<br>KSGTASVVCLLNNFYPREAKVQWKVDNALQSGNSQESVT<br>EQDSKDSTYSLSSTLTLSKADYEKHKVYACEVTHQGLSSPV<br>TKSFNRGEC | 25 |
| CD3$_{orig}$ VH-CL | EVQLLESGGGLVQPGGSLRLSCAASGFTFSTYAMNWVRQA<br>PGKGLEWVSRIRSKYNNYATYYADSVKGRFTISRDDSKNT<br>LYLQMNSLRAEDTAVYYCVRHGNFGNSYVSWFAYWGQG<br>TLVTVSSASVAAPSVFIFPPSDEQLKSGTASVVCLLNNFYPR<br>EAKVQWKVDNALQSGNSQESVTEQDSKDSTYSLSSTLTLS<br>KADYEKHKVYACEVTHQGLSSPVTKSFNRGEC | 26 |
| CD3$_{opt}$ VH-CL | EVQLLESGGGLVQPGGSLRLSCAASGFQFSSYAMNWVRQA<br>PGKGLEWVSRIRSKYNNYATYYADSVKGRFTISRDDSKNT<br>LYLQMNSLRAEDTAVYYCVRHTTFPSSYVSYYGYWGQGT<br>LVTVSSASVAAPSVFIFPPSDEQLKSGTASVVCLLNNFYPRE<br>AKVQWKVDNALQSGNSQESVTEQDSKDSTYSLSSTLTLSK<br>ADYEKHKVYACEVTHQGLSSPVTKSFNRGEC | 27 |
| Human CD3 epsilon stalk-Fc(knob) -Avi | QDGNEEMGGITQTPYKVSISGTTVILTCPQYPGSEILWQHN<br>DKNIGGDEDDKNIGSDEDHLSLKEFSELEQSGYYVCYPRGS<br>KPEDANFYLYLRARVSENCVDEQLYFQGGSPKSADKTHTC<br>PPCPAPELLGGPSVFLFPPKPKDTLMISRTPEVTCVVVDVSH<br>EDPEVKFNWYVDGVEVHNAKTKPREEQYNSTYRVVSVLT | 28 |

-continued

| | Amino Acid Sequence | SEQ ID NO |
|---|---|---|
| | VLHQDWLNGKEYKCKVSNKALPAPIEKTISKAKGQPREPQ VYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPGKSGGLNDIFEAQKIEWHE | |
| Human CD3 delta stalk - Fc (hole) - Avi | FKIPIEELEDRVFVNCNTSITWVEGTVGTLLSDITRLDLGKRI LDPRGIYRCNGTDIYKDKESTVQVHYRMCRSEQLYFQGDK THTCPPCPAPELLGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALPAPIEKTISKAKGQP REPQVCTLPPSRDELTKNQVSLSCAVKGFYPSDIAVEWESN GQPENNYKTTPPVLDSDGSFFLVSKLTVDKSRWQQGNVFS CSVMHEALHNHYTQKSLSLSPGKSGGLNDIFEAQKIEWHE | 29 |
| Cynomolgus CD3 epsilon stalk - Fc (knob) - Avi | QDGNEEMGSITQTPYQVSISGTTVILTCSQHLGSEAQWQHN GKNKEDSGDRLFLPEFSEMEQSGYYVCYPRGSNPEDASHH LYLKARVSENCVDEQLYFQGGSPKSADKTHTCPPCPAPELL GGPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPCR DELTKNQVSLWCLVKGFYPSDIAVEWESNGQPENNYKTTP PVLDSDGSFFLYSKLTVDKSRWQQGNVFSCSVMHEALHNH YTQKSLSLSPGKSGGLNDIFEAQKIEWHE | 30 |
| Cynomolgus CD3 delta stalk - Fc (hole) - Avi | FKIPVEELEDRVFVKCNTSVTWVEGTVGTLLTNNTRLDLG KRILDPRGIYRCNGTDIYKDKESAVQVHYRMSQNCVDEQL YFQGGSPKSADKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVCTLPPSRDELTKNQVSLSCAVKG FYPSDIAVEWESNGQPENNYKTTPPVLDSDGSFFLVSKLTV DKSRWQQGNVFSCSVMHEALHNHYTQKSLSLSPGKSGGL NDIFEAQKIEWHE | 31 |
| Human TYRP1 ECD - Fc (knob) - Avi | QFPRQCATVEALRSGMCCPDLSPVSGPGTDRCGSSSGRGRC EAVTADSRPHSPQYPHDGRDDREVWPLRFFNRTCHCNGNF SGHNCGTCRPGWRGAACDQRVLIVRRNLLDLSKEEKNHFV RALDMAKRTTHPLFVIATRRSEEILGPDGNTPQFENISIYNY FVWTHYYSVKKTFLGVGQESFGEVDFSHEGPAFLTWHRY HLLRLEKDMQEMLQEPSFSLPYWNFATGKNVCDICTDDLM GSRSNFDSTLISPNSVFSQWRVVCDSLEDYDTLGTLCNSTE DGPIRRNPAGNVARPMVQRLPEPQDVAQCLEVGLFDTPPF YSNSTNSFRNTVEGYSDPTGKYDPAVRSLHNLAHLFLNGT GGQTHLSPNDPIFVLLHTFTDAVFDEWLRRYNADISTFPLE NAPIGHNRQYNMVPFWPPVTNTEMFVTAPDNLGYTYEIQ WPSREFSVPEGSDKTHTCPPCPAPEAAGGPSVFLFPPKPKDT LMISRTPEVTCVVVDVSHEDPEVKFNWYVDGVEVHNAKT KPREEQYNSTYRVVSVLTVLHQDWLNGKEYKCKVSNKAL GAPIEKTISKAKGQPREPQVYTLPPCRDELTKNQVSLWCLV KGFYPSDIAVEWESNGQPENNYKTTPPVLDSDGSFFLYSKL TVDKSRWQQGNVFSCSVMHEALHNHYTQKSLSLSPGKSG GLNDIFEAQKIEWHE | 32 |
| Cynomolgus TYRP1 ECD - Fc (knob) - Avi | QFPRECATVEALRSGMCCPDLSPMSGPGTDRCGSSSGRGR CEAVTADSRPHSPRYPHDGRDDREVWPLRFFNRTCHCNGN FSGHNCGTCRPGWRGAACDQRVLVVRRNLLDLSKEEKNH FVRALDMAKRTTHPLFVIATRRSEEILGPDGNTPQFENISIY NYFVWTHYYSVKKTFLGAGQESFGEVDFSHEGPAFLTWH RYHLLRLEKDMQEMLQEPSFSLPYWNFATGKNVCDICTDD LMGSRSNFDSTLISPNSVFSQWRVVCDSLEDYDTLGTLCNS TESGPIRRNPAGNVARPMVQRLPEPQDVAQCLEVGLFDTPP FYSNSTNSFRNTVEGYSDPTGKYDPAVRSLHNLAHLFLNGT GGQTHLSPNDPIFVLLHTFTDAVFDEWLRRYNADISTFPLE NAPIGHNRQYNMVPFWPPVTNTEMFVTAPDNLGYTYEVQ WPSREFSVPGSDKTHTCPPCPAPEAAGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALG APIEKTISKAKGQPREPQVYTLPPCRDELTKNQVSLWCLVK GFYPSDIAVEWESNGQPENNYKTTPPVLDSDGSFFLYSKLT VDKSRWQQGNVFSCSVMHEALHNHYTQKSLSLSPGKSGG LNDIFEAQKIEWHE | 33 |
| Mouse TYRP1 ECD - Fc (knob) - | QFPRECANIEALRRGVCCPDLLPSSGPGTDPCGSSSGRGRC VAVIADSRPHSRHYPHDGKDDREAWPLRFFNRTCQCNDNF SGHNCGTCRPGWRGAACNQKILTVRRNLLDLSPEEKSHFV | 34 |

-continued

| | Amino Acid Sequence | SEQ ID NO |
|---|---|---|
| Avi | RALDMAKRTTHPQFVIATRRLEDILGPDGNTPQFENISVYN<br>YFVWTHYYSVKKTFLGTGQESFGDVDFSHEGPAFLTWHR<br>YHLLQLERDMQEMLQEPSFSLPYWNFATGKNVCDVCTDD<br>LMGSRSNFDSTLISPNSVFSQWRVVCESLEEYDTLGTLCNS<br>TEGGPIRRNPAGNVGRPAVQRLPEPQDVTQCLEVRVFDTPP<br>FYSNSTDSFRNTVEGYSAPTGKYDPAVRSLHNLAHLFLNGT<br>GGQTHLSPNDPIFVLLHTFTDAVFDEWLRRYNADISTFPLE<br>NAPIGHNRQYNMVPFWPPVTNTEMFVTAPDNLGYAYEVQ<br>WPGQEFTVSEGSDKTHTCPPCPAPEAAGGPSVFLFPPKPKD<br>TLMISRTPEVTCVVVDVSHEDPEVKFNWYVDGVEVHNAK<br>TKPREEQYNSTYRVVSVLTVLHQDWLNGKEYKCKVSNKA<br>LGAPIEKTISKAKGQPREPQVYTLPPCRDELTKNQVSLWCL<br>VKGFYPSDIAVEWESNGQPENNYKTTPPVLDSDGSFFLYSK<br>LTVDKSRWQQGNVFSCSVMHEALHNHYTQKSLSLSPGKS<br>GGLNDIFEAQKIEWHE | |
| Fc (hole) | DKTHTCPPCPAPEAAGGPSVFLFPPKPKDTLMISRTPEVTCV<br>VVDVSHEDPEVKFNWYVDGVEVHNAKTKPREEQYNSTYR<br>VVSVLTVLHQDWLNGKEYKCKVSNKALGAPIEKTISKAKG<br>QPREPQVCTLPPSRDELTKNQVSLSCAVKGFYPSDIAVEWE<br>SNGQPENNYKTTPPVLDSDGSFFLVSKLTVDKSRWQQGNV<br>FSCSVMHEALHNRFTQKSLSLSP | 35 |
| EGFRvIII ECD - Avi - His | LEEKKGNYVVTDHGSCVRACGADSYEMEEDGVRKCKKCE<br>GPCRKVCNGIGIGEFKDSLSINATNIKHFKNCTSISGDLHILP<br>VAFRGDSFTHTPPLDPQELDILKTVKEITGFLLIQAWPENRT<br>DLHAFENLEIIRGRTKQHGQFSLAVVSLNITSLGLRSLKEISD<br>GDVIISGNKNLCYANTINWKKLFGTSGQKTKIISNRGENSC<br>KATGQVCHALCSPEGCWGPEPRDCVSCRNVSRGRECVDK<br>CNLLEGEPREFVENSECIQCHPECLPQAMNITCTGRGPDNCI<br>QCAHYIDGPHCVKTCPAGVMGENNTLVWKYADAGHVCH<br>LCHPNCTYGCTGPGLEGCPTNGPKIPSVDGGSPTPPTPGGGS<br>GLNDIFEAQKIEWHEARAHHHHHH | 36 |
| EGFRvIII P056.021 HCDR1 | SYWIA | 37 |
| EGFRvIII P056.021 HCDR2 | VIHPYDSDTRYSPSFQG | 38 |
| EGFRvIII P056.021 HCDR3 | VSRSSYAFDY | 39 |
| EGFRvIII P056.021 VH | EVQLVQSGAEVKKPGESLKISCKGSGYSFDSYWIAWVRQM<br>PGKGLEWMGVIHPYDSDTRYSPSFQGQVTISADKSISTAYL<br>QWSSLKASDTAMYYCARVSRSSYAFDYWGQGTLVTVSS | 40 |
| EGFRvIII P056.021 LCDR1 | KSSQSVLYSSNNKNYLA | 41 |
| EGFRvIII P056.021 LCDR2 | WASTRES | 42 |
| EGFRvIII P056.021 LCDR3 | QQVHSGPPVT | 43 |
| EGFRvIII P056.021 VL | DIVMTQSPDSLAVSLGERATINCKSSQSVLYSSNNKNYLAW<br>YQQKPGQPPKLLIYWASTRESGVPDRFSGSGSGTDFTLTISS<br>LQAEDVAVYYCQQVHSGPPVTFGQGTKVEIK | 44 |
| EGFRvIII P056.052 HCDR1 | NYWIG | 45 |
| EGFRvIII P056.052 HCDR2 | TIYPGDSDRRYSPSFQG | 46 |

-continued

| | Amino Acid Sequence | SEQ ID NO |
|---|---|---|
| EGFRvIII P056.052 HCDR3 | VSRSSYAFDY | 47 |
| EGFRvIII P056.052 VH | EVQLVQSGAEVKKPGESLKISCKGSGYTFMNYWIGWVRQ MPGKGLEWMGTIYPGDSDRRYSPSFQGQVTLSADKSISTA YLQWSSLKASDTAMYYCARVSRSSYAFDYWGQGTLVTVS S | 48 |
| EGFRvIII P056.052 LCDR1 | KSSQSVLYSSNNKNYLA | 49 |
| EGFRvIII P056.052 LCDR2 | WASTRES | 50 |
| EGFRvIII P056.052 LCDR3 | QQVHSGPPVT | 51 |
| EGFRvIII P056.052 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 52 |
| EGFRvIII P047.019 HCDR1 | SIWIH | 53 |
| EGFRvIII P047.019 HCDR2 | TIYPGDSDTRYSPSFQG | 54 |
| EGFRvIII P047.019 HCDR3 | TGPGLAFDY | 55 |
| EGFRvIII P047.019 VH | EVQLVQSGAEVKKPGESLKISCKGSGYSFPSIWIHWVRQMP GKGLEWMGTIYPGDSDTRYSPSFQGQVTISADKSISTAYLQ WSSLKASDTAMYYCARTGPGLAFDYWGQGTLVTVSS | 56 |
| EGFRvIII P047.019 LCDR1 | KSSQSVLYSSNNKNYLA | 57 |
| EGFRVIII P047.019 LCDR2 | WASTRES | 58 |
| EGFRvIII P047.019 LCDR3 | QQSYSTPIT | 59 |
| EGFRvIII P047.019 VL | DIVMTQSPDSLAVSLGERATINCKSSQSVLYSSNNKNYLAW YQQKPGQPPKLLIYWASTRESGVPDRESGSGSGTDFTLTISS LQAEDVAVYYCQQSYSTPITFGQGTKVEIK | 60 |
| EGFRvIII P057.012 HCDR1 | NYWIA | 61 |
| EGFRvIII P057.012 HCDR2 | IIYPDDSDTRYSPSFQG | 62 |
| EGFRvIII P057.012 HCDR3 | ATNIASGGYFDY | 63 |
| EGFRvIII P057.012 VH | EVQLVQSGAEVKKPGESLKISCKGSGYSFANYWIAWVRQ MPGKGLEWMGIIYPDDSDTRYSPSFQGQVTISADKSISTAY LQWSSLKASDTAMYYCARATNIASGGYFDYWGQGTLVTV SS | 64 |

-continued

| | Amino Acid Sequence | SEQ ID NO |
|---|---|---|
| EGFRVIII P057.012 LCDR1 | KSSQSVLWNSNNKNYLA | 65 |
| EGFRvIII P057.012 LCDR2 | WASKRES | 66 |
| EGFRvIII P057.012 LCDR3 | QQSYSAPIT | 67 |
| EGFRvIII P057.012 VL | DIVMTQSPDSLAVSLGERATINCKSSQSVLWNSNNKNYLA WYQQKPGQPPKLLIYWASKRESGVPDRFSGSGSGTDFTLTI SSLQAEDVAVYYCQQSYSAPITFGQGTKVEIK | 68 |
| EGFRvIII P057.011 HCDR1 | RRWIA | 69 |
| EGFRvIII P057.011 HCDR2 | IIYPGDSDTRYSPSFQG | 70 |
| EGFRvIII P057.011 HCDR3 | ATNIASGGYFDY | 71 |
| EGFRvIII P057.011 VH | EVQLVQSGAEVKKPGESLKISCKGSGYNFGRRWIAWVRQ MPGKGLEWMGIIYPGDSDTRYSPSFQGQVTISADKSISTAY LQWSSLKASDTAMYYCARATNIASGGYFDYWGQGTLVTV SS | 72 |
| EGFRvIII P057.011 LCDR1 | KSSQSVLWNSNNKNYLA | 73 |
| EGFRvIII P057.011 LCDR2 | WASKRES | 74 |
| EGFRvIII P057.011 LCDR3 | QQSYSAPIT | 75 |
| EGFRvIII P057.011 VL | DIVMTQSPDSLAVSLGERATINCKSSQSVLWNSNNKNYLA WYQQKPGQPPKLLIYWASKRESGVPDRESGSGSGTDFTLTI SSLQAEDVAVYYCQQSYSAPITFGQGTKVEIK | 76 |
| EGFRvIII P056.027 HCDR1 | NNWIA | 77 |
| EGFRvIII P056.027 HCDR2 | VIYPGDSDKRYSPSFQG | 78 |
| EGFRvIII P056.027 HCDR3 | VSRSSYAFDY | 79 |
| EGFRvIII P056.027 VH | EVQLVQSGAEVKKPGESLKISCKGSGYTFGNNWIAWVRQ MPGKGLEWMGVIYPGDSDKRYSPSFQGQVTISADKSISTAY LQWSSLKASDTAMYYCARVSRSSYAFDYWGQGTLVTVSS | 80 |
| EGFRVIII P056.027 LCDR1 | KSSQSVLYSSNNKNYLA | 81 |
| EGFRvIII P056.027 LCDR2 | WASTRES | 82 |

-continued

| | Amino Acid Sequence | SEQ ID NO |
|---|---|---|
| EGFRvIII P056.027 LCDR3 | QQVHSGPPVT | 83 |
| EGFRvIII P056.027 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 84 |
| EGFRvIII P063.056 HCDR1 | SYWIA | 85 |
| EGFRvIII P063.056 HCDR2 | VIHPYDSDTRYSPSFQG | 86 |
| EGFRvIII P063.056 HCDR3 | VSRSSYAFDY | 87 |
| EGFRvIII P063.056 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSS | 88 |
| EGFRvIII P063.056 LCDR1 | KSSQSVLYSSNNKNYLA | 89 |
| EGFRvIII P063.056 LCDR2 | WASTRES | 90 |
| EGFRvIII P063.056 LCDR3 | QQQRDGPPVT | 91 |
| EGFRvIII P063.056 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQQRDGPPVTFGQGTKVEIK | 92 |
| EGFRvIII P064.078 HCDR1 | SYWIA | 93 |
| EGFRvIII P064.078 HCDR2 | VIHPYDSDTRYSPSFQG | 94 |
| EGFRvIII P064.078 HCDR3 | VSRLSYALDY | 95 |
| EGFRvIII P064.078 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRLSYALDYWGQGTLVTVSS | 96 |
| EGFRvIII P064.078 LCDR1 | KSSQSVLYSSNNKNYLA | 97 |
| EGFRvIII P064.078 LCDR2 | WASTRES | 98 |
| EGFRvIII P064.078 LCDR3 | QQVHSGPPVT | 99 |
| EGFRvIII P064.078 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 100 |
| EGFRvIII P065.036 HCDR1 | SYWIA | 101 |

-continued

| | Amino Acid Sequence | SEQ ID NO |
|---|---|---|
| EGFRvIII P065.036 HCDR2 | VIHPYDSDTRYSPSFQG | 102 |
| EGFRvIII P065.036 HCDR3 | VSRSSYALDY | 103 |
| EGFRvIII P065.036 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYALDYWGQGTLVTVSS | 104 |
| EGFRvIII P065.036 LCDR1 | KSSQSVLYSSNNKNYLA | 105 |
| EGFRvIII P065.036 LCDR2 | WASTRES | 106 |
| EGFRvIII P065.036 LCDR3 | QQVYSGPPVT | 107 |
| EGFRvIII P065.036 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVYSGPPVTFGQGTKVEIK | 108 |
| EGFRvIII VH-CH1(EE) CD3$_{orig}$/ CD3$_{opt}$ VL-CH1 - Fc (knob, PGLALA) | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDGGGGSGGGGSQAVVTQEPSL TVSPGGTVTLTCGSSTGAVTTSNYANWVQEKPGQAFRGLI GGTNKRAPGTPARFSGSLLGGKAALTLSGAQPEDEAEYYC ALWYSNLWVFGGGTKLTVLSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEPK SCDKTHTCPPCPAPEAAGGPSVFLFPPKPKDTLMISRTPEVT CVVVDVSHEDPEVKFNWYVDGVEVHNAKTKPREEQYNST YRVVSVLTVLHQDWLNGKEYKCKVSNKALGAPIEKTISKA KGQPREPQVYTLPPCRDELTKNQVSLWCLVKGFYPSDIAV EWESNGQPENNYKTTPPVLDSDGSFFLYSKLTVDKSRWQQ GNVFSCSVMHEALHNHYTQKSLSLSP | 109 |
| EGFRvIII VH-CH1(EE) -Fc (hole, PGLALA) | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKC KVSNKALGAPIEKTISKAKGQPREPQVCTLPPSRDELTKNQ VSLSCAVKGFYPSDIAVEWESNGQPENNYKTTPPVLDSDGS FFLVSKLTVDKSRWQQGNVFSCSVMHEALHNHYTQKSLSL SP | 110 |
| EGFRvIII VL-CL(RK) | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQQRDGPPVTFGQGTKVEIKRTVAAPSVF IFPPSDRKLKSGTASVVCLLNNFYPREAKVQWKVDNALQS GNSQESVTEQDSKDSTYSLSSTLTLSKADYEKHKVYACEV THQGLSSPVTKSFNRGEC | 111 |
| CD3$_{orig}$ VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 26 |

-continued

| | Amino Acid Sequence | SEQ ID NO |
|---|---|---|
| $CD3_{opt}$ VH-CL | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSSASVAAPSVFIFPPSDEQLKSGTASVVCLLNNFYPRE AKVQWKVDNALQSGNSQESVTEQDSKDSTYSLSSTLTLSK ADYEKHKVYACEVTHQGLSSPVTKSFNRGEC | 27 |
| Human CD3 | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGG LLLLVYYWSKNRKAKAKPVTRGAGAGGRQRGQNKERPPP VPNPDYEPIRKGQRDLYSGLNQRRI | 112 |
| Cynomolgus CD3 | QDGNEEMGSITQTPYQVSISGTTVILTCSQHLGSEAQWQHN GKNKEDSGDRLFLPEFSEMEQSGYYVCYPRGSNPEDASHH LYLKARVCENCMEMDVMAVATIVIVDICITLGLLLLVYYW SKNRKAKAKPVTRGAGAGGRQRGQNKERPPPVPNPDYEPI RKGQQDLYSGLNQRRI | 113 |
| Human TYRP1 | QFPRQCATVEALRSGMCCPDLSPVSGPGTDRCGSSSGRGRC EAVTADSRPHSPQYPHDGRDDREVWPLRFFNRTCHCNGNF SGHNCGTCRPGWRGAACDQRVLIVRRNLLDLSKEEKNHFV RALDMAKRTTHPLFVIATRRSEEILGPDGNTPQFENISIYNY FVWTHYYSVKKTFLGVGQESFGEVDFSHEGPAFLTWHRY HLLRLEKDMQEMLQEPSFSLPYWNFATGKNVCDICTDDLM GSRSNFDSTLISPNSVFSQWRVVCDSLEDYDTLGTLCNSTE DGPIRRNPAGNVARPMVQRLPEPQDVAQCLEVGLFDTPPF YSNSTNSFRNTVEGYSDPTGKYDPAVRSLHNLAHLFLNGT GGQTHLSPNDPIFVLLHTFTDAVFDEWLRRYNADISTFPLE NAPIGHNRQYNMVPFWPPVTNTEMFVTAPDNLGYTYEIQ WPSREFSVPEIIAIAVVGALLLVALIFGTASYLIRARRSMDE ANQPLLTDQYQCYAEEYEKLQNPNQSVV | 114 |
| Human EGFRvIII | LEEKKGNYVVTDHGSCVRACGADSYEMEEDGVRKCKKCE GPCRKVCNGIGIGEFKDSLSINATNIKHFKNCTSISGDLHILP VAFRGDSFTHTPPLDPQELDILKTVKEITGFLLIQAWPENRT DLHAFENLEIIRGRTKQHGQFSLAVVSLNITSLGLRSLKEISD GDVIISGNKNLCYANTINWKKLFGTSGQKTKIISNRGENSC KATGQVCHALCSPEGCWGPEPRDCVSCRNVSRGRECVDK CNLLEGEPREFVENSECIQCHPECLPQAMNITCTGRGPDNCI QCAHYIDGPHCVKTCPAGVMGENNTLVWKYADAGHVCH LCHPNCTYGCTGPGLEGCPTNGPKIPSIATGMVGALLLLLV VALGIGLFMRRRHIVRKRTLRRLLQERELVEPLTPSGEAPN QALLRILKETEFKKIKVLGSGAFGTVYKGLWIPEGEKVKIP VAIKELREATSPKANKEILDEAYVMASVDNPHVCRLLGICL TSTVQLITQLMPFGCLLDYVREHKDNIGSQYLLNWCVQIA KGMNYLEDRRLVHRDLAARNVLVKTPQHVKITDFGLAKL LGAEEKEYHAEGGKVPIKWMALESILHRIYTHQSDVWSYG VTVWELMTFGSKPYDGIPASEISSILEKGERLPQPPICTIDVY MIMVKCWMIDADSRPKFRELIIEFSKMARDPQRYLVIQGDE RMHLPSPTDSNFYRALMDEEDMDDVVDADEYLIPQQGFFS SPSTSRTPLLSSLSATSNNSTVACIDRNGLQSCPIKEDSFLQR YSSDPTGALTEDSIDDTFLPVPEYINQSVPKRPAGSVQNPVY HNQPLNPAPSRDPHYQDPHSTAVGNPEYLNTVQPTCVNST FDSPAHWAQKGSHQISLDNPDYQQDFFPKEAKPNGIFKGST AENAEYLRVAPQSSEFIGA | 115 |
| Human EGFR | LEEKKVCQGTSNKLTQLGTFEDHFLSLQRMFNNCEVVLGN LEITYVQRNYDLSFLKTIQEVAGYVLIALNTVERIPLENLQII RGNMYYENSYALAVLSNYDANKTGLKELPMRNLQEILHG AVRFSNNPALCNVESIQWRDIVSSDFLSNMSMDFQNHLGS CQKCDPSCPNGSCWGAGEENCQKLTKIICAQQCSGRCRGK SPSDCCHNQCAAGCTGPRESDCLVCRKFRDEATCKDTCPP LMLYNPTTYQMDVNPEGKYSFGATCVKKCPRNYVVTDHG SCVRACGADSYEMEEDGVRKCKKCEGPCRKVCNGIGIGEF KDSLSINATNIKHFKNCTSISGDLHILPVAFRGDSFTHTPPLD PQELDILKTVKEITGFLLIQAWPENRTDLHAFENLEIIRGRTK QHGQFSLAVVSLNITSLGLRSLKEISDGDVIISGNKNLCYAN TINWKKLFGTSGQKTKIISNRGENSCKATGQVCHALCSPEG CWGPEPRDCVSCRNVSRGRECVDKCNLLEGEPREFVENSE CIQCHPECLPQAMNITCTGRGPDNCIQCAHYIDGPHCVKTC PAGVMGENNTLVWKYADAGHVCHLCHPNCTYGCTGPGL EGCPTNGPKIPSIATGMVGALLLLLVVALGIGLFMRRRHIV RKRTLRRLLQERELVEPLTPSGEAPNQALLRILKETEFKKIK VLGSGAFGTVYKGLWIPEGEKVKIPVAIKELREATSPKANK | 116 |

-continued

| | Amino Acid Sequence | SEQ ID NO |
|---|---|---|
| | EILDEAYVMASVDNPHVCRLLGICLTSTVQLITQLMPFGCL LDYVREHKDNIGSQYLLNWCVQIAKGMNYLEDRRLVHRD LAARNVLVKTPQHVKITDFGLAKLLGAEEKEYHAEGGKVP IKWMALESILHRIYTHQSDVWSYGVTVWELMTFGSKPYDG IPASEISSILEKGERLPQPPICTIDVYMIMVKCWMIDADSRPK FRELIIEFSKMARDPQRYLVIQGDERMHLPSPTDSNFYRAL MDEEDMDDVVDADEYLIPQQGFFSSPSTSRTPLLSSLSATS NNSTVACIDRNGLQSCPIKEDSFLQRYSSDPTGALTEDSIDD TFLPVPEYINQSVPKRPAGSVQNPVYHNQPLNPAPSRDPHY QDPHSTAVGNPEYLNTVQPTCVNSTFDSPAHWAQKGSHQI SLDNPDYQQDFFPKEAKPNGIFKGSTAENAEYLRVAPQSSE FIGA | |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 117 |
| linker | GGGGSGGGGS | 118 |
| linker | DGGGGSGGGGS | 119 |
| Human kappa CL domain | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 120 |
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 121 |
| Human IgG1 heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 122 |

Bispecific CD3/FolR1 Antibody Sequences:
CDR Definition According to Kabat

| FOLR1_16D5 IgG_PGLALA | | |
|---|---|---|
| VH | EVQLVESGGGLVKPGGSLRLSCAASGFTFSNAWMSWVR QAPGKGLEWVGRIKSKTDGGTTDYAAPVKGRFTISRDDS KNTLYLQMNSLKTEDTAVYYCTTPWEWSWYDYWGQGT LVTVSS | 123 |
| CDRH1 | NAWMS | 124 |
| CDRH2 | RIKSKTDGGTTDYAAPVKG | 125 |
| CDRH3 | PWEWSWYDY | 126 |
| VL | QAVVTQEPSLTVSPGGTVTLTCGSSTGAVTTSNYANWVQ EKPGQAFRGLIGGTNKRAPGTPARFSGSLLGGKAALTLSG AQPEDEAEYYCALWYSNLWVFGGGTKLTVL | 11 |
| CDRL1 | GSSTGAVTTSNYAN | 8 |
| CDRL2 | GTNKRAP | 9 |
| CDRL3 | ALWYSNLWV | 10 |

| $CD3_{opt}$ IgG_PGLALA | | |
|---|---|---|
| VH | EVQLLESGGGLVQPGGSLRLSCAASGFQFSSYAMNWVRQ APGKGLEWVSRIRSKYNNYATYYADSVKGRFTISRDDSK NTLYLQMNSLRAEDTAVYYCVRHTTFPSSYVSYYGYWG QGTLVTVSS | 7 |
| CDRH1 | SYAMN | 2 |
| CDRH2 | RIRSKYNNYATYYADSVKG | 3 |
| CDRH3 | HTTFPSSYVSYYGY | 5 |
| VL | QAVVTQEPSLTVSPGGTVTLTCGSSTGAVTTSNYANWVQ EKPGQAFRGLIGGTNKRAPGTPARFSGSLLGGKAALTLSG AQPEDEAEYYCALWYSNLWVFGGGTKLTVL | 11 |

-continued

| | | |
|---|---|---|
| CDRL1 | GSSTGAVTTSNYAN | 8 |
| CDRL2 | GTNKRAP | 9 |
| CDRL3 | ALWYSNLWV | 10 |

FOLR1 TCB 16D5-CD3$_{opt}$ 2 + 1 classical format

| | | |
|---|---|---|
| K chain | EVQLLESGGGLVQPGGSLRLSCAASGFQFSSYAMNWVRQ | 127 |
| | APGKGLEWVSRIRSKYNNYATYYADSVKGRFTISRDDSK | |
| | NTLYLQMNSLRAEDTAVYYCVRHTTFPSSYVSYYGYWG | |
| | QGTLVTVSSASTKGPSVFPLAPSSKSTSGGTAALGCLVKD | |
| | YFPEPVTVSWNSGALTSGVHTFPAVLQSSGLYSLSSVVTV | |
| | PSSSLGTQTYICNVNHKPSNTKVDKKVEPKSCDGGGGSG | |
| | GGGSEVQLVESGGGLVKPGGSLRLSCAASGFTFSNAWMS | |
| | WVRQAPGKGLEWVGRIKSKTDGGTTDYAAPVKGRFTISR | |
| | DDSKNTLYLQMNSLKTEDTAVYYCTTPWEWSWYDYWG | |
| | QGTLVTVSSASTKGPSVFPLAPSSKSTSGGTAALGCLVKD | |
| | YFPEPVTVSWNSGALTSGVHTFPAVLQSSGLYSLSSVVTV | |
| | PSSSLGTQTYICNVNHKPSNTKVDKKVEPKSCDKTHTCPP | |
| | CPAPEAAGGPSVFLFPPKPKDTLMISRTPEVTCVVVDVSH | |
| | EDPEVKFNWYVDGVEVHNAKTKPREEQYNSTYRVVSVL | |
| | TVLHQDWLNGKEYKCKVSNKALGAPIEKTISKAKGQPRE | |
| | PQVYTLPPCRDELTKNQVSLWCLVKGFYPSDIAVEWESN | |
| | GQPENNYKTTPPVLDSDGSFFLYSKLTVDKSRWQQGNVF | |
| | SCSVMHEALHNHYTQKSLSLSP | |
| H chain | EVQLVESGGGLVKPGGSLRLSCAASGFTFSNAWMSWVR | 128 |
| | QAPGKGLEWVGRIKSKTDGGTTDYAAPVKGRFTISRDDS | |
| | KNTLYLQMNSLKTEDTAVYYCTTPWEWSWYDYWGQGT | |
| | LVTVSSASTKGPSVFPLAPSSKSTSGGTAALGCLVKDYFPE | |
| | PVTVSWNSGALTSGVHTFPAVLQSSGLYSLSSVVTVPSSS | |
| | LGTQTYICNVNHKPSNTKVDKKVEPKSCDKTHTCPPCPAP | |
| | EAAGGPSVFLFPPKPKDTLMISRTPEVTCVVVDVSHEDPE | |
| | VKFNWYVDGVEVHNAKTKPREEQYNSTYRVVSVLTVLH | |
| | QDWLNGKEYKCKVSNKALGAPIEKTISKAKGQPREPQVC | |
| | TLPPSRDELTKNQVSLSCAVKGFYPSDIAVEWESNGQPEN | |
| | NYKTTPPVLDSDGSFFLVSKLTVDKSRWQQGNVFSCSVM | |
| | HEALHNHYTQKSLSLSP | |
| Common | QAVVTQEPSLTVSPGGTVTLTCGSSTGAVTTSNYANWVQ | 129 |
| Light chain | EKPGQAFRGLIGGTNKRAPGTPARFSGSLLGGKAALTLSG | |
| | AQPEDEAEYYCALWYSNLWVFGGGTKLTVLGQPKAAPS | |
| | VTLFPPSSEELQANKATLVCLISDFYPGAVTVAWKADSSP | |
| | VKAGVETTTPSKQSNNKYAASSYLSLTPEQWKSHRSYSC | |
| | QVTHEGSTVEKTVAPTECS | |

FOLR1 TCB 16D5-CD3$_{opt}$ 2 + 1 inverted format

| | | |
|---|---|---|
| K chain | EVQLVESGGGLVKPGGSLRLSCAASGFTFSNAWMSWVR | 130 |
| | QAPGKGLEWVGRIKSKTDGGTTDYAAPVKGRFTISRDDS | |
| | KNTLYLQMNSLKTEDTAVYYCTTPWEWSWYDYWGQGT | |
| | LVTVSSASTKGPSVFPLAPSSKSTSGGTAALGCLVKDYFPE | |
| | PVTVSWNSGALTSGVHTFPAVLQSSGLYSLSSVVTVPSSS | |
| | LGTQTYICNVNHKPSNTKVDKKVEPKSCDGGGGSGGGGS | |
| | EVQLLESGGGLVQPGGSLRLSCAASGFQFSSYAMNWVRQ | |
| | APGKGLEWVSRIRSKYNNYATYYADSVKGRFTISRDDSK | |
| | NTLYLQMNSLRAEDTAVYYCVRHTTFPSSYVSYYGYWG | |
| | QGTLVTVSSASTKGPSVFPLAPSSKSTSGGTAALGCLVKD | |
| | YFPEPVTVSWNSGALTSGVHTFPAVLQSSGLYSLSSVVTV | |
| | PSSSLGTQTYICNVNHKPSNTKVDKKVEPKSCDKTHTCPP | |
| | CPAPEAAGGPSVFLFPPKPKDTLMISRTPEVTCVVVDVSH | |
| | EDPEVKFNWYVDGVEVHNAKTKPREEQYNSTYRVVSVL | |
| | TVLHQDWLNGKEYKCKVSNKALGAPIEKTISKAKGQPRE | |
| | PQVYTLPPCRDELTKNQVSLWCLVKGFYPSDIAVEWESN | |
| | GQPENNYKTTPPVLDSDGSFFLYSKLTVDKSRWQQGNVF | |
| | SCSVMHEALHNHYTQKSLSLSP | |
| H chain | FOLR1 TCB 16D5-CD3 cl22 2 + 1 classical format | 128 |
| L chain | FOLR1 TCB 16D5-CD3 cl22 2 + 1 classical format | 129 |

FOLR1 TCB 16D5-CD3$_{opt}$ 1 + 1 Head to tail inverted format

| | | |
|---|---|---|
| K chain | EVQLVESGGGLVKPGGSLRLSCAASGFTFSNAWMSWVR | 131 |
| | QAPGKGLEWVGRIKSKTDGGTTDYAAPVKGRFTISRDDS | |
| | KNTLYLQMNSLKTEDTAVYYCTTPWEWSWYDYWGQGT | |
| | LVTVSSASTKGPSVFPLAPSSKSTSGGTAALGCLVKDYFPE | |
| | PVTVSWNSGALTSGVHTFPAVLQSSGLYSLSSVVTVPSSS | |
| | LGTQTYICNVNHKPSNTKVDKKVEPKSCDGGGGSGGGGS | |
| | EVQLLESGGGLVQPGGSLRLSCAASGFQFSSYAMNWVRQ | |
| | APGKGLEWVSRIRSKYNNYATYYADSVKGRFTISRDDSK | |
| | NTLYLQMNSLRAEDTAVYYCVRHTTFPSSYVSYYGYWG | |
| | QGTLVTVSSASTKGPSVFPLAPSSKSTSGGTAALGCLVKD | |
| | YFPEPVTVSWNSGALTSGVHTFPAVLQSSGLYSLSSVVTV | |

-continued

| | | |
|---|---|---|
| | PSSSLGTQTYICNVNHKPSNTKVDKKVEPKSCDKTHTCPP<br>CPAPEAAGGPSVFLFPPKPKDTLMISRTPEVTCVVVDVSH<br>EDPEVKFNWYVDGVEVHNAKTKPREEQYNSTYRVVSVL<br>TVLHQDWLNGKEYKCKVSNKALGAPIEKTISKAKGQPRE<br>PQVYTLPPCRDELTKNQVSLWCLVKGFYPSDIAVEWESN<br>GQPENNYKTTPPVLDSDGSFFLYSKLTVDKSRWQQGNVF<br>SCSVMHEALHNHYTQKSLSLSP | |
| H chain | DKTHTCPPCPAPEAAGGPSVFLFPPKPKDTLMISRTPEVTC<br>VVVDVSHEDPEVKFNWYVDGVEVHNAKTKPREEQYNST<br>YRVVSVLTVLHQDWLNGKEYKCKVSNKALGAPIEKTISK<br>AKGQPREPQVCTLPPSRDELTKNQVSLSCAVKGFYPSDIA<br>VEWESNGQPENNYKTTPPVLDSDGSFFLVSKLTVDKSRW<br>QQGNVFSCSVMHEALHNHYTQKSLSLSP | 132 |
| L chain | FOLR1 TCB 16D5-CD3 cl22 2 + 1 classical format | 129 |

FOLR1 TCB 16D5-CD3$_{opt}$ 1 + 1 Head to tail classical format

| | | |
|---|---|---|
| K chain | EVQLLESGGGLVQPGGSLRLSCAASGFQFSSYAMNWVRQ<br>APGKGLEWVSRIRSKYNNYATYYADSVKGRFTISRDDSK<br>NTLYLQMNSLRAEDTAVYYCVRHTTFPSSYVSYYGYWG<br>QGTLVTVSSASTKGPSVFPLAPSSKSTSGGTAALGCLVKD<br>YFPEPVTVSWNSGALTSGVHTFPAVLQSSGLYSLSSVVTV<br>PSSSLGTQTYICNVNHKPSNTKVDKKVEPKSCDGGGGSG<br>GGGSEVQLVESGGGLVKPGGSLRLSCAASGFTFSNAWMS<br>WVRQAPGKGLEWVGRIKSKTDGGTTDYAAPVKGRFTISR<br>DDSKNTLYLQMNSLKTEDTAVYYCTTPWEWSWYDYWG<br>QGTLVTVSSASTKGPSVFPLAPSSKSTSGGTAALGCLVKD<br>YFPEPVTVSWNSGALTSGVHTFPAVLQSSGLYSLSSVVTV<br>PSSSLGTQTYICNVNHKPSNTKVDKKVEPKSCDKTHTCPP<br>CPAPEAAGGPSVFLFPPKPKDTLMISRTPEVTCVVVDVSH<br>EDPEVKFNWYVDGVEVHNAKTKPREEQYNSTYRVVSVL<br>TVLHQDWLNGKEYKCKVSNKALGAPIEKTISKAKGQPRE<br>PQVYTLPPCRDELTKNQVSLWCLVKGFYPSDIAVEWESN<br>GQPENNYKTTPPVLDSDGSFFLYSKLTVDKSRWQQGNVF<br>SCSVMHEALHNHYTQKSLSLSP | 133 |
| H chain | DKTHTCPPCPAPEAAGGPSVFLFPPKPKDTLMISRTPEVTC<br>VVVDVSHEDPEVKFNWYVDGVEVHNAKTKPREEQYNST<br>YRVVSVLTVLHQDWLNGKEYKCKVSNKALGAPIEKTISK<br>AKGQPREPQVCTLPPSRDELTKNQVSLSCAVKGFYPSDIA<br>VEWESNGQPENNYKTTPPVLDSDGSFFLVSKLTVDKSRW<br>QQGNVFSCSVMHEALHNHYTQKSLSLSP | 134 |
| L chain | FOLR1 TCB 16D5-CD3 cl22 2 + 1 classical format | 129 |

FOLR1 TCB 16D5-CD3$_{opt}$ 1 + 1 IgG like format

| | | |
|---|---|---|
| K chain | EVQLVESGGGLVKPGGSLRLSCAASGFTFSNAWMSWVR<br>QAPGKGLEWVGRIKSKTDGGTTDYAAPVKGRFTISRDDS<br>KNTLYLQMNSLKTEDTAVYYCTTPWEWSWYDYWGQGT<br>LVTVSSASTKGPSVFPLAPSSKSTSGGTAALGCLVKDYFPE<br>PVTVSWNSGALTSGVHTFPAVLQSSGLYSLSSVVTVPSSS<br>LGTQTYICNVNHKPSNTKVDKKVEPKSCDKTHTCPPCPAP<br>EAAGGPSVFLFPPKPKDTLMISRTPEVTCVVVDVSHEDPE<br>VKFNWYVDGVEVHNAKTKPREEQYNSTYRVVSVLTVLH<br>QDWLNGKEYKCKVSNKALGAPIEKTISKAKGQPREPQVY<br>TLPPCRDELTKNQVSLWCLVKGFYPSDIAVEWESNGQPE<br>NNYKTTPPVLDSDGSFFLYSKLTVDKSRWQQGNVFSCSV<br>MHEALHNHYTQKSLSLSP | 135 |
| H chain | EVQLVESGGGLVKPGGSLRLSCAASGFTFSNAWMSWVR<br>QAPGKGLEWVGRIKSKTDGGTTDYAAPVKGRFTISRDDS<br>KNTLYLQMNSLKTEDTAVYYCTTPWEWSWYDYWGQGT<br>LVTVSSASTKGPSVFPLAPSSKSTSGGTAALGCLVKDYFPE<br>PVTVSWNSGALTSGVHTFPAVLQSSGLYSLSSVVTVPSSS<br>LGTQTYICNVNHKPSNTKVDKKVEPKSCDKTHTCPPCPAP<br>EAAGGPSVFLFPPKPKDTLMISRTPEVTCVVVDVSHEDPE<br>VKFNWYVDGVEVHNAKTKPREEQYNSTYRVVSVLTVLH<br>QDWLNGKEYKCKVSNKALGAPIEKTISKAKGQPREPQVC<br>TLPPSRDELTKNQVSLSCAVKGFYPSDIAVEWESNGQPEN<br>NYKTTPPVLDSDGSFFLVSKLTVDKSRWQQGNVFSCSVM<br>HEALHNHYTQKSLSLSP | 136 |
| L chain | FOLR1 TCB 16D5-CD3 cl22 2 + 1 classical format | 129 |
| hu FolR1 | MAQRMTTQLLLLLVWVAVVGEAQTRIAWARTELLNVC<br>MNAKHHKEKPGPEDKLHEQCRPWRKNACCSTNTSQEAH<br>KDVSYLYRFNWNHCGEMAPACKRHFIQDTCLYECSPNLG<br>PWIQQVDQSWRKERVLNVPLCKEDCEQWWEDCRTSYTC<br>KSNWHKGWNWTSGFNKCAVGAACQPFHFYFPTPTVLCN<br>EIWTHSYKVSNYSRGSGRCIQMWFDPAQGNPNEEVARFY<br>AAAMSGAGPWAAWPFLLSLALMLLWLLS | 137 |

IV. Examples

The following are examples of methods and compositions of the invention. It is understood that various other aspects may be practiced, given the general description provided above.

Example 1—Generation of Optimized CD3 Binder

Starting from a previously described (see e.g. WO 2014/131712, incorporated herein by reference) CD3 binder, termed "$CD3_{orig}$" herein and comprising the VH and VL sequences of SEQ ID NOs 6 and 11, respectively, we aimed at optimizing properties of this binder by removal of two asparagine deamidation sequence motifs at Kabat positions 97 and 100 of the heavy chain CDR3. To this aim, we generated an antibody library, suitable for phage display, of the heavy chain with both asparagines at Kabat position 97 and 100 removed, and in addition the CDRs H1, H2, and H3 randomized in order to compensate for loss of affinity caused by replacing Asn97 and Asn100 through an affinity-maturation process.

This library was put on a filamentous phage via fusion to minor coat protein p3 (Marks et al. (1991) *J Mol Biol* 222, 581-597) and selected for binding to recombinant CD3ε.

10 candidate clones were identified in the initial screening, showing acceptable binding on recombinant antigen as measured by SPR as Fab fragments (produced in *E. coli*).

Only one of these clones, however, showed acceptable binding activity to CD3 expressing cells as measured by flow cytometry after conversion to IgG format.

The selected clone, termed "$CD3_{opt}$" herein and comprising the VH and VL sequences of SEQ ID NOs 7 and 11, respectively, was further evaluated and converted into bispecific format as described in the following.

Example 2—Binding of Optimized CD3 Binder to CD3

Binding to Recombinant CD3

Binding to recombinant CD3 was determined by surface plasmon resonance (SPR) for the optimized CD3 binder "$CD3_{opt}$" and the original CD3 binder "$CD3_{orig}$", both in human IgG1 format with P329G L234A L235A ("PGLALA", EU numbering) mutations in the Fc region (SEQ ID NOs 12 and 14 ($CD3_{orig}$) and SEQ ID NOs 13 and 14 ($CD3_{opt}$)).

In order to assess the effect of the deamidation site removal and its effect on the stability of the antibodies, binding of the original and the optimized CD3 binder to recombinant CD3 was tested after temperature stress for 14 days at 37 °C or 40 °C. Samples stored at −80 °C were used as reference. The reference samples and the samples stressed at 40 °C were in 20 mM His, 140 mM NaCl, pH 6.0, and the samples stressed at 37 °C in PBS, pH 7.4, all at a concentration of 1.2-1.3 mg/ml. After the stress period (14 days) samples in PBS were dialyzed back to 20 mM His, 140 mM NaCl, pH 6.0 for further analysis.

Relative Active Concentration (RAC) of the samples was determined by SPR as follows.

SPR was performed on a Biacore T200 instrument (GE Healthcare). Anti-Fab capturing antibody (GE Healthcare, #28958325) was immobilized on a Series S Sensor Chip CM5 (GE Healthcare) using standard amine coupling chemistry, resulting in a surface density of 4000-6000 resonance units (RU). As running and dilution buffer, HBS-P+(10 mM HEPES, 150 mM NaCl pH 7.4, 0.05% Surfactant P20) was used. CD3 antibodies with a concentration of 2 μg/ml were injected for 60 s at a flow rate of 5 μl/min. CD3 antigen (see below) was injected at a concentration of 10 μg/ml for 120 s and dissociation was monitored at a flow rate of 5 μl/min for 120 s. The chip surface was regenerated by two consecutive injections of 10 mM glycine pH 2.1 for 60 s each. Bulk refractive index differences were corrected by subtracting blank injections and by subtracting the response obtained from the blank control flow cell. For evaluation, the binding response was taken 5 seconds after injection end. To normalize the binding signal, the CD3 binding was divided by the anti-Fab response (the signal (RU) obtained upon capture of the CD3 antibody on the immobilized anti-Fab antibody). The relative active concentration was calculated by referencing each temperature stressed sample to the corresponding, non-stressed sample.

The antigen used was a heterodimer of CD3 delta and CD3 epsilon ectodomains fused to a human Fc domain with knob-into-hole modifications and a C-terminal Avi-tag (see SEQ ID NOs 28 and 29).

Figure 2:
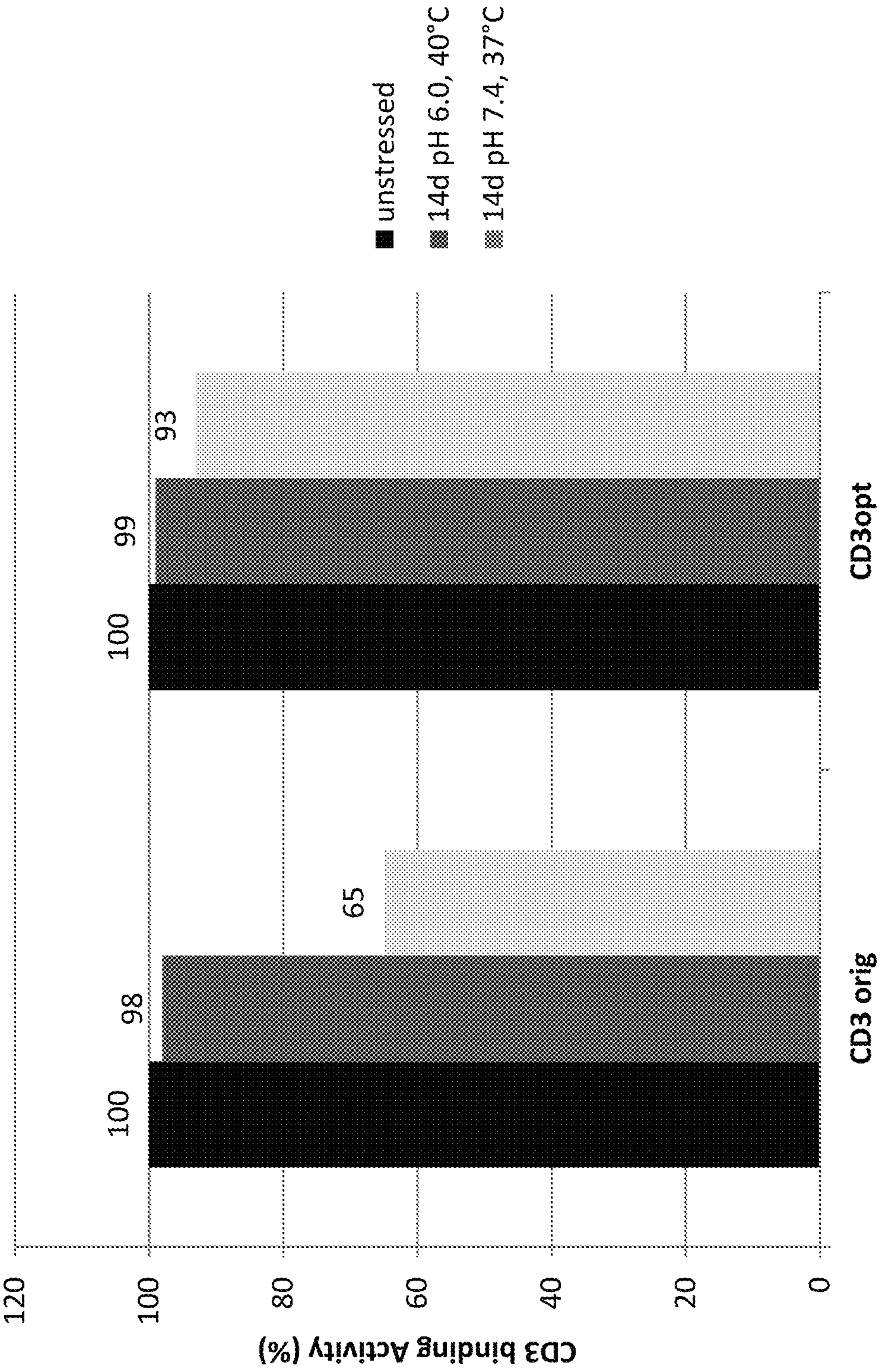
FIG. 2. Relative binding activity of original and optimized CD3 binders, $CD3_{orig}$ and $CD3_{opt}$, to recombinant CD3 as measured by SPR in unstressed condition, after 14 d at 40 °C. pH 6, or after 14 d at 37 °C. pH 7.4 (IgG format).

The results of this experiment are shown in FIG. 2. As can be seen, the optimized CD3 binder $CD3_{opt}$ showed strongly improved binding to CD3 after temperature stress (2 weeks at 37 °C, pH 7.4) as compared to the original CD3 binder $CD3_{orig}$. This result demonstrates that the deamidation site removal was successful, and has yielded an antibody with superior stability properties, relevant for in vivo half-life, as well as formulation of the antibody at neutral pH.

Binding to CD3 on Jurkat Cells

Binding to CD3 on the human reporter T-cell line Jurkat NFAT was determined by FACS for the optimized CD3 binder "$CD3_{opt}$" and the original CD3 binder "$CD3_{orig}$", both in human $IgG_1$ format with P329G L234A L235A ("PGLALA", EU numbering) mutations in the Fc region (SEQ ID NOs 12 and 14 ($CD3_{orig}$) and SEQ ID NOs 13 and 14 ($CD3_{opt}$)).

Jurkat-NFAT reporter cells (GloResponse Jurkat NFAT-RE-luc2P; Promega #CS176501) are a human acute lymphatic leukemia reporter cell line with a NFAT promoter, expressing human CD3. The cells were cultured in RPMI1640, 2 g/l glucose, 2 g/l $NaHCO_3$, 10% FCS, 25 mM HEPES, 2 mM L-glutamine, 1×NEAA, 1×sodium-pyruvate at 0.1-0.5 mio cells per ml. A final concentration of 200 μg per ml hygromycin B was added whenever cells were passaged.

For the binding assay, Jurkat NFAT cells were harvested, washed with PBS and resuspended in FACS buffer. The antibody staining was performed in a 96-well round bottom plate. Therefore 100'000 to 200'000 cells were seeded per well. The plate was centrifuged for 4 min at 400×g and the supernatant was removed. The test antibodies were diluted in FACS buffer and 20 μl of the antibody solution were added to the cells for 30 min at 4 °C. To remove unbound antibody, the cells were washed twice with FACS buffer before addition of the diluted secondary antibody (PE-conjugated AffiniPure F(ab')2 Fragment goat anti-human IgG Fcg Fragment Specific; Jackson ImmunoResearch #109-116-170). After 30 min incubation at 4 °C unbound secondary antibody was washed away. Before measurement the cells were resuspended in 200 μl FACS buffer and then analyzed by flow cytometry using a BD Canto II device.

Figure 3:
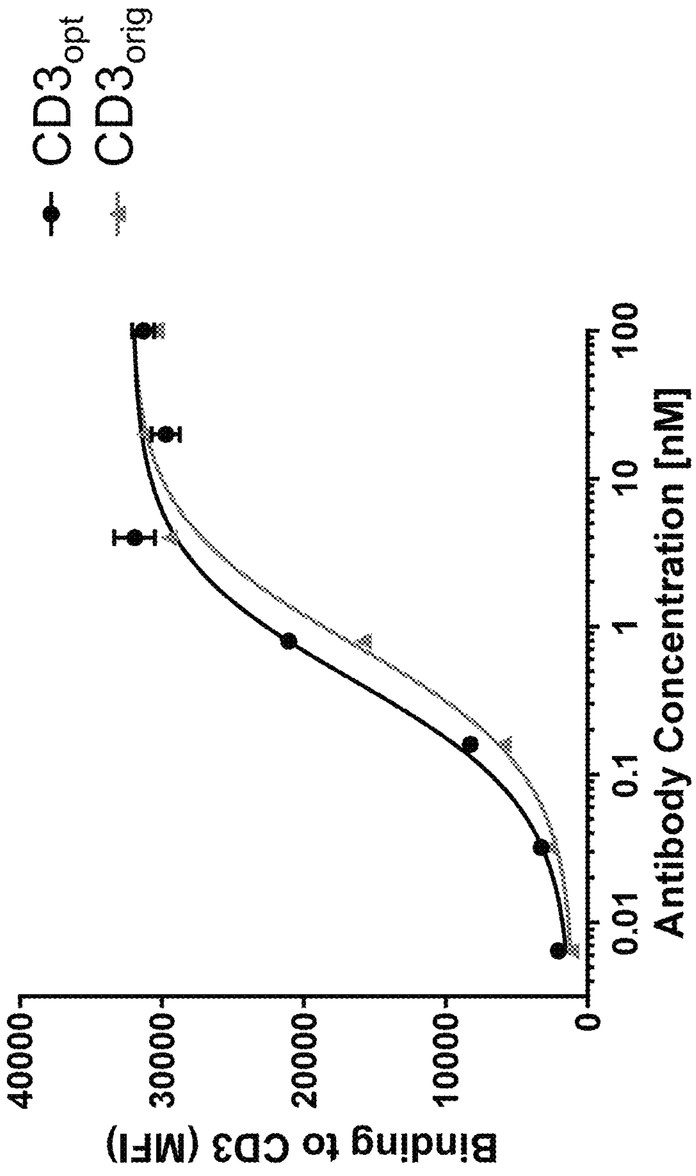
FIG. 3. Binding of original and optimized CD3 binders, $CD3_{orig}$ and $CD3_{opt}$, to Jurkat NFAT cells as measured by flow cytometry (IgG format). Antibodies bound to Jurkat NFAT cells were detected with a fluorescently labeled anti-human Fc specific secondary antibody.

As shown in FIG. 3, the optimized CD3 binder "$CD3_{opt}$" and the original CD3 binder "$CD3_{orig}$" bound comparably well to CD3 on Jurkat cells.

Example 3—Functional Activity of Optimized CD3 Binder

Figure 4:
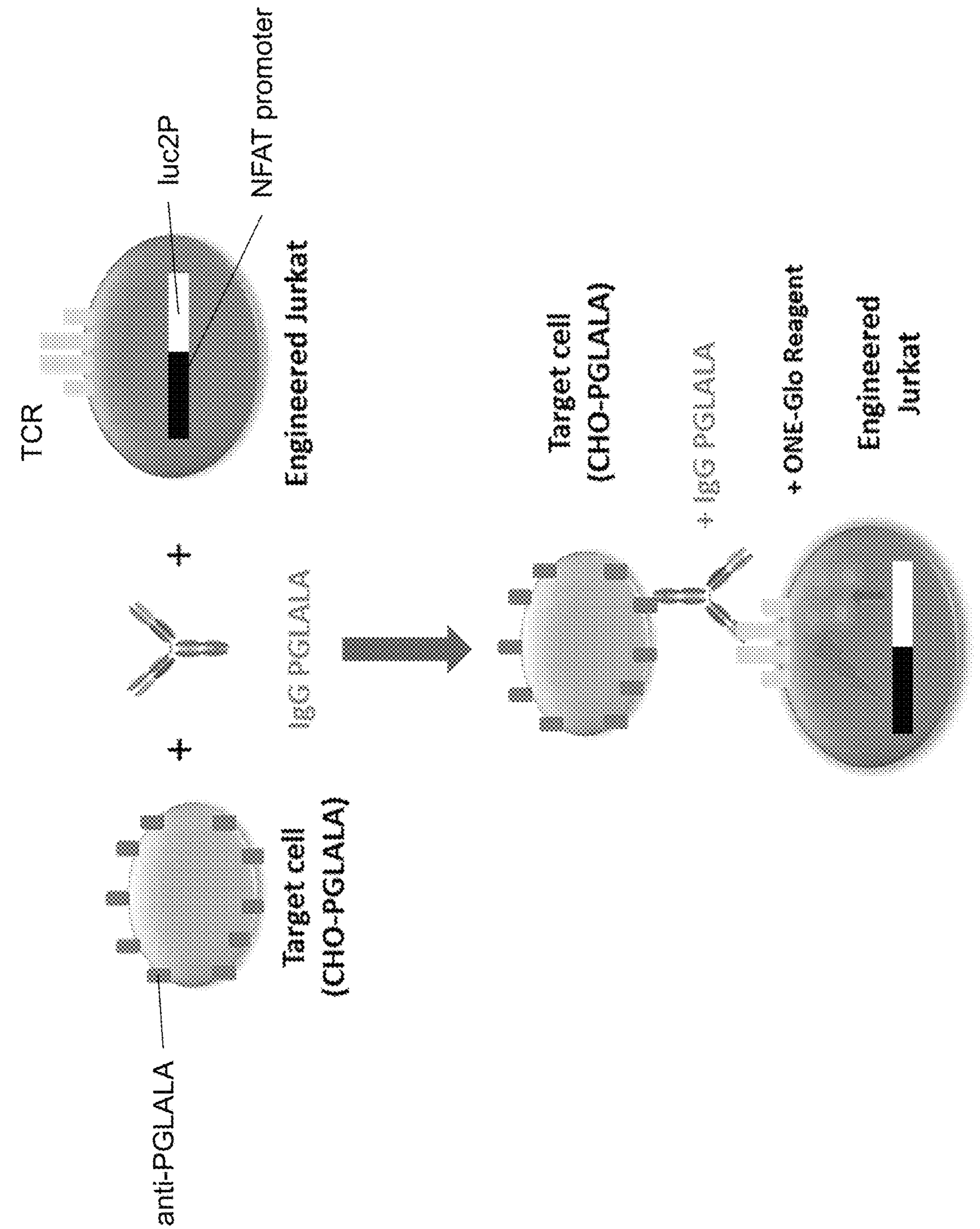
FIG. 4. Schematic illustration of the CD3 activation assay used in Example 3.

The functional activity of the optimized CD3 binder "$CD3_{opt}$" was tested in a Jurkat reporter cell assay and compared to the activity of the original CD3 binder "$CD3_{orig}$". To test the functional activity of the IgGs, anti-PGLALA expressing CHO cells were co-incubated with Jurkat NFAT reporter cells in the presence of increasing concentrations of $CD3_{opt}$ human IgG1 PGLALA or $CD3_{orig}$ human IgG1 PGLALA. Activation of CD3 on the Jurkat NFAT reporter cells upon T cell cross-linking induces the production of luciferase and luminescence can be measured as an activation marker. $CD3_{orig}$ human IgG1 wt was included as negative control which cannot bind to anti-PGLALA expressing CHO cells and therefore cannot be crosslinked on Jurkat NFAT cells. A schematic illustration of the assay is provided in FIG. 4.

Anti-PGLALA expressing CHO cells are CHO-K1 cells engineered to express on their surface an antibody that specifically binds human $IgG_1$ Fc(PGLALA) (see WO 2017/072210, incorporated herein by reference). These cells were cultured in DMEM/F12 medium containing 5% FCS+1% GluMax. The Jurkat NFAT reporter cells are as described in Example 2.

Upon simultaneous binding of the CD3 huIgG1 PGLALA to anti-PGLALA expressed on CHO and CD3 expressed on Jurkat-NFAT reporter cells, the NFAT promoter is activated and leads to expression of active firefly luciferase. The intensity of luminescence signal (obtained upon addition of luciferase substrate) is proportional to the intensity of CD3 activation and signaling. Jurkat-NFAT reporter cells grow in suspension and were cultured in RPMI1640, 2 g/l glucose, 2 g/l $NaHCO_3$, 10% FCS, 25 mM HEPES, 2 mM L-glutamin, 1×NEAA, 1×sodium-pyruvate at 0.1-0.5 mio cells per ml, 200 μg per ml hygromycin. For the assay, CHO cells were harvested and viability determined using ViCell. 30 000 target cells/well were plated in a flat-bottom, white-walled 96-well-plate (Greiner bio-one #655098) in 100 μl medium and 50 μl/well of diluted antibodies or medium (for controls) were added to the CHO cells. Subsequently, Jurkat-NFAT reporter cells were harvested and viability assessed using ViCell. Cells were resuspended at 1.2 mio cells/ml in cell culture medium without hygromycin B and added to CHO cells at 60 000 cells/well (50 μl/well) to obtain a final effector-to-target (E:T) ratio of 2:1 and a final volume of 200 μl per well. Then, 4 μl of GloSensor (Promega #E1291) was added to each well (2% of final volume). Cells were incubated for 24 h at 37 °C in a humidified incubator. At the end of incubation time, luminescence was detected using TECAN Spark 10M.

Figure 5:
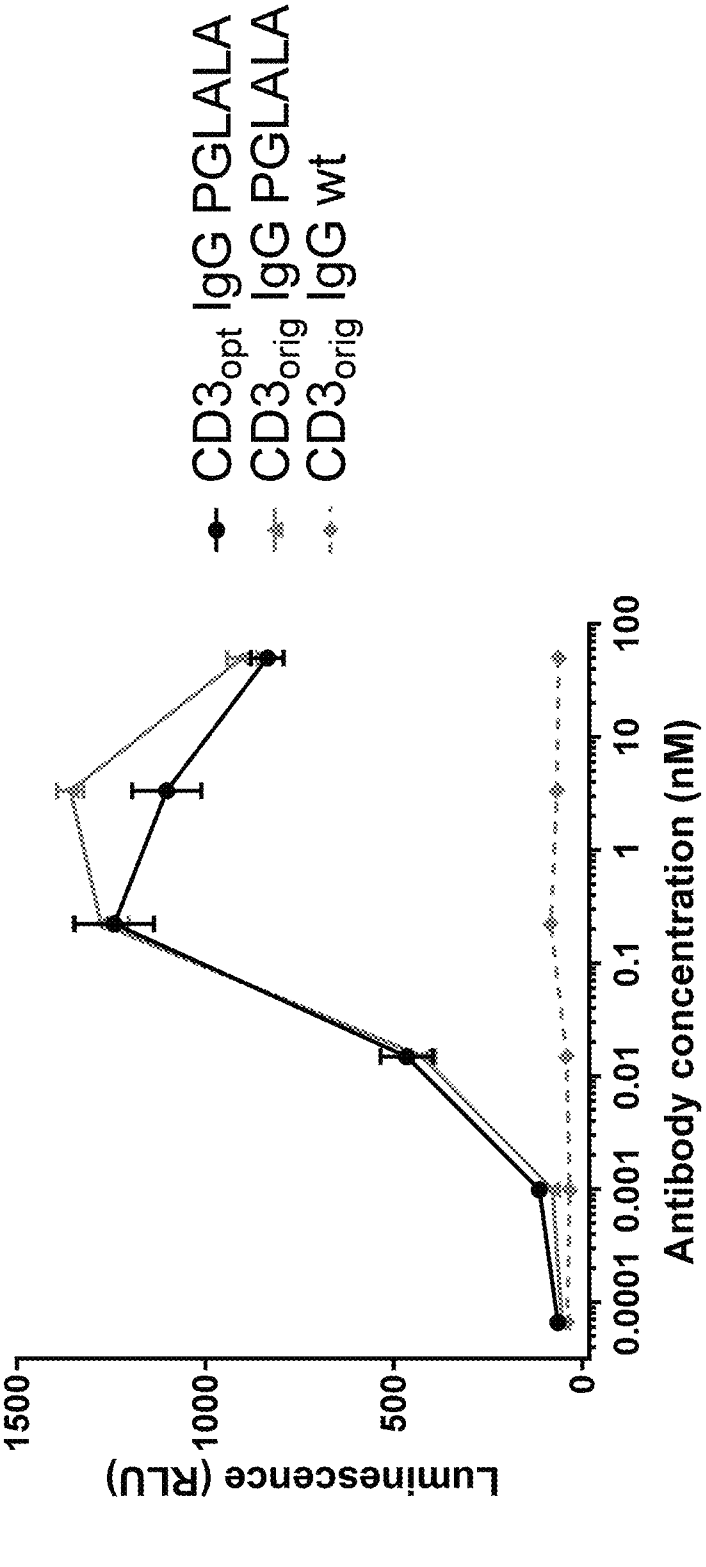
FIG. 5. Jurkat NFAT activation with original and optimized CD3 binders, $CD3_{orig}$ and $CD3_{opt}$ (IgG format). Jurkat NFAT reporter cells were co-incubated with anti-PGLALA expressing CHO (CHO-PGLALA) cells in the presence of $CD3_{orig}$ or $CD3_{opt}$ IgG PGLALA, or $CD3_{opt}$ IgG wt as negative control. CD3 activation was quantified by measuring luminescence after 24 h.

As shown in FIG. 5, the optimized CD3 binder $CD3_{opt}$ had a similar activity on Jurkat NFAT cells upon crosslinking as $CD3_{orig}$.

Example 4—Generation of T-Cell Bispecific Antibody Comprising Optimized CD3 Binder

TYRP1 TCB

The optimized CD3 binder identified in Example 1 ("$CD3_{opt}$", SEQ ID NOs 7 (VH) and 11 (VL)) was used to generate a T-cell bispecific antibody (TCB) targeting CD3 and TYRP1 ("TYRP1 TCB").

The TYRP1 binder comprised in this TCB was generated by humanization of the TYRP1 binder "TA99" (see GenBank entries AXQ57811 and AXQ57813 for the heavy and light chain, respectively), and comprises the heavy and light chain variable region sequences shown in SEQ ID NOs 18 and 22, respectively.

Figure 6:
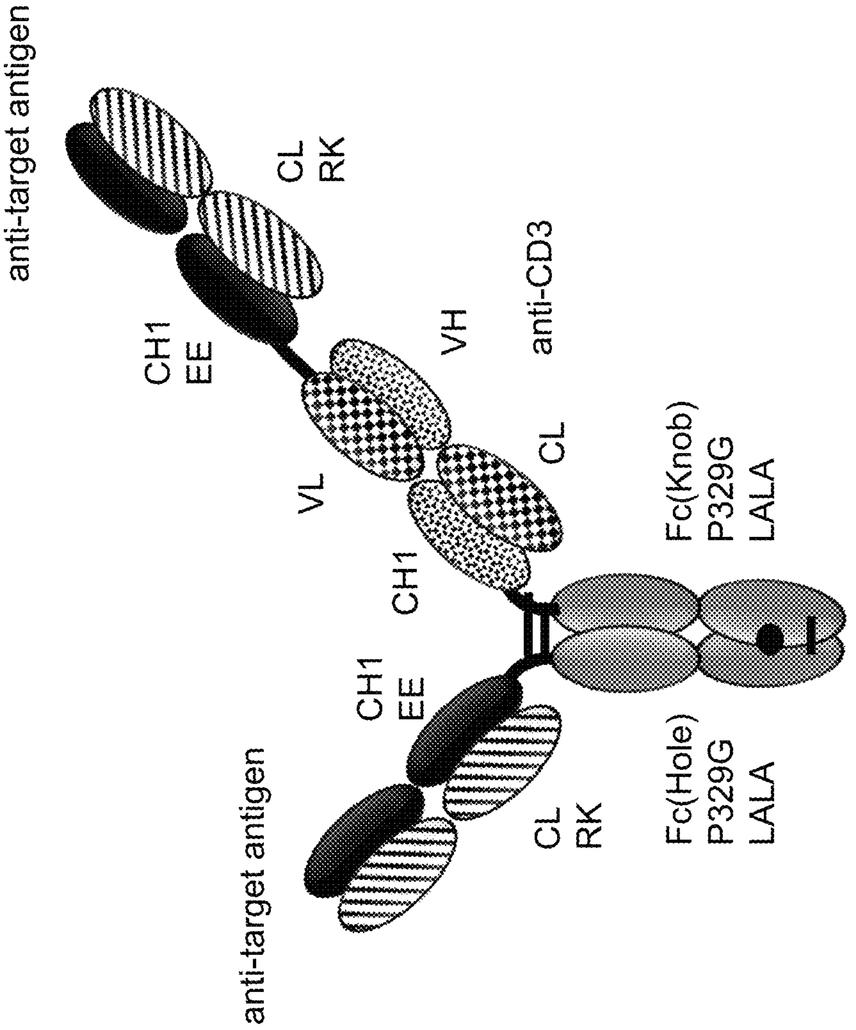
FIG. 6. Schematic illustration of the T-cell bispecific antibody (TCB) molecules prepared in the Examples. All tested TCB antibody molecules were produced as "2+1 IgG CrossFab, inverted" with charge modifications (VH/VL exchange in CD3 binder, charge modifications in target antigen binders, EE=147E, 213E; RK=123R, 124K).

A schematic illustration of the TCB molecule is provided in FIG. 6, and its full sequences are given in SEQ ID NOs 23, 24, 25 and 27.

An analogous molecule with the original CD3 binding sequences was also prepared (SEQ ID NOs 23, 24, 25 and 26).

Bispecific molecules were generated by transient transfection of HEK293 EBNA cells. The cells were transfected with the corresponding expression vectors in a 1:2:1:1 ratio ("vector heavy chain (VH-CH1-VL-CH1-CH2-CH3)": "vector light chain (VL-CL)": "vector heavy chain (VH-CH1-CH2-CH3)": "vector light chain (VH-CL)") Cells were centrifuged and medium was replaced by pre-warmed CD CHO medium (Thermo Fisher, #10743029). Expression vectors were mixed in CD CHO medium, PEI (polyethylenimine, Polysciences, #23966-1) was added, the solution vortexed and incubated for 10 minutes at room temperature. Afterwards, cells (2 mio/ml) were mixed with the vector/PEI solution, transferred to a flask and incubated for 3 hours at 37 °C in a shaking incubator with a 5% $CO_2$ atmosphere. After the incubation, Excell medium with supplements (80% of total volume) was added. One day after transfection, supplements (Feed, 12% of total volume) were added. Cell supernatants were harvested after 7 days by centrifugation and subsequent filtration (0.2 m filter).

Proteins were purified from filtered cell culture supernatants by standard methods. In brief, Fc containing proteins were purified from cell culture supernatants by Protein A-affinity chromatography (MabSelect Sure, GE Healthcare: equilibration buffer: 20 mM sodium citrate, 20 mM sodium phosphate, pH 7.5; elution buffer: 20 mM sodium citrate, 100 mM NaCl, 100 mM glycine pH 3.0). Elution was achieved at pH 3.0 followed by immediate pH neutralization of the sample. The protein was concentrated by centrifugation (Millipore Amicon® ULTRA-15 (#UFC903096)), and aggregated protein was separated from monomeric protein by size exclusion chromatography (Superdex 200, GE Healthcare) in 20 mM histidine, 140 mM sodium chloride, pH 6.0.

The concentration of purified proteins was determined by measuring the absorption at 280 nm using the mass extinction coefficient calculated on the basis of the amino acid sequence according to Pace et al. (1995), Protein Science 4, 2411-23. Purity and molecular weight of the proteins were analyzed by CE-SDS in the presence and absence of a reducing agent using a LabChipGXII (Perkin Elmer) (Table 1). Determination of the aggregate content was performed by HPLC chromatography at 25 °C using analytical size-exclusion column (TSKgel G3000 SW XL or UP-SW3000) equilibrated in running buffer (25 mM $K_2HPO_4$, 125 mM NaCl, 200 mM L-arginine monohydrochloride, pH 6.7 or 200 mM $KH_2PO_4$, 250 mM KCl pH 6.2, respectively) (Table 2).

TABLE 1

CE-SDS analyses (non-reduced) of TYRP1 TCBs.

| Molecule | Peak # | Size [kDa] | Purity [%] |
|---|---|---|---|
| TYRP1 TCB $CD3_{opt}$ | 1 | 221 | 100 |
| TYRP1 TCB $CD3_{orig}$ | 1 | 206 | 100 |

TABLE 2

Summary production and purification of TYRP1 TCBs.

| Molecule | Titer [mg/l] | Recovery [%] | Yield [mg/l] | Analytical SEC (HMW/Monomer/LMW) [%] |
|---|---|---|---|---|
| TYRP1 TCB $CD3_{opt}$ | 114 | 20 | 22.8 | 0.5/98.6/0.9 |
| TYRP1 TCB $CD3_{orig}$ | 72 | 12 | 8.7 | 0/97.5/2.5 |

Example 5—Binding of T-Cell Bispecific Antibody Comprising Optimized CD3 Binder to CD3 and TYRP1

Binding to Recombinant CD3

Binding of the TYRP1 TCB to recombinant CD3 was assessed by SPR, using the TCBs with either the optimized (TYRP1 TCB $CD3_{opt}$) or the original (TYRP1 TCB $CD3_{orig}$) CD3 binding sequences. SPR experiments were performed on a Biacore T200 with HBS-EP as running buffer (0.01 M HEPES pH 7.4, 0.15 M NaCl, 0.05% (v/v) Surfactant P20 (GE Healthcare)).

TYRP1 TCB was captured on a CM5 sensorchip surface with an immobilized antibody that specifically binds human $IgG_1$ Fc(PGLALA) (see WO 2017/072210, incorporated herein by reference). Capture antibody was coupled to the sensorchip surface by direct immobilization of around 8700 resonance units (RU) at pH 5.0 using the standard amine coupling kit (GE Healthcare). TCB molecules were captured for 30 s at 5 nM with a flow of 10 μl/min. The human and cynomolgus antigens (see below) were passed at a concentration of 12.35-3000 nM with a flow of 30 μl/min through the flow cells over 240 s. The dissociation phase was monitored for 240 s and triggered by switching from the sample solution to HBS-EP. The chip surface was regenerated after every cycle using one injection of 10 mM glycine pH 2.0 for 30 s. The antigens used were heterodimers of either human or cynomolgus CD3 delta and CD3 epsilon ectodomains fused to a human Fc domain with knob-into-hole modifications and a C-terminal Avi-tag (see SEQ ID NOs 28 and 29 (human CD3) and SEQ ID NOs 30 and 31 (cynomolgus CD3)). Bulk refractive index differences were corrected by subtracting the response obtained on the reference flow cell (no TCB captured). The affinity constants were derived from the kinetic rate constants by fitting to a 1:1 Langmuir binding using the BIAeval software (GE Healthcare).

The $K_D$ values for binding to human and cynomolgus CD3 were determined as 50 nM and 20 nM, respectively, for TYRP1 TCB $CD3_{opt}$ and were similar to the ones for TYRP1 TCB $CD3_{orig}$ (50 nM and 40 nM, respectively).

This shows that in unstressed condition both TCBs, comprising either $CD3_{opt}$ or $CD3_{orig}$, bound comparably well to recombinant CD3.

Binding of the TYRP1 TCB to recombinant human CD3 was also assessed after temperature stress for 14 days at 37 °C or 40 °C, using the TCBs with either the optimized or the original CD3 binding sequences. The experiment was performed as described in Example 2 above, using the TCB instead of IgG molecules.

Figure 7:
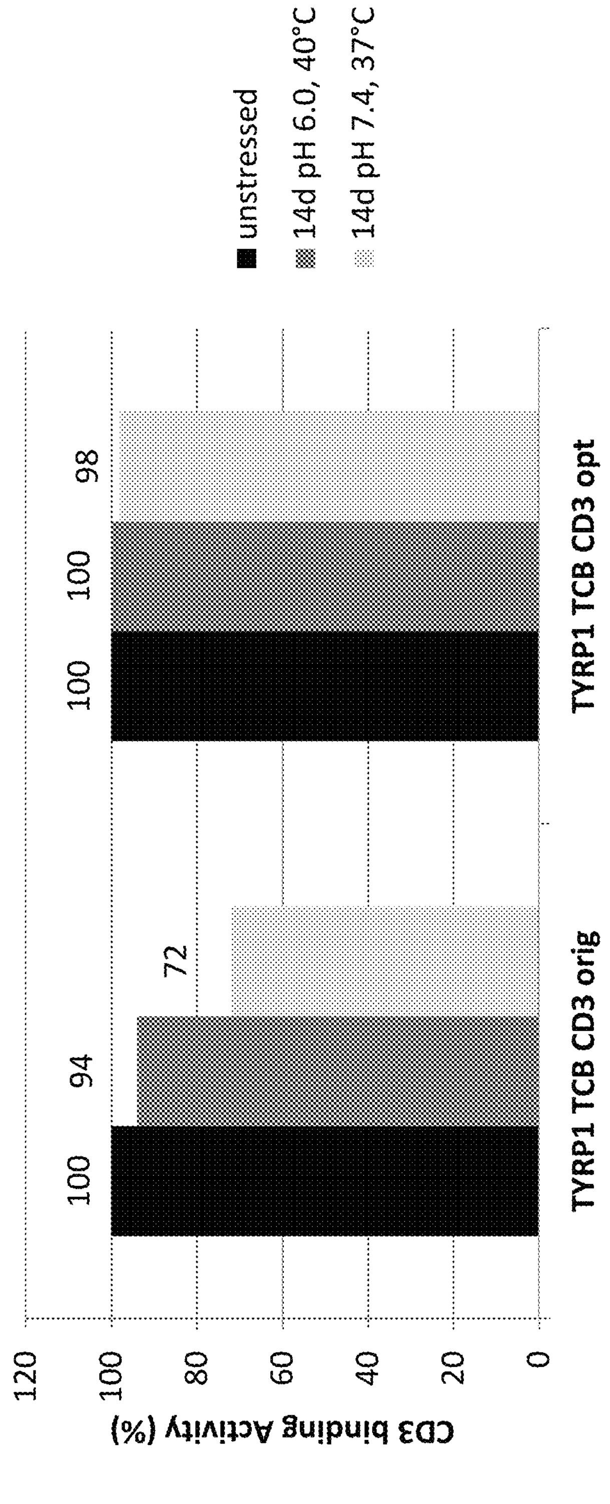
FIG. 7. Relative binding activity of TYRP1 TCBs comprising original or optimized CD3 binders, $CD3_{orig}$ or $CD3_{opt}$, to recombinant CD3 as measured by SPR in unstressed condition, after 14 d at 40 °C. pH 6, or after 14 d at 37 °C. pH 7.4.

The results of this experiment are shown in FIG. 7.

As can be seen in FIG. 7, the TCB comprising the optimized CD3 binder $CD3_{opt}$ showed strongly improved binding to CD3 after stress (2 weeks at 37 °C, pH 7.4) as compared to the TCB comprising the original CD3 binder $CD3_{orig}$. This result confirms that the improved properties of the optimized CD3 binder (see Example 2) are maintained at the TCB level.

Binding to Recombinant TYRP1

Binding to recombinant TYRP1 was assessed by SPR, using TYRP1 Fab fragments prepared by plasmin digestion of corresponding antibody.

SPR experiments were performed on a Biacore T200 with HBS-EP as running buffer (0.01 M HEPES pH 7.4, 0.15 M NaCl, 0.05% (v/v) Surfactant P20 (GE Healthcare)).

An antibody that specifically binds human $IgG_1$ Fc(PGLALA) (see WO 2017/072210, incorporated herein by reference) was directly coupled on a CM5 sensor chip at pH 5.0 using the standard amine coupling kit (GE Healthcare). Antigens (see below) were captured with a flow rate of 10 μl/min for 30 s. A 3-fold dilution series of the TYRP1 Fab fragments was passed on the flow cells at 30 μl/min for 180 s to record the association phase. The dissociation phase was monitored for 180 s or 1200 s and triggered by switching from the sample solution to HBS-EP. The chip surface was regenerated after every cycle using one injection of 10 mM glycine pH 2 for 30 s at 30 μl/min.

The antigens used were monomeric fusions of the human, cynomolgus or mouse TYRP1 extracellular domain (ECD) to a human Fc-domain with knob-into-hole (and PG LALA) modifications and a C-terminal Avi-tag (see SEQ ID NOs 32 and 35 (human TYRP1), SEQ ID NOs 33 and 35 (cynomolgus TYRP1) or SEQ ID NOs 34 and 35 (mouse TYRP1)).

Bulk refractive index differences were corrected by subtracting the response obtained on the reference flow cell (no antigen captured). The affinity constants ($K_D$) were derived from the kinetic rate constants by fitting to a 1:1 Langmuir binding using the BIAeval software (GE Healthcare). The $K_D$ values for binding to human, cynomolgus and mouse TYRP1 were determined as 130 pM, 180 pM and 530 pM, respectively, and were similar to the ones for the parental TA99 antibody (90 pM, 120 pM and 310 pM, respectively).

Binding of the TYRP1 TCB to recombinant TYRP1 was also assessed after temperature stress for 14 days at 37 °C or 40 °C, using the TCBs with either the optimized or the original CD3 binding sequences.

The experiment was performed as described above for the binding to CD3, using recombinant TYRP1 (Sino Biologicals) as antigen.

Figure 8:
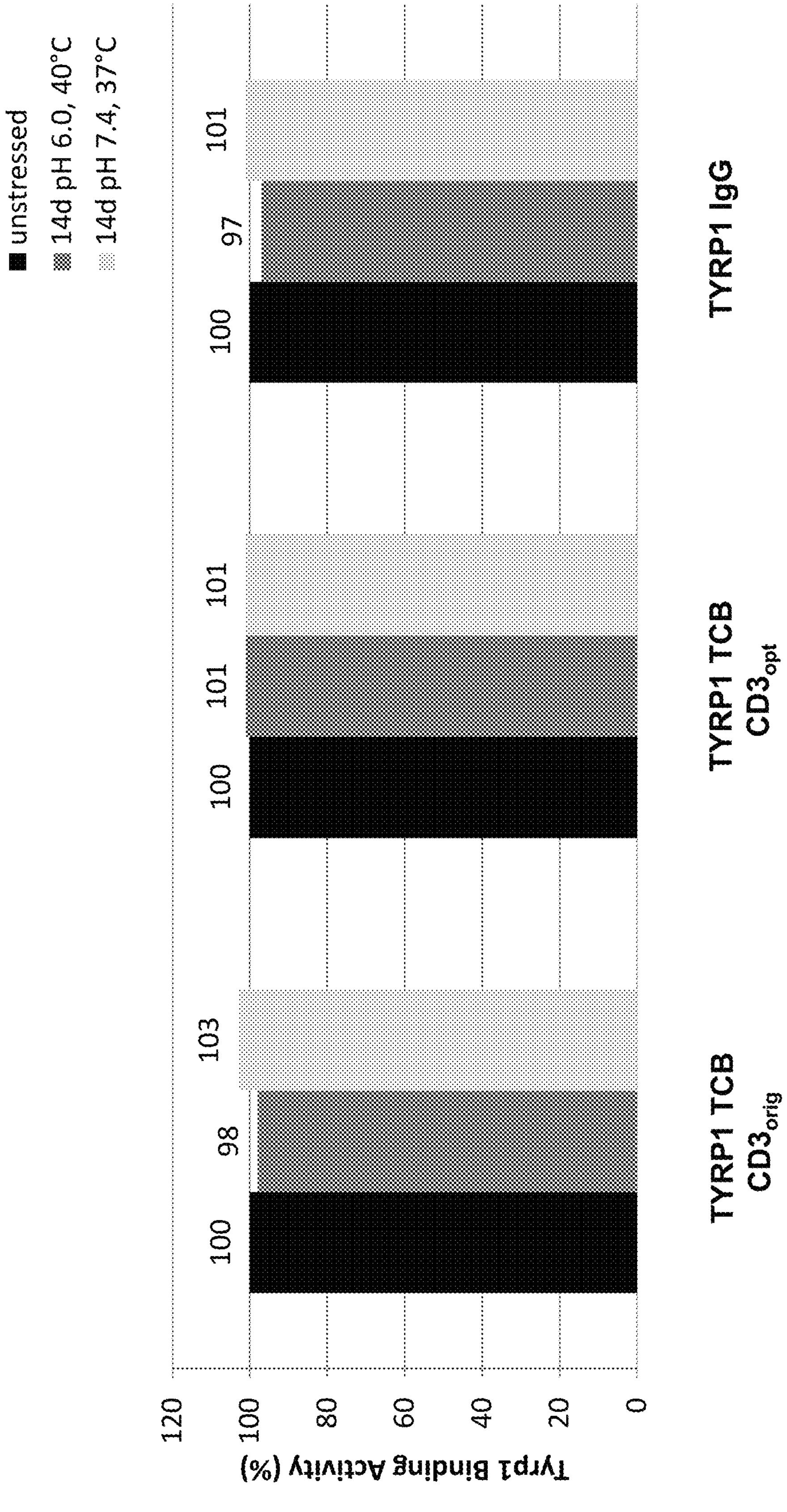
FIG. 8. Relative binding activity of TYRP1 TCBs comprising original or optimized CD3 binders, $CD3_{orig}$ or $CD3_{opt}$, or the corresponding TYRP1 IgG, to recombinant TYRP1 as measured by SPR in unstressed condition, after 14 d at 40 °C. pH 6, or after 14 d at 37 °C. pH 7.4.

The results of this experiment are shown in FIG. 8. They confirm that the binding to human TYRP1 for both TCBs (as well as for the corresponding TYRP1 binder in IgG format) is not affected by stress conditions.

Binding to CD3 on Jurkat Cells

Binding to CD3 on the human reporter T-cell line Jurkat NFAT was determined by FACS for TYRP1 TCBs comprising the optimized CD3 binder "$CD3_{opt}$" or the original CD3 binder "$CD3_{orig}$", as described above in Example 2.

Figure 9:
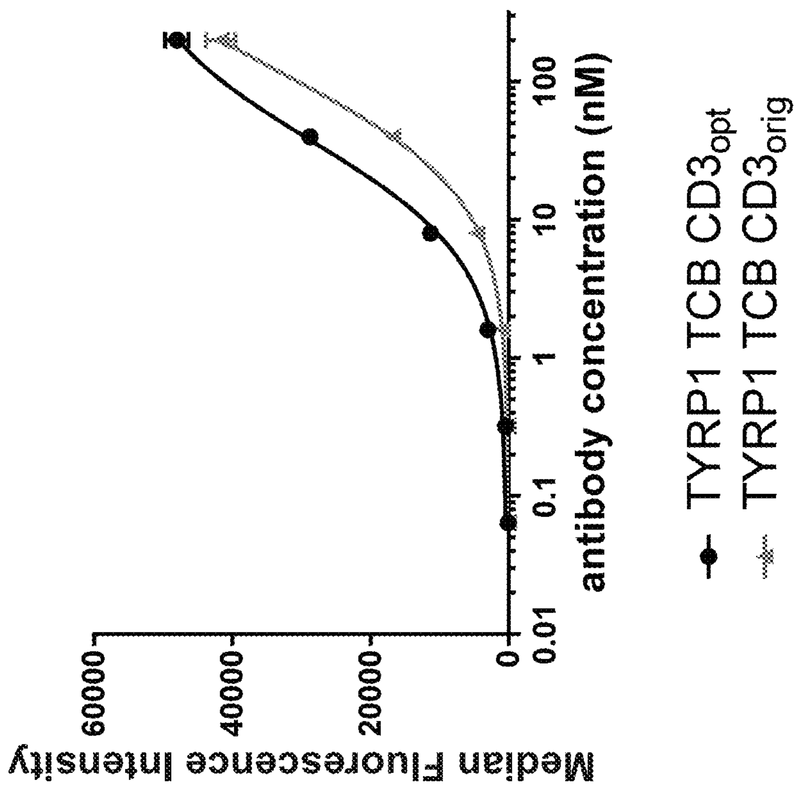
FIG. 9. Binding of TYRP1 TCBs comprising original or optimized CD3 binders, $CD3_{orig}$ or $CD3_{opt}$, to Jurkat NFAT cells as measured by flow cytometry. TCBs bound to Jurkat NFAT cells were detected with a fluorescently labeled anti-human Fc specific secondary antibody.

As shown in FIG. 9, the TCB comprising the optimized CD3 binder "$CD3_{opt}$" binds to CD3 on Jurkat cells at least comparably well to the TCB comprising the original CD3 binder "$CD3_{orig}$".

Example 6—Functional Activity of T-Cell Bispecific Antibody Comprising Optimized CD3 Binder CD3 Activation The TYRP1 TCBs containing either the optimized CD3 binder $CD3_{opt}$ or the original CD3 binder $CD3_{orig}$ (Example 4) were tested in the Jurkat NFAT reporter cell assay (see Example 3) in the presence of TYRP1 positive melanoma cells M150543 (primary melanoma cell line, obtained from the dermatology cell bank of the University of Zurich).

Upon simultaneous binding of TYRP1 TCB to TYRP1 positive target cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. The assay was performed as described in Example 3, using M150543 instead of anti-PGLALA expressing CHO cells.

Figure 10:
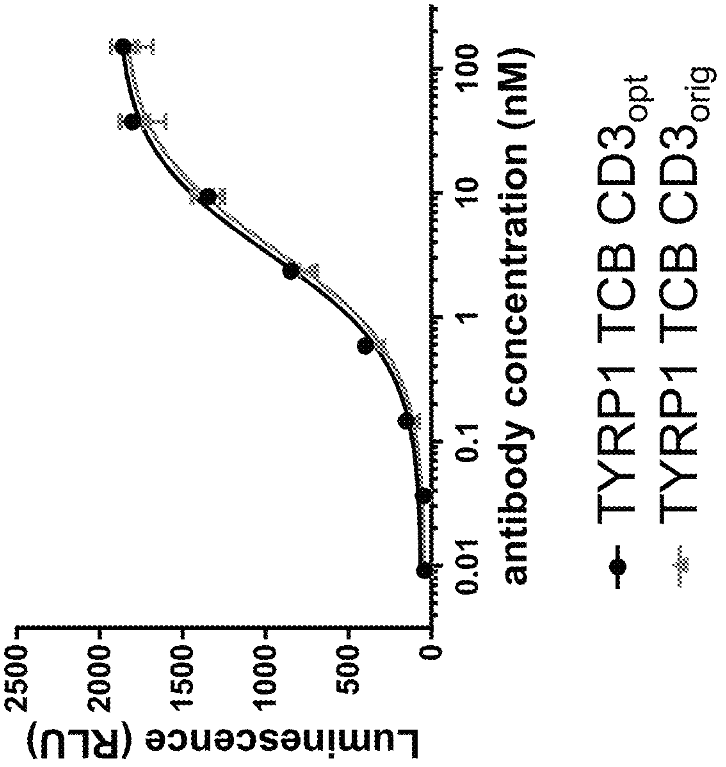
FIG. 10. Jurkat NFAT activation with TYRP1 TCBs comprising original or optimized CD3 binders. Jurkat NFAT reporter cells were co-incubated with the melanoma cell line M150543 in the presence of TYRP1 TCB $CD3_{orig}$ or TYRP1 TCB $CD3_{opt}$. CD3 activation in the presence of the TCBs was quantified by measuring luminescence after 24 h.

As seen for the IgGs (Example 3) both TCBs containing either $CD3_{opt}$ or $CD3_{orig}$ had a similar functional activity on the Jurkat NFAT reporter cells and induced CD3 activation in a concentration dependent manner (FIG. 10).

Target Cell Killing

In a next step, both TCB molecules were tested in a tumor cell killing assay with freshly isolated human PBMCs from three different donors, co-incubated with the human melanoma cell line M150543. Tumor cell lysis was determined by LDH release after 24 h and 48 h. Activation of CD4 and CD8 T cells was analyzed by upregulation of CD69 and CD25 on both cell subsets after 48 h.

Briefly, target cells were harvested with Trypsin/EDTA, washed, and plated at density of 30 000 cells/well using flat-bottom 96-well plates. Cells were left to adhere overnight. Peripheral blood mononuclear cells (PBMCs) were prepared by Histopaque density centrifugation of fresh blood obtained from healthy human donors. Fresh blood was diluted with sterile PBS and layered over Histopaque gradient (Sigma #H8889). After centrifugation (450×g, 30 minutes, room temperature), the plasma above the PBMC-containing interphase was discarded and PBMCs transferred into a new Falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom #K0302) at 37 °C, 5% $CO_2$ in cell incubator until further use (no longer than 24 h). For the killing assay, the antibodies were added at the indicated concentrations in triplicates. PBMCs were added to target cells at final effector-to-target (E:T) ratio of 10:1. Target cell killing was assessed after 24 h of incubation at 37 °C, 5% $CO_2$ by quantification of LDH released into cell supernatants by apoptotic/necrotic cells (LDH detection kit, Roche Applied Science #11 644 793 001). Maximal lysis of the target cells (=100%) was achieved by incubation of target cells with 1% Triton X-100. Minimal lysis (=0%) refers to target cells co-incubated with effector cells without bispecific construct.

Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend #300514), CD8 FITC (BioLegend #344704), CD25 BV421 (BioLegend #302630) and CD69 PE (BioLegend #310906) was performed according to the suppliers' indications. Cells were washed twice with 150 μl/well FACS buffer and fixed for 15 min at 4 °C using 100 μl/well fixation buffer (BD #554655). After centrifugation, the samples were resuspended in 200 μl/well FACS buffer. Samples were analyzed at BD FACS Fortessa.

Figures 11A, 11B:
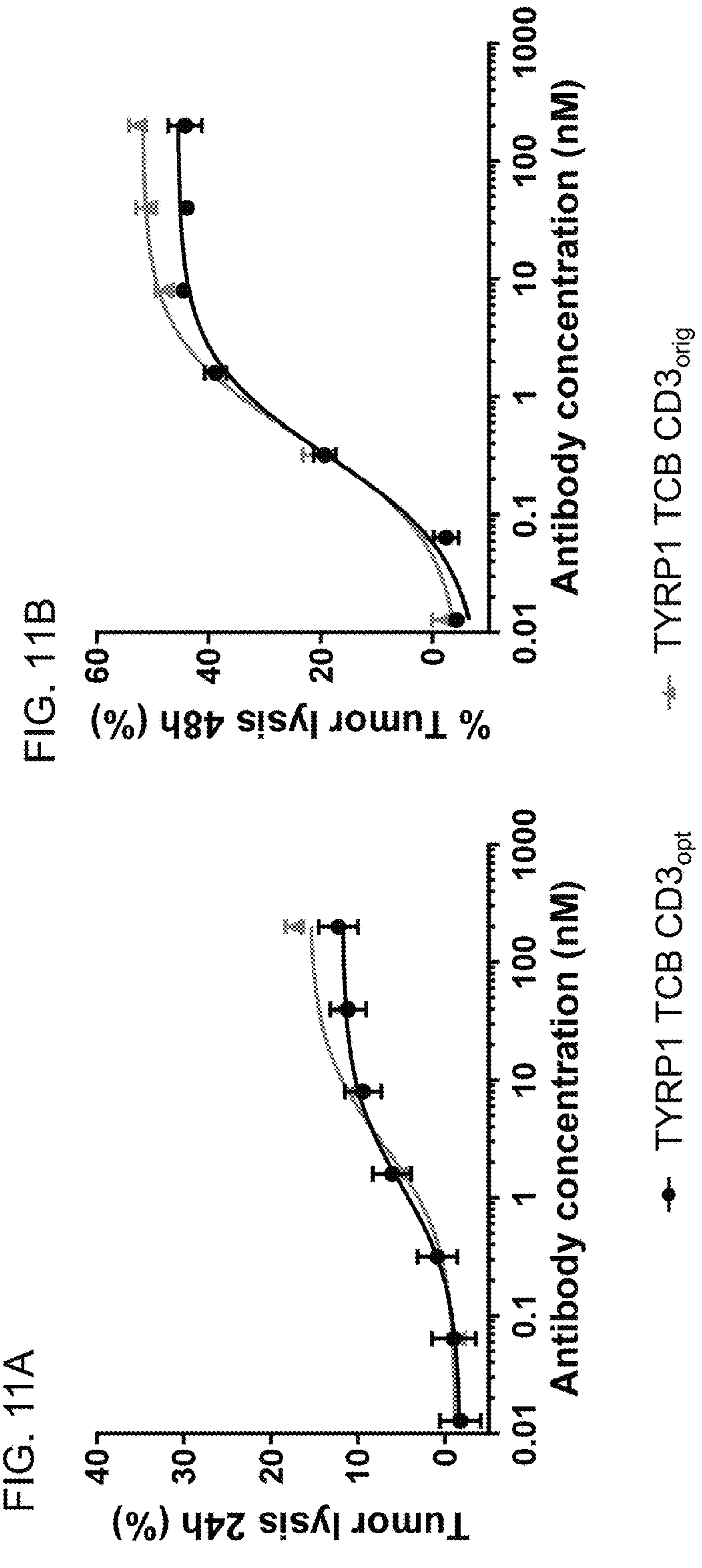
Figures 11C, 11D, 11E, 11F:
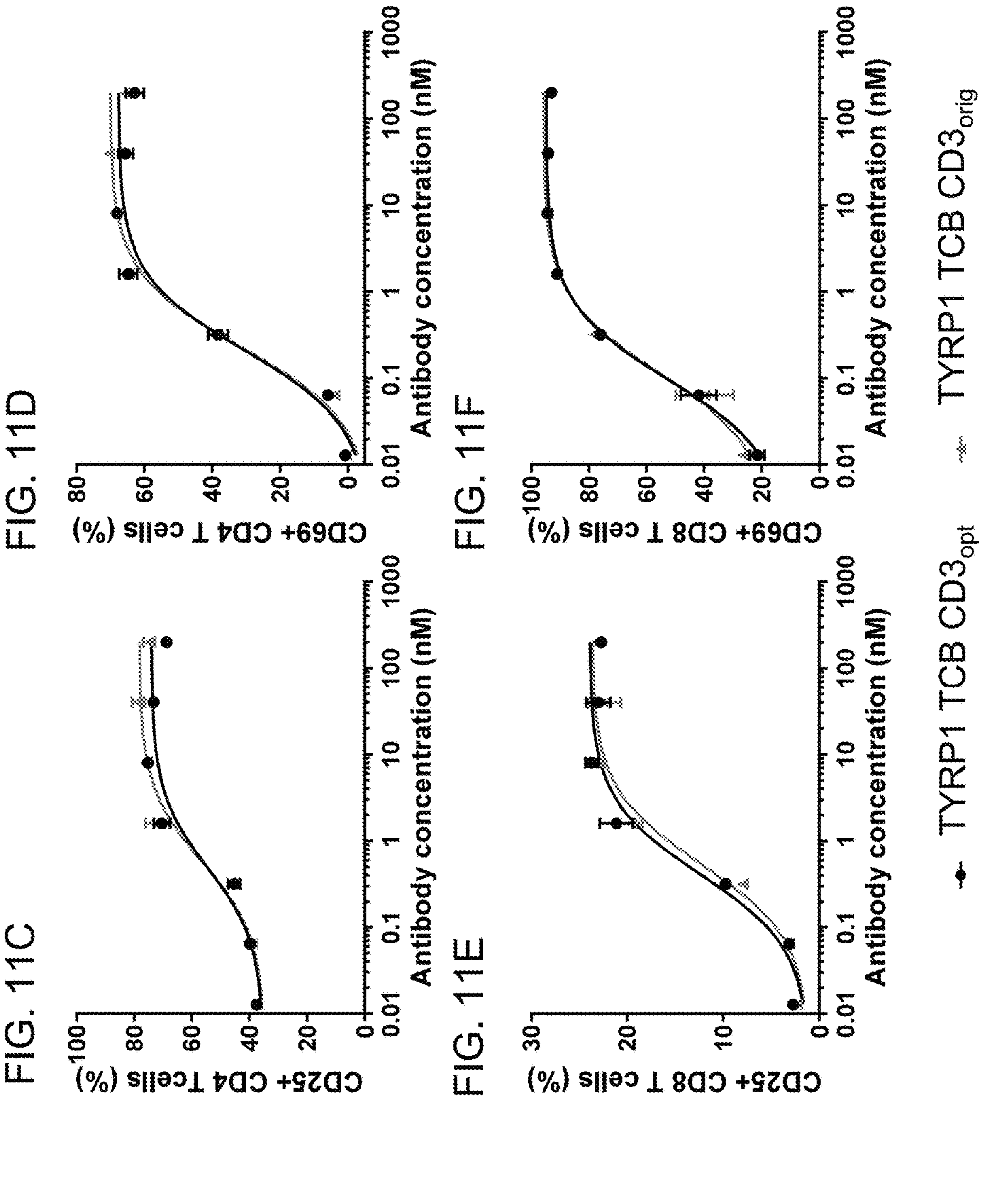
Figure 11G:
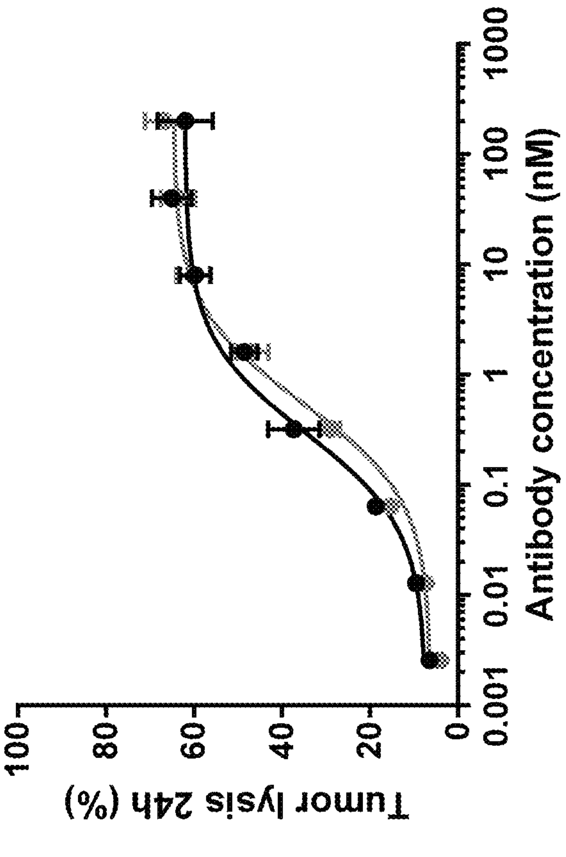
FIG. 11G-FIG. 11L: donor 2.
Figure 11H:
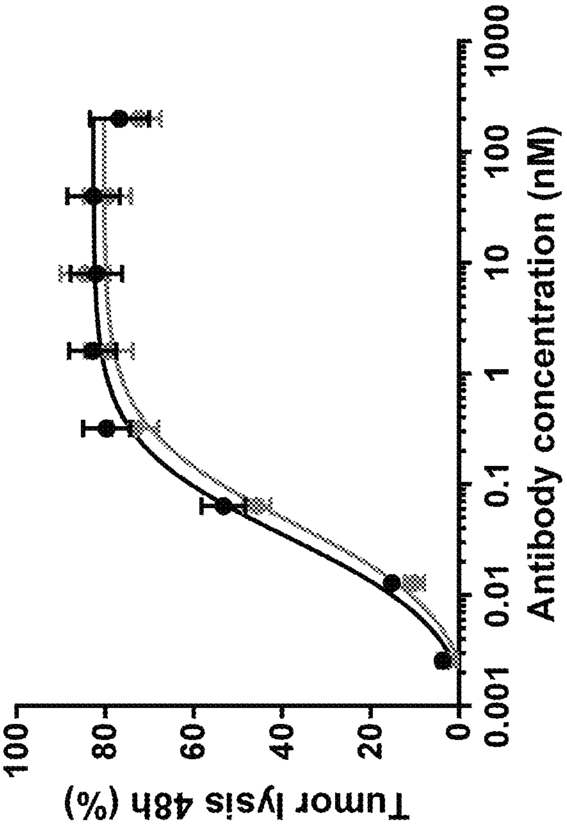
Figures 11I, 11J, 11K, 11L:
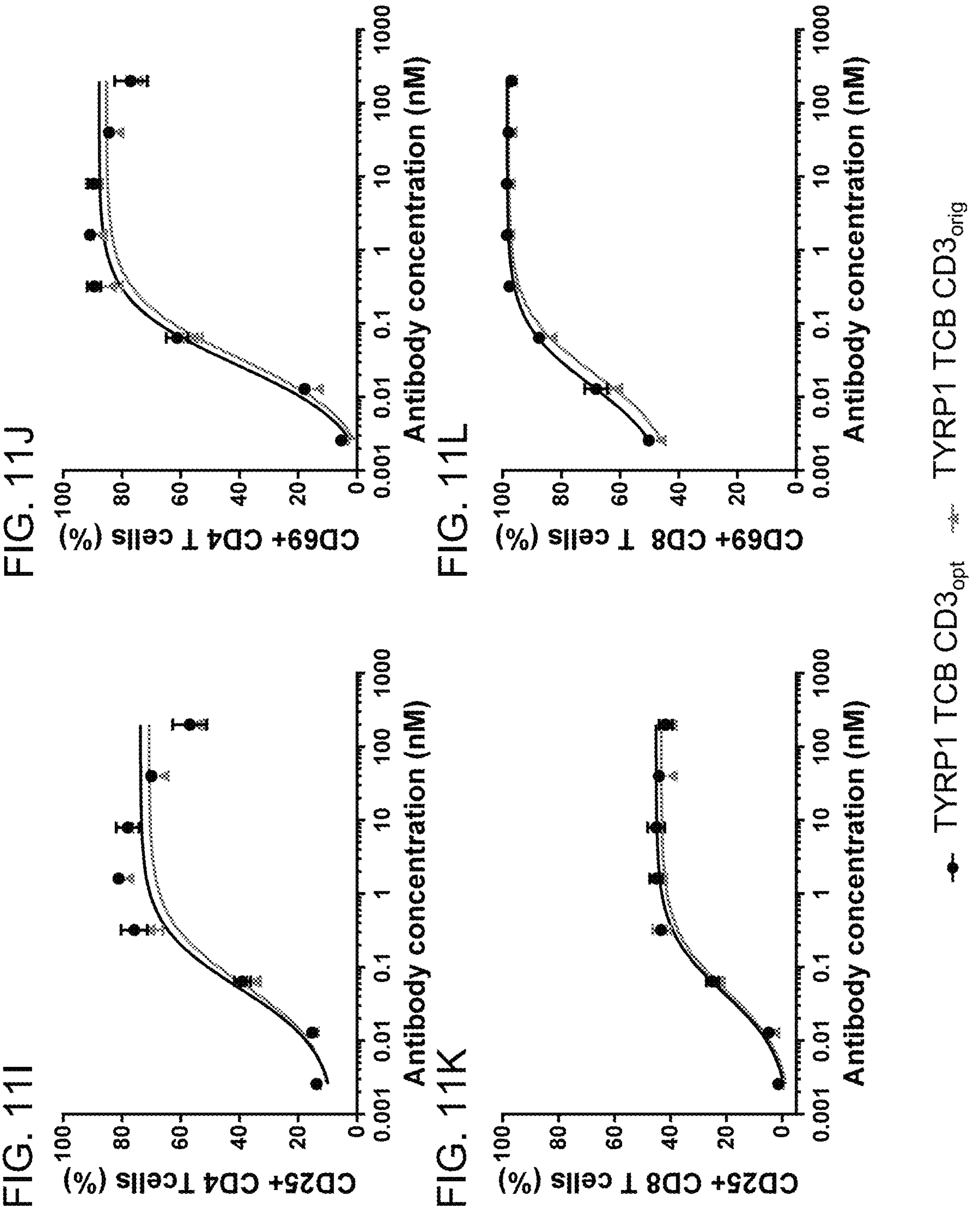
Figure 11M:
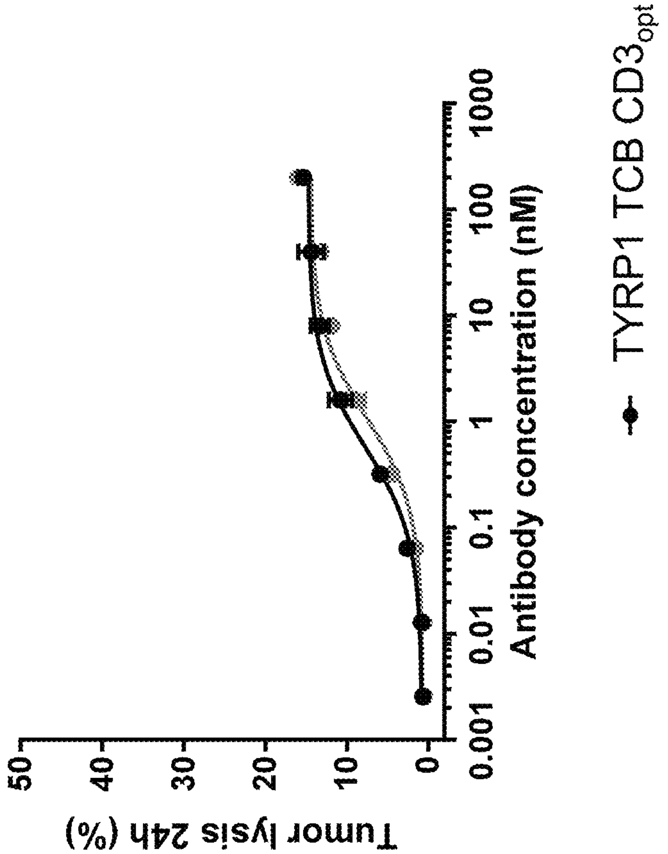
Figure 11N:
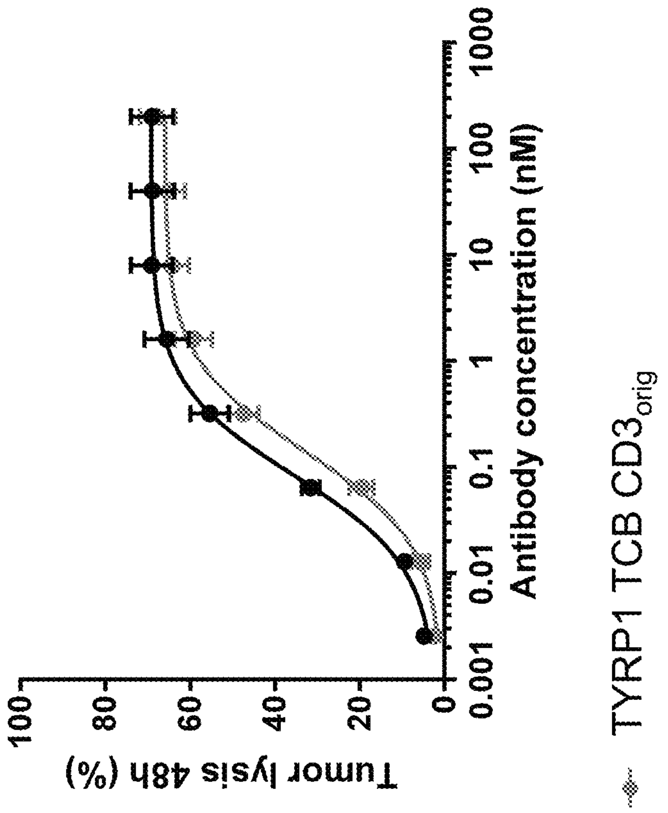
Figure 11O:
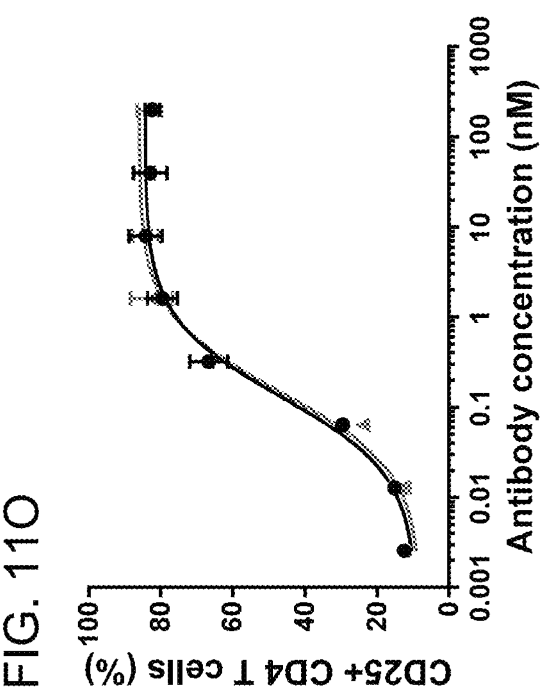
Figure 11P:
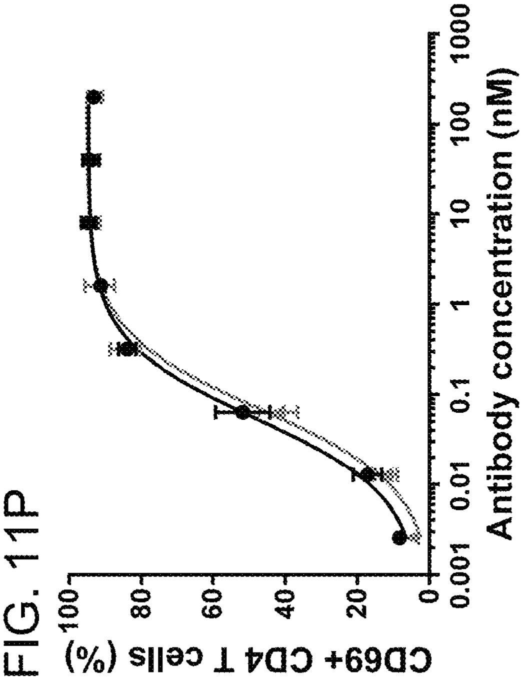
Figure 11Q:
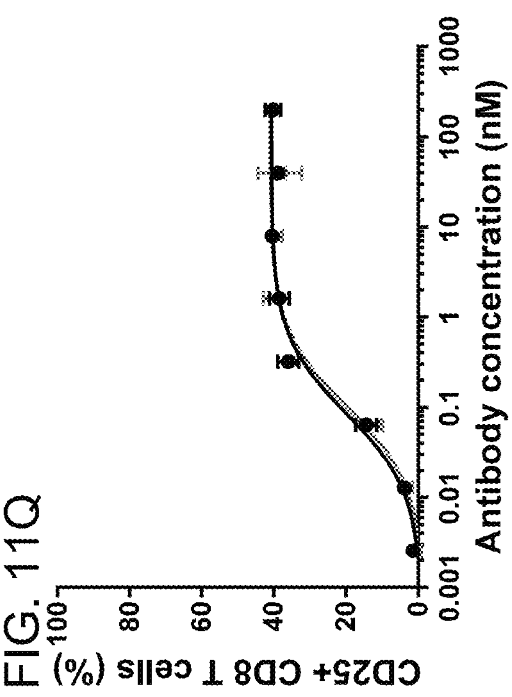
Figure 11R:
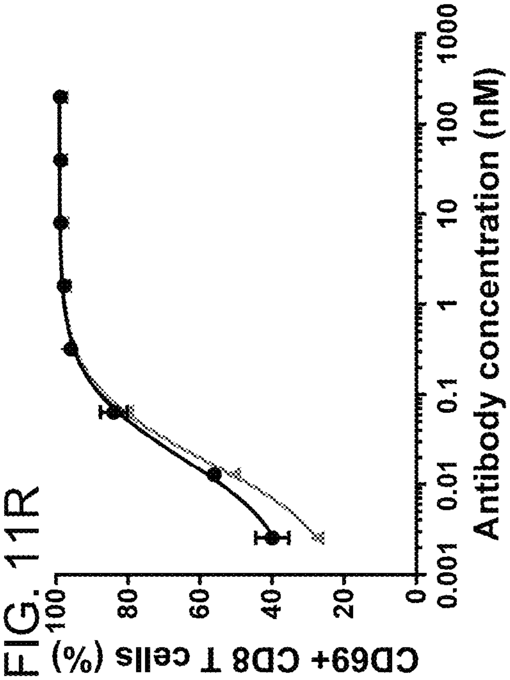

On all three donors both TCBs, comprising either the optimized or the original CD3 binder, induced T cell activation and tumor cell lysis in a comparable manner (FIG. 11A-FIG. 11R). The EC50 values of tumor cell lysis for all three donors after 48 h are summarized in Table 3.

TABLE 3

Summary of EC50 values of tumor cell killing with TYRP1 TCBs at 48 h.

| PBMC donor | TYRP1 TCB ($CD3_{opt}$) EC50 (95% confidence interval) | TYRP1 TCB ($CD3_{orig}$) EC50 (95% confidence interval) |
|---|---|---|
| Donor 1 | 0.31 nM (0.17 to 0.55) | 0.44 nM (0.28 to 0.70) |
| Donor 2 | 0.03 nM (0.02 to 0.06) | 0.05 nM (0.02 to 0.09) |
| Donor 3 | 0.08 nM (0.07 to 0.1) | 0.14 nM (0.11 to 0.18) |

Example 7—PK Study with T-Cell Bispecific Antibodies in Mice

The pharmacokinetics (PK) of the TYRP1 TCB with different CD3 binders ($CD3_{orig}$ and $CD3_{opt}$) was studied following intravenous bolus administration at 1 mg/kg to human FcRn transgenic (line32, homozygous) and FcRn knock-out mice (Jackson Laboratory strain numbers 003982 and 014565) (n=3/strain/test compound). Serial blood microsamples were taken from human FcRn transgenic (tg) mice up to 672 h (9 samples per mouse from 5 min to 672 h post dose) and up to 96 h in FcRn knockout (ko) mice (8 samples per mouse from 5 min to 96 h post-dose). Serum was prepared and stored frozen until analysis. Mouse serum samples were analysed with a generic ECLIA method specific for human Ig/Fab CH1/kappa domain using Cobas® e411 (Roche) instrument under non-GLP conditions. Pharmacokinetic evaluation was conducted using standard non-compartmental analysis.

The results of this study are shown in Table 4. This indicates that the engineering of the CDRs did not give rise to other sequence liability, that would affect antibody clearance. $CD3_{opt}$ is equally good in as $CD3_{orig}$ in terms of serum half-life, while having the additional benefit of increased CDR stability.

TABLE 4

Clearance data in huFcRn tg mice and FcRn ko mice (ml/day/kg; mean and (CV)).

| Mouse strain | TYRP1 TCB ($CD3_{orig}$) | TYRP1 TCB ($CD3_{opt}$) |
|---|---|---|
| hFcRn tg32 | 8.82 (10.0) | 6.68 (12.5) |
| FcRn ko | 66.4 (16.2) | 65.0 (6.5) |

Example 8—Generation of a Further T-Cell Bispecific Antibody Comprising Optimized CD3 Binder The optimized CD3 binder identified in Example 1 ("$CD3_{opt}$", SEQ ID NOs 7 (VH) and 11 (VL)) was used to generate a T-cell bispecific antibody (TCB) targeting CD3 and EGFRvIII ("EGFRvII TCB").

The EGFRvIII binder comprised in this TCB (P063.056) was derived from phage display followed by affinity maturation (see below), and comprises the heavy and light chain variable region sequences shown in SEQ ID NOs 88 and 92, respectively.

A schematic illustration of the TCB molecule is provided in FIG. 6, and its full sequences are given in SEQ ID NOs 109, 110, 111 and 27.

An analogous molecule with the original CD3 binding sequences was also prepared (SEQ ID NOs 109, 110, 111 and 26).

Bispecific molecules were generated by transient transfection of HEK293 EBNA cells, purified and analysed as described above in Example 4.

Furthermore, EGFRvIII antibodies derived from phage display were produced in human $IgG_1$ format in an analogous manner (transfecting the HEK EBNA cells with the expression vectors for the IgG heavy and light chains, in a 1:1 ratio), for use as described below.

All IgGs and TCB constructs were purified in comparable quality with a monomer content above 95% as determined by size exclusion chromatography.

Selection of EGFRvIII Antibody

Figure 12A:
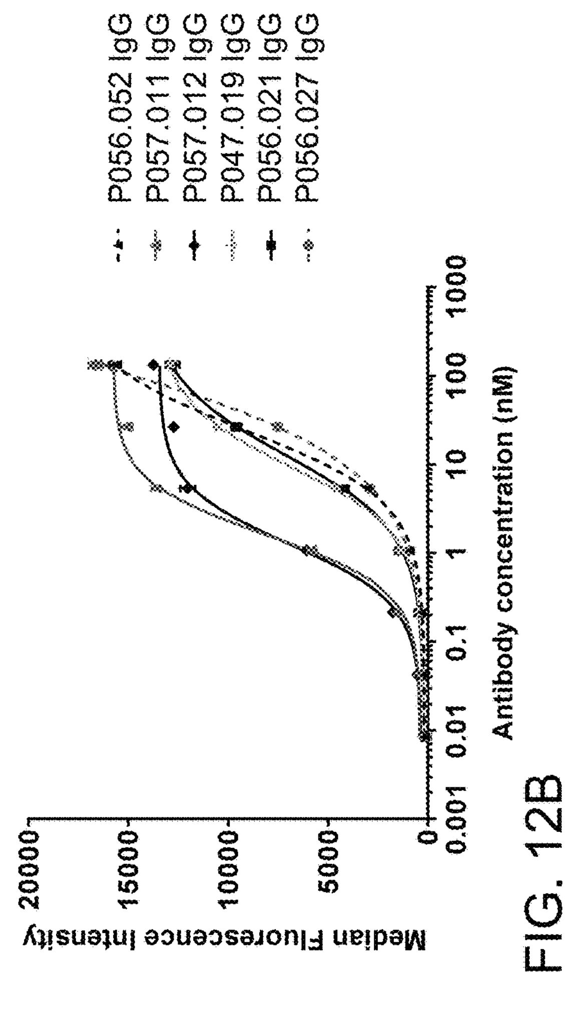
FIG. 12A-FIG. 12C. Specific binding of EGFRvIII IgG PGLALA. Specific binding of EGFRvIII IgG PGLALA antibodies to EGFRvIII without cross-reactivity to EGFRwt was tested by flow cytometry on CHO-EGFRvIII (FIG. 12A), EGFRvIII positive DK-MG (FIG. 12B) and EGFRwt expressing MKN-45 (FIG. 12C). Cetuximab was included as positive control for EGFRwt expression.
Figure 12B:
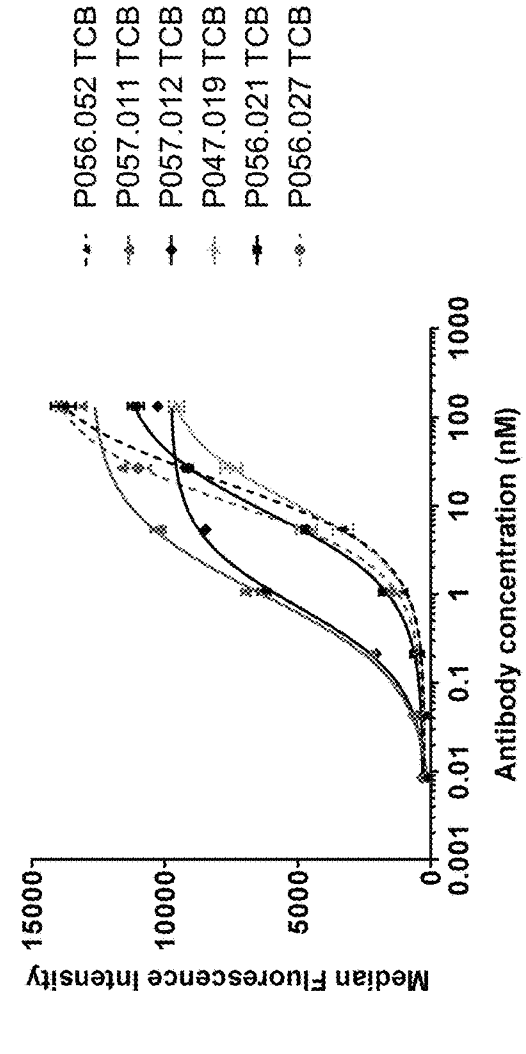
Figure 12C:
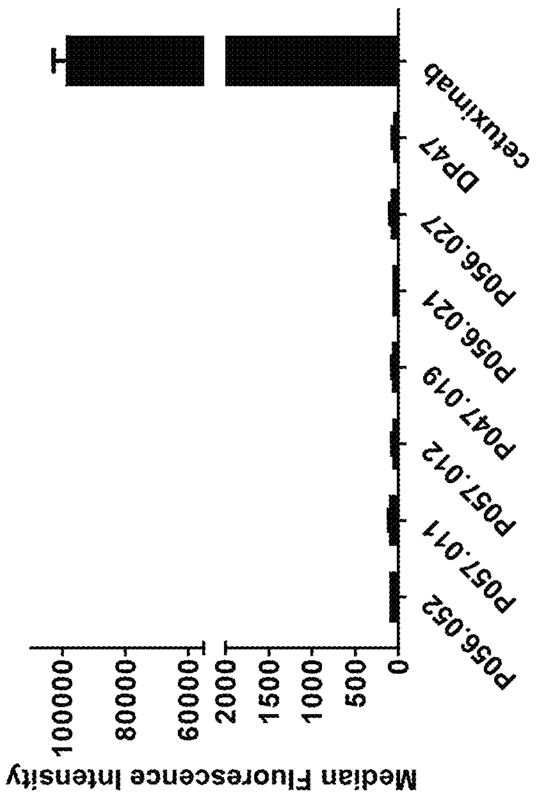

EGFRvIII antibodies were derived from phage display and affinity matured. Antibodies showing high affinity binding and specificity for EGFRvIII (P056.021 (SEQ ID NOs 40 and 44), P056.052 (SEQ ID NOs 48 and 52), P047.019 (SEQ ID NOs 56 and 60), P057.012 (SEQ ID NOs 64 and 68), P057.011 (SEQ ID NOs 72 and 76), P056.027 (SEQ ID NOs 80 and 84)) were tested for binding to EGFRvIII expressed on the cell surface using CHO cells stably expressing EGFRvIII and the EGFRvIII positive human glioblastoma cell line DK-MG. To confirm specificity and to exclude crossreactivity to wild-type EGFR (EGFRwt) the selected antibodies were tested for binding to the EGFRwt positive human tumor cell line MKN-45 (FIG. 12A-FIG. 12C). Cetuximab was included as positive control for binding to EGFRwt and the untargeted DP47 IgG as negative control. All selected antibodies specifically bound to EGFRvIII without crossreactivity to EGFRwt and were considered for further characterization.

Figure 13:
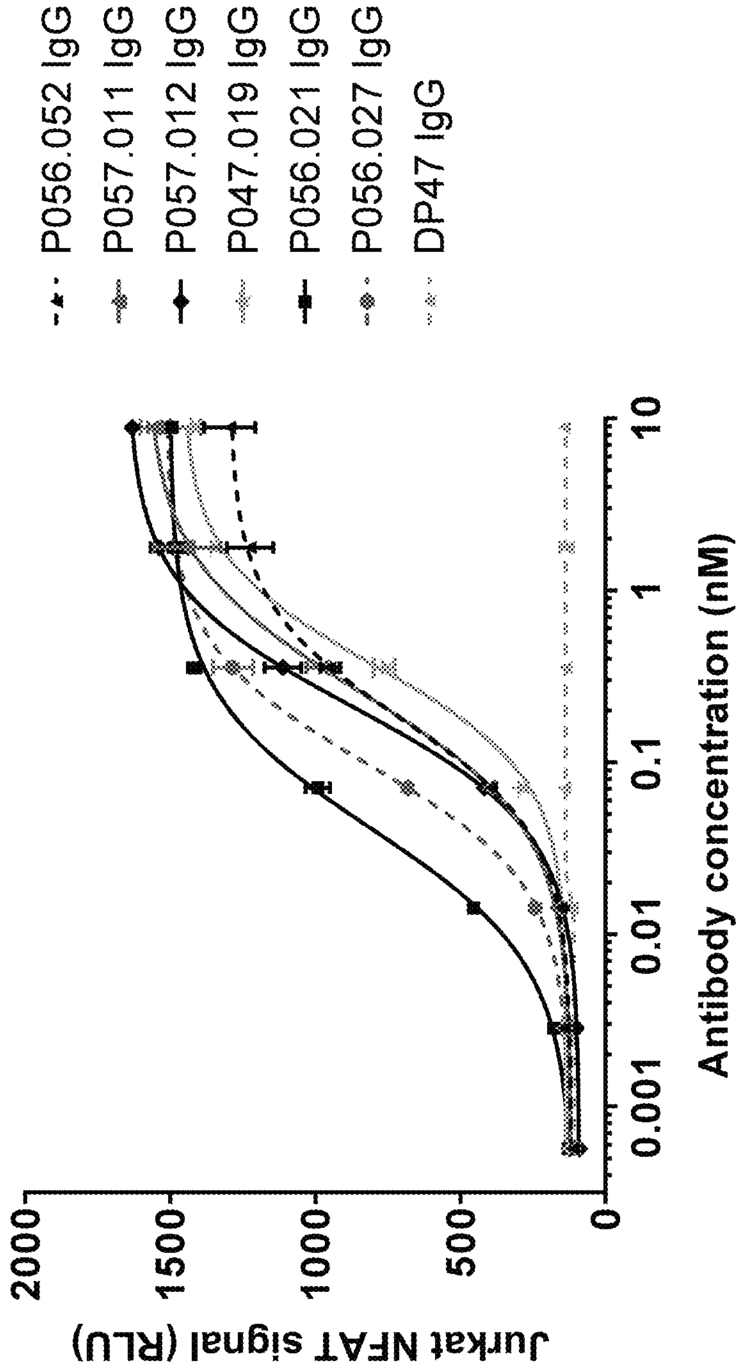
FIG. 13. CAR J activation with EGFRvIII IgG PGLALA. Jurkat NFAT reporter cells expressing anti-PGLALA CAR were co-incubated with EGFRvIII expressing DK-MG cells and EGFRvIII IgG PGLALA antibodies or DP47 IgG PGLALA as negative control. Activation of Jurkat NFAT cells was quantified by measuring luminescence after 22 h.

In a next step, the functional activity of these EGFRvIII antibodies as IgG1 PGLALA (human IgG1 format with P329G L234A L235A ("PGLALA", EU numbering) mutations in the Fc region) was assessed on DK-MG cells co-incubated with Jurkat NFAT reporter cells expressing an anti-PGLALA chimeric antigen receptor (CAR) by measuring luminescence (CAR J assay, see PCT application no. PCT/EP2018/086038, incorporated herein by reference in its entirety). DP47 IgG1 PGLALA was included as negative control. All tested EGFRvIII antibodies induced strong activation of the CAR-expressing Jurkat NFAT reporter cells (FIG. 13). All tested EGFRvIII antibodies, except for P047.019 which showed the weakest binding and activation, were selected for conversion into the TCB format (with $CD_{orig}$ as CD3 binder).

Figure 14A:
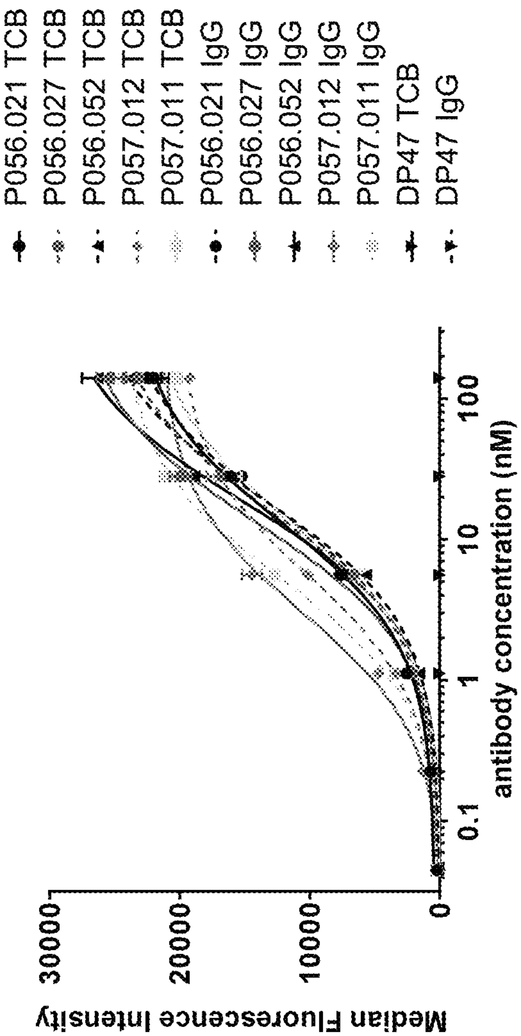
FIG. 14A and FIG. 14B. Binding of EGFRvIII IgG PGLALA and corresponding TCBs to EGFRvIII. Specific binding of EGFRvIII binders as IgG PGLALA and converted into TCBs to CHO-EGFRvIII (FIG. 14A) and MKN-45 (FIG. 14B) cells was measured by flow cytometry.
Figure 14B:
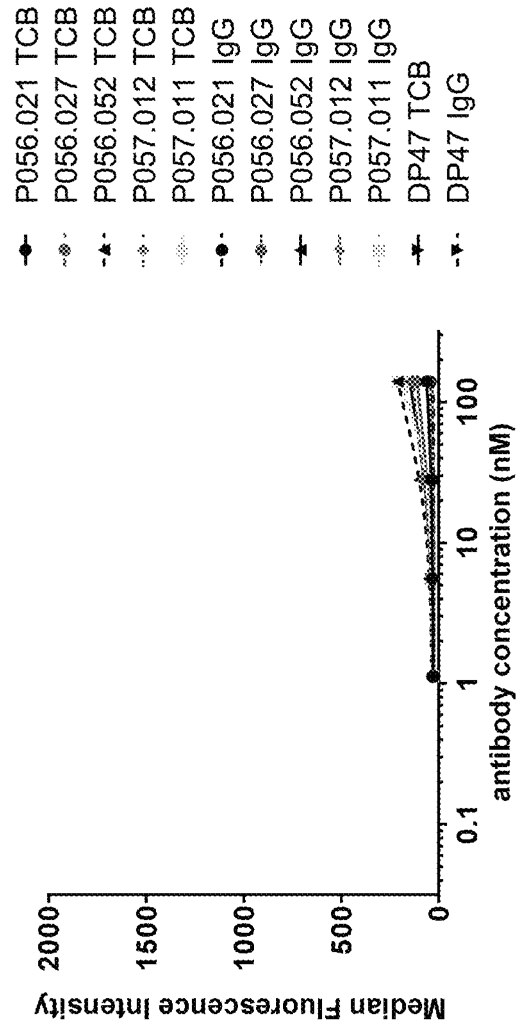

Binding of the selected EGFRvIII antibodies converted into the TCB format to CHO-EGFRvIII cells was compared to binding of the corresponding IgGs (FIG. 14A and FIG. 14B) to confirm that conversion into the TCB format has no impact on the binding capacities of the EGFRvIII antibodies. Most of the tested EGFRvIII clones retained their capacity to bind to EGFRvIII upon conversion into TCB format; only clone P057.011 showed slightly reduced binding to EGFRvIII in the TCB format compared to the corresponding IgG (Table 5).

TABLE 5

Binding of EGFRvIII IgG and TCB to CHO-EGFRvIII (EC50).

| EGFRvIII clone | EC50 IgG (nM) | EC50 TCB (nM) |
|---|---|---|
| P056.021 | 16.5 | 13.0 |
| P056.027 | 13.1 | 15.9 |
| P056.052 | 18.2 | 19.5 |
| P057.012 | 3.0 | 5.5 |
| P057.011 | 5.3 | 12.8 |

Figure 15:
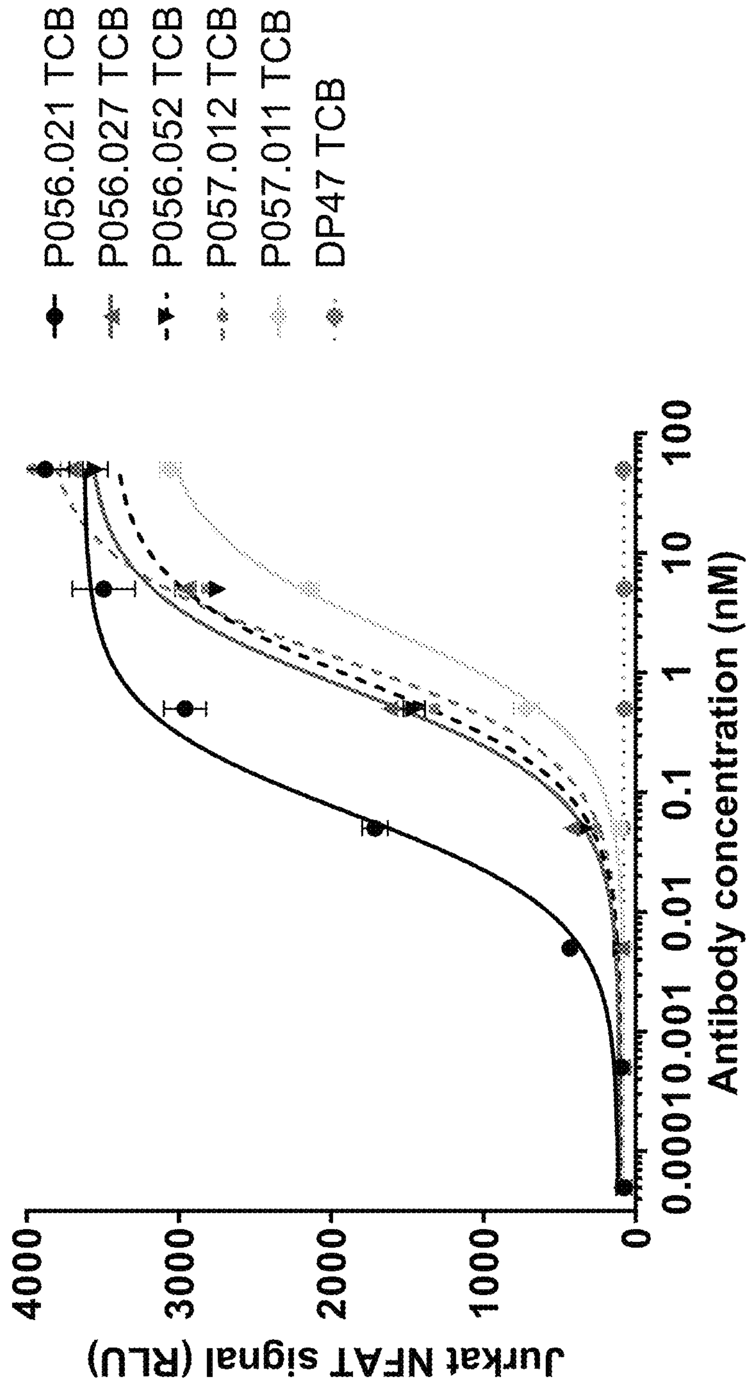
FIG. 15. Jurkat NFAT activation with EGFRvIII TCBs. Jurkat NFAT activation was determined as a maker for CD3 engagement with EGFRvIII TCBs in the presence of EGFRvIII positive DK-MG cells. DP47 TCB was included as negative control.

Subsequently the functional activity of the EGFRvIII TCBs was tested in a Jurkat NFAT reporter cell assay on EGFRvIII positive DK-MG cells (FIG. 15). All tested EGFRvIII TCBs had activity in the Jurkat NFAT reporter cell assay with P056.021 being the most potent one, followed by P056.027, P056.052 and P057.012 which had similar activity, and P057.011 which had the lowest activity. Next, the EGFRvIII TCBs were tested in a tumor cell lysis assay with PBMCs co-cultured with either DK-MG or MKN-45 cells to exclude crossreactivity of the EGFRvIII TCBs to EGFRwt (FIG. 16A-FIG. 16D). In this assay, apart from tumor cell lysis, T cell activation (FIG. 17A-FIG. 17H) and cytokine release (FIG. 18A-FIG. 18F) was measured as additional read-outs. As seen in the reporter cell assay before, EGFRvIII TCB P056.021 had the highest activity on EGFRvIII positive cells without having any activity on EGFRwt positive cells. EGFRvIII TCB P057.011 showed unspecific activity on EGFRwt cells and was therefore excluded. EGFRvIII TCBs P056.027, P056.052 and P057.012 had comparable activity. Based on these results, EGFRvIII binder P056.021 and P057.012 were selected for an additional round of affinity maturation.

No good binders could be derived from P057.012 (results not shown). Affinity and specificity to EGFRvIII of selected EGFRvIII binders derived from P056.021 as determined by SPR is shown in Table 6.

TABLE 6

Affinity and specificity to EGFRvIII of selected EGFRvIII binders as determined by SPR.

| Binder | Specificity (no binding to EGFRwt) | Binding to EGFRvIII (KD [nM]) |
|---|---|---|
| P056.021 (parental) | yes | 35 |
| P063.056 | yes | 10 |
| P064.078 | no | 15 |
| P065.036 | no | 10 |

Affinity matured EGFRvIII binders (P063.056 (SEQ ID NOs 88 and 92), P064.078 (SEQ ID NOs 96 and 100), P065.036 (SEQ ID NOs 104 and 108)) were also compared to the parental binder for specific binding to EGFRvIII on U87MG-EGFRvIII and MKN-45 cells (FIG. 19A and FIG. 19B). The best EGFRvIII binder in terms of affinity and specificity for EGFRvIII, P063.056, was selected for conversion into TCB format with either $CD3_{orig}$ or $CD3_{opt}$ as CD3 binder.

Functional activity of the EGFRvIII TCB P063.056 (with $CD3_{opt}$ or $CD3_{orig}$) was compared to the parental EGFRvIII TCB P056.021 in the Jurkat NFAT reporter cell assay on U87MG-EGFRvIII, DK-MG and MKN-45 cells (FIG. 20A-FIG. 20C). All three TCBs induce specific Jurkat NFAT activation only in the presence of EGFRvIII positive cells. The EGFRvIII TCB P063.056 had a slightly higher activity than the parental EGFRvIII TCB P056.021.

Methods

Surface Plasmon Resonance

Affinity of EGFRvIII antibodies to EGFRvIII was determined by surface plasmon resonance on Biacore T200 with HBS-EP as running buffer (0.01 M HEPES pH 7.4, 0.15 M NaCl, 0.005% (v/v) Surfactant P20; GE Healthcare) at 25 °C. Anti-EGFRvIII PGLALA IgGs were captured for 30 s at 25 nM with an antibody that specifically binds human $IgG_1$ Fc(PGLALA) (see WO 2017/072210, incorporated herein by reference) immobilized on a CM5 chip. The EGFRvIII-ECD avi his antigen (see below, Example 9) was passed at a concentration of 12.4-1000 nM with a flow of 30 μl/min through all flow cells over 200 s. The dissociation phase was monitored for 300 s and triggered by switching from the sample solution to HBS-EP. The chip surface was regenerated after every cycle using two injections of 10 mM glycine pH 2.0 for 30 s. Bulk refractive index differences were corrected by subtracting the response obtained on the reference flow cell. The affinity constants were derived from the kinetic rate constants by fitting to a 1:1 Langmuir binding using the BIAeval software (GE Healthcare).

For specificity determination EGFRvIII and EGFRwt ECD antigens were captured with an anti-his (Penta His, Qiagen) immobilized on a CM5 chip for 40 s at 100 nM. A single injection of anti-EGFRvIII antibodies at 500 nM for 60 s was performed, before regeneration with 10 mM glycine pH 2.0 for 60 s. Response units above 50 were observed for EGFRvIII binding. Responses above 5 response units (RU) were considered positive for EGFRwt binding and IgGs were categorized as specific with response below 5 RU for EGFRwt.

Cell Lines

Jurkat-NFAT reporter cells (GloResponse Jurkat NFAT-RE-luc2P; Promega #CS176501) are a human acute lymphatic leukemia reporter cell line with a NFAT promoter, expressing human CD3. The cells were cultured in RPMI1640, 2 g/l glucose, 2 g/l $NaHCO_3$, 10% FCS, 25 mM HEPES, 1% GlutaMAX, 1×NEAA, 1×sodium-pyruvate at 0.1-0.5 mio cells per ml. A final concentration of 200 μg per ml hygromycin B was added whenever cells were passaged.

Jurkat NFAT cells with PGLALA CAR were generated in house. The original cell line (Jurkat NFAT; Signosis) is a human acute lymphatic leukemia reporter cell line with a NFAT promoter leading to luciferase expression upon activation via human CD3. They were engineered to express a chimeric antigen receptor able to recognize the P293G LALA mutation. When cultured, the cells grow in suspension in RPMI1640 supplemented with 10% FCS and 1% glutamine and maintained between 0.4-1.5 mio cells per ml.

CHO-EGFRvIII cells were generated in house. CHO-K1 cells were stably transduced with EGFRvIII. Cells were cultured in DMEM/F12 medium containing 5% FCS, 1% GlutaMAX and 6 μg/ml puromycin.

DK-MG (DSMZ #ACC 277) is a human glioblastoma cell line. DK-MG cells were enriched by cell sorting for EGFRvIII expression. The cells were cultured in RPMI 1860, 10% FCS and 1% GlutaMAX.

U87MG-EGFRvII (ATCC HTB-14) is a human glioblastoma cell line which were stably transduced with EGFRvIII. The cells were cultured in DMEM, 10% FCS and 1% GlutaMAX. MKN-45 (DSMZ ACC 409) is a human gastric adenocarcinoma cells expressing high levels of EGFRwt. The cells were cultured in advanced RPMI1640 containing 2% FCS and 1% GlutaMAX.

Target Binding by Flow Cytometry

Cells used for binding experiments were harvested, washed with PBS and resuspended in FACS buffer. The antibody staining was performed in a 96-well round bottom plate. Cells were harvested, counted and 100 000 to 200 000 cells were seeded per well. The plate was centrifuged for 4 min at 400×g and the supernatant was removed. The test antibodies were diluted in FACS buffer and 20 μl of the antibody solution were added to the cells for 30 min at 4 °C. To remove unbound antibody the cells were washed twice with FACS buffer before addition of the diluted secondary antibody PE-conjugated AffiniPure F(ab')2 Fragment goat anti-human IgG Fcg Fragment Specific (Jackson ImmunoResearch, #109-116-170 or #109-116-098). After 30 min incubation on 4 °C unbound secondary antibody was washed away. Before measurement the cells were resuspended in 200 μl FACS buffer and analyzed by flow cytometry using BD Canto II or BD FACS Fortessa.

CAR J NFAT Reporter Cell Assay with EGFRvIII PGLALA IgGs

The potency of the EGFRvIII PGLALA IgGs to induce T cell activation was assessed using the CAR J NFAT reporter cell assay. The principle of the assay is to co-culture Jurkat-NFAT engineered effector cells with cancer cells expressing the tumor antigen. Only upon simultaneous binding of the IgGs to the CAR via the PGLALA mutation and the target antigen EGFRvIII, the NFAT promoter is activated and leads to increasing luciferase expression in the Jurkat effector cells. Upon addition of an adequate substrate, active Firefly Luciferase leads to emission of luminescence, which can be measured as a signal of CAR-mediated activation. Briefly, target cells were harvested and viability determined. 30 000 target cells/well were plated in a flat-bottom, white-walled 96-well-plate (Greiner bio-one, #655098) in 100 μl medium the day before the assay start. On the next day the medium was removed and 25 μl/well of diluted antibodies or medium (for controls) were added to the target cells. Subsequently, Jurkat-NFAT reporter cells were harvested and viability assessed using ViCell. Cells were resuspended at 1.5 mio cells/ml in cell culture medium and added to tumor cells at 75 000 cells/well (50 μl/well) to obtain a final effector-to-target (E:T) ratio of 2.5:1 and a final volume of 75 μl per well. Then 4 μl of GloSensor (Promega, #E1291) was added to each well (2% of end volume). Cells were incubated for 24 h at 37 °C in a humidified incubator. At the end of incubation time, the plates were adapted to room temperature (about 15 min). Then 25 μl/well of One-Glo Luciferase (Promega, #E6120) was added and the plate was incubated for 15 min in the dark before luminescence was detected using TECAN Spark.

Jurkat NFAT Reporter Cell Assay with EGFRvIII TCB

The capacity of EGFRvIII TCB with either the improved CD3 or the original CD3 binder to induce T cell cross-linking and subsequently T cell activation was assessed using EGFRvIII positive cells and Jurkat-NFAT reporter cells. Upon simultaneous binding of EGFRvIII TCB to EGFRvIII positive target cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. For the assay, target cells were harvested and viability determined. 30 000 target cells/well were plated in a flat-bottom, white-walled 96-well-plate (Greiner bio-one, #655098) in 100 μl medium and 50 μl/well of diluted antibodies or medium (for controls) were added to the target cells. Subsequently, Jurkat-NFAT reporter cells were harvested and viability assessed using ViCell. Cells were resuspended at 1.2 mio cells/ml in cell culture medium without hygromycin B and added to tumor cells at 60 000 cells/well (50 μl/well) to obtain a final effector-to-target (E:T) ratio of 2:1 and a final volume of 200 μl per well. Then 4 μl of GloSensor (Promega, #E1291) was added to each well (2% of end volume). Cells were incubated for 24 h at 37 °C in a humidified incubator. At the end of incubation time, luminescence was detected using TECAN Spark.

T-Cell Mediated Tumor Cell Killing

Target cells were harvested with Trypsin/EDTA, washed, and plated at density of 30 000 cells/well using flat-bottom 96-well plates. Cells were left to adhere overnight. Peripheral blood mononuclear cells (PBMCs) were prepared by Histopaque density centrifugation of fresh blood obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% GlutaMAX at 37 °C, 5% $CO_2$ in cell incubator until further use (not longer than 24 h). For the killing assay, the antibody was added at the indicated concentrations in triplicates. PBMCs were added to target cells at final effector to target (E:T) ratio of 10:1. Target cell killing was assessed after 24 h of incubation at 37 °C, 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend, #300514), CD8 FITC (BioLegend, #344704), CD25 BV421 (BioLegend, #302630) and CD69 PE (BioLegend, #310906) was performed according to the suppliers' indications. Cells were washed twice with 150 μl/well FACS buffer and fixed for 15 min at 4 °C using 100 μl/well fixation buffer (BD, #554655). After centrifugation, the samples were resuspended in 200 μl/well FACS buffer. Samples were analyzed at BD FACS Fortessa.

Cytokine secretion in the supernatant was measured by flow cytometry, using the cytometric bead array (CBA) according to the manufacturer's instructions but instead of 50 μl beads and sample only 25 μl of the supernatant and beads were used. The following CBA kits (BD Biosciences) were used: CBA human interferon gamma (IFNγ) Flex Set, CBA human Granzyme B Flex Set and CBA human TNF Flex Set. Samples were measured using the BD FACS Canto II or BD FACS Fortessa and analyses were performed using the Diva Software (BD Biosciences).

Example 9—Binding of T-Cell Bispecific Antibody Comprising Optimized CD3 Binder to CD3 and EGFRvIII Binding to Recombinant CD3

Binding of the EGFRvIII TCB to recombinant CD3 was assessed by SPR, using the TCBs with either the optimized (EGFRvIII TCB $CD3_{opt}$) or the original (EGFRvIII TCB $CD3_{orig}$) CD3 binding sequences, as described for TYRP1 TCB in Example 5 above. Capture antibody was coupled to the sensorchip surface by direct immobilization of around 5200 resonance units (RU) at pH 5.0 using the standard amine coupling kit (GE Healthcare), and TCB molecules were captured for 30 s at 20 nM with a flow of 10 μl/min.

The $K_D$ values for binding to human and cynomolgus CD3 were determined as 30 nM and 20 nM, respectively, for TYRP1 TCB $CD3_{opt}$ and were similar to the ones for TYRP1 TCB $CD3_{orig}$ (40 nM and 30 nM, respectively).

This shows that in unstressed condition both TCBs, comprising either $CD3_{opt}$ or $CD3_{orig}$, bound comparably well to recombinant CD3.

Binding of the EGFRvIII TCB to recombinant human CD3 was also assessed after temperature stress for 14 days at 37 °C or 40 °C, using the TCBs with either the optimized or the original CD3 binding sequences. The experiment was performed as described in Example 2 above, using the TCB instead of IgG molecules.

The results of this experiment are shown in FIG. 21.

As can be seen in FIG. 21, the TCB comprising the optimized CD3 binder $CD3_{opt}$ showed strongly improved binding to CD3 after stress (2 weeks at 37 °C, pH 7.4) as compared to the TCB comprising the original CD3 binder $CD3_{orig}$. This result again confirms that the improved properties of the optimized CD3 binder (see Example 2) are maintained at the TCB level.

Binding to Recombinant EGFRvIII

Binding of the EGFRvIII TCBs to recombinant EGFRvIII was assessed by SPR.

SPR experiments were performed on a Biacore T200 with HBS-EP as running buffer (0.01 M HEPES pH 7.4, 0.15 M NaCl, 0.05% (v/v) Surfactant P20 (GE Healthcare)).

An anti-Fc antibody (GE Healthcare) was directly coupled on a CM5 sensor chip at pH 5.0 using the standard amine coupling kit (GE Healthcare). EGFRvIII TCB (5 nM) was captured with a flow rate of 10 μl/min for 30 s. A 3-fold dilution series of the EGFRvIII antigen was passed on the flow cells at 30 μl/min for 200 s to record the association phase. The dissociation phase was monitored for 300 s and triggered by switching from the sample solution to HBS-EP. The chip surface was regenerated after every cycle using one injection of 3 M $MgCL_2$ for 30 s at 20 μl/min. The antigen used contains the extracellular domain of human EGFRvIII fused to an Avi-tag and a His-tag on the C-terminus (EGFRvIII-ECD avi his; SEQ ID NO: 36).

Bulk refractive index differences were corrected by subtracting the response obtained on the reference flow cell (no TCB captured). The affinity constants ($K_D$) were derived from the kinetic rate constants by fitting to a 1:1 Langmuir binding using the BIAeval software (GE Healthcare). The apparent avidity constant $K_D$ was approximated by kinetic analysis via the rate constants using a 1:1 binding fit on this 2:1 interaction.

The $K_D$ values (affinity) for binding to human EGFRvIII were determined as 6 nM for both the EGFRvIII TCB comprising either $CD3_{opt}$ or $CD3_{orig}$.

Binding of the EGFRvIII TCB to recombinant EGFRvIII was also assessed after temperature stress for 14 days at 37 °C or 40 °C, using the TCBs with either the optimized or the original CD3 binding sequences. The experiment was performed as described above in Example 5, using EGFRvIII-ECD avi his as antigen (see above).

The results of this experiment are shown in FIG. 22. They confirm that the binding to human EGFRvIII for both TCBs is not affected by stress conditions.

Binding to CD3 on Jurkat Cells

Binding to CD3 on the human reporter T-cell line Jurkat NFAT was determined by FACS for EGFRvIII TCBs comprising the optimized CD3 binder "$CD3_{opt}$" or the original CD3 binder "$CD3_{orig}$", as described above in Example 2.

As shown in FIG. 23, the TCBs comprising either the optimized CD3 binder "$CD3_{opt}$" or the original CD3 binder "$CD3_{orig}$" bound comparably well to CD3 on Jurkat cells.

Binding to EGFRvIII on U87MG-EGFRvII Cells

Binding to EGFRvIII on the human glioblastoma cell line U87MG-EGFRvII was determined by FACS for EGFRvIII TCBs comprising the EGFRvIII binder P063.056 with either $CD3_{opt}$ or $CD3_{orig}$, or the EGFRvIII clone P056.021 with $CD3_{orig}$. The EGFRvIII binder P063.056 was included also in IgG format.

As shown in FIG. 24 all three TCBs bind with high affinity to EGFRvIII expressed on U87MG-EGFRvIII cells and binding is not impaired by the conversion into the TCB format.

Example 10—Functional Activity of T-Cell Bispecific Antibody Comprising Optimized CD3 Binder CD3 Activation The EGFRvIII TCBs containing the selected EGFRvIII binder (P063.056) and either the optimized CD3 binder $CD3_{opt}$ or the original CD3 binder $CD3_{orig}$ were tested in the Jurkat NFAT reporter cell assay in the presence of EGFRvIII positive glioblastoma cells DK-MG, U87MG-huEGFRvIII and EGFRwt positive MKN45 cells as described above in Example 8.

As seen for the IgGs (Example 3) both TCBs containing either $CD3_{opt}$ or $CD3_{orig}$ had a similar functional activity on the Jurkat NFAT reporter cells and induced CD3 activation in a concentration dependent manner (FIG. 20A-FIG. 20C).

Target Cell Killing

The EGFRvIII TCBs containing the selected EGFRvIII binder (P063.056) and either the optimized CD3 binder $CD3_{opt}$ or the original CD3 binder $CD3_{orig}$ were compared to the EGFRvIII TCB containing the parental EGFRvIII binder P056.021 and the CD3 binder $CD3_{orig}$ in a tumor cell killing experiment in the presence of the glioblastoma cell line U87MG-EGFRvII and PBMCs as described above in Example 8. As seen on the Jurkat NFAT reporter cells, the functional activity of the TCBs with either the $CD3_{opt}$ or $CD3_{orig}$ is similar with regard to induction of tumor cell lysis and activation of CD4 and CD8 T cells as measured by CD69 upregulation (FIG. 20A-FIG. 25D).

In addition, the functional activity of the EGFRvIII TCB with the EGFRvIII binder P063.056 and the optimized CD3 binder $CD3_{opt}$ in the "2+1 format" (as illustrated in FIG. 6) was compared to an EGFRvIII TCB with the same EGFRvIII and CD3 binder in the "1+1 head-to-tail format" (schematically depicted in FIG. 1G). These two EGFRvIII TCBs were tested in the Jurkat NFAT reporter cell assay and in a tumor cell killing assay with the glioblastoma cell line U87MG-EGFRvIII as described in Example 8. The EGFRvIII TCB in the 2+1 format had a superior functional activity both in CD3 activation measured in the Jurkat NFAT reporter cell assay (FIG. 26) and in the induction of tumor cell killing and T cell activation in the killing assay with PBMCs (FIG. 27A-FIG. 27D).

Example 11—Functional Characterization of T-Cell Bispecific Antibodies Comprising Optimized CD3 Binder T Cell Proliferation and Activation by EGFRvIII TCB Functional activity of the EGFRvIII TCBs containing the selected EGFR binder (P063.056) and either the optimized CD3 binder $CD3_{opt}$ or the original CD3 binder $CD3_{orig}$ was compared to the EGFRvIII TCB containing the parental EGFRvIII binder P056.021 and the CD3 binder $CD3_{orig}$ in a T cell proliferation assay on U87MG-EGFRvIII cells (FIG. 28A-FIG. 28D). All three TCBs induced strong proliferation and activation of CD4 T cells and CD8 T cells. The P063.056 EGFRvIII TCB with $CD3_{opt}$ had a higher activity than the other two EGFRvIII TCBs.

Tumor Cell Lysis by EGFRvIII TCB

Next, the EGFRvIII TCB containing the selected EGFR binder (P063.056) and the optimized CD3 binder $CD3_{opt}$ and the EGFRvIII TCB containing the parental EGFRvIII binder P056.021 and the CD3 binder $CD3_{orig}$ were tested in a tumor cell lysis assay with PBMCs co-cultured with DK-MG cells (FIG. 29A-FIG. 29F). In this assay, apart from tumor cell lysis, T cell activation and cytokine release was measured as additional read-outs. As seen before, the P063.056 EGFRvIII TCB with $CD3_{opt}$ had a higher activity than the P056.021 EGFRvIII TCB with $CD3_{orig}$ with regard to tumor cell lysis, T cell activation and release of IFNγ and TNFα.

T Cell Activation and Tumor Cell Lysis by TYRP1 TCB

The functional property of TYRP1 TCB to induce cytokine release was tested by co-cultivation of the primary melanoma cell line M150543 with PBMCs isolated from a healthy donor. Tumor cell lysis mediated by T cells via TYRP1 TCB was analyzed after 24 h and 48 h of treatment (FIG. 30A-FIG. 30F). Release of IFNγ and TNFα into the supernatant as well as CD4 and CD8 T cell activation was analyzed after 48 h of treatment. TYRP1 TCB was able to induce potent tumor cell lysis already after 24 h. This was accompanied by strong activation of CD4 and CD8 T cells determined by upregulation of CD25 as well as significant release of IFNγ and TNFα.

Methods

PBMC Isolation

Peripheral blood mononuclear cells (PBMCs) were prepared by Histopaque density centrifugation of fresh blood obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% GlutaMAX at 37 °C, 5% $CO_2$ in cell incubator until further use (not longer than 24 h) or frozen and stored in liquid nitrogen until further use. The day before use frozen PBMCs were thawed and cultured overnight in medium at 37 °C.

T Cell Proliferation

Briefly, target cells harvested, counted and washed twice with PBS. Cells were resuspended at 5 mio cells per ml in PBS. Cells were stained with the cell proliferation dye eFluor 670 (eBioscience, #65-0840-85) with a final concentration of 5 μM for 10 min at 37 °C. To stop the staining reaction, 4 volumes of cold complete cell culture medium were added to the cell suspension and incubated for 5 min at 4 °C and then washed three times with medium. Labeled target cells were counted and adjusted to 0.1 mio cells per ml in RPMI1640, 10% FCS and 1% GlutaMax. 10'000 target cells per well were seeded into a 96 well plate. Then the treatment was added at the indicated concentrations and at the end 100'000 PBMCs isolated from a healthy donor were added per well. The cells were incubated for 5 days at 37 °C, then PBMCs were harvested and stained with CD3 BUV395 (BioLegend, #563548), CD4 PE (BioLegend, #300508), CD8 APC (BioLegend, #344722), CD25 PE/Cy7 (BioLegend, #302612). Proliferation was determined by dilution of the eFluor 670 dye in CD4 T cells and CD8 T cells measured by flow cytometry (FACS Fortessa, BD Bioscience) and activation of CD4 and CD8 T cells by measuring CD25 upregulation.

T Cell Mediated Tumor Cell Killing

Target cells were harvested with trypsin/EDTA, washed, and plated at density of 30 000 cells/well using flat-bottom 96-well plates. Cells were left to adhere overnight. For the killing assay, the antibodies were added at the indicated concentrations in triplicates. PBMCs were added to target cells at final effector to target (E:T) ratio of 10:1. Target cell killing was assessed after 24 h of incubation at 37 °C, 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

T Cell Activation

Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend, #300514), CD8 FITC (#344704, BioLegend), CD25 BV421 (BioLegend, #302630) and CD69 PE (BioLegend, #310906) was performed according to the suppliers' indications. Cells were washed twice with 150 μl/well FACS buffer and fixed for 15 min at 4 °C using 100 μl/well fixation buffer (BD, #554655). After centrifugation, the samples were resuspended in 200 μl/well FACS buffer. Samples were analyzed at BD FACS Fortessa.

Cytokine Secretion

Cytokine secretion in the supernatant was measured by flow cytometry, using the cytometric bead array (CBA) according to the manufacturer's instructions but instead of 50 μl beads and sample only 25 μl of the supernatant and beads were used. The following CBA kits (BD Biosciences) were used: CBA human interferon gamma (IFNγ) Flex Set and CBA human TNF Flex Set. Samples were measured using the BD FACS Canto II or BD FACS Fortessa and analyses were performed using the Diva Software (BD Biosciences).

Example 13—In Vivo Efficacy of T-Cell Bispecific Antibodies Comprising Optimized CD3 Binder The TYRP1 TCB (comprising the optimized CD3 binder identified in Example 1) was tested for its anti-tumoral efficacy in a xenograft mouse model of a human tumor cell line, the IGR-1 melanoma xenograft model.

IGR-1 cells (human melanoma) were cultured in DMEM medium containing 10% FCS (Sigma). The cells were cultured at 37 °C in a water-saturated atmosphere at 5% $CO_2$. Passage 6 was used for transplantation. Cell viability was 96.7%. $2\times10^6$ cells per animal were injected subcutaneously in 100 μl of RPMI cell culture medium (Gibco) into the flank of mice using a 1 ml tuberculin syringe (BD Biosciences, Germany).

Fully humanized NSG female mice (Roche Glycart AG, Switzerland) were maintained under specific-pathogen-free condition with daily cycles of 12 h light/12 h darkness according to committed guidelines (GV-Solas; Felasa; TierschG). The experimental study protocol was reviewed and approved by local government (ZH223/2017). Continuous health monitoring was carried out on a regular basis.

Mice were injected subcutaneously on study day 0 with $2\times10^6$ of IGR-1 cells, randomized and weighed. Twenty days after the tumor cell injection (tumor volume >200 $mm^3$), mice were injected i.v. with 10 μg (0.5 mg/kg) TYRP1 TCB twice weekly for five weeks. All mice were injected i.v. with 200 μl of the appropriate solution. The mice in the vehicle group were injected with histidine buffer and the treatment group with the TYRP1 TCB construct. To obtain the proper amount of antibody per 200 μl, the stock solutions were diluted with histidine buffer when necessary. Tumor size was measured with a caliper three times a week and plotted with GrahPad Prism software as volume in $mm^3$+/−SEM. Statistical analysis was performed with JMP12 software.

FIG. 31 shows that TYRP1 TCB mediated significant efficacy in terms of tumor growth inhibition compared to the vehicle group (68% TGI, p=0.0058*).

The EGFRvII TCB (comprising the optimized CD3 binder identified in Example 1) was likewise tested for its anti-tumoral efficacy in a xenograft mouse model of a human tumor cell line, the U87-EGFRvII glioblastoma xenograft model.

U87 cells (human glioblastoma) were originally obtained from ATCC (Manassas, USA) and stably transfected to express the human EGFRvII protein (Roche Glycart AG, Switzerland). After expansion the cells were deposited in the Roche Glycart internal cell bank. The U87-EGFRvII cell line was cultured in DMEM medium containing 10% FCS (Sigma) and 0.5 μg/ml Puromycin (Invitrogen). The cells were cultured at 37 °C in a water-saturated atmosphere at 5% $CO_2$. Passage 8 was used for transplantation. Cell viability was 94.7%. $5\times10^5$ cells per animal were injected subcutaneously in 100 μl of RPMI cell culture medium (Gibco) into the flank of mice using a 1 ml tuberculin syringe (BD Biosciences, Germany).

Fully humanized NSG female mice (Roche Glycart AG, Switzerland) were maintained under specific-pathogen-free condition with daily cycles of 12 h light/12 h darkness according to committed guidelines (GV-Solas; Felasa; TierschG). The experimental study protocol was reviewed and approved by local government (ZH223/2017). Continuous health monitoring was carried out on a regular basis.

Mice were injected subcutaneously on study day 0 with $5\times10^5$ of U87-EGFRvIII cells, randomized and weighed. Two weeks after the tumor cell injection (tumor volume >200 $mm^3$), mice were injected i.v. with 10 μg (0.5 mg/kg) EGFRvIII TCB twice weekly for three weeks. All mice were injected i.v. with 200 μl of the appropriate solution. The mice in the vehicle group were injected with histidine buffer and the treatment group with the EGFRvIII TCB construct. To obtain the proper amount of antibody per 200 µl, the stock solutions were diluted with histidine buffer when necessary. Tumor size was measured with a caliper three times a week and plotted with GrahPad Prism software as volume in $mm^3$+/−SEM.

FIG. 32 shows that EGFRvIII TCB mediated significant efficacy in terms of tumor growth control with all mice achieving complete remission.

Example 14—PK Study with EGFRvIII TCB in Mice

The pharmacokinetics (PK) of the EGFRvIII TCB comprising the optimized CD3 binder, $CD3_{opt}$, was studied following intravenous bolus administration at 1 mg/kg to human FcRn transgenic (line32, homozygous) and NOD-SCID mice. Serial blood microsamples were taken from human FcRn transgenic (tg) mice and NOD-SCID mice up to 672 h (9 samples per mouse from 5 min to 672 h post dose). Samples of mouse serum treated with EGFRvIII TCB were analyzed using a specific enzyme-linked immunosorbent assay (ELISA) under non-GLP conditions. Capture of EGFRvIII TCB was done with biotinylated EGFRvIII antigen (huEGFRvIII his biotin) on streptavidin-coated microtiter plates (SA-MTP). Bound EGFRvIII TCB was detected with digoxigenin-labeled monoclonal antibody against human IgG1 Fc(PGLALA) (see Example 3) followed by addition of an anti-digoxigenin-POD secondary detection antibody. Signals were generated by addition of peroxidase substrate (ABTS). The calibration range was 2.35 ng/ml to 150 ng/ml with 2.5 ng/ml being the lower limit of quantification (LLOQ).

The results of this study are shown in Table 7. The PK profile of EGFRvIII TCB is within the expected range for both tested mouse strains. This indicates that the engineering of the CDRs of the CD3 binder did not give rise to other sequence liability, that would affect antibody clearance.

TABLE 7

Clearance data in huFcRn tg mice and NOD-SCID mice (ml/day/kg; mean).

| Mouse strain | EGFRVIII TCB ($CD3_{opt}$) |
|---|---|
| hFcRn tg32 | 12.4 |
| NOD-SCID | 10.1 |

Example 15—FOLR1 TCB with $CD3_{opt}$ as CD3 Binder

Conversion and Production of a FOLR1 TCB with $CD3_{opt}$ as CD3 Binder

For production of $CD3_{opt}$ FOLR1 TCB ('classical 2+1 format'=CD3 Fab outside, FOLR1 Fab inside of Fc knob chain, FIG. 33A, SEQ ID Nos 127, 128, 129) the variable domains of the CD3 binder $CD3_{opt}$ were inserted into suitable expression vectors. The molecule consists of a human IgG1 backbone with mutations in the Fc region (LL234/235AA and P329G) to abrogate Fc effector functions. The T cell bispecific molecules were produced in the proprietary 2+1 heterodimer format based on the knob-into-hole technology (two binding moieties for the target antigen and one for the CD3).

Transfection and Expression of FOLR1 TCBs with $CD3_{opt}$ as CD3 Binder

Expression of FOLR1 TCB was performed by transient transfection of ExpiCHO-S™ cells (ExpiCHO™ Expression System; Thermo/Gibco #A29133). ExpiCHO-S cells were pre cultured according to the manufacturer's instructions. On the day of transfection, 500 ml cells were seeded with 6×10E6 viable cells/mL in sterile disposable shaker flasks. For optimal transfection, a total amount of 1.0 µg plasmid DNA and 0.64 µl ExpiFectamine™ CHO Reagent per mL of culture volume was used.

Separate dilutions of ExpiFectamine™ CHO Reagent in cold OptiPRO™ Medium and DNA in cold OptiPRO™ Medium were incubated for 5 minutes at room temperature. Diluted ExpiFectamine™ CHO Reagent was added to the diluted DNA, thoroughly mixed and incubated for another 5 minutes at room temperature. Subsequently, the complexmix is added to the cells and incubated in a 37 °C incubator with ≥80% relative humidity and 8% CO2 on an orbital shaker platform.

According to the supplier's recommendations, High Titer Protocol was used for protein expression: addition of ExpiFectamine™ CHO Enhancer and single feed on Day 1 post-transfection; shift cells to 32 °C on Day 1 post transfection. On Day 8 post-transfection cell supernatant was harvested for purification.

Purification of FOLR1 TCB

The FOLR1 TCB was purified by protein A affinity chromatography, followed by ion exchange and size exclusion chromatography. In brief, supernatants were loaded on a HiTrap MabSelect SuRe column (GE Healthcare), which was equilibrated with 1×PBS pH7.4. After a washing step with the equilibration buffer with 5 column volumes, the proTCBs were eluted using 100 mM sodium acetate pH3.0. The flow rate was set to 5 ml/min. The pooled fractions were diluted with water (1:5 v/v) and loaded on a POROS HS 50 column (ThermoFisher Scientific), which was equilibrated with 40 mM sodium acetate pH5.5. After washing with equilibration buffer, the TCB was eluted using a sodium acetate gradient from 40 mM up to 1 M over 27 column volumes. The flow rate was set to 7 ml/min. The collected fractions were analyzed by analytical size exclusion chromatography (Waters BioSuite) and pooled according to the content of monomeric species. Subsequently, the pooled fractions were concentrated using an Amicon Ultra device (Millipore) to a final volume of 15 ml. The concentrated pool was loaded on a HiLoad 26/60 Superdex prep grade column (GE Healthcare), column volume 320 ml. The running buffer was 20 mM histidine-HCl, 140 mM NaCl pH6.0, the flow rate was set to 3 ml/min. Fractions were pooled according to the content of monomeric species.

TABLE 8

Production/purification results for FOLR1 TCB with cl22 as CD3 binder

| Molecule | Clone ID | Yield [mg/L] | Product peak SEC [%] | Main peak CE-SDS [%] | Endotoxin [EU/ml] |
|---|---|---|---|---|---|
| FOLR1 TCB_cl22 | P1AF1257 | 58.8 | 98.5 | 96.9 | <0.2 |

Example 16—Jurkat NFAT Activation Mediated by FOLR1-TCB ($CD3_{opt}$)

FOLR1-TCB containing CD3 clone22 binder was first tested in Jurkat NFAT reporter assay. FOLR1 targeting T cell bispecific antibody (TCB) simultaneously binds to huFOLR1 coated beads and CD3epsilon on T cell (Jurkat NFAT) thereby inducing T cell activation. T cell activation can be measured as luminescence as the Jurkat NFAT luciferase cells express luciferase upon activation via CD3epsilon (CD3ε). Jurkat-NFAT reporter cell line (Promega) is a human acute lymphatic leukemia reporter cell line with a NFAT promoter, expressing human CD3R. If TCB binds tumor target and CD3 (crosslinkage) binds CD3R Luciferase expression can be measured in Luminescence after addition of One-Glo substrate (Promega).

Jurkat NFAT assay medium: RPMI1640, 2 g/l Glucose, 2 g/l $NaHCO_3$, 10% FCS, 25 mM HEPES, 2 mM L-Glutamin, 1×NEAA, 1×Sodium-pyruvate Jurkat NFAT cultivation medium: RPMI1640, 2 g/l Glucose, 2 g/l $NaHCO_3$, 10% FCS, 25 mM HEPES, 2 mM L-Glutamin, 1×NEAA, 1×Sodium-pyruvate; freshly added Hygromycine B 200 μg/ml.

65 μl Streptavidin Dynabeads were diluted in 10 ml PBS. The beads were centrifuged at 400rcf for 4 min and supernatant was removed. Then 30 μg of biotinylated FolR1 antigen were added to 1.5 ml DPBS and then added to the Streptavidin Beads. The bead-antigen mixture was incubated for 1 h at 4 °C, slowly rotating. After incubation, 10 ml DPBS were added to the bead-ag conjugates, centrifuged (4 min, 400 rcf) and the supernatant discarded. The conjugates were again washed with 5 ml DPBS and the pellet then resuspended in 6 ml assay medium. Effector cells (Jurkat NFAT) were harvested, counted and checked for viability. Cells were centrifuged at 350 rcf for 4 minutes before cells were resuspended in 12 ml assay medium. cAMP was added to effector cells suspension (2% end volume).

Coated beads (in 10 μl/well) and Jurkat NFAT effector cells (20.000 cells/well in 20 μl/well) with cAMP were mixed and added to a 384-well white walled clear bottom plate (Greiner BioOne). FOLR1-TCB was diluted in jurkat assay medium before a dilution row was prepared and 10 μl per well were added. Cells were incubated with beads and TCB/medium at 37 °C for 5.5 h in a humidified incubator before they were taken out of the incubator for about 10 min to adapt to room temperature prior to Luminescence read out in Tecan Spark using 0.5 sec/well as detection time.

FOLR1-TCB induced dose-dependent Jurkat NFAT activation using huFOLR1-coated beads for crosslinking (FIG. 34).

Example 17—T Cell Killing Mediated by FOLR1 Pro-TCB (CD3 Clone22)

To assess potency of FOLR1-TCB with $CD3_{opt}$, the target cell cytotoxicity and T cell activation mediated by FOLR1-TCB was assessed using FOLR1 positive Ovcar-3 cells. Human PBMCs were used as effector cells and T cell activation markers were stained after 48 h of incubation with the molecules and cells. Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube subsequently filled with 50 ml of PBS. The mixture was centrifuged (400×g, 10 minutes, room temperature), the supernatant discarded and the PBMC pellet resuspended in 2 ml ACK buffer for Erythrocytes lysis. After incubation at 37 °C for about 2-3 minutes the tubes were filled with sterile PBS to 50 ml and centrifuged at 350×g for 10 minutes. This washing step was repeated once prior to resuspension of PBMCs in advanced RPMI1640 medium containing 2% FCS, 1×GlutaMax and 10% DMSO. PBMCs were slowly frozen in CoolCell® Cell Freezing Containers (BioCision) at −80 °C and then transferred to liquid nitrogen. One day before assay start adherent target cells were harvested with Trypsin/EDTA, counted, checked for viability and resuspended in assay medium (RPMI1640, 2% FCS, 1×GlutaMax). About 24 h before assay start PBMCs were thawed in RPMI1640 medium (10% FCS, 1×GlutaMax). PBMCs were centrifuged at 350 g for 7 min and resuspended in fresh medium (RPMI1640, 10% FCS, 1×GlutaMax). PBMCs were kept for a maximum of 24 hours before they were used for an assay. The assay medium was RPMI+2% FCS+1% GlutaMax.

Target cells were plated at a density of 20 000 cells/well (in 50 μl/well in assay medium) using 96-well flat-bottom plates. Cells were incubated over night in a humidified incubator at 37 °C. The molecules were diluted in assay medium and added at the indicated concentrations in triplicates. PBMCS were harvested and centrifuged at 350 g for 7 min before they were resuspended in assay medium. 0.2 mio huPBMCs in 100 μl/well (E:T 10:1, based on the number of seeded target cells) were added before plates were incubated at 37 °C for 48 h. Target cell killing was assessed after 48 h of incubation at 37 °C, 5% CO2 by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 for 1 h before LDH readout. Minimal lysis (=0%) refers to target cells co-incubated with effector cells without any TCB. LDH release was measured by measuring absorbance (A492 nm-A650 nm).

T-cell activation was assessed after 48 h of incubation at 37 °C, 5% $CO_2$ by quantification of CD69 on CD4 positive and CD8 positive T cells.

DPBS was added to wells containing the PBMCs before the plates were centrifuged for 4 min at 400×g. Supernatant was aspirated and cells were washed again with PBS, centrifuged, supernatant removed and the cell pellet was resuspended by vortexing the plate carefully. 5 μl of LIVE/DEAD™ Fixable Aqua Dead Cell Stain were diluted 1:1000 in DPBS. 50 μl of the diluted dye were added to the wells containing the PBMCs. One empty well was prepared by adding 1 drop of compensation beads (Invitrogen Arc™, reactive beads) and 1 μl undiluted LIVE/DEAD dye was added. The plate was incubated for 30 minutes at 4 °C. To remove excess color, the cells were washed twice, first time with 150 μl PBS and second time with 150 μl FACS buffer. The plates were centrifuged for 4 min at 400×g. The supernatant was removed and the cells were resuspended by careful vortexing. 1 drop of negative beads (Invitrogen Arc™, negative beads) was added to the compensation control well containing the LIVE stained beads. 25 μl of the diluted CD4/CD8/CD25/CD69 antibody mixture (0.8 μl of each color/well), single antibodies (for compensation controls; 0.8 μl AB+24 μl FACS buffer) or FACS buffer (for unstained control) was added to the resuspended cells in the wells and the plate was incubated for 60 min at 4 °C. To remove unbound antibody, the cells were washed twice with 150 μl FACS buffer per well. After the centrifugation the supernatant was removed and the cells were resuspended bycareful vortexing. The cells were fixed in 150 ul FACS+ 1% PFA buffer overnight for analysis the next week. The next day the cells were re-suspended in 150 μl FACS buffer. Fluorescence was measured using FACS LSR Fortessa.

Dose-dependent target cell killing could be shown for Ovcar-3 cells incubated with huPBMCs and FOLR1-TCB ($CD3_{opt}$) (FIG. 35A). Dotted line shows huPBMCs incubated with target cells but without TCB. Target cell cytotoxicity correlates with T cell activation measured by CD69 for CD4 and CD8 positive T cells (FIG. 35B).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A bispecific antibody that binds to CD3 and Folate receptor 1 (FolR1), wherein the bispecific antibody comprises:

(i) a first antigen binding domain capable of specific binding to CD3, comprising a heavy chain variable region (VH) comprising a heavy chain complementary determining region (HCDR) 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a light chain variable region (VL) comprising a light chain complementarity determining region (LCDR) 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, and (ii) a second antigen binding domain capable of specific binding to FolR1, comprising a VH comprising an HCDR 1 comprising the amino acid sequence of SEQ ID NO: 124, an HCDR 2 comprising the amino acid sequence of SEQ ID NO: 125, and an HCDR 3 comprising the amino acid sequence of SEQ ID NO: 126, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10.

2. The bispecific antibody of claim 1, wherein the VH of the first antigen binding domain comprises an amino acid sequence that is at least about 95% identical to the amino acid sequence of SEQ ID NO: 7, and the VL comprises an amino acid sequence that is at least about 95% identical to the amino acid sequence of SEQ ID NO: 11.

3. A bispecific antibody that binds to CD3 and FolR1, wherein the bispecific antibody comprises:

(i) a first antigen binding domain capable of specific binding to CD3, comprising a VH comprising the amino acid sequence of SEQ ID NO: 7 and a VL comprising the amino acid sequence of SEQ ID NO: 11, and (ii) a second antigen binding domain capable of specific binding to FolR1, comprising a VH comprising the amino acid sequence of SEQ ID NO: 123 and a VL comprising the amino acid sequence of SEQ ID NO: 11.

4. The bispecific antibody of claim 1, wherein the first antigen binding domain is a Fab molecule, and wherein the bispecific antibody further comprises an Fc domain composed of a first and a second subunit.

5. The bispecific antibody of claim 4, comprising a third antigen binding domain capable of specific binding to FolR1.

6. The bispecific antibody of claim 5, wherein:

(i) the second and the third antigen binding domains are each a Fab molecule; and (ii) the first antigen binding domain is a Fab molecule wherein the variable domains VL and VH or the constant domains CL and CH1 of the Fab light chain and the Fab heavy chain are replaced by each other.

7. The bispecific antibody of claim 6, wherein the variable domains VL and VH of the Fab light chain and the Fab heavy chain are replaced by each other.

8. The bispecific antibody of claim 6, wherein the second and the third antigen binding domains are each a conventional Fab molecule.

9. The bispecific antibody of claim 8, wherein the second and the third antigen binding domains are each a Fab molecule wherein:

in the constant domain CL the amino acid at position 124 is substituted independently by lysine (K), arginine (R), or histidine (H) (numbering according to Kabat) and the amino acid at position 123 is substituted independently by lysine (K), arginine (R), or histidine (H) (numbering according to Kabat), and in the constant domain CH1 the amino acid at position 147 is substituted independently by glutamic acid (E) or aspartic acid (D) (numbering according to Kabat EU index) and the amino acid at position 213 is substituted independently by glutamic acid (E) or aspartic acid (D) (numbering according to Kabat EU index).

10. The bispecific antibody of claim 5, wherein the first and the second antigen binding domains are fused to each other.

11. The bispecific antibody of claim 10, wherein the first and the second antigen binding domains are fused to each other via a peptide linker.

12. The bispecific antibody of claim 5, wherein the first and the second antigen binding domains are each a Fab molecule and wherein:

(i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.

13. The bispecific antibody of claim 5, wherein the first, the second, and the third antigen binding domains are each a Fab molecule and the bispecific antibody comprises an Fc domain composed of a first and a second subunit; and wherein:

(i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and the third antigen binding domain, where present, is fused at the C-terminus of the Fab heavy chain to the N-terminus of the second subunit of the Fc domain.

14. The bispecific antibody of claim 5, wherein the Fc domain is an IgG Fc domain and/or a human Fc domain.

15. The bispecific antibody of claim 5, wherein the Fc domain is an $IgG_1$ Fc domain.

16. The bispecific antibody of claim 5, wherein:

(i) the Fc comprises a modification promoting the association of the first and the second subunit of the Fc domain; and/or (ii) the Fc domain comprises one or more amino acid substitutions that reduces binding to an Fc receptor and/or an effector function.

17. The bispecific antibody of claim 5, wherein the second and the third antigen binding domains each comprises a VH comprising an HCDR 1 comprising the amino acid sequence of SEQ ID NO: 124, an HCDR 2 comprising the amino acid sequence of SEQ ID NO: 125, and an HCDR 3 comprising the amino acid sequence of SEQ ID NO: 126, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10.

18. The bispecific antibody of claim 5, wherein the second and the third antigen binding domains each comprises a VH comprising an amino acid sequence that is at least about 95% identical to the amino acid sequence of SEQ ID NO: 123 and a VL comprising an amino acid sequence that is at least about 95% identical to the amino acid sequence of SEQ ID NO: 11.

19. A pharmaceutical composition comprising the bispecific antibody of claim 17.

20. A pharmaceutical composition comprising the bispecific antibody of claim 18.

21. A method of treating a cancer in an individual comprising administering to the subject the bispecific antibody of claim 1.

22. A method of treating a cancer in an individual comprising administering to the subject the bispecific antibody of claim 17.

23. A method of treating a cancer in an individual comprising administering to the subject the bispecific antibody of claim 18.

24. A bispecific antibody comprising:

(i) a first antigen binding domain capable of specific binding to CD3, comprising a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, (ii) a second antigen binding domain capable of specific binding to FolR1, and (iii) a third antigen binding domain capable of specific binding to FolR1, wherein the second and the third antigen binding domains each comprises a VH comprising a HCDR 1 of SEQ ID NO: 124, a HCDR 2 of SEQ ID NO: 125, and a HCDR 3 of SEQ ID NO: 126, and a VL comprising a LCDR 1 of SEQ ID NO: 8, a LCDR 2 of SEQ ID NO: 9 and a LCDR 3 of SEQ ID NO: 10;

wherein the first, second, and third antigen binding domains are each a Fab molecule, wherein the second and third are each a conventional Fab molecule;

wherein in the first antigen binding domain the variable domains VL and VH of the Fab light chain and the Fab heavy chain are replaced by each other;

wherein in each of the second and the third antigen binding domains:

(a) in the constant domain CL, the amino acid at position 124 is substituted independently by lysine (K), arginine (R), or histidine (H) (numbering according to Kabat) and the amino acid at position 123 is substituted independently by lysine (K), arginine (R), or histidine (H) (numbering according to Kabat), and (b) in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index);

wherein:

(a) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (b) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and the third antigen binding domain is fused at the C-terminus of the Fab heavy chain to the N-terminus of the second subunit of the Fc domain;

wherein the bispecific antibody comprises an Fc domain composed of a first and a second subunit; and wherein the Fc domain is an IgG comprising a modification promoting the association of the first and the second subunit of the Fc domain and further comprising one or more amino acid substitutions that reduces binding to an Fc receptor and/or reduces an effector function.

25. The bispecific antibody of claim 24, wherein the first antigen binding domain comprises a VH comprising an amino acid sequence that is at least about 95% identical to the amino acid sequence of SEQ ID NO: 7 and a VL comprising an amino acid sequence that is at least about 95% identical to the amino acid sequence of SEQ ID NO: 11; and the second and the third antigen binding domains each comprises a VH comprising an amino acid sequence that is at least about 95% identical to the amino acid sequence of SEQ ID NO: 123 and a VL comprising an amino acid sequence that is at least about 95% identical to the amino acid sequence of SEQ ID NO: 11.

26. The bispecific antibody of claim 24, wherein the Fc domain is an $IgG_1$.

27. The bispecific antibody of claim 24, wherein the Fc domain is a human Fc domain.

28. A pharmaceutical composition comprising the bispecific antibody of claim 24.

29. A method of treating a cancer in an individual comprising administering to the subject the bispecific antibody of claim 24.

30. The bispecific antibody of claim 1, wherein the first antigen binding domain comprises a VH comprising the amino acid sequence of SEQ ID NO: 7 and a VL comprising the amino acid sequence of SEQ ID NO: 11.

31. The bispecific antibody of claim 1, wherein the second antigen binding domain comprises a VH comprising an amino acid sequence that is at least about 95% identical to the amino acid sequence of SEQ ID NO: 123 and a VL comprising an amino acid sequence that is at least about 95% identical to the amino acid sequence of SEQ ID NO: 11.

32. The bispecific antibody of claim 1, wherein the second antigen binding domain comprises a VH comprising the amino acid sequence of SEQ ID NO: 123 and a VL comprising the amino acid sequence of SEQ ID NO: 11.

33. The bispecific antibody of claim 24, wherein the Fc domain is a human $IgG_1$ Fc domain.

34. The bispecific antibody of claim 24, wherein the first and the second antigen binding domains are fused to each other via a peptide linker.

35. The bispecific antibody of claim 24, wherein the first antigen binding domain comprises a VH comprising the amino acid sequence of SEQ ID NO: 7 and a VL comprising the amino acid sequence of SEQ ID NO: 11; and the second and the third antigen binding domains each comprises a VH comprising the amino acid sequence of SEQ ID NO: 123 and a VL comprising the amino acid sequence of SEQ ID NO: 11.

36. The bispecific antibody of claim 35, wherein the Fc domain is a human $IgG_1$ Fc domain, and wherein the first and the second antigen binding domains are fused to each other via a peptide linker.

37. A pharmaceutical composition comprising the bispecific antibody of claim 33.

38. A pharmaceutical composition comprising the bispecific antibody of claim 34.

39. A pharmaceutical composition comprising the bispecific antibody of claim 35.

40. A pharmaceutical composition comprising the bispecific antibody of claim 36.

41. A method of treating a cancer in an individual comprising administering to the subject the bispecific antibody of claim 33.

42. A method of treating a cancer in an individual comprising administering to the subject the bispecific antibody of claim 34.

43. A method of treating a cancer in an individual comprising administering to the subject the bispecific antibody of claim 35.

44. A method of treating a cancer in an individual comprising administering to the subject the bispecific antibody of claim 36.

* * * * *

SEQUENCE LISTING

```
Sequence total quantity: 137
SEQ ID NO: 1            moltype = AA  length = 5
FEATURE                 Location/Qualifiers
REGION                  1..5
                        note = CD3orig HCDR1
source                  1..5
                        mol_type = protein
                        organism = synthetic construct
SEQUENCE: 1
TYAMN                                                         5

SEQ ID NO: 2            moltype = AA  length = 5
FEATURE                 Location/Qualifiers
REGION                  1..5
                        note = CD3opt HCDR1
source                  1..5
                        mol_type = protein
                        organism = synthetic construct
SEQUENCE: 2
SYAMN                                                         5

SEQ ID NO: 3            moltype = AA  length = 19
FEATURE                 Location/Qualifiers
REGION                  1..19
                        note = CD3orig / CD3opt HCDR2
source                  1..19
                        mol_type = protein
                        organism = synthetic construct
SEQUENCE: 3
RIRSKYNNYA TYYADSVKG                                          19

SEQ ID NO: 4            moltype = AA  length = 14
FEATURE                 Location/Qualifiers
REGION                  1..14
                        note = CD3orig HCDR3
source                  1..14
                        mol_type = protein
                        organism = synthetic construct
SEQUENCE: 4
HGNFGNSYVS WFAY                                               14

SEQ ID NO: 5            moltype = AA  length = 14
FEATURE                 Location/Qualifiers
REGION                  1..14
                        note = CD3opt HCDR3
source                  1..14
                        mol_type = protein
                        organism = synthetic construct
SEQUENCE: 5
HTTFPSSYVS YYGY                                               14

SEQ ID NO: 6            moltype = AA  length = 125
FEATURE                 Location/Qualifiers
REGION                  1..125
                        note = CD3orig VH
source                  1..125
                        mol_type = protein
                        organism = synthetic construct
SEQUENCE: 6
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSS                                                         125
```

```
SEQ ID NO: 7            moltype = AA  length = 125
FEATURE                 Location/Qualifiers
REGION                  1..125
                        note = CD3opt VH
source                  1..125
                        mol_type = protein
                        organism = synthetic construct
SEQUENCE: 7
EVQLLESGGG LVQPGGSLRL SCAASGFQFS SYAMNWVRQA PGKGLEWVSR IRSKYNNYAT  60
YYADSVKGRF TISRDDSKNT LYLQMNSLRA EDTAVYYCVR HTTFPSSYVS YYGYWGQGTL  120
VTVSS                                                             125

SEQ ID NO: 8            moltype = AA  length = 14
FEATURE                 Location/Qualifiers
REGION                  1..14
                        note = CD3orig / CD3opt LCDR1
source                  1..14
                        mol_type = protein
                        organism = synthetic construct
SEQUENCE: 8
GSSTGAVTTS NYAN                                                   14

SEQ ID NO: 9            moltype = AA  length = 7
FEATURE                 Location/Qualifiers
REGION                  1..7
                        note = CD3orig / CD3opt LCDR2
source                  1..7
                        mol_type = protein
                        organism = synthetic construct
SEQUENCE: 9
GTNKRAP                                                           7

SEQ ID NO: 10           moltype = AA  length = 9
FEATURE                 Location/Qualifiers
REGION                  1..9
                        note = CD3orig / CD3opt LCDR3
source                  1..9
                        mol_type = protein
                        organism = synthetic construct
SEQUENCE: 10
ALWYSNLWV                                                         9

SEQ ID NO: 11           moltype = AA  length = 109
FEATURE                 Location/Qualifiers
REGION                  1..109
                        note = CD3orig / CD3opt VL
source                  1..109
                        mol_type = protein
                        organism = synthetic construct
SEQUENCE: 11
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVL             109

SEQ ID NO: 12           moltype = AA  length = 453
FEATURE                 Location/Qualifiers
REGION                  1..453
                        note = CD3orig IgG HC
source                  1..453
                        mol_type = protein
                        organism = synthetic construct
SEQUENCE: 12
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSP                               453

SEQ ID NO: 13           moltype = AA  length = 453
FEATURE                 Location/Qualifiers
REGION                  1..453
                        note = CD3opt IgG HC
source                  1..453
                        mol_type = protein
                        organism = synthetic construct
SEQUENCE: 13
EVQLLESGGG LVQPGGSLRL SCAASGFQFS SYAMNWVRQA PGKGLEWVSR IRSKYNNYAT  60
```

```
YYADSVKGRF TISRDDSKNT LYLQMNSLRA EDTAVYYCVR HTTFPSSYVS YYGYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSP                              453

SEQ ID NO: 14          moltype = AA  length = 216
FEATURE                Location/Qualifiers
REGION                 1..216
                       note = CD3orig / CD3opt IgG LC
source                 1..216
                       mol_type = protein
                       organism = synthetic construct
SEQUENCE: 14
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 15          moltype = AA  length = 5
FEATURE                Location/Qualifiers
REGION                 1..5
                       note = TYRP1 HCDR1
source                 1..5
                       mol_type = protein
                       organism = synthetic construct
SEQUENCE: 15
DYFLH                                                             5

SEQ ID NO: 16          moltype = AA  length = 17
FEATURE                Location/Qualifiers
REGION                 1..17
                       note = TYRP1 HCDR2
source                 1..17
                       mol_type = protein
                       organism = synthetic construct
SEQUENCE: 16
WINPDNGNTV YAQKFQG                                                17

SEQ ID NO: 17          moltype = AA  length = 12
FEATURE                Location/Qualifiers
REGION                 1..12
                       note = TYRP1 HCDR3
source                 1..12
                       mol_type = protein
                       organism = synthetic construct
SEQUENCE: 17
RDYTYEKAAL DY                                                     12

SEQ ID NO: 18          moltype = AA  length = 121
FEATURE                Location/Qualifiers
REGION                 1..121
                       note = TYRP1 VH
source                 1..121
                       mol_type = protein
                       organism = synthetic construct
SEQUENCE: 18
QVQLVQSGAE VKKPGASVKV SCKASGFNIK DYFLHWVRQA PGQGLEWMGW INPDNGNTVY  60
AQKFQGRVTM TADTSTSTVY MELSSLRSED TAVYYCTRRD YTYEKAALDY WGQGTLVTVS  120
S                                                                 121

SEQ ID NO: 19          moltype = AA  length = 11
FEATURE                Location/Qualifiers
REGION                 1..11
                       note = TYRP1 LCDR1
source                 1..11
                       mol_type = protein
                       organism = synthetic construct
SEQUENCE: 19
RASGNIYNYL A                                                      11

SEQ ID NO: 20          moltype = AA  length = 7
FEATURE                Location/Qualifiers
REGION                 1..7
                       note = TYRP1 LCDR2
source                 1..7
                       mol_type = protein
```

```
                       organism = synthetic construct
SEQUENCE: 20
DAKTLAD                                                     7

SEQ ID NO: 21          moltype = AA  length = 9
FEATURE                Location/Qualifiers
REGION                 1..9
                       note = TYRP1 LCDR3
source                 1..9
                       mol_type = protein
                       organism = synthetic construct
SEQUENCE: 21
QHFWSLPFT                                                   9

SEQ ID NO: 22          moltype = AA  length = 107
FEATURE                Location/Qualifiers
REGION                 1..107
                       note = TYRP1 VL
source                 1..107
                       mol_type = protein
                       organism = synthetic construct
SEQUENCE: 22
DIQMTQSPSS LSASVGDRVT ITCRASGNIY NYLAWYQQKP GKVPKLLIYD AKTLADGVPS  60
RFSGSGSGTD FTLTISSLQP EDVATYYCQH FWSLPFTFGQ GTKLEIK                107

SEQ ID NO: 23          moltype = AA  length = 674
FEATURE                Location/Qualifiers
REGION                 1..674
                       note = TYRP1 VH-CH1(EE) - CD3orig/CD3opt VL-CH1 - Fc (knob,
                        PGLALA)
source                 1..674
                       mol_type = protein
                       organism = synthetic construct
SEQUENCE: 23
QVQLVQSGAE VKKPGASVKV SCKASGFNIK DYFLHWVRQA PGQGLEWMGW INPDNGNTVY  60
AQKFQGRVTM TADTSTSTVY MELSSLRSED TAVYYCTRRD YTYEKAALDY WGQGTLVTVS  120
SASTKGPSVF PLAPSSKSTS GGTAALGCLV EDYFPEPVTV SWNSGALTSG VHTFPAVLQS  180
SGLYSLSSVV TVPSSSLGTQ TYICNVNHKP SNTKVDEKVE PKSCDGGGGS GGGGSQAVVT  240
QEPSLTVSPG GTVTLTCGSS TGAVTTSNYA NWVQEKPGQA FRGLIGGTNK RAPGTPARFS  300
GSLLGGKAAL TLSGAQPEDE AEYYCALWYS NLWVFGGGTK LTVLSSASTK GPSVFPLAPS  360
SKSTSGGTAA LGCLVKDYFP EPVTVSWNSG ALTSGVHTFP AVLQSSGLYS LSSVVTVPSS  420
SLGTQTYICN VNHKPSNTKV DKKVEPKSCD KTHTCPPCPA PEAAGGPSVF LFPPKPKDTL  480
MISRTPEVTC VVVDVSHEDP EVKFNWYVDG VEVHNAKTKP REEQYNSTYR VVSVLTVLHQ  540
DWLNGKEYKC KVSNKALGAP IEKTISKAKG QPREPQVYTL PPCRDELTKN QVSLWCLVKG  600
FYPSDIAVEW ESNGQPENNY KTTPPVLDSD GSFFLYSKLT VDKSRWQQGN VFSCSVMHEA  660
LHNHYTQKSL SLSP                                                    674

SEQ ID NO: 24          moltype = AA  length = 449
FEATURE                Location/Qualifiers
REGION                 1..449
                       note = TYRP1 VH-CH1(EE) -Fc (hole, PGLALA)
source                 1..449
                       mol_type = protein
                       organism = synthetic construct
SEQUENCE: 24
QVQLVQSGAE VKKPGASVKV SCKASGFNIK DYFLHWVRQA PGQGLEWMGW INPDNGNTVY  60
AQKFQGRVTM TADTSTSTVY MELSSLRSED TAVYYCTRRD YTYEKAALDY WGQGTLVTVS  120
SASTKGPSVF PLAPSSKSTS GGTAALGCLV EDYFPEPVTV SWNSGALTSG VHTFPAVLQS  180
SGLYSLSSVV TVPSSSLGTQ TYICNVNHKP SNTKVDEKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSP                                    449

SEQ ID NO: 25          moltype = AA  length = 214
FEATURE                Location/Qualifiers
REGION                 1..214
                       note = TYRP1 VL-CL(RK)
source                 1..214
                       mol_type = protein
                       organism = synthetic construct
SEQUENCE: 25
DIQMTQSPSS LSASVGDRVT ITCRASGNIY NYLAWYQQKP GKVPKLLIYD AKTLADGVPS  60
RFSGSGSGTD FTLTISSLQP EDVATYYCQH FWSLPFTFGQ GTKLEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 26          moltype = AA  length = 232
FEATURE                Location/Qualifiers
```

```
REGION                 1..232
                       note = CD3orig VH-CL
source                 1..232
                       mol_type = protein
                       organism = synthetic construct
SEQUENCE: 26
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSSASVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 27          moltype = AA  length = 232
FEATURE                Location/Qualifiers
REGION                 1..232
                       note = CD3opt VH-CL
source                 1..232
                       mol_type = protein
                       organism = synthetic construct
SEQUENCE: 27
EVQLLESGGG LVQPGGSLRL SCAASGFQFS SYAMNWVRQA PGKGLEWVSR IRSKYNNYAT  60
YYADSVKGRF TISRDDSKNT LYLQMNSLRA EDTAVYYCVR HTTFPSSYVS YYGYWGQGTL  120
VTVSSASVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 28          moltype = AA  length = 360
FEATURE                Location/Qualifiers
REGION                 1..360
                       note = Human CD3 epsilon stalk - Fc(knob) - Avi
source                 1..360
                       mol_type = protein
                       organism = synthetic construct
SEQUENCE: 28
QDGNEEMGGI TQTPYKVSIS GTTVILTCPQ YPGSEILWQH NDKNIGGDED DKNIGSDEDH  60
LSLKEFSELE QSGYYVCYPR GSKPEDANFY LYLRARVSEN CVDEQLYFQG GSPKSADKTH  120
TCPPCPAPEL LGGPSVFLFP PKPKDTLMIS RTPEVTCVVV DVSHEDPEVK FNWYVDGVEV  180
HNAKTKPREE QYNSTYRVVS VLTVLHQDWL NGKEYKCKVS NKALPAPIEK TISKAKGQPR  240
EPQVYTLPPC RDELTKNQVS LWCLVKGFYP SDIAVEWESN GQPENNYKTT PPVLDSDGSF  300
FLYSKLTVDK SRWQQGNVFS CSVMHEALHN HYTQKSLSLS PGKSGGLNDI FEAQKIEWHE  360

SEQ ID NO: 29          moltype = AA  length = 325
FEATURE                Location/Qualifiers
REGION                 1..325
                       note = Human CD3 delta stalk - Fc (hole) - Avi
source                 1..325
                       mol_type = protein
                       organism = synthetic construct
SEQUENCE: 29
FKIPIEELED RVFVNCNTSI TWVEGTVGTL LSDITRLDLG KRILDPRGIY RCNGTDIYKD  60
KESTVQVHYR MCRSEQLYFQ GDKTHTCPPC PAPELLGGPS VFLFPPKPKD TLMISRTPEV  120
TCVVVDVSHE DPEVKFNWYV DGVEVHNAKT KPREEQYNST YRVVSVLTVL HQDWLNGKEY  180
KCKVSNKALP APIEKTISKA KGQPREPQVC TLPPSRDELT KNQVSLSCAV KGFYPSDIAV  240
EWESNGQPEN NYKTTPPVLD SDGSFFLVSK LTVDKSRWQQ GNVFSCSVMH EALHNHYTQK  300
SLSLSPGKSG GLNDIFEAQK IEWHE                                        325

SEQ ID NO: 30          moltype = AA  length = 351
FEATURE                Location/Qualifiers
REGION                 1..351
                       note = Cynomolgus CD3 epsilon stalk - Fc (knob) - Avi
source                 1..351
                       mol_type = protein
                       organism = synthetic construct
SEQUENCE: 30
QDGNEEMGSI TQTPYQVSIS GTTVILTCSQ HLGSEAQWQH NGKNKEDSGD RLFLPEFSEM  60
EQSGYYVCYP RGSNPEDASH HLYLKARVSE NCVDEQLYFQ GGSPKSADKT HTCPPCPAPE  120
LLGGPSVFLF PPKPKDTLMI SRTPEVTCVV VDVSHEDPEV KFNWYVDGVE VHNAKTKPRE  180
EQYNSTYRVV SVLTVLHQDW LNGKEYKCKV SNKALPAPIE KTISKAKGQP REPQVYTLPP  240
CRDELTKNQV SLWCLVKGFY PSDIAVEWES NGQPENNYKT TPPVLDSDGS FFLYSKLTVD  300
KSRWQQGNVF SCSVMHEALH NHYTQKSLSL SPGKSGGLND IFEAQKIEWH E           351

SEQ ID NO: 31          moltype = AA  length = 334
FEATURE                Location/Qualifiers
REGION                 1..334
                       note = Cynomolgus CD3 delta stalk - Fc (hole) - Avi
source                 1..334
                       mol_type = protein
                       organism = synthetic construct
SEQUENCE: 31
FKIPVEELED RVFVKCNTSV TWVEGTVGTL LTNNTRLDLG KRILDPRGIY RCNGTDIYKD  60
KESAVQVHYR MSQNCVDEQL YFQGGSPKSA DKTHTCPPCP APELLGGPSV FLFPPKPKDT  120
```

```
LMISRTPEVT CVVVDVSHED PEVKFNWYVD GVEVHNAKTK PREEQYNSTY RVVSVLTVLH  180
QDWLNGKEYK CKVSNKALPA PIEKTISKAK GQPREPQVCT LPPSRDELTK NQVSLSCAVK  240
GFYPSDIAVE WESNGQPENN YKTTPPVLDS DGSFFLVSKL TVDKSRWQQG NVFSCSVMHE  300
ALHNHYTQKS LSLSPGKSGG LNDIFEAQKI EWHE                             334

SEQ ID NO: 32          moltype = AA  length = 699
FEATURE                Location/Qualifiers
REGION                 1..699
                       note = Human TYRP1 ECD - Fc (knob) - Avi
source                 1..699
                       mol_type = protein
                       organism = synthetic construct
SEQUENCE: 32
QFPRQCATVE ALRSGMCCPD LSPVSGPGTD RCGSSSGRGR CEAVTADSRP HSPQYPHDGR  60
DDREVWPLRF FNRTCHCNGN FSGHNCGTCR PGWRGAACDQ RVLIVRRNLL DLSKEEKNHF  120
VRALDMAKRT THPLFVIATR RSEEILGPDG NTPQFENISI YNYFVWTHYY SVKKTFLGVG  180
QESFGEVDFS HEGPAFLTWH RYHLLRLEKD MQEMLQEPSF SLPYWNFATG KNVCDICTDD  240
LMGSRSNFDS TLISPNSVFS QWRVVCDSLE DYDTLGTLCN STEDGPIRRN PAGNVARPMV  300
QRLPEPQDVA QCLEVGLFDT PPFYSNSTNS FRNTVEGYSD PTGKYDPAVR SLHNLAHLFL  360
NGTGGQTHLS PNDPIFVLLH TFTDAVFDEW LRRYNADIST FPLENAPIGH NRQYNMVPFW  420
PPVTNTEMFV TAPDNLGYTY EIQWPSREFS VPEGSDKTHT CPPCPAPEAA GGPSVFLFPP  480
KPKDTLMISR TPEVTCVVVD VSHEDPEVKF NWYVDGVEVH NAKTKPREEQ YNSTYRVVSV  540
LTVLHQDWLN GKEYKCKVSN KALGAPIEKT ISKAKGQPRE PQVYTLPPCR DELTKNQVSL  600
WCLVKGFYPS DIAVEWESNG QPENNYKTTP PVLDSDGSFF LYSKLTVDKS RWQQGNVFSC  660
SVMHEALHNH YTQKSLSLSP GKSGGLNDIF EAQKIEWHE                        699

SEQ ID NO: 33          moltype = AA  length = 698
FEATURE                Location/Qualifiers
REGION                 1..698
                       note = Cynomolgus TYRP1 ECD - Fc (knob) - Avi
source                 1..698
                       mol_type = protein
                       organism = synthetic construct
SEQUENCE: 33
QFPRECATVE ALRSGMCCPD LSPMSGPGTD RCGSSSGRGR CEAVTADSRP HSPRYPHDGR  60
DDREVWPLRF FNRTCHCNGN FSGHNCGTCR PGWRGAACDQ RVLVVRRNLL DLSKEEKNHF  120
VRALDMAKRT THPLFVIATR RSEEILGPDG NTPQFENISI YNYFVWTHYY SVKKTFLGAG  180
QESFGEVDFS HEGPAFLTWH RYHLLRLEKD MQEMLQEPSF SLPYWNFATG KNVCDICTDD  240
LMGSRSNFDS TLISPNSVFS QWRVVCDSLE DYDTLGTLCN STESGPIRRN PAGNVARPMV  300
QRLPEPQDVA QCLEVGLFDT PPFYSNSTNS FRNTVEGYSD PTGKYDPAVR SLHNLAHLFL  360
NGTGGQTHLS PNDPIFVLLH TFTDAVFDEW LRRYNADIST FPLENAPIGH NRQYNMVPFW  420
PPVTNTEMFV TAPDNLGYTY EVQWPSREFS VPGSDKTHTC PPCPAPEAAG GPSVFLFPPK  480
PKDTLMISRT PEVTCVVVDV SHEDPEVKFN WYVDGVEVHN AKTKPREEQY NSTYRVVSVL  540
TVLHQDWLNG KEYKCKVSNK ALGAPIEKTI SKAKGQPREP QVYTLPPCRD ELTKNQVSLW  600
CLVKGFYPSD IAVEWESNGQ PENNYKTTPP VLDSDGSFFL YSKLTVDKSR WQQGNVFSCS  660
VMHEALHNHY TQKSLSLSPG KSGGLNDIFE AQKIEWHE                         698

SEQ ID NO: 34          moltype = AA  length = 699
FEATURE                Location/Qualifiers
REGION                 1..699
                       note = Mouse TYRP1 ECD - Fc (knob) - Avi
source                 1..699
                       mol_type = protein
                       organism = synthetic construct
SEQUENCE: 34
QFPRECANIE ALRRGVCCPD LLPSSGPGTD PCGSSSGRGR CVAVIADSRP HSRHYPHDGK  60
DDREAWPLRF FNRTCQCNDN FSGHNCGTCR PGWRGAACNQ KILTVRRNLL DLSPEEKSHF  120
VRALDMAKRT THPQFVIATR RLEDILGPDG NTPQFENISV YNYFVWTHYY SVKKTFLGTG  180
QESFGDVDFS HEGPAFLTWH RYHLLQLERD MQEMLQEPSF SLPYWNFATG KNVCDVCTDD  240
LMGSRSNFDS TLISPNSVFS QWRVVCESLE EYDTLGTLCN STEGGPIRRN PAGNVGRPAV  300
QRLPEPQDVT QCLEVRVFDT PPFYSNSTDS FRNTVEGYSA PTGKYDPAVR SLHNLAHLFL  360
NGTGGQTHLS PNDPIFVLLH TFTDAVFDEW LRRYNADIST FPLENAPIGH NRQYNMVPFW  420
PPVTNTEMFV TAPDNLGYAY EVQWPGQEFT VSEGSDKTHT CPPCPAPEAA GGPSVFLFPP  480
KPKDTLMISR TPEVTCVVVD VSHEDPEVKF NWYVDGVEVH NAKTKPREEQ YNSTYRVVSV  540
LTVLHQDWLN GKEYKCKVSN KALGAPIEKT ISKAKGQPRE PQVYTLPPCR DELTKNQVSL  600
WCLVKGFYPS DIAVEWESNG QPENNYKTTP PVLDSDGSFF LYSKLTVDKS RWQQGNVFSC  660
SVMHEALHNH YTQKSLSLSP GKSGGLNDIF EAQKIEWHE                        699

SEQ ID NO: 35          moltype = AA  length = 225
FEATURE                Location/Qualifiers
REGION                 1..225
                       note = Fc (hole)
source                 1..225
                       mol_type = protein
                       organism = synthetic construct
SEQUENCE: 35
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSRDELTK NQVSLSCAVK GFYPSDIAVE WESNGQPENN YKTTPPVLDS  180
```

```
DGSFFLVSKL TVDKSRWQQG NVFSCSVMHE ALHNRFTQKS LSLSP                 225

SEQ ID NO: 36           moltype = AA  length = 393
FEATURE                 Location/Qualifiers
REGION                  1..393
                        note = EGFRvIII ECD - Avi - His
source                  1..393
                        mol_type = protein
                        organism = synthetic construct
SEQUENCE: 36
LEEKKGNYVV TDHGSCVRAC GADSYEMEED GVRKCKKCEG PCRKVCNGIG IGEFKDSLSI  60
NATNIKHFKN CTSISGDLHI LPVAFRGDSF THTPPLDPQE LDILKTVKEI TGFLLIQAWP  120
ENRTDLHAFE NLEIIRGRTK QHGQFSLAVV SLNITSLGLR SLKEISDGDV IISGNKNLCY  180
ANTINWKKLF GTSGQKTKII SNRGENSCKA TGQVCHALCS PEGCWGPEPR DCVSCRNVSR  240
GRECVDKCNL LEGEPREFVE NSECIQCHPE CLPQAMNITC TGRGPDNCIQ CAHYIDGPHC  300
VKTCPAGVMG ENNTLVWKYA DAGHVCHLCH PNCTYGCTGP GLEGCPTNGP KIPSVDGGSP  360
TPPTPGGGSG LNDIFEAQKI EWHEARAHHH HHH                              393

SEQ ID NO: 37           moltype = AA  length = 5
FEATURE                 Location/Qualifiers
REGION                  1..5
                        note = EGFRvIII P056.021 HCDR1
source                  1..5
                        mol_type = protein
                        organism = synthetic construct
SEQUENCE: 37
SYWIA                                                             5

SEQ ID NO: 38           moltype = AA  length = 17
FEATURE                 Location/Qualifiers
REGION                  1..17
                        note = EGFRvIII P056.021 HCDR2
source                  1..17
                        mol_type = protein
                        organism = synthetic construct
SEQUENCE: 38
VIHPYDSDTR YSPSFQG                                                17

SEQ ID NO: 39           moltype = AA  length = 10
FEATURE                 Location/Qualifiers
REGION                  1..10
                        note = EGFRvIII P056.021 HCDR3
source                  1..10
                        mol_type = protein
                        organism = synthetic construct
SEQUENCE: 39
VSRSSYAFDY                                                        10

SEQ ID NO: 40           moltype = AA  length = 119
FEATURE                 Location/Qualifiers
REGION                  1..119
                        note = EGFRvIII P056.021 VH
source                  1..119
                        mol_type = protein
                        organism = synthetic construct
SEQUENCE: 40
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RSSYAFDYWG QGTLVTVSS   119

SEQ ID NO: 41           moltype = AA  length = 17
FEATURE                 Location/Qualifiers
REGION                  1..17
                        note = EGFRvIII P056.021 LCDR1
source                  1..17
                        mol_type = protein
                        organism = synthetic construct
SEQUENCE: 41
KSSQSVLYSS NNKNYLA                                                17

SEQ ID NO: 42           moltype = AA  length = 7
FEATURE                 Location/Qualifiers
REGION                  1..7
                        note = EGFRvIII P056.021 LCDR2
source                  1..7
                        mol_type = protein
                        organism = synthetic construct
SEQUENCE: 42
WASTRES                                                           7
```

```
SEQ ID NO: 43          moltype = AA  length = 10
FEATURE                Location/Qualifiers
REGION                 1..10
                       note = EGFRvIII P056.021 LCDR3
source                 1..10
                       mol_type = protein
                       organism = synthetic construct
SEQUENCE: 43
QQVHSGPPVT                                                        10

SEQ ID NO: 44          moltype = AA  length = 114
FEATURE                Location/Qualifiers
REGION                 1..114
                       note = EGFRvIII P056.021 VL
source                 1..114
                       mol_type = protein
                       organism = synthetic construct
SEQUENCE: 44
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQVHSG PPVTFGQGTK VEIK        114

SEQ ID NO: 45          moltype = AA  length = 5
FEATURE                Location/Qualifiers
REGION                 1..5
                       note = EGFRvIII P056.052 HCDR1
source                 1..5
                       mol_type = protein
                       organism = synthetic construct
SEQUENCE: 45
NYWIG                                                             5

SEQ ID NO: 46          moltype = AA  length = 17
FEATURE                Location/Qualifiers
REGION                 1..17
                       note = EGFRvIII P056.052 HCDR2
source                 1..17
                       mol_type = protein
                       organism = synthetic construct
SEQUENCE: 46
TIYPGDSDRR YSPSFQG                                                17

SEQ ID NO: 47          moltype = AA  length = 10
FEATURE                Location/Qualifiers
REGION                 1..10
                       note = EGFRvIII P056.052 HCDR3
source                 1..10
                       mol_type = protein
                       organism = synthetic construct
SEQUENCE: 47
VSRSSYAFDY                                                        10

SEQ ID NO: 48          moltype = AA  length = 119
FEATURE                Location/Qualifiers
REGION                 1..119
                       note = EGFRvIII P056.052 VH
source                 1..119
                       mol_type = protein
                       organism = synthetic construct
SEQUENCE: 48
EVQLVQSGAE VKKPGESLKI SCKGSGYTFM NYWIGWVRQM PGKGLEWMGT IYPGDSDRRY  60
SPSFQGQVTL SADKSISTAY LQWSSLKASD TAMYYCARVS RSSYAFDYWG QGTLVTVSS   119

SEQ ID NO: 49          moltype = AA  length = 17
FEATURE                Location/Qualifiers
REGION                 1..17
                       note = EGFRvIII P056.052 LCDR1
source                 1..17
                       mol_type = protein
                       organism = synthetic construct
SEQUENCE: 49
KSSQSVLYSS NNKNYLA                                                17

SEQ ID NO: 50          moltype = AA  length = 7
FEATURE                Location/Qualifiers
REGION                 1..7
                       note = EGFRvIII P056.052 LCDR2
source                 1..7
                       mol_type = protein
                       organism = synthetic construct
```

```
SEQUENCE: 50
WASTRES                                                             7

SEQ ID NO: 51           moltype = AA  length = 10
FEATURE                 Location/Qualifiers
REGION                  1..10
                        note = EGFRvIII P056.052 LCDR3
source                  1..10
                        mol_type = protein
                        organism = synthetic construct
SEQUENCE: 51
QQVHSGPPVT                                                          10

SEQ ID NO: 52           moltype = AA  length = 114
FEATURE                 Location/Qualifiers
REGION                  1..114
                        note = EGFRvIII P056.052 VL
source                  1..114
                        mol_type = protein
                        organism = synthetic construct
SEQUENCE: 52
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQVHSG PPVTFGQGTK VEIK        114

SEQ ID NO: 53           moltype = AA  length = 5
FEATURE                 Location/Qualifiers
REGION                  1..5
                        note = EGFRvIII P047.019 HCDR1
source                  1..5
                        mol_type = protein
                        organism = synthetic construct
SEQUENCE: 53
SIWIH                                                               5

SEQ ID NO: 54           moltype = AA  length = 17
FEATURE                 Location/Qualifiers
REGION                  1..17
                        note = EGFRvIII P047.019 HCDR2
source                  1..17
                        mol_type = protein
                        organism = synthetic construct
SEQUENCE: 54
TIYPGDSDTR YSPSFQG                                                  17

SEQ ID NO: 55           moltype = AA  length = 9
FEATURE                 Location/Qualifiers
REGION                  1..9
                        note = EGFRvIII P047.019 HCDR3
source                  1..9
                        mol_type = protein
                        organism = synthetic construct
SEQUENCE: 55
TGPGLAFDY                                                           9

SEQ ID NO: 56           moltype = AA  length = 118
FEATURE                 Location/Qualifiers
REGION                  1..118
                        note = EGFRvIII P047.019 VH
source                  1..118
                        mol_type = protein
                        organism = synthetic construct
SEQUENCE: 56
EVQLVQSGAE VKKPGESLKI SCKGSGYSFP SIWIHWVRQM PGKGLEWMGT IYPGDSDTRY  60
SPSFQGQVTI SADKSISTAY LQWSSLKASD TAMYYCARTG PGLAFDYWGQ GTLVTVSS    118

SEQ ID NO: 57           moltype = AA  length = 17
FEATURE                 Location/Qualifiers
REGION                  1..17
                        note = EGFRvIII P047.019 LCDR1
source                  1..17
                        mol_type = protein
                        organism = synthetic construct
SEQUENCE: 57
KSSQSVLYSS NNKNYLA                                                  17

SEQ ID NO: 58           moltype = AA  length = 7
FEATURE                 Location/Qualifiers
REGION                  1..7
                        note = EGFRvIII P047.019 LCDR2
```

```
source                  1..7
                        mol_type = protein
                        organism = synthetic construct
SEQUENCE: 58
WASTRES                                                           7

SEQ ID NO: 59           moltype = AA  length = 9
FEATURE                 Location/Qualifiers
REGION                  1..9
                        note = EGFRvIII P047.019 LCDR3
source                  1..9
                        mol_type = protein
                        organism = synthetic construct
SEQUENCE: 59
QQSYSTPIT                                                         9

SEQ ID NO: 60           moltype = AA  length = 113
FEATURE                 Location/Qualifiers
REGION                  1..113
                        note = EGFRvIII P047.019 VL
source                  1..113
                        mol_type = protein
                        organism = synthetic construct
SEQUENCE: 60
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQSYST PITFGQGTKV EIK         113

SEQ ID NO: 61           moltype = AA  length = 5
FEATURE                 Location/Qualifiers
REGION                  1..5
                        note = EGFRvIII P057.012 HCDR1
source                  1..5
                        mol_type = protein
                        organism = synthetic construct
SEQUENCE: 61
NYWIA                                                             5

SEQ ID NO: 62           moltype = AA  length = 17
FEATURE                 Location/Qualifiers
REGION                  1..17
                        note = EGFRvIII P057.012 HCDR2
source                  1..17
                        mol_type = protein
                        organism = synthetic construct
SEQUENCE: 62
IIYPDDSDTR YSPSFQG                                                17

SEQ ID NO: 63           moltype = AA  length = 12
FEATURE                 Location/Qualifiers
REGION                  1..12
                        note = EGFRvIII P057.012 HCDR3
source                  1..12
                        mol_type = protein
                        organism = synthetic construct
SEQUENCE: 63
ATNIASGGYF DY                                                     12

SEQ ID NO: 64           moltype = AA  length = 121
FEATURE                 Location/Qualifiers
REGION                  1..121
                        note = EGFRvIII P057.012 VH
source                  1..121
                        mol_type = protein
                        organism = synthetic construct
SEQUENCE: 64
EVQLVQSGAE VKKPGESLKI SCKGSGYSFA NYWIAWVRQM PGKGLEWMGI IYPDDSDTRY  60
SPSFQGQVTI SADKSISTAY LQWSSLKASD TAMYYCARAT NIASGGYFDY WGQGTLVTVS  120
S                                                                 121

SEQ ID NO: 65           moltype = AA  length = 17
FEATURE                 Location/Qualifiers
REGION                  1..17
                        note = EGFRvIII P057.012 LCDR1
source                  1..17
                        mol_type = protein
                        organism = synthetic construct
SEQUENCE: 65
KSSQSVLWNS NNKNYLA                                                17
```

```
SEQ ID NO: 66           moltype = AA  length = 7
FEATURE                 Location/Qualifiers
REGION                  1..7
                        note = EGFRvIII P057.012 LCDR2
source                  1..7
                        mol_type = protein
                        organism = synthetic construct
SEQUENCE: 66
WASKRES                                                    7

SEQ ID NO: 67           moltype = AA  length = 9
FEATURE                 Location/Qualifiers
REGION                  1..9
                        note = EGFRvIII P057.012 LCDR3
source                  1..9
                        mol_type = protein
                        organism = synthetic construct
SEQUENCE: 67
QQSYSAPIT                                                  9

SEQ ID NO: 68           moltype = AA  length = 113
FEATURE                 Location/Qualifiers
REGION                  1..113
                        note = EGFRvIII P057.012 VL
source                  1..113
                        mol_type = protein
                        organism = synthetic construct
SEQUENCE: 68
DIVMTQSPDS LAVSLGERAT INCKSSQSVL WNSNNKNYLA WYQQKPGQPP KLLIYWASKR  60
ESGVPDRFSG SGSGTDFTLT ISSLQAEDVA VYYCQQSYSA PITFGQGTKV EIK         113

SEQ ID NO: 69           moltype = AA  length = 5
FEATURE                 Location/Qualifiers
REGION                  1..5
                        note = EGFRvIII P057.011 HCDR1
source                  1..5
                        mol_type = protein
                        organism = synthetic construct
SEQUENCE: 69
RRWIA                                                      5

SEQ ID NO: 70           moltype = AA  length = 17
FEATURE                 Location/Qualifiers
REGION                  1..17
                        note = EGFRvIII P057.011 HCDR2
source                  1..17
                        mol_type = protein
                        organism = synthetic construct
SEQUENCE: 70
IIYPGDSDTR YSPSFQG                                         17

SEQ ID NO: 71           moltype = AA  length = 12
FEATURE                 Location/Qualifiers
REGION                  1..12
                        note = EGFRvIII P057.011 HCDR3
source                  1..12
                        mol_type = protein
                        organism = synthetic construct
SEQUENCE: 71
ATNIASGGYF DY                                              12

SEQ ID NO: 72           moltype = AA  length = 121
FEATURE                 Location/Qualifiers
REGION                  1..121
                        note = EGFRvIII P057.011 VH
source                  1..121
                        mol_type = protein
                        organism = synthetic construct
SEQUENCE: 72
EVQLVQSGAE VKKPGESLKI SCKGSGYNFG RRWIAWVRQM PGKGLEWMGI IYPGDSDTRY  60
SPSFQGQVTI SADKSISTAY LQWSSLKASD TAMYYCARAT NIASGGYFDY WGQGTLVTVS  120
S                                                          121

SEQ ID NO: 73           moltype = AA  length = 17
FEATURE                 Location/Qualifiers
REGION                  1..17
                        note = EGFRvIII P057.011 LCDR1
source                  1..17
                        mol_type = protein
```

```
                         organism = synthetic construct
SEQUENCE: 73
KSSQSVLWNS NNKNYLA                                                17

SEQ ID NO: 74            moltype = AA  length = 7
FEATURE                  Location/Qualifiers
REGION                   1..7
                         note = EGFRvIII P057.011 LCDR2
source                   1..7
                         mol_type = protein
                         organism = synthetic construct
SEQUENCE: 74
WASKRES                                                           7

SEQ ID NO: 75            moltype = AA  length = 9
FEATURE                  Location/Qualifiers
REGION                   1..9
                         note = EGFRvIII P057.011 LCDR3
source                   1..9
                         mol_type = protein
                         organism = synthetic construct
SEQUENCE: 75
QQSYSAPIT                                                         9

SEQ ID NO: 76            moltype = AA  length = 113
FEATURE                  Location/Qualifiers
REGION                   1..113
                         note = EGFRvIII P057.011 VL
source                   1..113
                         mol_type = protein
                         organism = synthetic construct
SEQUENCE: 76
DIVMTQSPDS LAVSLGERAT INCKSSQSVL WNSNNKNYLA WYQQKPGQPP KLLIYWASKR  60
ESGVPDRFSG SGSGTDFTLT ISSLQAEDVA VYYCQQSYSA PITFGQGTKV EIK         113

SEQ ID NO: 77            moltype = AA  length = 5
FEATURE                  Location/Qualifiers
REGION                   1..5
                         note = EGFRvIII P056.027 HCDR1
source                   1..5
                         mol_type = protein
                         organism = synthetic construct
SEQUENCE: 77
NNWIA                                                             5

SEQ ID NO: 78            moltype = AA  length = 17
FEATURE                  Location/Qualifiers
REGION                   1..17
                         note = EGFRvIII P056.027 HCDR2
source                   1..17
                         mol_type = protein
                         organism = synthetic construct
SEQUENCE: 78
VIYPGDSDKR YSPSFQG                                                17

SEQ ID NO: 79            moltype = AA  length = 10
FEATURE                  Location/Qualifiers
REGION                   1..10
                         note = EGFRvIII P056.027 HCDR3
source                   1..10
                         mol_type = protein
                         organism = synthetic construct
SEQUENCE: 79
VSRSSYAFDY                                                        10

SEQ ID NO: 80            moltype = AA  length = 119
FEATURE                  Location/Qualifiers
REGION                   1..119
                         note = EGFRvIII P056.027 VH
source                   1..119
                         mol_type = protein
                         organism = synthetic construct
SEQUENCE: 80
EVQLVQSGAE VKKPGESLKI SCKGSGYTFG NNWIAWVRQM PGKGLEWMGV IYPGDSDKRY  60
SPSFQGQVTI SADKSISTAY LQWSSLKASD TAMYYCARVS RSSYAFDYWG QGTLVTVSS   119

SEQ ID NO: 81            moltype = AA  length = 17
FEATURE                  Location/Qualifiers
REGION                   1..17
```

```
                        note = EGFRvIII P056.027 LCDR1
source                  1..17
                        mol_type = protein
                        organism = synthetic construct
SEQUENCE: 81
KSSQSVLYSS NNKNYLA                                               17

SEQ ID NO: 82           moltype = AA  length = 7
FEATURE                 Location/Qualifiers
REGION                  1..7
                        note = EGFRvIII P056.027 LCDR2
source                  1..7
                        mol_type = protein
                        organism = synthetic construct
SEQUENCE: 82
WASTRES                                                          7

SEQ ID NO: 83           moltype = AA  length = 10
FEATURE                 Location/Qualifiers
REGION                  1..10
                        note = EGFRvIII P056.027 LCDR3
source                  1..10
                        mol_type = protein
                        organism = synthetic construct
SEQUENCE: 83
QQVHSGPPVT                                                       10

SEQ ID NO: 84           moltype = AA  length = 114
FEATURE                 Location/Qualifiers
REGION                  1..114
                        note = EGFRvIII P056.027 VL
source                  1..114
                        mol_type = protein
                        organism = synthetic construct
SEQUENCE: 84
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQVHSG PPVTFGQGTK VEIK        114

SEQ ID NO: 85           moltype = AA  length = 5
FEATURE                 Location/Qualifiers
REGION                  1..5
                        note = EGFRvIII P063.056 HCDR1
source                  1..5
                        mol_type = protein
                        organism = synthetic construct
SEQUENCE: 85
SYWIA                                                            5

SEQ ID NO: 86           moltype = AA  length = 17
FEATURE                 Location/Qualifiers
REGION                  1..17
                        note = EGFRvIII P063.056 HCDR2
source                  1..17
                        mol_type = protein
                        organism = synthetic construct
SEQUENCE: 86
VIHPYDSDTR YSPSFQG                                               17

SEQ ID NO: 87           moltype = AA  length = 10
FEATURE                 Location/Qualifiers
REGION                  1..10
                        note = EGFRvIII P063.056 HCDR3
source                  1..10
                        mol_type = protein
                        organism = synthetic construct
SEQUENCE: 87
VSRSSYAFDY                                                       10

SEQ ID NO: 88           moltype = AA  length = 119
FEATURE                 Location/Qualifiers
REGION                  1..119
                        note = EGFRvIII P063.056 VH
source                  1..119
                        mol_type = protein
                        organism = synthetic construct
SEQUENCE: 88
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RSSYAFDYWG QGTLVTVSS   119
```

```
SEQ ID NO: 89          moltype = AA  length = 17
FEATURE                Location/Qualifiers
REGION                 1..17
                       note = EGFRvIII P063.056 LCDR1
source                 1..17
                       mol_type = protein
                       organism = synthetic construct
SEQUENCE: 89
KSSQSVLYSS NNKNYLA                                                17

SEQ ID NO: 90          moltype = AA  length = 7
FEATURE                Location/Qualifiers
REGION                 1..7
                       note = EGFRvIII P063.056 LCDR2
source                 1..7
                       mol_type = protein
                       organism = synthetic construct
SEQUENCE: 90
WASTRES                                                           7

SEQ ID NO: 91          moltype = AA  length = 10
FEATURE                Location/Qualifiers
REGION                 1..10
                       note = EGFRvIII P063.056 LCDR3
source                 1..10
                       mol_type = protein
                       organism = synthetic construct
SEQUENCE: 91
QQQRDGPPVT                                                        10

SEQ ID NO: 92          moltype = AA  length = 114
FEATURE                Location/Qualifiers
REGION                 1..114
                       note = EGFRvIII P063.056 VL
source                 1..114
                       mol_type = protein
                       organism = synthetic construct
SEQUENCE: 92
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQQRDG PPVTFGQGTK VEIK        114

SEQ ID NO: 93          moltype = AA  length = 5
FEATURE                Location/Qualifiers
REGION                 1..5
                       note = EGFRvIII P064.078 HCDR1
source                 1..5
                       mol_type = protein
                       organism = synthetic construct
SEQUENCE: 93
SYWIA                                                             5

SEQ ID NO: 94          moltype = AA  length = 17
FEATURE                Location/Qualifiers
REGION                 1..17
                       note = EGFRvIII P064.078 HCDR2
source                 1..17
                       mol_type = protein
                       organism = synthetic construct
SEQUENCE: 94
VIHPYDSDTR YSPSFQG                                                17

SEQ ID NO: 95          moltype = AA  length = 10
FEATURE                Location/Qualifiers
REGION                 1..10
                       note = EGFRvIII P064.078 HCDR3
source                 1..10
                       mol_type = protein
                       organism = synthetic construct
SEQUENCE: 95
VSRLSYALDY                                                        10

SEQ ID NO: 96          moltype = AA  length = 119
FEATURE                Location/Qualifiers
REGION                 1..119
                       note = EGFRvIII P064.078 VH
source                 1..119
                       mol_type = protein
                       organism = synthetic construct
SEQUENCE: 96
```

```
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RLSYALDYWG QGTLVTVSS   119

SEQ ID NO: 97          moltype = AA  length = 17
FEATURE                Location/Qualifiers
REGION                 1..17
                       note = EGFRvIII P064.078 LCDR1
source                 1..17
                       mol_type = protein
                       organism = synthetic construct
SEQUENCE: 97
KSSQSVLYSS NNKNYLA                                                17

SEQ ID NO: 98          moltype = AA  length = 7
FEATURE                Location/Qualifiers
REGION                 1..7
                       note = EGFRvIII P064.078 LCDR2
source                 1..7
                       mol_type = protein
                       organism = synthetic construct
SEQUENCE: 98
WASTRES                                                           7

SEQ ID NO: 99          moltype = AA  length = 10
FEATURE                Location/Qualifiers
REGION                 1..10
                       note = EGFRvIII P064.078 LCDR3
source                 1..10
                       mol_type = protein
                       organism = synthetic construct
SEQUENCE: 99
QQVHSGPPVT                                                        10

SEQ ID NO: 100         moltype = AA  length = 114
FEATURE                Location/Qualifiers
REGION                 1..114
                       note = EGFRvIII P064.078 VL
source                 1..114
                       mol_type = protein
                       organism = synthetic construct
SEQUENCE: 100
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQVHSG PPVTFGQGTK VEIK        114

SEQ ID NO: 101         moltype = AA  length = 5
FEATURE                Location/Qualifiers
REGION                 1..5
                       note = EGFRvIII P065.036 HCDR1
source                 1..5
                       mol_type = protein
                       organism = synthetic construct
SEQUENCE: 101
SYWIA                                                             5

SEQ ID NO: 102         moltype = AA  length = 17
FEATURE                Location/Qualifiers
REGION                 1..17
                       note = EGFRvIII P065.036 HCDR2
source                 1..17
                       mol_type = protein
                       organism = synthetic construct
SEQUENCE: 102
VIHPYDSDTR YSPSFQG                                                17

SEQ ID NO: 103         moltype = AA  length = 10
FEATURE                Location/Qualifiers
REGION                 1..10
                       note = EGFRvIII P065.036 HCDR3
source                 1..10
                       mol_type = protein
                       organism = synthetic construct
SEQUENCE: 103
VSRSSYALDY                                                        10

SEQ ID NO: 104         moltype = AA  length = 119
FEATURE                Location/Qualifiers
REGION                 1..119
                       note = EGFRvIII P065.036 VH
source                 1..119
```

```
                        mol_type = protein
                        organism = synthetic construct
SEQUENCE: 104
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RSSYALDYWG QGTLVTVSS   119

SEQ ID NO: 105          moltype = AA  length = 17
FEATURE                 Location/Qualifiers
REGION                  1..17
                        note = EGFRvIII P065.036 LCDR1
source                  1..17
                        mol_type = protein
                        organism = synthetic construct
SEQUENCE: 105
KSSQSVLYSS NNKNYLA                                                 17

SEQ ID NO: 106          moltype = AA  length = 7
FEATURE                 Location/Qualifiers
REGION                  1..7
                        note = EGFRvIII P065.036 LCDR2
source                  1..7
                        mol_type = protein
                        organism = synthetic construct
SEQUENCE: 106
WASTRES                                                            7

SEQ ID NO: 107          moltype = AA  length = 10
FEATURE                 Location/Qualifiers
REGION                  1..10
                        note = EGFRvIII P065.036 LCDR3
source                  1..10
                        mol_type = protein
                        organism = synthetic construct
SEQUENCE: 107
QQVYSGPPVT                                                         10

SEQ ID NO: 108          moltype = AA  length = 114
FEATURE                 Location/Qualifiers
REGION                  1..114
                        note = EGFRvIII P065.036 VL
source                  1..114
                        mol_type = protein
                        organism = synthetic construct
SEQUENCE: 108
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQVYSG PPVTFGQGTK VEIK        114

SEQ ID NO: 109          moltype = AA  length = 672
FEATURE                 Location/Qualifiers
REGION                  1..672
                        note = EGFRvIII VH-CH1(EE) - CD3orig/CD3opt VL-CH1 - Fc
                         (knob, PGLALA)
source                  1..672
                        mol_type = protein
                        organism = synthetic construct
SEQUENCE: 109
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RSSYAFDYWG QGTLVTVSSA  120
STKGPSVFPL APSSKSTSGG TAALGCLVED YFPEPVTVSW NSGALTSGVH TFPAVLQSSG  180
LYSLSSVVTV PSSSLGTQTY ICNVNHKPSN TKVDEKVEPK SCDGGGGSGG GGSQAVVTQE  240
PSLTVSPGGT VTLTCGSSTG AVTTSNYANW VQEKPGQAFR GLIGGTNKRA PGTPARFSGS  300
LLGGKAALTL SGAQPEDEAE YYCALWYSNL WVFGGGTKLT VLSSASTKGP SVFPLAPSSK  360
STSGGTAALG CLVKDYFPEP VTVSWNSGAL TSGVHTFPAV LQSSGLYSLS SVVTVPSSSL  420
GTQTYICNVN HKPSNTKVDK KVEPKSCDKT HTCPPCPAPE AAGGPSVFLF PPKPKDTLMI  480
SRTPEVTCVV VDVSHEDPEV KFNWYVDGVE VHNAKTKPRE EQYNSTYRVV SVLTVLHQDW  540
LNGKEYKCKV SNKALGAPIE KTISKAKGQP REPQVYTLPP CRDELTKNQV SLWCLVKGFY  600
PSDIAVEWES NGQPENNYKT TPPVLDSDGS FFLYSKLTVD KSRWQQGNVF SCSVMHEALH  660
NHYTQKSLSL SP                                                      672

SEQ ID NO: 110          moltype = AA  length = 447
FEATURE                 Location/Qualifiers
REGION                  1..447
                        note = EGFRvIII VH-CH1(EE) -Fc (hole, PGLALA)
source                  1..447
                        mol_type = protein
                        organism = synthetic construct
SEQUENCE: 110
EVQLVQSGAE VKKPGESLKI SCKGSGYSFD SYWIAWVRQM PGKGLEWMGV IHPYDSDTRY  60
SPSFQGQVTI SADKSISTAY LQWSSLKASD TAMYYCARVS RSSYAFDYWG QGTLVTVSSA  120
```

```
STKGPSVFPL APSSKSTSGG TAALGCLVED YFPEPVTVSW NSGALTSGVH TFPAVLQSSG  180
LYSLSSVVTV PSSSLGTQTY ICNVNHKPSN TKVDEKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL GAPIEKTISK AKGQPREPQV CTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSP                                      447

SEQ ID NO: 111         moltype = AA  length = 221
FEATURE                Location/Qualifiers
REGION                 1..221
                       note = EGFRvIII VL-CL(RK)
source                 1..221
                       mol_type = protein
                       organism = synthetic construct
SEQUENCE: 111
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQQRDG PPVTFGQGTK VEIKRTVAAP  120
SVFIFPPSDR KLKSGTASVV CLLNNFYPRE AKVQWKVDNA LQSGNSQESV TEQDSKDSTY  180
SLSSTLTLSK ADYEKHKVYA CEVTHQGLSS PVTKSFNRGE C                      221

SEQ ID NO: 112         moltype = AA  length = 186
FEATURE                Location/Qualifiers
source                 1..186
                       mol_type = protein
                       organism = Homo sapiens
SEQUENCE: 112
QDGNEEMGGI TQTPYKVSIS GTTVILTCPQ YPGSEILWQH NDKNIGGDED DKNIGSDEDH  60
LSLKEFSELE QSGYYVCYPR GSKPEDANFY LYLRARVCEN CMEMDVMSVA TIVIVDICIT  120
GGLLLLVYYW SKNRKAKAKP VTRGAGAGGR QRGQNKERPP PVPNPDYEPI RKGQRDLYSG  180
LNQRRI                                                             186

SEQ ID NO: 113         moltype = AA  length = 177
FEATURE                Location/Qualifiers
source                 1..177
                       mol_type = protein
                       organism = Macaca fascicularis
SEQUENCE: 113
QDGNEEMGSI TQTPYQVSIS GTTVILTCSQ HLGSEAQWQH NGKNKEDSGD RLFLPEFSEM  60
EQSGYYVCYP RGSNPEDASH HLYLKARVCE NCMEMDVMAV ATIVIVDICI TLGLLLLVYY  120
WSKNRKAKAK PVTRGAGAGG RQRGQNKERP PPVPNPDYEP IRKGQQDLYS GLNQRRI      177

SEQ ID NO: 114         moltype = AA  length = 513
FEATURE                Location/Qualifiers
source                 1..513
                       mol_type = protein
                       organism = Homo sapiens
SEQUENCE: 114
QFPRQCATVE ALRSGMCCPD LSPVSGPGTD RCGSSSGRGR CEAVTADSRP HSPQYPHDGR  60
DDREVWPLRF FNRTCHCNGN FSGHNCGTCR PGWRGAACDQ RVLIVRRNLL DLSKEEKNHF  120
VRALDMAKRT THPLFVIATR RSEEILGPDG NTPQFENISI YNYFVWTHYY SVKKTFLGVG  180
QESFGEVDFS HEGPAFLTWH RYHLLRLEKD MQEMLQEPSF SLPYWNFATG KNVCDICTDD  240
LMGSRSNFDS TLISPNSVFS QWRVVCDSLE DYDTLGTLCN STEDGPIRRN PAGNVARPMV  300
QRLPEPQDVA QCLEVGLFDT PPFYSNSTNS FRNTVEGYSD PTGKYDPAVR SLHNLAHLFL  360
NGTGGQTHLS PNDPIFVLLH TFTDAVFDEW LRRYNADIST FPLENAPIGH NRQYNMVPFW  420
PPVTNTEMFV TAPDNLGYTY EIQWPSREFS VPEIIAIAVV GALLLVALIF GTASYLIRAR  480
RSMDEANQPL LTDQYQCYAE EYEKLQNPNQ SVV                               513

SEQ ID NO: 115         moltype = AA  length = 919
FEATURE                Location/Qualifiers
source                 1..919
                       mol_type = protein
                       organism = Homo sapiens
SEQUENCE: 115
LEEKKGNYVV TDHGSCVRAC GADSYEMEED GVRKCKKCEG PCRKVCNGIG IGEFKDSLSI  60
NATNIKHFKN CTSISGDLHI LPVAFRGDSF THTPPLDPQE LDILKTVKEI TGFLLIQAWP  120
ENRTDLHAFE NLEIIRGRTK QHGQFSLAVV SLNITSLGLR SLKEISDGDV IISGNKNLCY  180
ANTINWKKLF GTSGQKTKII SNRGENSCKA TGQVCHALCS PEGCWGPEPR DCVSCRNVSR  240
GRECVDKCNL LEGEPREFVE NSECIQCHPE CLPQAMNITC TGRGPDNCIQ CAHYIDGPHC  300
VKTCPAGVMG ENNTLVWKYA DAGHVCHLCH PNCTYGCTGP GLEGCPTNGP KIPSIATGMV  360
GALLLLLVVA LGIGLFMRRR HIVRKRTLRR LLQERELVEP LTPSGEAPNQ ALLRILKETE  420
FKKIKVLGSG AFGTVYKGLW IPEGEKVKIP VAIKELREAT SPKANKEILD EAYVMASVDN  480
PHVCRLLGIC LTSTVQLITQ LMPFGCLLDY VREHKDNIGS QYLLNWCVQI AKGMNYLEDR  540
RLVHRDLAAR NVLVKTPQHV KITDFGLAKL LGAEEKEYHA EGGKVPIKWM ALESILHRIY  600
THQSDVWSYG VTVWELMTFG SKPYDGIPAS EISSILEKGE RLPQPPICTI DVYMIMVKCW  660
MIDADSRPKF RELIIEFSKM ARDPQRYLVI QGDERMHLPS PTDSNFYRAL MDEEDMDDVV  720
DADEYLIPQQ GFFSSPSTSR TPLLSSLSAT SNNSTVACID RNGLQSCPIK EDSFLQRYSS  780
DPTGALTEDS IDDTFLPVPE YINQSVPKRP AGSVQNPVYH NQPLNPAPSR DPHYQDPHST  840
AVGNPEYLNT VQPTCVNSTF DSPAHWAQKG SHQISLDNPD YQQDFFPKEA KPNGIFKGST  900
AENAEYLRVA PQSSEFIGA                                               919
```

```
SEQ ID NO: 116          moltype = AA  length = 1186
FEATURE                 Location/Qualifiers
source                  1..1186
                        mol_type = protein
                        organism = Homo sapiens
SEQUENCE: 116
LEEKKVCQGT SNKLTQLGTF EDHFLSLQRM FNNCEVVLGN LEITYVQRNY DLSFLKTIQE  60
VAGYVLIALN TVERIPLENL QIIRGNMYYE NSYALAVLSN YDANKTGLKE LPMRNLQEIL  120
HGAVRFSNNP ALCNVESIQW RDIVSSDFLS NMSMDFQNHL GSCQKCDPSC PNGSCWGAGE  180
ENCQKLTKII CAQQCSGRCR GKSPSDCCHN QCAAGCTGPR ESDCLVCRKF RDEATCKDTC  240
PPLMLYNPTT YQMDVNPEGK YSFGATCVKK CPRNYVVTDH GSCVRACGAD SYEMEEDGVR  300
KCKKCEGPCR KVCNGIGIGE FKDSLSINAT NIKHFKNCTS ISGDLHILPV AFRGDSFTHT  360
PPLDPQELDI LKTVKEITGF LLIQAWPENR TDLHAFENLE IIRGRTKQHG QFSLAVVSLN  420
ITSLGLRSLK EISDGDVIIS GNKNLCYANT INWKKLFGTS GQKTKIISNR GENSCKATGQ  480
VCHALCSPEG CWGPEPRDCV SCRNVSRGRE CVDKCNLLEG EPREFVENSE CIQCHPECLP  540
QAMNITCTGR GPDNCIQCAH YIDGPHCVKT CPAGVMGENN TLVWKYADAG HVCHLCHPNC  600
TYGCTGPGLE GCPTNGPKIP SIATGMVGAL LLLLVVALGI GLFMRRRHIV RKRTLRRLLQ  660
ERELVEPLTP SGEAPNQALL RILKETEFKK IKVLGSGAFG TVYKGLWIPE GEKVKIPVAI  720
KELREATSPK ANKEILDEAY VMASVDNPHV CRLLGICLTS TVQLITQLMP FGCLLDYVRE  780
HKDNIGSQYL LNWCVQIAKG MNYLEDRRLV HRDLAARNVL VKTPQHVKIT DFGLAKLLGA  840
EEKEYHAEGG KVPIKWMALE SILHRIYTHQ SDVWSYGVTV WELMTFGSKP YDGIPASEIS  900
SILEKGERLP QPPICTIDVY MIMVKCWMID ADSRPKFREL IIEFSKMARD PQRYLVIQGD  960
ERMHLPSPTD SNFYRALMDE EDMDDVVDAD EYLIPQQGFF SSPSTSRTPL LSSLSATSNN  1020
STVACIDRNG LQSCPIKEDS FLQRYSSDPT GALTEDSIDD TFLPVPEYIN QSVPKRPAGS  1080
VQNPVYHNQP LNPAPSRDPH YQDPHSTAVG NPEYLNTVQP TCVNSTFDSP AHWAQKGSHQ  1140
ISLDNPDYQQ DFFPKEAKPN GIFKGSTAEN AEYLRVAPQS SEFIGA                1186

SEQ ID NO: 117          moltype = AA  length = 225
FEATURE                 Location/Qualifiers
REGION                  1..225
                        note = hIgG1 Fc region
source                  1..225
                        mol_type = protein
                        organism = synthetic construct
SEQUENCE: 117
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSP                 225

SEQ ID NO: 118          moltype = AA  length = 10
FEATURE                 Location/Qualifiers
REGION                  1..10
                        note = Linker GGGGSGGGGS
source                  1..10
                        mol_type = protein
                        organism = synthetic construct
SEQUENCE: 118
GGGGSGGGGS                                                        10

SEQ ID NO: 119          moltype = AA  length = 11
FEATURE                 Location/Qualifiers
REGION                  1..11
                        note = Linker DGGGGSGGGGS
source                  1..11
                        mol_type = protein
                        organism = synthetic construct
SEQUENCE: 119
DGGGGSGGGG S                                                      11

SEQ ID NO: 120          moltype = AA  length = 107
FEATURE                 Location/Qualifiers
REGION                  1..107
                        note = Human kappa CL domain
source                  1..107
                        mol_type = protein
                        organism = synthetic construct
SEQUENCE: 120
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 121          moltype = AA  length = 105
FEATURE                 Location/Qualifiers
REGION                  1..105
                        note = Human lambda CL domain
source                  1..105
                        mol_type = protein
                        organism = synthetic construct
```

```
SEQUENCE: 121
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                 105

SEQ ID NO: 122         moltype = AA  length = 328
FEATURE                Location/Qualifiers
REGION                 1..328
                       note = Human IgG1 heavy chain constant region (CH1-CH2-CH3)
source                 1..328
                       mol_type = protein
                       organism = synthetic construct
SEQUENCE: 122
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                    328

SEQ ID NO: 123         moltype = AA  length = 120
FEATURE                Location/Qualifiers
REGION                 1..120
                       note = 16D5 VH
source                 1..120
                       mol_type = protein
                       organism = synthetic construct
SEQUENCE: 123
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120

SEQ ID NO: 124         moltype = AA  length = 5
FEATURE                Location/Qualifiers
REGION                 1..5
                       note = 16D5 CDRH1
source                 1..5
                       mol_type = protein
                       organism = synthetic construct
SEQUENCE: 124
NAWMS                                                             5

SEQ ID NO: 125         moltype = AA  length = 19
FEATURE                Location/Qualifiers
REGION                 1..19
                       note = 16D5 CDRH2
source                 1..19
                       mol_type = protein
                       organism = synthetic construct
SEQUENCE: 125
RIKSKTDGGT TDYAAPVKG                                              19

SEQ ID NO: 126         moltype = AA  length = 9
FEATURE                Location/Qualifiers
REGION                 1..9
                       note = 16D5 CDRH3
source                 1..9
                       mol_type = protein
                       organism = synthetic construct
SEQUENCE: 126
PWEWSWYDY                                                         9

SEQ ID NO: 127         moltype = AA  length = 687
FEATURE                Location/Qualifiers
REGION                 1..687
                       note = FOLR1 TCB 16D5-CD3opt 2+1 classical format K chain
source                 1..687
                       mol_type = protein
                       organism = synthetic construct
SEQUENCE: 127
EVQLLESGGG LVQPGGSLRL SCAASGFQFS SYAMNWVRQA PGKGLEWVSR IRSKYNNYAT  60
YYADSVKGRF TISRDDSKNT LYLQMNSLRA EDTAVYYCVR HTTFPSSYVS YYGYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDG GGGSGGGGSE  240
VQLVESGGGL VKPGGSLRLS CAASGFTFSN AWMSWVRQAP GKGLEWVGRI KSKTDGGTTD  300
YAAPVKGRFT ISRDDSKNTL YLQMNSLKTE DTAVYYCTTP WEWSWYDYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL GAPIEKTISK AKGQPREPQV YTLPPCRDEL  600
TKNQVSLWCL VKGFYPSDIA VEWESNGQPE NNYKTTPPVL DSDGSFFLYS KLTVDKSRWQ  660
```

```
QGNVFSCSVM HEALHNHYTQ KSLSLSP                                687

SEQ ID NO: 128          moltype = AA  length = 448
FEATURE                 Location/Qualifiers
REGION                  1..448
                        note = FOLR1 TCB 16D5-CD3opt 2+1 classical format H chain
source                  1..448
                        mol_type = protein
                        organism = synthetic construct
SEQUENCE: 128
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSP                               448

SEQ ID NO: 129          moltype = AA  length = 215
FEATURE                 Location/Qualifiers
REGION                  1..215
                        note = Common Light chain
source                  1..215
                        mol_type = protein
                        organism = synthetic construct
SEQUENCE: 129
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                        215

SEQ ID NO: 130          moltype = AA  length = 687
FEATURE                 Location/Qualifiers
REGION                  1..687
                        note = FOLR1 TCB 16D5-CD3opt 2+1 inverted format K chain
source                  1..687
                        mol_type = protein
                        organism = synthetic construct
SEQUENCE: 130
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDGGGGSG GGGSEVQLLE  240
SGGGLVQPGG SLRLSCAASG FQFSSYAMNW VRQAPGKGLE WVSRIRSKYN NYATYYADSV  300
KGRFTISRDD SKNTLYLQMN SLRAEDTAVY YCVRHTTFPS SYVSYYGYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL GAPIEKTISK AKGQPREPQV YTLPPCRDEL  600
TKNQVSLWCL VKGFYPSDIA VEWESNGQPE NNYKTTPPVL DSDGSFFLYS KLTVDKSRWQ  660
QGNVFSCSVM HEALHNHYTQ KSLSLSP                                687

SEQ ID NO: 131          moltype = AA  length = 687
FEATURE                 Location/Qualifiers
REGION                  1..687
                        note = FOLR1 TCB 16D5-CD3opt 1+1 Head to tail inverted
                         format K chain
source                  1..687
                        mol_type = protein
                        organism = synthetic construct
SEQUENCE: 131
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDGGGGSG GGGSEVQLLE  240
SGGGLVQPGG SLRLSCAASG FQFSSYAMNW VRQAPGKGLE WVSRIRSKYN NYATYYADSV  300
KGRFTISRDD SKNTLYLQMN SLRAEDTAVY YCVRHTTFPS SYVSYYGYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL GAPIEKTISK AKGQPREPQV YTLPPCRDEL  600
TKNQVSLWCL VKGFYPSDIA VEWESNGQPE NNYKTTPPVL DSDGSFFLYS KLTVDKSRWQ  660
QGNVFSCSVM HEALHNHYTQ KSLSLSP                                687

SEQ ID NO: 132          moltype = AA  length = 225
FEATURE                 Location/Qualifiers
REGION                  1..225
                        note = FOLR1 TCB 16D5-CD3opt 1+1 Head to tail inverted
```

```
                         format H chain
source                  1..225
                        mol_type = protein
                        organism = synthetic construct
SEQUENCE: 132
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSP                 225

SEQ ID NO: 133          moltype = AA  length = 687
FEATURE                 Location/Qualifiers
REGION                  1..687
                        note = FOLR1 TCB 16D5-CD3opt 1+1 Head to tail classical
                         format K chain
source                  1..687
                        mol_type = protein
                        organism = synthetic construct
SEQUENCE: 133
EVQLLESGGG LVQPGGSLRL SCAASGFQFS SYAMNWVRQA PGKGLEWVSR IRSKYNNYAT  60
YYADSVKGRF TISRDDSKNT LYLQMNSLRA EDTAVYYCVR HTTFPSSYVS YYGYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDG GGGSGGGGSE  240
VQLVESGGGL VKPGGSLRLS CAASGFTFSN AWMSWVRQAP GKGLEWVGRI KSKTDGGTTD  300
YAAPVKGRFT ISRDDSKNTL YLQMNSLKTE DTAVYYCTTP WEWSWYDYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL GAPIEKTISK AKGQPREPQV YTLPPCRDEL  600
TKNQVSLWCL VKGFYPSDIA VEWESNGQPE NNYKTTPPVL DSDGSFFLYS KLTVDKSRWQ  660
QGNVFSCSVM HEALHNHYTQ KSLSLSP                                      687

SEQ ID NO: 134          moltype = AA  length = 225
FEATURE                 Location/Qualifiers
REGION                  1..225
                        note = FOLR1 TCB 16D5-CD3opt 1+1 Head to tail classical
                         format H chain
source                  1..225
                        mol_type = protein
                        organism = synthetic construct
SEQUENCE: 134
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSP                 225

SEQ ID NO: 135          moltype = AA  length = 448
FEATURE                 Location/Qualifiers
REGION                  1..448
                        note = FOLR1 TCB 16D5-CD3opt 1+1 IgG like format K chain
source                  1..448
                        mol_type = protein
                        organism = synthetic construct
SEQUENCE: 135
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 136          moltype = AA  length = 448
FEATURE                 Location/Qualifiers
REGION                  1..448
                        note = FOLR1 TCB 16D5-CD3opt 1+1 IgG like format H chain
source                  1..448
                        mol_type = protein
                        organism = synthetic construct
SEQUENCE: 136
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT PWEWSWYDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSP                                     448
```

-continued

```
SEQ ID NO: 137          moltype = AA  length = 257
FEATURE                 Location/Qualifiers
source                  1..257
                        mol_type = protein
                        organism = Homo sapiens
SEQUENCE: 137
MAQRMTTQLL LLLVWVAVVG EAQTRIAWAR TELLNVCMNA KHHKEKPGPE DKLHEQCRPW  60
RKNACCSTNT SQEAHKDVSY LYRFNWNHCG EMAPACKRHF IQDTCLYECS PNLGPWIQQV  120
DQSWRKERVL NVPLCKEDCE QWWEDCRTSY TCKSNWHKGW NWTSGFNKCA VGAACQPFHF  180
YFPTPTVLCN EIWTHSYKVS NYSRGSGRCI QMWFDPAQGN PNEEVARFYA AAMSGAGPWA  240
AWPFLLSLAL MLLWLLS                                                257
```